US011984200B2

(12) United States Patent
Bagaev et al.

(10) Patent No.: US 11,984,200 B2
(45) Date of Patent: *May 14, 2024

(54) SYSTEMS AND METHODS FOR GENERATING, VISUALIZING AND CLASSIFYING MOLECULAR FUNCTIONAL PROFILES

(71) Applicant: BostonGene Corporation, Waltham, MA (US)

(72) Inventors: Alexander Bagaev, Moscow (RU); Feliks Frenkel, Moscow (RU); Nikita Kotlov, Moscow (RU); Ravshan Ataullakhanov, Moscow (RU); Olga Isaeva, Leiden (NL)

(73) Assignee: BostonGene Corporation, Waltham, MA (US)

( * ) Notice: Subject to any disclaimer, the term of this patent is extended or adjusted under 35 U.S.C. 154(b) by 1632 days.

This patent is subject to a terminal disclaimer.

(21) Appl. No.: 16/006,481

(22) Filed: Jun. 12, 2018

(65) Prior Publication Data

US 2018/0357373 A1 Dec. 13, 2018
US 2020/0175134 A9 Jun. 4, 2020

Related U.S. Application Data

(60) Provisional application No. 62/598,440, filed on Dec. 13, 2017, provisional application No. 62/518,787, filed on Jun. 13, 2017.

(51) Int. Cl.
*G16B 45/00* (2019.01)
*C12Q 1/6886* (2018.01)
(Continued)

(52) U.S. Cl.
CPC ......... *G16B 45/00* (2019.02); *C12Q 1/6886* (2013.01); *G06F 16/285* (2019.01); *G06F 17/18* (2013.01);
(Continued)

(58) Field of Classification Search
CPC ......... G16B 45/00; G16B 25/10; G16B 5/20; G16B 5/00; G16B 20/00; G16B 40/00;
(Continued)

(56) References Cited

U.S. PATENT DOCUMENTS 8,068,994 B2 11/2011 Draghici
10,311,967 B2 6/2019 Bagaev et al.
(Continued)

FOREIGN PATENT DOCUMENTS

CN 101389957 A 3/2009
CN 101932724 A 12/2010
(Continued)

OTHER PUBLICATIONS

Extended European Search Report for European Application No. 22155044.5 dated May 12, 2022.
(Continued)

*Primary Examiner* — Jesse P Frumkin
(74) *Attorney, Agent, or Firm* — Wolf, Greenfield & Sacks, P.C.

(57) ABSTRACT

Various methods, systems, computer readable media, and graphical user interfaces (GUIs) are presented and described that enable a subject, doctor, or user to characterize or classify various types of cancer precisely. Additionally, described herein are methods, systems, computer readable media, and GUIs that enable more effective specification of treatment and improved outcomes for patients with identified types of cancer. Some embodiments of the methods, systems, computer readable media, and GUIs described herein comprise obtaining RNA expression data and/or whole exome sequencing (WES) data for a biological sample from a plurality of subjects, determining a respective plurality of molecular-functional (MF) profiles for the plurality of subjects, and storing the plurality of MF profiles in
(Continued)

association with information identifying the particular cancer type.

20 Claims, 98 Drawing Sheets

(51) Int. Cl.
| | |
|---|---|
| *G06F 16/28* | (2019.01) |
| *G06F 17/18* | (2006.01) |
| *G16B 5/00* | (2019.01) |
| *G16B 5/20* | (2019.01) |
| *G16B 20/00* | (2019.01) |
| *G16B 25/10* | (2019.01) |
| *G16B 30/00* | (2019.01) |
| *G16B 40/00* | (2019.01) |
| *G16B 40/20* | (2019.01) |
| *G16B 40/30* | (2019.01) |
| *G16B 50/00* | (2019.01) |
| *G16B 50/30* | (2019.01) |
| *G16H 10/20* | (2018.01) |
| *G16H 20/00* | (2018.01) |
| *G16H 20/10* | (2018.01) |
| *G16H 20/40* | (2018.01) |
| *G16H 50/20* | (2018.01) |
| *G16H 50/30* | (2018.01) |
| *G16H 50/50* | (2018.01) |
| *G16H 50/70* | (2018.01) |
| *G16H 70/20* | (2018.01) |

(52) U.S. Cl.
CPC ............... *G16B 5/00* (2019.02); *G16B 5/20* (2019.02); *G16B 20/00* (2019.02); *G16B 25/10* (2019.02); *G16B 30/00* (2019.02); *G16B 40/00* (2019.02); *G16B 40/20* (2019.02); *G16B 40/30* (2019.02); *G16B 50/00* (2019.02); *G16B 50/30* (2019.02); *G16H 10/20* (2018.01); *G16H 20/00* (2018.01); *G16H 20/10* (2018.01); *G16H 20/40* (2018.01); *G16H 50/20* (2018.01); *G16H 50/30* (2018.01); *G16H 50/50* (2018.01); *G16H 50/70* (2018.01); *G16H 70/20* (2018.01); *C12Q 2600/156* (2013.01); *C12Q 2600/158* (2013.01)

(58) Field of Classification Search
CPC ........ G16B 50/00; G16B 25/00; G16B 25/20; G16B 25/30; G16B 99/00; G16B 5/10; G16B 5/30; G16B 20/10; G16B 20/20; G16B 20/30; G16B 20/40; G16B 20/50; G16B 40/10; G16B 40/20; G16B 40/30; G16B 50/10; G16B 50/20; G16B 50/30; G16B 50/40; G16B 50/50; G06F 16/285; G06F 17/18; G06F 19/30; G06F 19/32; G06F 19/34; G06F 19/3456; G06F 19/3481; G06F 19/325; G06F 19/36; G16H 20/00; G16H 50/50; G16H 20/10; G16H 20/40; G16H 70/20; G16H 10/20; G16H 50/30; G16H 50/20; G16H 50/70; G16H 50/00; G16H 50/80; C12Q 1/6886; C12Q 2600/156; C12Q 2600/158; Y02A 90/10; G06Q 50/22; G06Q 50/24
See application file for complete search history.

(56) References Cited

U.S. PATENT DOCUMENTS

| | | |
|---|---|---|
| 10,395,761 B1 | 8/2019 | Bagaev et al. |
| 10,580,517 B2 | 3/2020 | Bagaev et al. |
| 10,650,911 B2 | 5/2020 | Bagaev et al. |
| 11,302,420 B2 | 4/2022 | Bagaev et al. |
| 11,322,226 B2 | 5/2022 | Bagaev et al. |
| 11,367,509 B2 | 6/2022 | Bagaev et al. |
| 11,373,733 B2 | 6/2022 | Bagaev et al. |
| 11,430,545 B2 | 8/2022 | Bagaev et al. |
| 2006/0127928 A1 | 6/2006 | Bacus et al. |
| 2007/0172844 A1 | 7/2007 | Lancaster et al. |
| 2008/0153098 A1 | 6/2008 | Rimm et al. |
| 2009/0105167 A1 | 4/2009 | Potti et al. |
| 2012/0220580 A1 | 8/2012 | Li et al. |
| 2013/0065789 A1 | 3/2013 | Tsao et al. |
| 2013/0165337 A1 | 6/2013 | Robinson et al. |
| 2014/0220580 A1 | 8/2014 | Brown et al. |
| 2014/0342924 A1 | 11/2014 | Harkin et al. |
| 2015/0317430 A1 | 11/2015 | Olson |
| 2016/0123964 A1 | 5/2016 | Tumeh et al. |
| 2016/0312286 A1 | 10/2016 | Brandon et al. |
| 2017/0218068 A1 | 8/2017 | Lesterhuis et al. |
| 2018/0100201 A1 | 4/2018 | Garraway et al. |
| 2018/0357372 A1 | 12/2018 | Bagaev et al. |
| 2018/0357374 A1 | 12/2018 | Bagaev et al. |
| 2018/0357376 A1 | 12/2018 | Bagaev et al. |
| 2018/0357377 A1 | 12/2018 | Bagaev et al. |
| 2018/0357378 A1 | 12/2018 | Bagaev et al. |
| 2019/0252046 A1 | 8/2019 | Bagaev et al. |
| 2020/0175134 A9 | 6/2020 | Bagaev et al. |
| 2020/0273543 A1 | 8/2020 | Bagaev et al. |
| 2020/0335180 A1 | 10/2020 | Bagaev et al. |
| 2020/0347456 A1 | 11/2020 | Regev et al. |
| 2021/0174908 A1 | 6/2021 | Benjamin et al. |
| 2022/0186318 A1 | 6/2022 | Meerson et al. |
| 2022/0389512 A1 | 12/2022 | Bagaev et al. |
| 2023/0085564 A1* | 3/2023 | Morrison ............... G16B 20/20 |
| 2023/0290440 A1 | 9/2023 | Mikheecheva et al. |

FOREIGN PATENT DOCUMENTS

| | | |
|---|---|---|
| CN | 104039343 A | 9/2014 |
| JP | 2006-524502 | 11/2006 |
| JP | 2008-502365 | 1/2008 |
| WO | WO 2004/078035 A2 | 9/2004 |
| WO | WO 2005/123993 A2 | 12/2005 |
| WO | WO 2012/095448 A1 | 7/2012 |
| WO | WO 2015/073896 A2 | 5/2015 |
| WO | WO 2016/109546 A2 | 7/2016 |
| WO | WO 2017/004153 A1 | 1/2017 |
| WO | WO 2017/013436 A1 | 1/2017 |
| WO | WO 2017/093764 A1 | 6/2017 |
| WO | WO 2017/194556 A1 | 11/2017 |
| WO | WO 2018/231771 A1 | 12/2018 |

OTHER PUBLICATIONS

Wolf et al., Gene co-expression modules as clinically relevant hallmarks of breast cancer diversity. PloS one. Feb. 7, 2014;9(2):e88309.
Abba et al., Gene expression signature of estrogen receptor alpha status in breast cancer. BMC Genomics. 2005;6(37):1-13.
Alizadeh et al., Doxorubicin Eliminates Myeloid-Derived Suppressor Cells and Enhances the Efficacy of Adoptive T-Cell Transfer in Breast Cancer. Cancer Research. 2013;74:104-118.
Bieche et al., CXC chemokines located in the 4q21 region are up-regulated in breast cancer. Endocrine-Realted Cancer. 2007;14:1039-52.
Bieche et al., Molecular Profiling of Inflammatory Breast Cancer: Identification of a Poor-Prognosis Gene Expression Signature. Clinical Cancer Research. 2004;10:6789-95.
Burris, III et al., Phase II Study of the Antibody Drug Conjugate Trastuzumab-DM1 for the Treatment of Human Epidermal Growth Factor Receptor 2 (HER2)-Positive Breast Cancer After Prior

(56) References Cited

OTHER PUBLICATIONS

HER2-Directed Therapy. Journal of Clinical Oncology. 2010;29(4):398-405.

Casey et al., Molecular signatures suggest a major role for stromal cells in development of invasive breast cancer. Breast Cancer Research and Treatment. 2009;114:47-62.

Elsheikh et al., CCND1 amplification and cyclin D1 expression in breast cancer and their relation with proteomic subgroups and patient outcome. Breast Cancer Research and Treatment. 2008;109:325-35.

Emens et al., Breast cancer immunobiology driving immunotherapy: vaccines and immune checkpoint blockade. Expert Reviews in Anticancer Therapy. 2012;12:1597-611.

Fackler et al., Genome-wide Methylation Analysis Identifies Genes Specific to Breast Cancer Hormone Receptor Status and Risk of Recurrence. Cancer Research. 2011;71:6195-207.

Findlay et al., Effective oral chemotherapy for breast cancer: pillars of strength. Annals of Oncology. 2008;19:212-22.

Folgueira et al., Gene Expression Profile Associated with Response to Doxorubicin-Based Therapy in Breast Cancer. Cancer Therapy: Clinical. 2005;11:7434-43.

Kaufmann et al., International Expert Panel on the Use of Primary (Preoperative) Systemic Treatment of Operable Breast Cancer: Review and Recommendations. Journal of Clinical Oncology. 2003;21:2600-8.

Li et al., PD-L1 Expression is Associated with Tumor FOXP3+ Regulatory T-Cell Infiltration of Breast Cancer and Poor Prognosis of Patient. Journal of Cancer. 2016;7(7):784-93.

Nishidate et al., Genome-wide gene-expression profiles of breast-cancer cells purified with laser microbeam microdissection: Identification of genes associated with progression and metastasis. International Journal of Oncology. 2004;25:797-819.

Parr et al., Placenta growth factor is over-expressed and has prognostic value in human breast cancer. European Journal of Cancer. 2005;41:2819-27.

Salvucci et al., The role of CXCR4 receptor expression in breast cancer: a large tissue microarray study. Breast Cancer Research and Treatment. 2006;97:275-83.

Siggelkow et al., Expression of aurora kinase A is associated with metastasis-free survival in node-negative breast cancer patients. BMC Cancer. 2012;12:1-11.

Soria et al., The inflammatory chemokines CCL2 and CCL5 in breast cancer. Cancer Letters. 2008;267:271-85.

Sorlie, Molecular portraits of breast cancer: tumour subtypes as distinct disease entities. European Journal of Cancer. 2004;40:2667-75.

Sun et al., IntegratedAnalysis of Gene Expression, CpG Island Methylation, and Gene Copy Number in Breast Cancer Cells by Deep Sequencing. PLoS one. 2011;6(2):1-18.

Tchou et al., Fibroblast activation protein expression by stromal cells and tumor-associated macrophages in human breast cancer. Human Pathology. 2013;44:2549-57.

Yu et al., Cytotoxic T lymphocyte antigen 4 expression in human breast cancer: implications for prognosis. Cancer Immunol Immunotherapy. 2015;64:853-60.

Cancer Genome Atlas Network, Comprehensive molecular portraits of human breast tumours. Nature. Oct. 2012;490(7418):61.

Cardoso et al., 70-gene signature as an aid to treatment decisions in early-stage breast cancer. New England Journal of Medicine. Aug. 25, 2016;375(8):717-29.

Desmedt et al., Biological processes associated with breast cancer clinical outcome depend on the molecular subtypes. Clinical cancer research. Aug. 15, 2008;14(16):5158-65.

Gao et al., Integrative analysis of complex cancer genomics and clinical profiles using the cBioPortal. Science signaling. Apr. 2, 2013;6(269):34 pages.

Kuperstein et al., Atlas of Cancer Signalling Network: a systems biology resource for integrative analysis of cancer data with Google Maps. Oncogenesis. Jul. 2015;4(7):e160.

Rhodes et al., Oncomine 3.0: genes, pathways, and networks in a collection of 18,000 cancer gene expression profiles. Neoplasia (New York, NY). Feb. 2007;9(2):166-180.

Rosa et al., VAMP: visualization and analysis of array-CGH, transcriptome and other molecular profiles. Bioinformatics. Sep. 1, 2006;22(17):2066-73.

Russo et al., RNASeqGUI: a GUI for analysing RNA-Seq data. Bioinformatics. Sep. 1, 2014;30(17):2514-6.

Shankavaram et al., CellMiner: a relational database and query tool for the NCI-60 cancer cell lines. BMC genomics. Dec. 1, 2009;10(1):277.

[No Author Listed] Atezolizumab (Tecentriq). FDA U.S. Food & Drug Administration. https://www.fda.gov/drugs/informationondrugs/approveddrugs/ucm525780.htm Last updated Oct. 19, 2016. Last accessed Jul. 26, 2018. 2 pages.

[No Author Listed] Bevacizumab. FDA U.S. Food & Drug Administration. https://web.archive.org/web/20170111231723/https://www.fda.gov/Drugs/InformationOnDrugs/ApprovedDrugs/ucm336763.htm Last updated Oct. 9, 2015. Last accessed via WayBackMachine Jul. 26, 2018. 1 page.

[No Author Listed] Elotuzumab. FDA U.S. Food & Drug Administration. https://web.archive.org/web/20170118085702/http://www.fda.gov/Drugs/InformationOnDrugs/ApprovedDrugs/ucm474719.htm Last updated Nov. 30, 2015. Last accessed via WayBackMachine Jul. 26, 2018. 1 page.

[No Author Listed] Nivolumab (Opdivo). FDA U.S. Food & Drug Administration. https://web.archive.org/web/20170118085700/https://www.fda.gov/Drugs/InformationOnDrugs/ApprovedDrugs/ucm436566.htm Last updated Apr. 6, 2015. Last accessed via WayBackMachine Jul. 26, 2018. 1 page.

[No Author Listed] Olaratumab (Lartruvo). FDA U.S. Food & Drug Administration. https://www.fda.gov/Drugs/InformationOnDrugs/ApprovedDrugs/ucm526087.htm Last updated Oct. 20, 2016. Last accessed Jul. 26, 2018. 2 pages.

[No Author Listed] Osimertinib. FDA U.S. Food & Drug Administration. https://web.archive.org/web/20170227152135/https://www.fda.gov/Drugs/InformationOnDrugs/ApprovedDrugs/ucm472565.htm Last updated Nov. 13, 2015. Last accessed via WayBackMachine Jul. 26, 2018. 1 page.

[No Author Listed] Pembrolizumab (Keytruda) Checkpoint Inhibitor. FDA U.S. Food & Drug Administration. https://www.fda.gov/Drugs/InformationOnDrugs/ApprovedDrugs/ucm526430.htm Last updated Oct. 25, 2016. Last accessed Jul. 26, 2018. 2 pages.

[No Author Listed] Rituximab Infusion. FDA U.S. Food & Drug Administration. https://web.archive.org/web/20161211125252/http://www.fda.gov:80/Drugs/InformationOnDrugs/ApprovedDrugs/ucm324890.htm Last updated May 4, 2016. Last accessed via WayBackMachine Jul. 26, 2018. 1 page.

[No Author Listed], A Phase 3 Study of Pembrolizumab + Epacadostat or Placebo in Subjects With Unresectable or Metastatic Melanoma (Keynote-252 / ECHO-301). Clinical Trials. https://clinicaltrials.gov/ct2/show/NCT02752074 Last updated May 8, 2018. Last accessed Jul. 26, 2018. 7 pages.

[No Author Listed], A Pilot Study to Evaluate the Safety of a 3 Weeks Sitagliptin Treatment in HCC Patients Undergoing Liver Resection (HCC-DPPIV). Clinical Trials. https://clinicaltrials.gov/ct2/show/NCT02650427 Last updated Sep. 28, 2017. Last accessed Jul. 26, 2018. 7 pages.

[No Author Listed], Combination of Interferon-gamma and Nivolumab for Advanced Solid Tumors. Clinical Trials. https://clinicaltrials.gov/ct2/show/NCT02614456 Last updated Feb. 7, 2018. Last accessed Jul. 26, 2018. 8 pages.

[No Author Listed], Evaluation of MGN1703 Maintenance Treatment in Patients with mCRC With Tumor Reduction During Induction Treatment (Impala). Clinical Trials. https://clinicaltrials.gov/ct2/show/NCT02077868 Last updated Jun. 23, 2017. Last accessed Jul. 26, 2018. 7 pages.

[No Author Listed], FDA Approves Merck's Keytruda® (pembrolizumab) as First-Line Combination Therapy with Pemetrexed and Carboplatin for Patients with Metastatic Nonsquamous Non-Small Cell Lung Cancer (NSCLC), Irrespective of PD-L1 Expression. Merck. http://investors.merck.com/news/press-release-details/2017/FDA-Approves-Mercks-KEYTRUDA-pembrolizumab-as-First-Line-Combination-Therapy-with-Pemetrexed-and-Carboplatin-for-

(56) References Cited

OTHER PUBLICATIONS

Patients-with-Metastatic-Nonsquamous-Non-Small-Cell-Lung-Cancer-NSCLC-Irrespective-of-PD-L1-Expression/default.aspx May 10, 2017. Last accessed Jul. 27, 2018. 10 pages.

[No Author Listed], FDA grants accelerated approval to pembrolizumab for first tissue/site agnostic indication. FDA U.S. Food & Drug Administration. https://www.fda.gov/drugs/informationondrugs/approveddrugs/ucm560040.htm Last updated May 30, 2017. Last accessed Jul. 27, 2018. 2 pages.

[No Author Listed], Immunotherapy Combination Study in Advanced Previously Treated Non-Small Cell Lung Cancer. Clinical Trials. https://clinicaltrials.gov/ct2/show/NCT02460367 Last updated Feb. 4, 2016. Last accessed Jul. 26, 2018. 9 pages.

[No Author Listed], L-NMMA Plus Docetaxel in Refractory Locally Advanced or Metastatic Triple Negative Breast Cancer Patients. Clinical Trials. https://clinicaltrials.gov/ct2/show/NCT02834403 Last updated Mar. 29, 2018. Last accessed Jul. 26, 2018. 10 pages.

[No Author Listed], NHS-IL12 for Solid Tumors. Clinical Trials. https://clinicaltrials.gov/ct2/show/NCT01417546 Last updated Jul. 6, 2018. Last accessed Jul. 26, 2018. 11 pages.

[No Author Listed], Ph2 NK Cell Enriched DCIs w/wo RLR9 Agonist, DUK-CPG-001 From Donors Following Allogeneic SCT (NK-DCI). Clinical Trials. https://clinicaltrials.gov/ct2/show/NCT02452697 Last updated Jul. 25, 2018. Last accessed Jul. 26, 2018. 10 pages.

[No Author Listed], Provenge Followed by Docetaxel in Castration-Resistant Prostate Cancer. Clinical Trials. https://clinicaltrials.gov/ct2/show/NCT02793219 Last updated Oct. 30, 2017. Last accessed Jul. 26, 2018. 11 pages.

[No Author Listed], SABR-ATAC: A Trial of TGF-beta Inhibition and Stereotactic Ablative Radiotherapy for Early Stage Non-small Cell Lung Cancer. Clinical Trials. https://clinicaltrials.gov/ct2/show/NCT02581787 Last updated May 7 04, 2018. Last accessed Jul. 26, 2018. 8 pages.

[No Author Listed], Study Evaluating the Safety and Pharmacokinetics of JCAR017 in B-cell Non-Hodgkin Lymphoma (TRANSCEND-NHL-001). Clinical Trials. https://clinicaltrials.gov/ct2/show/NCT02631044 Last updated Jun. 8, 2018. Last accessed Jul. 26, 2018. 12 pages.

[No Author Listed], Study of AM0010 With FOLFOX Compared to FOLFOX Alone Second-line Tx in Pts With Metastatic Pancreatic Cancer (Sequoia). Clinical Trials. https://clinicaltrials.gov/ct2/show/NCT02923921 Last updated Jul. 17, 2018. Last accessed Jul. 26, 2018. 6 pages.

[No Author Listed], The R Project for Statistical Computing. Getting Started. https://www.r-project.org/ last accessed Jul. 26, 2018. 5 pages.

[No Author Listed], Trial of TRX518 (Anti-GITR mAb) in Stage III or IV Malignant Melanoma or Other Solid Tumors (TRX518-001). Clinical Trials. https://clinicaltrials.gov/ct2/show/NCT01239134 Last updated Mar. 3, 2017. Last accessed Jul. 26, 2018. 9 pages.

Akbani et al., Genomic Classification of Cutaneous Melanoma. Cell. Jun. 18, 2015;161(7):1681-96. doi: 10.1016/j.cell.2015.05.044.

Aran et al., Systematic pan-cancer analysis of tumour purity. Nat Commun. Dec. 4, 2015;6:8971. doi: 10.1038/ncomms9971. 11 pages.

Ayers et al., Relationship between immune gene signatures and clinical response to PD-1 blockade with pembrolizumab (MK-3475) in patients with advanced solid tumors. Journal for Immuno Therapy of Cancer. 2015;3(22):1-2.

Barbie et al., Systematic RNA interference reveals that oncogenic KRAS-driven cancers require TBK1. Nature. 2009. 462. 108-12.

Becht et al., Estimating the population abundance of tissue-infiltrating immune and stromal cell populations using gene expression. Genome Biol. Oct. 20, 2016;17(1):218.

Blank et al., The "cancer immunogram" Science. 2016;352:658-60.

Blondel et al., Fast unfolding of communities in large networks. J Stat Mech Theory Exp. 2008. P10008. 12 pages.

Bolotin et al., Antigen receptor repertoire profiling from RNA-seq data. Nat Biotechnol. Oct. 11, 2017;35(10):908-911. doi: 10.1038/nbt.3979.

Bray et al. Near-optimal probabilistic RNA-seq quantification. Nature Biotechnology vol. 34, pp. 525-527 (2016).

Brown et al., Regression of Glioblastoma after Chimeric Antigen Receptor T-Cell Therapy. The New England Journal of Medicine. 2016. 9 pages.

Cantoni et al., NK Cells, Tumor Cell Transition, and Tumor Progression in Solid Malignancies: New Hints for NK-Based Immunotherapy. Journal of Immunology Research. 2016. 13 pages.

Carter et al., Absolute quantification of somatic DNA alterations in human cancer. Nat Biotechnol. May 2012; 30(5): 413-421.

Chanmee et al., Tumor-associated macrophages as major players in the tumor microenvironment. Cancers (Basel). Aug. 13, 2014;6(3):1670-90. doi: 10.3390/cancers6031670.

Charoentong et al., Pan-cancer Immunogenomic Analyses Reveal Genotype-Immunophenotye Relationships and Predictors of Response To Checkpoint Blockade. Cell Rep. Cold Spring Harbor Labs Journals. 2017;18:248-62.

Chaudhary et al., Regulatory T Cells in the Tumor Microenvironment and Cancer Progression: Role and Therapeutic Targeting. Vaccines (Basel). Aug. 6, 2016;4(3). pii: E28. doi: 10.3390/vaccines4030028. 25 pages.

Filatenkov et al., Ablative Tumor Radiation Can Change the Tumor Immune Cell Microenvironment to Induce Durable Complete Remissions. Clin Cancer Res. Aug. 15, 2015;21(16):3727-39. doi: 10.1158/1078-0432.CCR-14-2824. Epub Apr. 13, 2015.

Gordon et al., Using gene expression ratios to predict outcome among patients with mesothelioma. J Natl Cancer Inst. Apr. 16, 2003;95(8):598-605.

Grossman et al., Toward a Shared Vision for Cancer Genomic Data. Perspective. Sep. 22, 2016. 4 pages.

Haabeth et al., Inflammation driven by tumour-specific Th1 cells protects against B-cell cancer. Nat Commun. 2011;2:240. doi: 10.1038/ncomms1239. 12 pages.

Hagberg et al., Exploring network structure, dynamics, and function using NetworkX. Proceedings of the 7th Python in Science Conference (SciPy 2008). 5 pages.

Hanzelmann et al., GSVA: gene set variation analysis for microarray and RNA-seq data. BMC Bioinformatics. Jan. 16, 2013;14:7. doi: 10.1186/1471-2105-14-7.

Hua et al., Accumulation of FoxP3+ T regulatory cells in the tumor microenvironment of human colorectal adenomas. Pathol Res Pract. Feb. 2016;212(2):106-12. doi: 10.1016/j.prp.2015.12.002. Epub Dec. 14, 2015.

Hugo et al., Genomic and Transcriptomic Features of Response to Anti-PD-1 Therapy in Metastatic Melanoma. Cell. 2016;165(1):35-44.

Hunter, Matplotlib: A 2D Graphics Environment. Comput Sci Eng. 2007;9:90-5.

Jacquelot et al., Predictors of responses to immune checkpoint blockade in advanced melanoma. Nature Communications. 2017. 13 pages.

Ji et al., An immune-active tumor microenvironment favors clinical response to ipilimumab. Cancer Immunology, Immunotherapy. 2012;61(7):1019-31.

Kandoth et al., Mutational landscape and significance across 12 major cancer types. Nature. Oct. 17, 2013;502(7471):333-339. doi: 10.1038/nature12634.

Kaporis et al., Human basal cell carcinoma is associated with Foxp3+ T cells in a Th2 dominant microenvironment. J Invest Dermatol. Oct. 2007;127(10):2391-8. Epub May 17, 2007.

Kemper et al., BRAF(V600E) Kinase Domain Duplication Identified in Therapy-Refractory Melanoma Patient-Derived Xenografts. Cell Rep. Jun. 28, 2016;16(1):263-277. doi: 10.1016/j.celrep.2016.05.064. Epub Jun. 16, 2016.

Le et al., PD-1 Blockade in Tumors with Mismatch-Repair Deficiency. N Engl J Med. Jun. 25, 2015;372(26):2509-20. doi: 10.1056/NEJMoa1500596. Epub May 30, 2015.

Lu et al., Identification of Gene Expression Biomarkers for Predicting Radiation Exposure. Sci Rep 2015;4(1):6293. 7 pages.

(56) References Cited

OTHER PUBLICATIONS

Marvel et al., Myeloid-derived suppressor cells in the tumor microenvironment: expect the unexpected. J Clin Invest. Sep. 2015;125(9):3356-64. doi: 10.1172/JCI80005. Epub Jul. 13, 2015.
McKinney, Data Structures for Statistical Computing in Python. Proc. of the 9th Python in Science Conf. SCIPY 2010;51.
Nathanson et al., Somatic Mutations and Neoepitope Homology in Melanomas Treated with CTLA-4 Blockade. Cancer Immunology Research. 2017. 9 pages.
Newman et al., Robust enumeration of cell subsets from tissue expression profiles. Nat Methods. May 2015;12(5):453-7. doi: 10.1038/nmeth.3337. Epub Mar. 30, 2015.
Noguera et al., Extracellular matrix, biotensegrity and tumor microenvironment. An update and overview. Histol Histopathol. Jun. 2012;27(6):693-705. doi: 10.14670/HH-27.693.
O'Leary et al., Reference sequence (RefSeq) database at NCBI: current status, taxonomic expansion, and functional annotation. Nucleic Acids Res. Jan. 4, 2016;44(D1):D733-45. doi: 10.1093/nar/gkv1189. Epub Nov. 8, 2015.
Palmieri et al., Genetic instability and increased mutational load: which diagnostic tool best direct patients with cancer to immunotherapy? J Transl Med. 2017; 15: 17. 4 pages.
Papageorgis, TGFβ Signaling in Tumor Initiation, Epithelial-to-Mesenchymal Transition, and Metastasis. J Oncol. 2015;2015:587193. doi: 10.1155/2015/587193. Epub Mar. 25, 2015. 15 pages.
Passiglia et al., PD-L1 expression as predictive biomarker in patients with NSCLC: a pooled analysis. Oncotarget. Apr. 12, 2016;7(15):19738-47. doi: 10.18632/oncotarget.7582.
Pedregosa et al., Scikit-learn: Machine Learning in Python. J Mach Learn Res. Oct. 12:2825-2830, 2011.
Quail et al., Microenvironmental regulation of tumor progression and metastasis. Nat Med. Nov. 2013;19(11):1423-37. doi: 10.1038/nm.3394.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.
Rizvi et al., Cancer immunology. Mutational landscape determines sensitivity to PD-1 blockade in non-small cell lung cancer. Science. Apr. 3, 2015;348(6230):124-8. doi: 10.1126/science.aaa1348. Epub Mar. 12, 2015.
Roh et al., Integrated molecular analysis of tumor biopsies on sequential CTLA-4 and PD-1 blockade reveals markers of response and resistance. Cancer. Sci Transl Med. 2017. 13 pages.
Sato et al., Integrated molecular analysis of clear-cell renal cell carcinoma. Nat Genet. Aug. 2013;45(8):860-7. doi: 10.1038/ng.2699. Epub Jun. 24, 2013.
Schumacher et al., Editorial overview: Cancer immunology: genomics & biomarkers: Cancer immunity through the prism of genomics and proteomics. Curr Opin Immunol. Aug. 2016;41:ix-x. doi: 10.1016/j.coi.2016.07.006. Epub Aug. 6, 2016.
Senbabaoglu et al., Tumor immune microenvironment characterization in clear cell renal cell carcinoma identifies prognostic and immunotherapeutically relevant messenger RNA signatures. Genome Biol. Nov. 17, 2016;17(1):231. 25 pages.
Shalapour et al., Immunosuppressive plasma cells impede T-cell-dependent immunogenic chemotherapy. Nature. May 7, 2015;521(7550):94-8. doi: 10.1038/nature14395. Epub Apr. 29, 2015.
Shannon et al., Cytoscape: a software environment for integrated models of biomolecular interaction networks. Genome Res. Nov. 2003;13(11):2498-504.
Shiga et al., Cancer-Associated Fibroblasts: Their Characteristics and Their Roles in Tumor Growth. Cancers (Basel). Dec. 11, 2015;7(4):2443-58. doi: 10.3390/cancers7040902.
Singel et al., Neutrophils in the tumor microenvironment: trying to heal the wound that cannot heal. Immunol Rev. Sep. 2016;273(1):329-43. doi: 10.1111/imr.12459.

Snyder et al., Genetic Basis for Clinical Response to CTLA-4 Blockade in Melanoma. N Engl J Med. 2014;371(23):2189-99.
Subramanian et al., Gene set enrichment analysis: a knowledge-based approach for interpreting genome-wide expression profiles. Proc Natl Acad Sci U S A. Oct. 25, 2005;102(43):15545-50. Epub Sep. 30, 2005.
Tappeiner et al., TIminer: NGS data mining pipeline for cancer immunology and immunotherapy. Bioinformatics. Oct. 1, 2017;33(19):3140-3141. doi: 10.1093/bioinformatics/btx377.
Tirosh et al., Dissecting the multicellular ecosystem of metastatic melanoma by single-cell RNA-seq. Science. Apr. 8, 2016;352(6282):189-96. doi: 10.1126/science.aad0501.
Umansky et al., Tumor microenvironment and myeloid-derived suppressor cells. Cancer Microenviron. Aug. 2013;6(2):169-77. doi: 10.1007/s12307-012-0126-7. Epub Dec. 16, 2012.
Van Allen et al., Genomic correlates of response to CTLA-4 blockade in metastatic melanoma. Science. Oct. 9, 2015;350(6257):207-211 doi: 10.1126/science.aad0095. Epub Sep. 10, 2015.
Van Der Maaten, Accelerating t-SNE using Tree-Based Algorithms. Journal of Machine Learning Research. 2014;15:3221-3245.
Van Der Maaten, Visualizing Data using t-SNE. Journal of Machine Learning Research. 2008;9:2579-2605.
Van Der Walt et al., The NumPy Array: A Structure for Efficient Numerical Computation. Computing in Science and Engineering. 2011;13(2):22-30.
Vilgelm et al,. Combinatorial approach to cancer immunotherapy: strength in numbers. JLB. 2016. 16 pages.
Wargo et al., Monitoring immune responses in the tumor microenvironment. Curr Opin Immunol. Aug. 2016;41:23-31. doi: 10.1016/j.coi.2016.05.006. Epub May 27, 2016.
Yu et al., Cancer-associated fibroblasts induce epithelial-mesenchymal transition of breast cancer cells through paracrine TGF-β signalling. Br J Cancer. Feb. 4, 2014;110(3):724-32. doi: 10.1038/bjc.2013.768. Epub Dec. 12, 2013.
Zhang et al., Starved and Asphyxiated: How Can CD8(+) T Cells within a Tumor Microenvironment Prevent Tumor Progression. Front Immunol. Feb. 10, 2016;7:32. doi: 10.3389/fimmu.2016.00032. eCollection 2016.
International Search Report and Written Opinion for International Application No. PCT/US2018/037008 dated Sep. 21, 2018.
International Search Report and Written Opinion for International Application No. PCT/US2018/037018 dated Sep. 21, 2018.
International Search Report and Written Opinion for International Application No. PCT/US2018/037017 dated Sep. 25, 2018.
Bao et al., AbsCN-seq: a statistical method to estimate tumor purity, ploidy and absolute copy numbers from next-generation sequencing data. Bioinformatics. 2014;30(8):1056-063.
Beck et al., Significance Analysis of Prognostic Signatures. PLOS Computational Biology. 2013;9(1):1-17.
Burke, Predicting Clinical Outcomes Using Molecular Biomarkers. Biomarkers in Cancer. 2016;8:89-99.
Ding, Visualization and Integrative Analysis of Cancer Multi-Omics Data. Dissertation. The Ohio State University. 2016. 150 pages.
Feng et al., Differentially expressed genes between primary cancer and paired lymph node metastases predict clinical outcome of node-positive breast cancer patients. Breast Cancer Research and Treatment. 2007;103:319-29.
Finak et al., Stromal gene expression predicts clinical outcome in breast cancer. Nature Medicine. 2008;14:518-527.
Gyorffy et al., An online survival analysis tool to rapidly assess the effect of 22,277 genes on breast cancer prognosis using microarray date of 1,809 patients. Breast Cancer Research and Treatment. 2010;123:725-31.
Hermann et al., Analysis and Visualization of Gene Expression Data. Dissertation. Tubingen. 2011. 180 pages.
Jansen et al., Molecular Classification of Tamoxifen-Resistant Breast Carcinomas by Gene Expression Profiling. Journal of Clinical Oncology. 2005;23(4):732-40.
McArt et al., PICan: An integromics framework for dynamic cancer biomarker discovery. Molecular Oncology. 2015;9(6):1234-40.
Merico et al., Enrichment Map: A Network-Based Method for Gene-Set Enrichment Visualization and Interpretation. Plos One. 2010;5(11):1-12.

(56) References Cited

OTHER PUBLICATIONS

Mustacchi et al., Identification and Validation of a New Set of Five Genes for Prediction of Risk in Early Breast Cancer. International Journal of Molecular Science. 2013;14:9686-702.

Nam et al., A pathway-based approach for identifying biomarkers of tumor progression to trastuzumab-resistant breast cancer. Cancer Letters. 2015;356:880-90.

Panse et al., Chemokine CXCLI3 is overexpressed in the tumor tissue and in the peripheral blood of breast cancer patients. British Journal of Cancer. 2008;99:930-38.

Pardoll, The blockade of immune checkpoints in cancer immunotherapy. Nature Reviews Cancer. 2012;12(4):252-64.

Sturm et al., Discovering Medical Knowledge Using Visual Analytics. Eurographics Workshop on Visual Computing for Biology and Medicine. 2015. 10 pages.

Tamburini et al., Gene expression profiling identifies inflammation and angiogenesis as distinguishing features of canine hemangiosarcoma. BMC Cancer. 2010;10(1):619. 16 pages.

Van Der Auwera et al., Increased Angiogenesis and Lymphangiogenesis in Inflammatory versus Noninflammatory Breast Cancer by Real-Time Reverse Transcriptase-PCR Gene Expression Quantification. Clinical Cancer Research. 2004;10:7965-971.

Vuaroqueaux et al. Low E2F1 transcript levels are a strong determinant of favorable breast cancer outcome. Breast Cancer Research 2007. 2007;9:1-10.

West et al., Tumor-infiltrating lymphocytes predict response to anthracycline-based chemotherapy in estrogen receptor-negative breast cancer. Breast Cancer Research. 2011;12:13 pages.

Darby et al., Early Breast Cancer Trialists' Collaborative G: Effect of radiotherapy after breast-conserving surgery on 10-year recurrence and 15-year breast cancer death: meta-analysis of individual patient data for 10,801 women in 17 randomised trials. Lancet. 2011;378(9804):1707-16.

Fumagalli et al., Transfer of clinically relevant gene expression signatures in breast cancer: from Affymetrix microarray to Illumina RNA-Sequencing technology. BMC genomics. Dec. 1, 2014;15(1):1008.

Lee et al., Post-treatment tumor gene expression signatures are more predictive of treatment outcomes than baseline signatures in breast cancer. Pharmacogenetics and genomics. Nov. 1, 2009;19(11):833-42.

International Preliminary Report on Patentability for International Application No. PCT/US2018/037017 dated Dec. 26, 2019.

[No Author Listed], Quickly understand the Gene Ontology (GO) database in one article. Health information station. 2021. 10 pages. https://zhuanlan.zhihu.com/p/99789859 (Last accessed Mar. 31, 2023).

International Search Report and Written Opinion for International Application No. PCT/US2021/062961 mailed Apr. 13, 2022.

International Preliminary Report on Patentability for International Application No. PCT/US2021/062961 mailed Jun. 22, 2023.

International Search Report and Written Opinion for International Application No. PCT/US2023/013002 mailed Jun. 7, 2023.

Byers et al., Clinical quantitation of immune signature in follicular lymphoma by RT-PCR-based gene expression profiling. Blood, The Journal of the American Society of Hematology. May 1, 2008;111(9):4764-70.

Dave et al., Prediction of survival in follicular lymphoma based on molecular features of tumor-infiltrating immune cells. New England Journal of Medicine. Nov. 18, 2004;351(21):2159-69.

Dybkær et al., Diffuse large B-cell lymphoma classification system that associates normal B-cell subset phenotypes with prognosis. Journal of Clinical Oncology. Apr. 20, 2015;33(12):1379.

Glas et al., Gene-expression and immunohistochemical study of specific T-cell subsets and accessory cell types in the transformation and prognosis of follicular lymphoma. Journal of clinical oncology. 2007;25(4):390-8.

Gribben, Implications of the tumor microenvironment on survival and disease response in follicular lymphoma. Current opinion in oncology. Sep. 1, 2010;22(5):424-30.

Hakimi et al., Transcriptomic Profiling of the Tumor Microenvironment Reveals Distinct Subgroups of Clear Cell Renal Cell Cancer: Data from a Randomized Phase III TrialGenomic Predictors of TKI Response in the COMPARZ Trial. Cancer discovery. Apr. 1, 2019;9(4):510-25.

Sugimoto et al., Follicular lymphoma: the role of the tumor microenvironment in prognosis. Journal of Clinical and Experimental Hematopathology. 2016;56(1). 19 pages.

Sweis et al., Molecular Drivers of the Non-T-cell-Inflamed Tumor Microenvironment in Urothelial Bladder CancerDrivers of Non-T-cell-Inflamed Bladder Cancer. Cancer immunology research. Jul. 1, 2016;4(7):563-8.

Communication pursuant to Article 94(3) EPC for European Application No. 21843825.7 dated Oct. 18, 2023.

Harjunpää et al., Differential gene expression in non-malignant tumour microenvironment is associated with outcome in follicular lymphoma patients treated with rituximab and CHOP. British journal of haematology. Oct. 2006;135(1):33-42.

U.S. Appl. No. 16/920,226, filed Jul. 2, 2020, Bagaev et al.
U.S. Appl. No. 16/006,462, filed Jun. 12, 2018, Bagaev et al.
U.S. Appl. No. 16/006,518, filed Jun. 12, 2018, Bagaev et al.
U.S. Appl. No. 16/006,555, filed Jun. 12, 2018, Bagaev et al.
U.S. Appl. No. 16/006,572, filed Jun. 12, 2018, Bagaev et al.
U.S. Appl. No. 16/006,593, filed Jun. 12, 2018, Bagaev et al.
U.S. Appl. No. 16/006,085, filed Jun. 12, 2018, Frenkel et al.
U.S. Appl. No. 16/006,129, filed Jun. 12, 2018, Frenkel et al.
U.S. Appl. No. 16/006,200, filed Jun. 12, 2018, Bagaev et al.
U.S. Appl. No. 16/006,279, filed Jun. 12, 2018, Bagaev et al.
U.S. Appl. No. 16/006,340, filed Jun. 12, 2018, Bagaev et al.
U.S. Appl. No. 16/006,381, filed Jun. 12, 2018, Bagaev et al.
U.S. Appl. No. 16/391,221, filed Apr. 22, 2019, Bagaev et al.
U.S. Appl. No. 16/523,808, filed Jul. 26, 2019, Bagaev et al.
U.S. Appl. No. 16/871,755, filed May 11, 2020, Bagaev et al.

\* cited by examiner

DATAFILES

GENOME sequencing — illumina
WES (Whole exome sequencing) (x209)
illumina
Uploaded: 11.11.2016/calculated Affimetrix biopsy analysis — affymetrix
55690 genes counted
Uploaded: 07.12.2016

RNAseq (transcriptome) — illumina
(82M reads)
65610 genes counted
Uploaded: 03.04.2017/calculated

OVERALL STATUS

Name: Hugo 27
BG-CM-HG27
M / 83 years

DISEASE CHARACTERISTICS

Malignant cutaneous melanoma
Stage IV / M1c
ECOG: 1

GENERAL RECCOMENDATIONS

Previous: ipililumab/2014
Next possible NCCN: ##

BostonGene

LAUNCH ANALYSIS

START

Time line
Delete

PATIENT OVERVIEW

Hugo27

Stage: IV
T4N0M1c
ECOG:1
- Distant metastatic disease
- Adrenal metastases
- No brain metastases Histology Ulceration status: —
Breslow thickness: 6mm
Clark level: 4
EHR: connected Blood analysis
EHR: connected MRI
EHR: connected BRAF: negative
EHR: connected

FIG. 10

SYSTEMS AND METHODS FOR GENERATING, VISUALIZING AND CLASSIFYING MOLECULAR FUNCTIONAL PROFILES

RELATED APPLICATIONS

This application claims the benefit under 35 U.S.C. § 119(e) of the filing date of U.S. provisional patent application Ser. No. 62/518,787, entitled "Systems and Methods for Identifying Cancer Treatments from Sequence Data", filed Jun. 13, 2017 and U.S. provisional patent application Ser. No. 62/598,440, entitled "Systems and Methods Identifying Cancer Treatments from Sequence Data," filed Dec. 13, 2017, the entire contents of which are incorporated herein by reference.

This application is filed on the same day as International Application No.: PCT/US18/37017, entitled "SYSTEMS AND METHODS FOR GENERATING, VISUALIZING AND CLASSIFYING MOLECULAR FUNCTIONAL PROFILES"; International Application No.: PCT/US18/37018, entitled "SYSTEMS AND METHODS FOR IDENTIFYING RESPONDERS AND NON-RESPONDERS TO IMMUNE CHECKPOINT BLOCKADE THERAPY"; and International Application No.: PCT/US18/37008, entitled "SYSTEMS AND METHODS FOR IDENTIFYING CANCER TREATMENTS FROM NORMALIZED BIOMARKER SCORES", the entire contents of each of which are incorporated herein by reference.

FIELD

Aspects of the technology described herein relate to generating, visualizing and classifying molecular-functional (MF) profiles of cancer patients.

Some aspects of the technology described herein relate to generating a graphical user interface (GUI) for visualizing a molecular-functional profile of a cancer patient.

Some aspects of the technology described herein relate to identifying the type of MF profile of a patient, and predicting prognoses, identifying therapies, and/or otherwise aiding in the personalized care of the patient using the identified type.

BACKGROUND

Correctly characterizing the type or types of cancer a patient or subject has and, potentially, selecting one or more effective therapies for the patient can be crucial for the survival and overall wellbeing of that patient. Advances in characterizing cancers, predicting prognoses, identifying effective therapies, and otherwise aiding in personalized care of patients with cancer are needed.

SUMMARY

Provided herein, inter alia, are systems and methods for generating a molecular-functional (MF) profile for a subject and identifying an existing MF profile cluster that is associated with the generated MF profile. Such information, in some embodiments, is output to a user in a graphical user interface (GUI).

Systems and methods for identifying a molecular-functional (MF) profile cluster with which to associate a MF profile for a subject comprises, in some embodiments, obtaining RNA expression data and/or whole exome sequencing (WES) data for the subject; determining a MF profile for the subject, in part, by determining a gene group expression level for each gene group in a set of gene groups using the RNA expression data and/or WES data, the set of gene groups comprising gene groups associated with cancer malignancy and different gene groups associated with cancer microenvironment; and identifying a MF profile cluster with which to associate the MF profile for the subject from among multiple MF profile clusters that were generated by determining a plurality of MF profiles for a respective plurality of subjects using RNA expression data obtained from biological samples for the plurality of subjects, each of the plurality of MF profiles containing a gene group expression level for each gene group in the set of gene groups, and clustering the plurality of MF profiles to obtain the MF profile clusters. Provided herein, inter alia, are systems and methods for generating MF profile clusters. Such information, in some embodiments, is stored in one or more databases.

Systems and methods for generating MF profile clusters comprises, in some embodiments, obtaining RNA expression data and/or whole exome sequencing (WES) data for a plurality of subjects having a cancer of a particular type; determining a respective plurality of MF profiles for the plurality of subjects, in part, by determining, for each subject, a respective gene group expression level for each gene group in a set of gene groups using the RNA expression data and/or WES data, the set of gene groups comprising gene groups associated with cancer malignancy and different gene groups associated with cancer microenvironment; clustering the plurality of MF profiles to obtain MF profile clusters comprising a first MF profile cluster, a second MF profile cluster, a third MF profile cluster, and a fourth MF profile cluster; and storing the plurality of MF profiles in association with information identifying the particular cancer type.

Provided herein, inter alia, are systems and methods for generating a molecular-functional (MF) profile for a subject using at least four (e.g., at least five) gene group expression levels and identifying an existing MF profile cluster that is associated with the generated MF profile. Such information, in some embodiments, is output to a user in a graphical user interface (GUI).

Systems and methods for identifying a molecular-functional (MF) profile cluster with which to associate a MF profile for a subject comprises, in some embodiments, obtaining RNA expression data and/or whole exome sequencing (WES) data for the subject; determining a MF profile for the subject, in part, by determining a gene group expression level for each gene group in a set of gene groups using the RNA expression data and/or WES data, the set of gene groups comprising gene groups associated with cancer malignancy that consists of a tumor properties group and gene groups associated with cancer microenvironment that consists of a tumor-promoting immune microenvironment group, a an anti-tumor immune microenvironment group, an angiogenesis group, and a fibroblasts group; and identifying a MF profile cluster with which to associate the MF profile for the subject from among multiple MF profile clusters that were generated by determining a plurality of MF profiles for a respective plurality of subjects using RNA expression data obtained from biological samples for the plurality of subjects, each of the plurality of MF profiles containing a gene group expression level for each gene group in the set of gene groups, and clustering the plurality of MF profiles to obtain the MF profile clusters.

Provided herein, inter alia, are systems and methods for generating molecular-functional (MF) profile clusters, generating MF profiles for a subject, and associating the patient's MF profile with the MF profile cluster. Such information, in some embodiments, is output to a user in a graphical user interface (GUI).

Systems and methods for generating molecular-functional (MF) profile clusters, generating MF profiles for a subject, and associating the patient's MF profile with the MF profile cluster comprises, in some embodiments, obtaining RNA expression data and/or whole exome sequencing (WES) data for a plurality of subjects; determining a respective plurality of MF profiles for the plurality of subjects, in part, by determining, for each subject, a respective gene group expression level for each gene group in a set of gene groups using the RNA expression data and/or WES data, the set of gene groups comprising gene groups associated with cancer malignancy and different gene groups associated with cancer microenvironment; clustering the plurality of MF profiles to obtain MF profile clusters comprising a first MF profile cluster, a second MF profile cluster, a third MF profile cluster, and a fourth MF profile cluster; obtaining second RNA expression data from a subject, determining a MF profile for the subject, in part, by determining a gene group expression level for each gene group in the set of gene groups using the second RNA expression data; and identifying a MF profile cluster with which to associate the MF profile for the subject from among multiple MF profile clusters.

Provided herein, inter alia, are systems and methods for generating a MF profile and generating a MF portrait for visualizing the MF profile in a graphical user interface (GUI).

Systems and methods for generating a MF profile and generating a MF portrait for visualizing the MF profile in a graphical user interface (GUI) comprises, in some embodiments, obtaining RNA expression data and/or whole exome sequencing (WES) data for a subject; determining a MF profile for the subject, in part, by determining a gene group expression level for each gene group in a set of gene groups using the RNA expression data and/or WES data, the set of gene groups comprising gene groups associated with cancer malignancy and different gene groups associated with cancer microenvironment; determining a first visual characteristic for a first GUI element using the first gene group expression level; determining a second visual characteristic for a second GUI element using the second gene group expression level; generating a personalized GUI personalized to the subject; and presenting the generated personalized GUI to a user.

Provided herein, inter alia, are systems and methods for generating a MF profile by determining expression levels for e.g., four or five gene groups and generating a MF portrait for visualizing the MF profile in a graphical user interface (GUI).

Systems and methods for generating a MF profile by determining expression levels for e.g., four or five gene groups and generating a MF portrait for visualizing the MF profile in a graphical user interface (GUI) comprises, in some embodiments, obtaining RNA expression data and/or whole exome sequencing (WES) data for a subject; determining a MF profile for the subject, in part, by determining a gene group expression level for each gene group in a set of gene groups using the RNA expression data and/or WES data, the set of gene groups comprising gene groups associated with cancer malignancy that consists of X and gene groups associated with cancer microenvironment that consist of a tumor-promoting immune microenvironment group, an anti-tumor immune microenvironment group, an angiogenesis group, and a fibroblasts group; determining a first visual characteristic for a first GUI element using the first gene group expression level; determining a second visual characteristic for a second GUI element using the second gene group expression level; generating a personalized GUI personalized to the subject; and presenting the generated personalized GUI to a user.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising gene groups associated with cancer malignancy and different gene groups associated with cancer microenvironment; and identifying, from among multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using RNA expression data obtained from biological samples from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising gene groups associated with cancer malignancy and different gene groups associated with cancer microenvironment; and identifying, from among multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using RNA expression data obtained from biological samples from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising gene groups associated with cancer malignancy and different gene groups associated with cancer microenvironment; and identifying, from among multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using RNA expression data obtained from biological samples from the plurality of subjects, each of the plurality of MF profiles containing a gene group expression level for each gene group in the set of gene groups; and clustering the plurality of MF profiles to obtain the MF profile clusters.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data from biological samples from a plurality of subjects, at least some of the subjects having a cancer of a particular type; determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample; and storing the plurality of MF profiles in association with information identifying the particular cancer type.

In one aspect, provided herein is a method, comprising: using at least one computer hardware processor to perform: obtaining RNA expression data and/or whole exome sequencing (WES) data from biological samples from a plurality of subjects, at least some of the subjects having a cancer of a particular type; determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample; and storing the plurality of MF profiles in association with information identifying the particular cancer type.

In one aspect, provided herein is at least one non-transitory computer-readable storage medium storing processor-executable instructions that, when executed by at least one computer hardware processor, cause at least one computer hardware processor to perform: obtaining RNA expression data and/or whole exome sequencing (WES) data from biological samples from a plurality of subjects, at least some of the subjects having a cancer of a particular type; determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample; and storing the plurality of MF profiles in association with information identifying the particular cancer type.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising a first gene group associated with cancer malignancy and a second gene group associated with cancer microenvironment, wherein the first and second gene groups are different, the determining comprising: determining a first gene group expression level for the first gene group, and determining a second gene group expression level for the second gene group; determining a first visual characteristic for a first graphical user interface (GUI) element using the first gene group expression level; determining a second visual characteristic for a second GUI element using the second gene group expression level; generating a personalized GUI personalized to the subject, the GUI comprising: a first GUI portion associated with cancer malignancy and containing the first GUI element having the first visual characteristic, and a second GUI portion associated with cancer microenvironment and containing the second GUI element having the second visual characteristic; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising a first gene group associated with cancer malignancy and a second gene group associated with cancer microenvironment, wherein the first and second gene groups are different, the determining comprising: determining a first gene group expression level for the first gene group, and determining a second gene group expression level for the second gene group; determining a first visual characteristic for a first graphical user interface (GUI) element using the first gene group expression level; determining a second visual characteristic for a second GUI element using the second gene group expression level; generating a personalized GUI personalized to the subject, the GUI comprising: a first GUI portion associated with cancer malignancy and containing the first GUI element having the first visual characteristic, and a second GUI portion associated with cancer microenvironment and containing the second GUI element having the second visual characteristic; and presenting the generated personalized GUI to a user.

In one aspect, provided herein is at least one non-transitory computer-readable storage medium storing processor-executable instructions that, when executed by at least one computer hardware processor, cause at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising a first gene group associated with cancer malignancy and a second gene group associated with cancer microenvironment, wherein the first and second gene groups are different, the determining comprising: determining a first gene group expression level for the first gene group, and determining a second gene group expression level for the second gene group; determining a first visual characteristic for a first graphical user interface (GUI) element using the first gene group expression level; determining a second visual characteristic for a second GUI element using the second gene group expression level; generating a personalized GUI personalized to the subject, the GUI comprising: a first GUI portion associated with cancer malignancy and containing the first GUI element having the first visual characteristic, and a second GUI portion associated with cancer microenvironment and containing the second GUI element having the second visual characteristic; and presenting the generated personalized GUI to a user.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the tumor properties group; and determining, using the RNA expression data and the reference RNA expression data, a gene group expression level for each gene group in a second set of gene groups associated with cancer microenvironment and consisting of the tumor-promoting immune microenvironment group, the anti-tumor immune microenvironment group, the angiogenesis group, and the fibroblasts group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the tumor properties group; and determining, using the RNA expression data and the reference RNA expression data, a gene group expression level for each gene group in a second set of gene groups associated with cancer microenvironment and consisting of the tumor-promoting immune microenvironment group, the anti-tumor immune microenvironment group, the angiogenesis group, and the fibroblasts group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the tumor properties group; and determining, using the RNA expression data and the reference RNA expression data, a gene group expression level for each gene group in a second set of gene groups associated with cancer microenvironment and consisting of the tumor-promoting immune microenvironment group, the anti-tumor immune microenvironment group, the angiogenesis group, and the fibroblasts group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining first RNA expression data and/or first whole exome sequencing (WES) data from biological samples from a plurality of subjects; determining a respective plurality of molecular-functional (MF) profiles for the plurality of subjects at least in part by, for each of the plurality of subjects, determining, using the first RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters including: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples; obtaining second RNA expression data for a biological sample from a subject; determining a molecular-functional (MF) profile for the subject at least in part by determining, using the second RNA expression data, a gene group expression level for each group in the set of gene groups; and identifying, from among the MF profile clusters, a particular MF profile cluster with which to associate the MF profile for the subject.

In one aspect, provided herein is a method, comprising: using at least one computer hardware processor to perform: obtaining first RNA expression data and/or first whole exome sequencing (WES) data from biological samples from a plurality of subjects; determining a respective plurality of molecular-functional (MF) profiles for the plurality of subjects at least in part by, for each of the plurality of subjects, determining, using the first RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters including: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples; obtaining second RNA expression data for a biological sample from a subject; determining a molecular-functional (MF) profile for the subject at least in part by determining, using the second RNA expression data, a gene group expression level for each group in the set of gene groups; and identifying, from among the MF profile clusters, a particular MF profile cluster with which to associate the MF profile for the subject.

In one aspect, provided herein is at least one non-transitory computer-readable storage medium storing processor-executable instructions that, when executed by at least one computer hardware processor, cause the at least one computer hardware processor to perform: obtaining first RNA expression data and/or first whole exome sequencing (WES) data from biological samples from a plurality of subjects; determining a respective plurality of molecular-functional (MF) profiles for the plurality of subjects at least in part by, for each of the plurality of subjects, determining, using the first RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters including: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples; obtaining second RNA expression data for a biological sample from a subject; determining a molecular-functional (MF) profile for the subject at least in part by determining, using the second RNA expression data, a gene group expression level for each group in the set of gene groups; and identifying, from among the MF profile clusters, a particular MF profile cluster with which to associate the MF profile for the subject.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the tumor properties group; and second gene groups associated with cancer microenvironment consisting of the tumor-promoting immune microenvironment group, the anti-tumor immune microenvironment group, the angiogenesis group, and the fibroblasts group, determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the tumor properties group; and second gene groups associated with cancer microenvironment consisting of the tumor-promoting immune microenvironment group, the anti-tumor immune microenvironment group, the angiogenesis group, and the fibroblasts group, determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the tumor properties group; and second gene groups associated with cancer microenvironment consisting of the tumor-promoting immune microenvironment group, the anti-tumor immune microenvironment group, the angiogenesis group, and the fibroblasts group, determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and second gene groups associated with cancer microenvironment consisting of the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and second gene groups associated with cancer microenvironment consisting of the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and second gene groups associated with cancer microenvironment consisting of the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and second gene groups associated with cancer microenvironment consisting of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and second gene groups associated with cancer microenvironment consisting of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and second gene groups associated with cancer microenvironment consisting of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

BRIEF DESCRIPTION OF THE DRAWINGS

Various aspects and embodiments will be described with reference to the following figures. The figures are not necessarily drawn to scale.

FIG. 4 is a screenshot of the user's account profile screen presented to the user in response to the user logging into the software program.

FIG. 6 is a screenshot presenting that the patient's tumor biopsy sequencing data was downloaded (as shown in the lower right panel).

FIG. 10 is a screenshot presenting information relating to the mutational burden biomarker (as shown in the middle panel) provided in response to the user selecting the mutational burden biomarker.

DETAILED DESCRIPTION

Figure 1A:
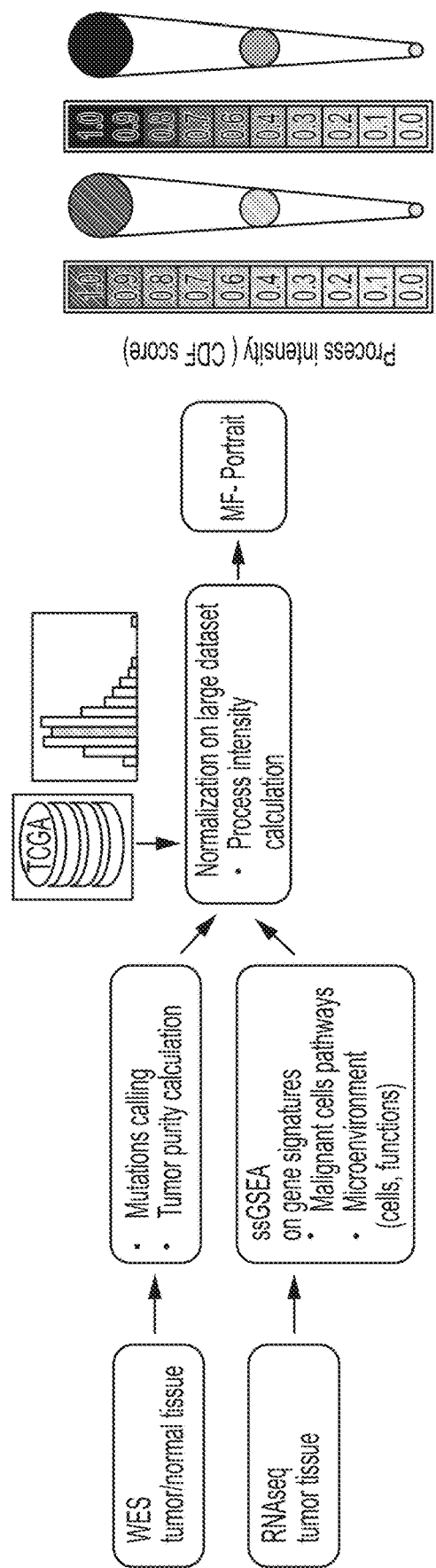
FIG. 1A is a graphical representation of an exemplary bioinformatics pipeline for determining tumor functional properties in a molecular functional profile (MF profile), in accordance with some embodiments of the technology described herein.

Recent advances in personalized genomic sequencing and cancer genomic sequencing technologies have made it possible to obtain patient-specific information about cancer cells (e.g., tumor cells) and cancer microenvironments from one or more biological samples obtained from individual patients. This information can be used to characterize the type or types of cancer a patient or subject has and, potentially, select one or more effective therapies for the patient. This information may also be used to determine how a patient is responding over time to a treatment and, if necessary, to select a new therapy or therapies for the patient as necessary. This information may also be used to determine whether a patient should be included or excluded from participating in a clinical trial.

The inventors have recognized and appreciated that many different types of cancer including, but not limited to melanoma, sarcoma, and glioblastoma, may be characterized as or classified into one of four molecular function (MF) profiles, herein identified as first MF profile ($1^{st}$ MF profile), second MF profile ($2^{nd}$ MF profile), third MF profile ($3^{rd}$ MF profile), and fourth MF profile ($4^{th}$ MF profile).

First MF profile cancers may also be described as "inflamed/vascularized" and/or "inflamed/fibroblast-enriched"; Second MF profile cancers may also be described as "inflamed/non-vascularized" and/or "inflamed/non-fibroblast-enriched"; Third MF profile cancers may also be described as "non-inflamed/vascularized" and/or "non-inflamed/fibroblast-enriched"; and Fourth MF profile cancers may also be described as "non-inflamed/non-vascularized" and/or "non-inflamed/non-fibroblast-enriched" and/or "immune desert." Such characteristics of MF clusters may be calculated in a number of ways.

As used herein, "inflamed" refers to the level of compositions and processes related to inflammation in a cancer (e.g., a tumor). In some embodiments, inflamed cancers (e.g., tumors) are highly infiltrated by immune cells, and are highly active with regard to antigen presentation and T-cell activation. In some embodiments, inflamed cancers (e.g., tumors) may have an NK cell and/or a T cell z score of, for example, at least 0.60, at least 0.65, at least 0.70, at least 0.75, at least 0.80, at least 0.85, at least 0.90, at least 0.91, at least 0.92, at least 0.93, at least 0.94, at least 0.95, at least 0.96, at least 0.97, at least 0.98, or at least 0.99. In some embodiments, inflamed cancers (e.g., tumors) may have an NK cell and/or a T cell z score of, for example, not less than 0.60, not less than 0.65, not less than 0.70, not less than 0.75, not less than 0.80, not less than 0.85, not less than 0.90, not less than 0.91, not less than 0.92, not less than 0.93, not less than 0.94, not less than 0.95, not less than 0.96, not less than 0.97, not less than 0.98, or not less than 0.99. In some embodiments, non-inflamed tumors are poorly infiltrated by immune cells, and have low activity with regard to antigen presentation and T-cell activation. In some embodiments, non-inflamed cancers (e.g., tumors) may have an NK cell and/or a T cell z score of, for example, less than −0.20, less than −0.25, less than −0.30, less than −0.35, less than −0.40, less than −0.45, less than −0.50, less than −0.55, less than −0.60, less than −0.65, less than −0.70, less than −0.75, less than −0.80, less than −0.85, less than −0.90, less than −0.91, less than −0.92, less than −0.93, less than −0.94, less than −0.95, less than −0.96, less than −0.97, less than −0.98, or less than −0.99. In some embodiments, non-inflamed cancers (e.g., tumors) may have an NK cell and/or a T cell z score of, for example, not more than −0.20, not more than −0.25, not more than −0.30, not more than −0.35, not more than −0.40, not more than −0.45, not more than −0.50, not more than −0.55, not more than −0.60, not more than −0.65, not more than −0.70, not more than −0.75, not more than −0.80, not more than −0.85, not more than −0.90, not more than −0.91, not more than −0.92, not more than −0.93, not more than −0.94, not more than −0.95, not more than −0.96, not more than −0.97, not more than −0.98, or not more than −0.99.

As used herein, "vascularized" refers to the formation of blood vessels in a cancer (e.g., a tumor). In some embodiments, vascularized cancers (e.g., tumors) comprise high levels of cellular compositions and process related to blood vessel formation. In some embodiments, vascularized cancers (e.g., tumors) may have an angiogenesis z score of, for example, at least 0.60, at least 0.65, at least 0.70, at least 0.75, at least 0.80, at least 0.85, at least 0.90, at least 0.91, at least 0.92, at least 0.93, at least 0.94, at least 0.95, at least 0.96, at least 0.97, at least 0.98, or at least 0.99. In some embodiments, vascularized cancers (e.g., tumors) may have an NK cell and/or a T cell z score of, for example, not less than 0.60, not less than 0.65, not less than 0.70, not less than 0.75, not less than 0.80, not less than 0.85, not less than 0.90, not less than 0.91, not less than 0.92, not less than 0.93, not less than 0.94, not less than 0.95, not less than 0.96, not less than 0.97, not less than 0.98, or not less than 0.99. In some embodiments, non-vascularized cancers (e.g., tumors) comprise few or no compositions and processes related to blood vessel formation. In some embodiments, non-vascularized cancers (e.g., tumors) may have an angiogenesis z score of, for example, less than −0.20, less than −0.25, less than −0.30, less than −0.35, less than −0.40, less than −0.45, less than −0.50, less than −0.55, less than −0.60, less than −0.65, less than −0.70, less than −0.75, less than −0.80, less than −0.85, less than −0.90, less than −0.91, less than −0.92, less than −0.93, less than −0.94, less than −0.95, less than −0.96, less than −0.97, less than −0.98, or less than −0.99. In some embodiments, non-vascularized cancers (e.g., tumors) may have an angiogenesis z score of, for example, not more than −0.20, not more than −0.25, not more than −0.30, not more than −0.35, not more than −0.40, not more than −0.45, not more than −0.50, not more than −0.55, not more than −0.60, not more than −0.65, not more than −0.70, not more than −0.75, not more than −0.80, not more than −0.85, not more than −0.90, not more than −0.91, not more than −0.92, not more than −0.93, not more than −0.94, not more than −0.95, not more than −0.96, not more than −0.97, not more than −0.98, or not more than −0.99.

As used herein, "fibroblast enriched" refers to the level or amount of fibroblasts in a cancer (e.g., a tumor). In some embodiments, fibroblast enriched tumors comprise high levels of fibroblast cells. In some embodiments, fibroblast enriched cancers (e.g., tumors) may have a fibroblast (cancer associated fibroblast) z score of, for example, at least 0.60, at least 0.65, at least 0.70, at least 0.75, at least 0.80, at least 0.85, at least 0.90, at least 0.91, at least 0.92, at least 0.93, at least 0.94, at least 0.95, at least 0.96, at least 0.97, at least 0.98, or at least 0.99. In some embodiments, fibroblast enriched cancers (e.g., tumors) may have an NK cell and/or a T cell z score of, for example, not less than 0.60, not less than 0.65, not less than 0.70, not less than 0.75, not less than 0.80, not less than 0.85, not less than 0.90, not less than 0.91, not less than 0.92, not less than 0.93, not less than 0.94, not less than 0.95, not less than 0.96, not less than 0.97, not less than 0.98, or not less than 0.99. In some embodiments, non-fibroblast-enriched cancers (e.g., tumors) comprise few or no fibroblast cells. In some embodiments, non-fibroblast-enriched cancers (e.g., tumors) may have a fibroblast (cancer associated fibroblast) z score of, for example, less than −0.20, less than −0.25, less than −0.30, less than −0.35, less than −0.40, less than −0.45, less than −0.50, less than −0.55, less than −0.60, less than −0.65, less than −0.70, less than −0.75, less than −0.80, less than −0.85, less than −0.90, less than −0.91, less than −0.92, less than −0.93, less than −0.94, less than −0.95, less than −0.96, less than −0.97, less than −0.98, or less than −0.99. In some embodiments, non-fibroblast-enriched cancers (e.g., tumors) may have a fibroblast (cancer associated fibroblast) z score of, for example, not more than −0.20, not more than −0.25, not more than −0.30, not more than −0.35, not more than −0.40, not more than −0.45, not more than −0.50, not more than −0.55, not more than −0.60, not more than −0.65, not more than −0.70, not more than −0.75, not more than −0.80, not more than −0.85, not more than −0.90, not more than −0.91, not more than −0.92, not more than −0.93, not more than −0.94, not more than −0.95, not more than −0.96, not more than −0.97, not more than −0.98, or not more than −0.99.

Each subject biological sample may be assigned to one of four predefined MF profile clusters using a k-nearest neighbors classifier. The classifier may be trained on the data by which the MF profile clusters are defined and on their corresponding labels. Sample vectors for the k-nearest neighbors classifier may be found in Table 1, below. The classifier may then predict the type of MF profile (MF profile cluster) for the subject sample utilizing its relative processes intensity values. Relative processes intensity values may be calculated as Z-values (arguments of the standard normal distribution over training set of samples) of ssGSEA algorithm outputs inferred from the RNA sequence data from the subject sample as described herein.

TABLE 1

Sample vectors for the k-nearest neighbors classifier (z-scores).

| MF profile type | First | Second | Third | Fourth |
|---|---|---|---|---|
| Angiogenesis | 0.727815 | −0.5907 | 0.71314 | −0.42704 |
| Cancer Associated Fibroblasts | 0.596986 | −0.4871 | 0.82218 | −0.49264 |
| Receptor_tyrosine_kinases | 0.370197 | −0.4366 | 0.75614 | −0.33472 |
| NK_cells | 0.624648 | 0.75725 | −0.3987 | −0.89695 |
| Checkpoint_inhibition | 0.671491 | 0.74881 | −0.3928 | −0.92683 |
| Effector_cells | 0.652837 | 0.77783 | −0.3953 | −0.93822 |
| T_cells | 0.701067 | 0.74591 | −0.3827 | −0.9518 |
| Proliferation_rate | −0.44244 | 0.10307 | −0.457 | 0.509505 |

The identification and classification of $1^{st}$-$4^{th}$ MF profile cluster types as described herein were not known in the art, and such classifications provide more precise diagnoses that might not be seen by the use of any single marker or less complex combination of elements. The methods, systems, and graphical user interfaces (GUIs) based on such classifications described herein are newly available and no previously described techniques or methods existed to perform the elements of these techniques. Further, the four molecular function (MF) profiles were not known previously to exist and there could therefore be no motivation in the art to define these cancer types. Additionally, the types of analyses described herein would have been considered too involved, costly, and/or time consuming to perform without understanding the potential benefits that could be derived from such complex analyses based on the multiplicity and mutability of the involved factors.

The inventors have recognized and appreciated that several of the elements described herein add something more than what is well understood, routine, or conventional activity proposed by others in the field. These meaningful non-routine steps result in the improvements seen in the methods, systems, and GUIs described herein and include, but are not limited to: the analysis of gene expression levels and gene group expression levels for both cancer malignancy and cancer microenvironment; the combination(s) of specific genes used in the gene groups (or modules) provided herein; the recognition that many different cancers can be classified such that they are identifiable as one of $1^{st}$-$4^{th}$ MF profile cancer types; technical improvements in analyses that allow for more precise identification of cancers and resulting improvements in outcome for the patient; the creation of improved graphical user interfaces to aid in the analysis of an individual patient's cancer into cancer $1^{st}$-$4^{th}$ MF profile cancer types; the specification of treatments for individual patients based on the identified classification of one or more cancers in the patient (i.e., $1^{st}$-$4^{th}$ MF profile cancer types) and/or additional information about the patient or the patient's cancer.

Therefore, aspects of the present disclosure relate to methods and compositions for characterizing one or more cancers (e.g., tumors) of or in a patient. In some embodiments, characterizing a cancer (e.g., a tumor) comprises determining differentially expressed genes in a sample from a subject (e.g., a patient) having a cancer (e.g., a tumor). In some embodiments, characterizing a cancer (e.g., a tumor) comprises determining whether one or more genes are mutated in a sample from a subject having a cancer (e.g., a tumor). In certain embodiments, characterizing a cancer (e.g., a tumor) comprises identifying the cancer (e.g., a tumor) as a specific subtype of cancer selected from a $1^{st}$ MF profile cancer type (inflamed/vascularized and/or inflamed/fibroblast enriched); a $2^{nd}$ MF profile cancer type (inflamed/non-vascularized and/or inflamed/non-fibroblast enriched); a $3^{rd}$ MF profile cancer type (non-inflamed/vascularized and/or non-inflamed/fibroblast enriched); and a $4^{th}$ MF profile cancer type (non-inflamed/non-vascularized and/or non-inflamed/non-fibroblast enriched; also identified herein as "immune desert").

Such methods and compositions may be useful for clinical purposes including, for example, selecting a treatment, monitoring cancer progression, assessing the efficacy of a treatment against a cancer, evaluating suitability of a patient for participating in a clinical trial, or determining a course of treatment for a subject (e.g., a patient).

The methods and compositions described herein may also be useful for non-clinical applications including (as a non-limiting example) research purposes such as, e.g., studying the mechanism of cancer development and/or biological pathways and/or biological processes involved in cancer, and developing new therapies for cancer based on such studies.

Further, systems which present this information in a comprehensive and useable format will be needed to facilitate treatment of patients with such conditions. Therefore, provided herein are models and systems of cancer-immunity interrelationships for a particular patient that result in a profile designed to concisely and clearly describe important characteristics of cancerous cells (e.g., tumor cells) of the patient (referred to herein as, for example, "cancer malignancy"), as well as all the key processes in the cancer (e.g., tumor) microenvironment (discussed herein as, for example, "cancer microenvironment").

Such a model may take into consideration the full spectrum of non-malignant components in the cancer microenvironment, including fibroblasts and extracellular matrices, the network of blood and lymphatic vessels, tissue macrophages, dendritic and mast cells, different kinds of leukocytes/lymphocytes migrated to or proliferating within tumor, as well as intrinsic properties of malignant cells.

Certain aspects of the described model or system present the cellular composition of the cancerous cells (e.g., the tumor), while other aspects reflect the intensity of processes of the cancerous (e.g., the tumor) cells of the biological sample and/or patient. The presence and number of any cell type is an important but insufficient parameter because it is also necessary to understand how these cells function within the processes that make up the cancer (e.g., the tumor). The size of particular functional modules including, e.g., the intensity of processes ongoing in these modules, actually comprises both concentration and functional activity of the cell type. Therefore, a cancer (e.g., a tumor) "profile" that comprises a set of functional modules with an estimate of their intensity implicitly reflects the content of the different cell types within the cancer (e.g., the tumor).

Therefore, in some embodiments the model described herein enables the study of the structural-functional composition of a particular patient's tumor and/or cancerous cells and also allows the comparison of the same across different patients and groups of patients. As a non-limiting example, the described model has been used to compare human skin cutaneous melanoma (SKCM) tumors from 470 melanoma patients. Four general types of tumors were revealed (described here as tumor types $1^{st}$ MF profile type, $2^{nd}$ MF profile type, $3^{rd}$ MF profile type, and $4^{th}$ MF profile type) pertaining to 22%, 28%, 24%, and 24% of melanoma patients, respectively (representing 98% of total patients). Tumor types $1^{st}$ MF profile type and $2^{nd}$ MF profile type are characterized by excessive infiltration with cells of the immune system (so-called "inflamed" or "hot" tumors), and $3^{rd}$ MF profile type and $4^{th}$ MF profile type are considered poorly infiltrated (so-called "non-inflamed" or "cold" tumors), meaning they have no obvious signs of inflammation or recruitment of immune cells.

Generally, techniques described herein provide for improvements over conventional computer-implemented techniques for analysis of medical data such as evaluation of expression data (e.g., RNA expression data) and determining whether one or more therapies (e.g., targeted therapies and/or immunotherapies) will be effective in treating the subject. Additionally, some embodiments of the technology provided herein are directed to graphical user interfaces that present oncological data in a new way which is compact and highly informative. These graphical user interfaces not only reduce the cognitive load on users working with them, but may serve to reduce clinician errors and improve the functionality of a computer by providing all needed information in a single interactive interface. This eliminates the need for a clinician to consult different sources of information (e.g., view multiple different webpages, use multiple different application programs, etc.), which would otherwise place an additional burden on the processing, memory, and communications resources of the computer(s) used by the clinician.

As described herein, some embodiments relate to a software program for providing information related to a patient's cancer to a user (e.g., an oncologist or other doctor, a healthcare provider, a researcher, a patient, etc.). The software program may provide information about the patient, e.g., the patient's age, overall status, diagnosis, and treatment history.

In another aspect, the software program may provide information about the patient's cancer, e.g., tumor histology, tumor purity, tumor clone evolution, tumor cell composition, tumor cell infiltrate, gene expression levels, gene mutations, the results of medical examinations (e.g., MRI results) and sequencing data (e.g., RNA sequencing data and/or whole exome sequencing (WES) data).

In another aspect, the software program may provide information about potential treatments (e.g., immunotherapies, targeted therapies, etc.) and information related to potential treatments, e.g., prognostic factors, therapeutic efficacy, clinical trial efficacy, ongoing clinical trials, and relevant publications.

In another aspect, the software program may provide information about the patient's biomarkers (e.g., genetic biomarkers, cellular biomarkers, and expression biomarkers) and information related to the patient's biomarkers (e.g., a description of the biomarker, how the biomarker value was calculated, the patient's particular biomarker value compared to other patients, and related publications).

In yet another aspect, the software program may also allow the user to interactively design a panel of sequencing results (e.g., results related to the sequences or levels of specified biomarkers or genes) specific to the patient and/or a combination therapy for the patient.

As used herein, the term "patient" means any mammal, including mice, rabbits, and humans. In one embodiment, the patient is a human or non-human primate. The terms "individual" or "subject" may be used interchangeably with "patient."

Obtaining Expression Data

Expression data (e.g., RNA expression data and/or whole exome sequencing (WES) data) as described herein may be obtained from a variety of sources. In some embodiments, expression data may be obtained by analyzing a biological sample from a patient. The biological sample may be analyzed prior to performance of the techniques described herein including the techniques for generating MF clusters, associating a patient's MF profile with one of the MF clusters, and generating an MF portrait from a patient's MF profile to provide a visualization for the MF profile. In some such embodiments, data obtained from the biological sample may be stored (e.g., in a database) and accessed during performance of the techniques described herein. In some embodiments, expression data is obtained from a database containing expression data for at least one patient.

Biological Samples

Any of the methods, systems, assays, or other claimed elements may use or be used to analyze any biological sample from a subject (i.e., a patient or individual). In some embodiments, the biological sample may be any sample from a subject known or suspected of having cancerous cells or pre-cancerous cells.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue).

The biological sample may be any type of sample including, for example, a sample of a bodily fluid, one or more cells, a piece of tissue, or some or all of an organ. In some embodiments, the sample may be from a cancerous tissue or organ or a tissue or organ suspected of having one or more cancerous cells. In some embodiments, the sample may be from a healthy (e.g., non-cancerous) tissue or organ. In some embodiments, a sample from a subject (e.g., a biopsy from a subject) may include both healthy and cancerous cells and/or tissue. In certain embodiments, one sample will be taken from a subject for analysis. In some embodiments, more than one (e.g., 2, 3, 4, 5, 6, 7, 8, 9, 10, 11, 12, 13, 14, 15, 16, 17, 18, 19, 20, or more) samples may be taken from a subject for analysis. In some embodiments, one sample from a subject will be analyzed. In certain embodiments, more than one (e.g., 2, 3, 4, 5, 6, 7, 8, 9, 10, 11, 12, 13, 14, 15, 16, 17, 18, 19, 20, or more) samples may be analyzed. If more than one sample from a subject is analyzed, the samples may be procured at the same time (e.g., more than one sample may be taken in the same procedure), or the samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure). A second or subsequent sample may be taken or obtained from the same region (e.g., from the same tumor or area of tissue) or a different region (including, e.g., a different tumor). A second or subsequent sample may be taken or obtained from the subject after one or more treatments, and may be taken from the same region or a different region. As a non-limiting example, the second or subsequent sample may be useful in determining whether the cancer in each sample has different characteristics (e.g., in the case of samples taken from two physically separate tumors in a patient) or whether the cancer has responded to one or more treatments (e.g., in the case of two or more samples from the same tumor prior to and subsequent to a treatment).

Any of the biological samples described herein may be obtained from the subject using any known technique. In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy). In some embodiments, each of the at least one biological samples is a bodily fluid sample, a cell sample, or a tissue biopsy.

In some embodiments, one or more than one cell (i.e., a cell sample) is obtained from a subject using a scrape or brush method. The cell sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) samples from one or more tumors or tissues known or suspected of having cancerous cells.

Sample Analysis

Methods and compositions described herein are based, at least in part, on the identification and characterization of certain biological processes and/or molecular and cellular compositions that are present within and/or surrounding the cancer (e.g., the tumor).

Biological processes within and/or surrounding cancer (e.g., a tumor) include, but are not limited to, angiogenesis, metastasis, proliferation, cell activation (e.g., T cell activation), tumor invasion, immune response, cell signaling (e.g., HER2 signaling), and apoptosis.

Molecular and cellular compositions within and/or surrounding cancer (e.g., a tumor) include, but are not limited to, nucleic acids (e.g., DNA and/or RNA), molecules (e.g., hormones), proteins (e.g., wild-type and/or mutant proteins), and cells (e.g., malignant and/or non-malignant cells).

The cancer microenvironment, as used herein, refers to the molecular and cellular environment in which the cancer (e.g., a tumor) exists including, but not limited to, blood vessels that surround and/or are internal to a tumor, immune cells, fibroblasts, bone marrow-derived inflammatory cells, lymphocytes, signaling molecules, and the extracellular matrix (ECM).

The molecular and cellular composition and biological processes present within and/or surrounding the tumor may be directed toward promoting cancer (e.g., tumor) growth and survival (e.g., pro-tumor) and/or inhibiting cancer (e.g., tumor) growth and survival (e.g., anti-tumor).

The cancer (e.g., tumor) microenvironment may comprise cellular compositions and biological processes directed toward promoting cancer (e.g., tumor) growth and survival (e.g., pro-tumor microenvironment) and/or inhibiting cancer (e.g., tumor) growth and survival (e.g., anti-tumor microenvironment). In some embodiments, the cancer (e.g., tumor) microenvironment comprises a pro-cancer (e.g., tumor) microenvironment. In some embodiments, the cancer (e.g., tumor) microenvironment comprises an anti-cancer (e.g., tumor) microenvironment. In some embodiments, the cancer (e.g., tumor) microenvironment comprises a pro-cancer (e.g., tumor) microenvironment and an anti-cancer (e.g., tumor) microenvironment. Any information relating to molecular and cellular compositions, and biological processes that are present within and/or surrounding cancer (e.g., a tumor) may be used in methods and compositions for characterization of cancers (e.g., tumors) as described herein. In some embodiments, cancer (e.g., a tumor) may be characterized based on gene group expression level (e.g., on gene group RNA expression level). In some embodiments, cancer (e.g., a tumor) is characterized based on protein expression. In some embodiments, cancer (e.g., a tumor) is characterized based on absence or presence of at least one mutation (e.g., mutational load). In some embodiments, the mutational load is estimated from whole exome sequencing data (WES). In some embodiments, cancer (e.g., a tumor) is characterized based on histology. In some embodiments, cancer (e.g., a tumor) is characterized based on tumor purity. Tumor purity may be determined using any means known in the art including, but not limited to, cell sorting-based technology (e.g., Fluorescent-Activated Cell Sorting (FACS)). In some embodiments, tumor purity is determined from whole exome sequencing (WES) data of paired tumor and non-cancerous (e.g., normal) tissue. In some embodiments, cancer (e.g., a tumor) is characterized based on the number of neoantigens. The number of neoantigens may be determined using any means known in the art including, but not limited to, the use of whole exome sequencing (WES) data of paired cancer (e.g., tumor) and non-cancerous tissues.

Methods and compositions for characterization of cancers as described herein may be applied to any cancer (e.g., any tumor). Exemplary cancers include, but are not limited to, adrenocortical carcinoma, bladder urothelial carcinoma, breast invasive carcinoma, cervical squamous cell carcinoma, endocervical adenocarcinoma, colon adenocarcinoma, esophageal carcinoma, kidney renal clear cell carcinoma, kidney renal papillary cell carcinoma, liver hepatocellular carcinoma, lung adenocarcinoma, lung squamous cell carcinoma, ovarian serous cystadenocarcinoma, pancreatic adenocarcinoma, prostate adenocarcinoma, rectal adenocarcinoma, skin cutaneous melanoma, stomach adenocarcinoma, thyroid carcinoma, uterine corpus endometrial carcinoma, and cholangiocarcinoma.

In one embodiment, cancers of any type (including all the types of cancer listed herein) may be classified as being 1st MF profile type (inflamed/vascularized and/or inflamed/fibroblast enriched), 2nd MF profile type (inflamed/non-vascularized and/or inflamed/non-fibroblast enriched), 3rd MF profile type (non-inflamed/vascularized and/or non-inflamed/fibroblast enriched), or 4th MF profile type (non-inflamed/non-vascularized and/or non-inflamed/non-fibroblast enriched) cancers (e.g., tumors).

Expression Data

Expression data (e.g., indicating expression levels) for a plurality of genes may be used for any of the methods or compositions described herein. The number of genes which may be examined may be up to and inclusive of all the genes of the subject. In some embodiments, expression levels may be examined for all of the genes of a subject. As a non-limiting example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein. As another set of non-limiting examples, at least four, at least five, at least six, at least seven, at least eight, at least nine, at least ten, at least eleven, at least twelve, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 125, at least 150, at least 175, at least 200, at least 225, at least 250, at least 275, or at least 300 genes may be used for any evaluation described herein. In some embodiments, at least two, at least three, at least four, at least five, at least six, at least seven, at least eight, at least nine, at least ten, at least eleven, at least twelve, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 125, at least 150, at least 175, at least 200, at least 225, at least 250, at least 275, or at least 300 genes may be examined for each gene group or module evaluation described herein. In some embodiments, up to 50 modules (e.g., up to two, up to three, up to four, up to five, up to six, up to seven, up to eight, up to nine, up to ten, up to eleven, up to twelve, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 31, up to 32, up to 33, up to 34, up to 35, up to 36, up to 37, up to 38, up to 39, up to 40, up to 41, up to 42, up to 43, up to 44, up to 45, up to 46, up to 47, up to 48, up to 49, or up to 50) modules or gene groups may be used for any evaluation described herein.

Any method may be used on a sample from a subject in order to acquire expression data (e.g., indicating expression levels) for the plurality of genes. As a set of non-limiting examples, the expression data may be RNA expression data, DNA expression data, or protein expression data.

DNA expression data, in some embodiments, refers to a level of DNA in a sample from a subject. The level of DNA in a sample from a subject having cancer may be elevated compared to the level of DNA in a sample from a subject not having cancer, e.g., a gene duplication in a cancer patient's sample. The level of DNA in a sample from a subject having cancer may be reduced compared to the level of DNA in a sample from a subject not having cancer, e.g., a gene deletion in a cancer patient's sample.

DNA expression data, in some embodiments, refers to data for DNA (or gene) expressed in a sample, for example, sequencing data for a gene that is expressed in a patient's sample. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Any technique used in the art to sequence DNA may be used with the methods and compositions described herein. As a set of non-limiting examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data comprises whole exome sequencing (WES) data. In some embodiments, the expression data comprises whole genome sequencing (WGS) data. In some embodiments, the expression data comprises next-generation sequencing (NGS) data. In some embodiments, the expression data comprises microarray data.

In some embodiments, expression data is used to determine gene group expression levels. In some embodiments, the gene group expression levels are calculated as a gene set enrichment analysis (GSEA) score for the gene group. In some embodiments, GSEA comprises calculating an enrichment score (ES), assessing ES significance, adjusting ES for multiple hypothesis testing, and weighting each gene. In some embodiments, each gene is weighted equally. In some embodiments, each gene is weighted according to their association with a phenotype.

In some embodiments, calculating an ES comprises ranking genes by their expression difference, calculating cumulative sum over ranked genes, and recording maximum deviation from zero as ES. In some embodiments, calculating cumulative sum over ranked genes comprises an increase in sum when a gene is present in a gene group and a decrease in sum when a gene is absent from gene group. In some embodiments, magnitude of increment depends on correlation of a gene and a phenotype.

In some embodiments, assessing ES significance comprises permutating phenotype labels. In some embodiments, assessing ES significance comprises calculating ES for permutated data. In some embodiments, assessing ES significance comprises comparing ES for non-permutated data to ES for permutated data.

In some embodiments, adjusting ES for multiple hypothesis testing comprises determining a normalized enrichment score (NES). In some embodiments, adjusting ES for multiple hypothesis testing determining a false discovery rate (FDR) for the NES. In some embodiments, determining FDR comprises comparing tail of the observed and null distributions for the NES. In some embodiments, GSEA score is calculated at least once. In some embodiments, GSEA score is calculated at least twice. In some embodiments, GSEA score is calculated once for positively scoring gene groups and once for negatively score gene groups.

Datasets

Any dataset containing expression data may be used to generate MF profiles as described herein. In some embodiments, expression data may be obtained from one or more databases and/or any other suitable electronic repository of data. Examples of databases include, but are not limited to, CGP (Cancer Genome Project), CPTAC (Clinical Proteomic Tumor Analysis Consortium), ICGC (International Cancer Genome Consortium), and TCGA (The Cancer Genome Atlas). In some embodiments, expression data may be obtained from data associated with a clinical trial. In some embodiments, expression data may be predicted in association with a clinical trial based on one or more similar drugs (e.g., drugs of a similar class such as PD-1 inhibitors). In some embodiments, expression data may be obtained from a hospital database. In some embodiments, expression data may be obtained from a commercial sequencing supplier. In some embodiments, expression data may be obtained from a subject (e.g., a patient) and/or a subject's (e.g., a patient's) relative, guardian, or caretaker.

Assays

Any of the biological samples described herein can be used for obtaining expression data using conventional assays or those described herein. Expression data, in some embodiments, includes gene expression levels. Gene expression levels may be detected by detecting a product of gene expression such as mRNA and/or protein.

In some embodiments, gene expression levels are determined by detecting a level of a protein in a sample and/or by detecting a level of activity of a protein in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

The level of a protein may be measured using an immunoassay. Examples of immunoassays include any known assay (without limitation), and may include any of the following: immunoblotting assay (e.g., Western blot), immunohistochemical analysis, flow cytometry assay, immunofluorescence assay (IF), enzyme linked immunosorbent assays (ELIS As) (e.g., sandwich ELISAs), radioimmune assays, electrochemiluminescence-based detection assays, magnetic immunoassays, lateral flow assays, and related techniques. Additional suitable immunoassays for detecting a level of a protein provided herein will be apparent to those of skill in the art.

Such immunoassays may involve the use of an agent (e.g., an antibody) specific to the target protein. An agent such as an antibody that "specifically binds" to a target protein is a term well understood in the art, and methods to determine such specific binding are also well known in the art. An antibody is said to exhibit "specific binding" if it reacts or associates more frequently, more rapidly, with greater duration and/or with greater affinity with a particular target protein than it does with alternative proteins. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen. In some embodiments, a sample may be contacted, simultaneously or sequentially, with more than one binding agent that binds different proteins (e.g., multiplexed analysis).

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source including, but not limited to, primate (human and non-human primate) and primatized (such as humanized) antibodies.

In some embodiments, the antibodies as described herein can be conjugated to a detectable label and the binding of the detection reagent to the peptide of interest can be determined based on the intensity of the signal released from the detectable label. Alternatively, a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., (β-galactosidase) that produces a colored product from a colorless substrate.

It will be apparent to those of skill in the art that this disclosure is not limited to immunoassays. Detection assays that are not based on an antibody, such as mass spectrometry, are also useful for the detection and/or quantification of a protein and/or a level of protein as provided herein. Assays that rely on a chromogenic substrate can also be useful for the detection and/or quantification of a protein and/or a level of protein as provided herein.

Alternatively, the level of nucleic acids encoding a gene in a sample can be measured via a conventional method. In some embodiments, measuring the expression level of nucleic acid encoding the gene comprises measuring mRNA. In some embodiments, the expression level of mRNA encoding a gene can be measured using real-time reverse transcriptase (RT) Q-PCR or a nucleic acid microarray. Methods to detect nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some embodiments, the level of nucleic acids encoding a gene in a sample can be measured via a hybridization assay. In some embodiments, the hybridization assay comprises at least one binding partner. In some embodiments, the hybridization assay comprises at least one oligonucleotide binding partner. In some embodiments, the hybridization assay comprises at least one labeled oligonucleotide binding partner. In some embodiments, the hybridization assay comprises at least one pair of oligonucleotide binding partners. In some embodiments, the hybridization assay comprises at least one pair of labeled oligonucleotide binding partners.

Any binding agent that specifically binds to a desired nucleic acid or protein may be used in the methods and kits described herein to measure an expression level in a sample. In some embodiments, the binding agent is an antibody or an aptamer that specifically binds to a desired protein. In other embodiments, the binding agent may be one or more oligonucleotides complementary to a nucleic acid or a portion thereof. In some embodiments, a sample may be contacted, simultaneously or sequentially, with more than one binding agent that binds different proteins or different nucleic acids (e.g., multiplexed analysis).

To measure an expression level of a protein or nucleic acid, a sample can be in contact with a binding agent under suitable conditions. In general, the term "contact" refers to an exposure of the binding agent with the sample or cells collected therefrom for suitable period sufficient for the formation of complexes between the binding agent and the target protein or target nucleic acid in the sample, if any. In some embodiments, the contacting is performed by capillary action in which a sample is moved across a surface of the support membrane.

In some embodiments, an assay may be performed in a low-throughput platform, including single assay format. In some embodiments, an assay may be performed in a high-throughput platform. Such high-throughput assays may comprise using a binding agent immobilized to a solid support (e.g., one or more chips). Methods for immobilizing a binding agent will depend on factors such as the nature of the binding agent and the material of the solid support and may require particular buffers. Such methods will be evident to one of ordinary skill in the art.

Genes

The various genes recited herein are, in general, named using human gene naming conventions. The various genes, in some embodiments, are described in publically available resources such as published journal articles. The gene names may be correlated with additional information (including sequence information) through use of, for example, the NCBI GenBank® databases available at www <dot> ncbi <dot> nlm <dot> nih <dot> gov; the HUGO (Human Genome Organization) Gene Nomination Committee (HGNC) databases available at www <dot> genenames <dot> org; the DAVID Bioinformatics Resource available at www <dot> david <dot> ncifcrf <dot> gov. The gene names may also be correlated with additional information through printed publications from the foregoing organizations, which are incorporated by reference herein for this purpose. It should be appreciated that a gene may encompass all variants of that gene. For organisms or subjects other than human subjects, corresponding specific-specific genes may be used. Synonyms, equivalents, and closely related genes (including genes from other organisms) may be identified using similar databases including the NCBI GenBank® databases described above.

In some embodiments, gene MK167 may be identified as GenBank® Accession number NM_002417.4 or NM_001145966.1; gene ESCO2 may be identified as GenBank® Accession number NM_001017420.2; gene CETN3 may be identified as GenBank® Accession number NM_001297765.1, NM_004365.3 or NM_001297768.1; gene CDK2 may be identified as GenBank® Accession number NM_001798.4, NM_052827.3 or NM_001290230.1; gene CCND1 may be identified as GenBank® Accession number NM_053056.2; gene CCNE1 may be identified as GenBank® Accession number NM_001238.3, NM_001322259.1, NM_001322261.1 or NM_001322262.1; gene AURKA may be identified as GenBank® Accession number NM_198433.2, NM_003600.3, NM_198434.2, NM_198435.2, NM_198436.2, NM_198437.2, NM_001323303.1, NM_001323304.1, or NM_001323305.1; gene AURKB may be identified as GenBank® Accession number NM_004217.3, NM_001256834.2, NM_001284526.1, NM_001313950.1, NM_001313951.1NM_001313952.1, NM_001313954.1, NM_001313953.2 or NM_001313955.1; gene CDK4 may be identified as GenBank® Accession number NM_000075.3; gene CDK6 may be identified as GenBank® Accession number NM_001145306.1; gene PRC1 may be identified as GenBank® Accession number NM_199413.2 or NM_003981.3; gene E2F1 may be identified as GenBank® Accession number NM_005225.2; gene MYBL2 may be identified as GenBank® Accession number NM_002466.3 or NM_001278610.1; gene BUB1 may be identified as GenBank® Accession number NM_004336.4, NM_001278616.1, NM_001278617.1; gene PLK1 may be identified as GenBank® Accession number NM_005030.5; gene CCNB1 may be identified as GenBank® Accession number NM_031966.3, NM_001354845.1, NM_001354844.1; gene MCM2 may be identified as GenBank® Accession number NM_004526.3; gene MCM6 may be identified as GenBank® Accession number NM_005915.5; gene PIK3CA may be identified as GenBank® Accession number NM_006218.3; gene PIK3CB may be identified as GenBank® Accession number NM_006219.2 or NM_001256045.1; gene PIK3CG may be identified as GenBank® Accession number NM_002649.3, NM_001282427.1 or NM_001282426.1; gene PIK3CD may be identified as GenBank® Accession number NM_005026.4, NM_001350234.1, or NM_001350235.1; gene AKT1 may be identified as GenBank® Accession number NM_005163.2, NM_001014431.1, or NM_001014432.1; gene MTOR may be identified as GenBank® Accession number NM_004958.3; gene PTEN may be identified as GenBank® Accession number NM_001304717.2, NM_000314.6 or NM_001304718.1; gene PRKCA may be identified as GenBank® Accession number NM_002737.2; gene AKT2 may be identified as GenBank® Accession number NM_001330511.1, NM_001243027.2, NM_001243028.2, NM_001626.5; gene AKT3 may be identified as GenBank® Accession number NM_005465.4, NM_181690.2 or NM_001206729.1; gene BRAF may be identified as GenBank® Accession number NM_001354609.1 or NM_004333.5; gene FNTA may be identified as GenBank® Accession number NM_002027.2; gene FNTB may be identified as GenBank® Accession number NM_002028.3; gene MAP2K1 may be identified as GenBank® Accession number NM_002755.3; gene MKNK1 may be identified as GenBank® Accession number NM_003684.6, NM_198973.4 or NM_001135553.3; gene MKNK2 may be identified as GenBank® Accession number NM_017572.3 or NM_199054.2.

MF Profiles

A "molecular functional tumor portrait (MF profile)," as described herein, refers to a graphical depiction of a tumor with regard to molecular and cellular composition, and biological processes that are present within and/or surrounding the tumor. Related compositions and processes present within and/or surrounding a tumor are presented in functional modules (also described herein as "gene groups") of a MF profile.

Figure 1B:
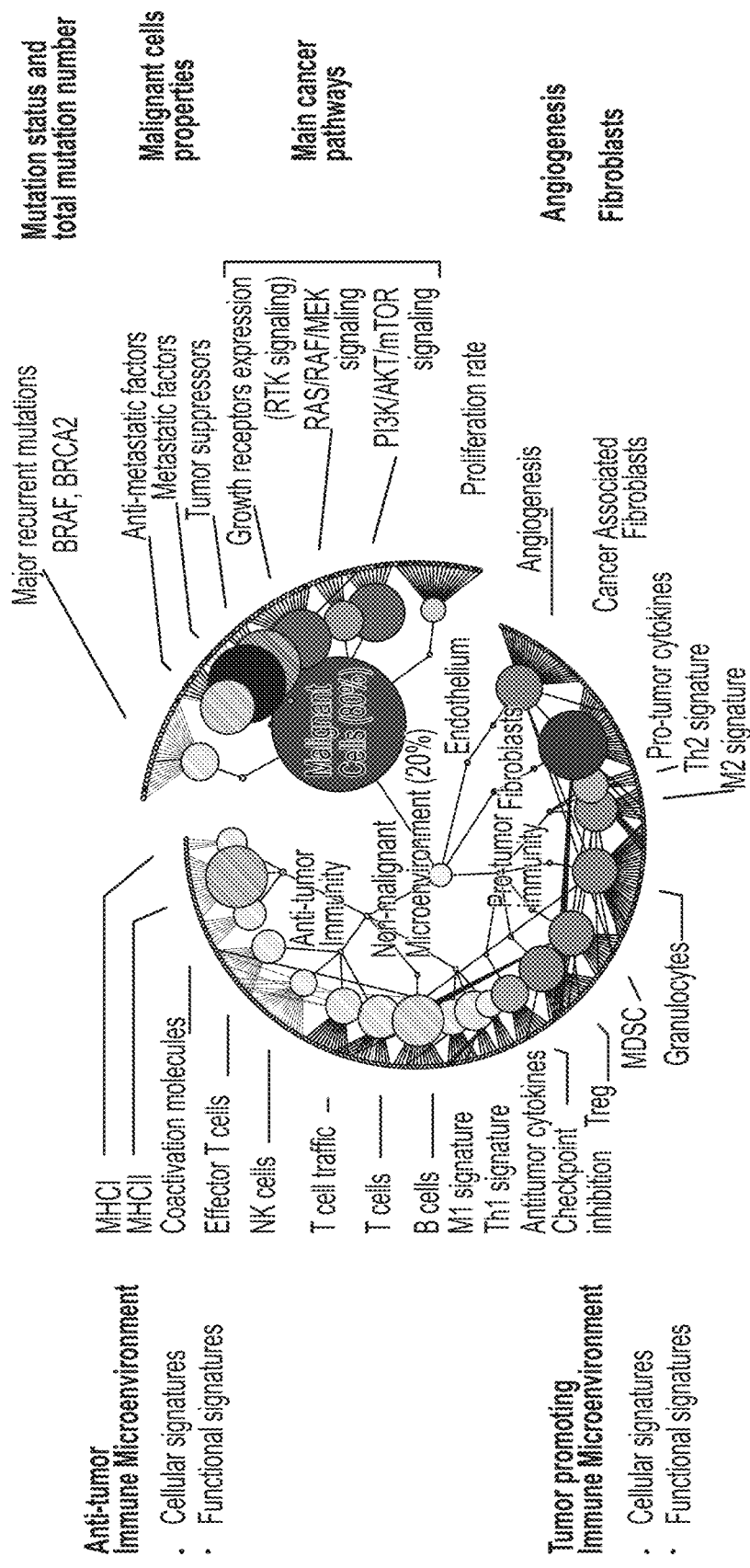
FIG. 1B is a graphical representation of tumor functional properties in a MF profile comprising 28 functional modules, in accordance with some embodiments of the technology described herein. The size of the modules correspond to their intensity rate. Colors reflect the module pro- or anticancer activity. Solid shades without cross-marking are assigned to the modules that promote tumor growth, while shades of with cross-marking are assigned to those having anticancer activity. The malignancy modules are collected in the Tumor Burden sector, which are located in the right top quarter of the graphical representation.

MF profiles may be constructed, in some embodiments, from gene expression data (for example sequencing data, e.g., whole exome sequencing data, RNA sequencing data, or other gene expression data) of normal tissue and/or tumor tissue. FIG. 1A shows an exemplary bioinformatics pipeline for constructing a tumor portrait from sequencing data. MF profiles produced in accordance with the bioinformatics pipeline in FIG. 1A may comprise functional modules depicted as circles and arrange in an circular pattern as shown in FIG. 1B. Each circle of the MF profile in FIG. 1B represents a functional module, which are labeled using lines. Related functional modules may be combined into a single functional module. For example, FIG. 1B shows that the anti-metastatic factors module, the metastatic factors module, and the tumor suppressors module may be combined into the malignant cell properties module.

Figure 1C:
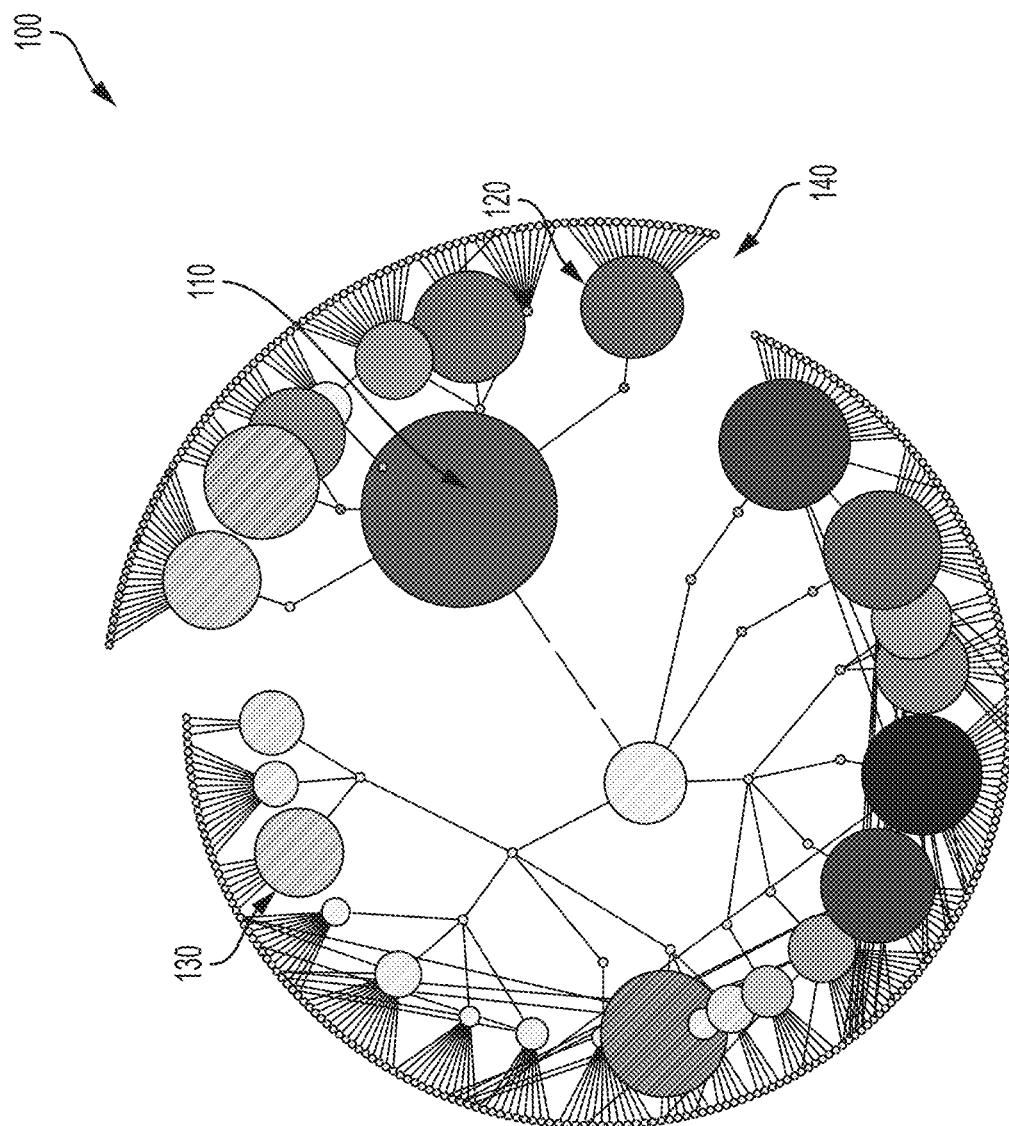
FIG. 1C shows an exemplary MF profile, in accordance with some embodiments of the technology described herein.

FIG. 1C shows one embodiment of an MF profile as provided herein. As shown in FIG. 1C, the MF profile 100 comprises 28 functional modules, three of which are labeled as 110, 120 and 130. Module size indicates module intensity. For example, module 110 is larger than module 120 indicating that module 110 has increased module intensity as compared to module 120. The presence or absence of cross-hatching of the module indicates whether the module is a pro-tumor module or an anti-tumor module. Pro-tumor modules (e.g., module 120) are shown in solid shades without cross-marking thereof, and anti-tumor modules (e.g., module 130) are shown with cross-marking thereof. The depth of shading of the module indicates module intensity. Modules relating to tumor malignancy 140 are depicted in the top right quarter of the circle.

MF Profile Modules

A "functional module" or "gene group," as described herein, refers to related compositions and processes present within and/or surrounding a tumor.

For example, an immune response/inflammation module provides information related to immune system composition and activity within a tumor. Examples of immune system composition and activity within a tumor presented in the immune response/inflammation module include, but are not limited to, the number of unique tumor antigens, MHC-restricted antigen presentation, expression of co-stimulatory compounds that are involved in T cell activation, intensities of activation and effector phases of adaptive and innate immune responses, proportions of different lymphoid and myeloid cell populations within a tumor, expression rates of cancer-promoting and anti-cancer cytokines, and intensities of immune response processes (e.g., activities of immunosuppressive cells and expression of immune checkpoint inhibitory molecules).

Exemplary modules in a MF profile may include, but are not limited to, Major histocompatibility complex I (MHCI) module, Major histocompatibility complex II (MHCII) module, Coactivation molecules module, Effector cells module, Effector T cell module; Natural killer cells (NK cells) module, T cell traffic module, T cells module, B cells module, B cell traffic module, Benign B cells module, Malignant B cell marker module, M1 signatures module, Th1 signature module, Antitumor cytokines module, Checkpoint inhibition (or checkpoint molecules) module, Follicular dendritic cells module, Follicular B helper T cells module, Protumor cytokines module, Regulatory T cells (Treg) module, Treg traffic module, Myeloid-derived suppressor cells (MDSCs) module, MDSC and TAM traffic module, Granulocytes module, Granulocytes traffic module, Eosinophil signature model, Neutrophil signature model, Mast cell signature module, M2 signature module, Th2 signature module, Th17 signature module, Protumor cytokines module, Complement inhibition module, Fibroblastic reticular cells module, Cancer associated fibroblasts (CAFs) module, Matrix formation (or Matrix) module, Angiogenesis module, Endothelium module, Hypoxia factors module, Coagulation module, Blood endothelium module, Lymphatic endothelium module, Proliferation rate (or Tumor proliferation rate) module, Oncogenes module, PI3K/AKT/mTOR signaling module, RAS/RAF/MEK signaling module, Receptor tyrosine kinases expression module, Growth Factors module, Tumor suppressors module, Metastasis signature module, Antimetastatic factors module, and Mutation status module. In certain embodiments, the modules may be described as "gene groups".

In some embodiments, the gene groups of the modules may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same.

In some embodiments, the modules in a MF profile may comprise or consist of: Major histocompatibility complex I (MHCI) module, Major histocompatibility complex II (MHCII) module, Coactivation molecules module, Effector cells (or Effector T cell) module, Natural killer cells (NK cells) module, T cells module, B cells module, M1 signatures module, Th1 signature module, Antitumor cytokines module, Checkpoint inhibition (or checkpoint molecules) module, Regulatory T cells (Treg) module, Myeloid-derived suppressor cells (MDSCs) module, Neutrophil signature model, M2 signature module, Th2 signature module, Protumor cytokines module, Complement inhibition module, Cancer associated fibroblasts (CAFs) module, Angiogenesis module, Endothelium module, Proliferation rate (or Tumor proliferation rate) module, PI3K/AKT/mTOR signaling module, RAS/RAF/MEK signaling module, Receptor tyrosine kinases expression module, Growth Factors module, Tumor suppressors module, Metastasis signature module, and Antimetastatic factors module. The MF profile may additionally include: T cell traffic module, Antitumor cytokines module, Treg traffic module, MDSC and TAM traffic module, Granulocytes or Granulocyte traffic module, Eosinophil signature model, Mast cell signature module, Th17 signature module, Matrix formation (or Matrix) module, and Hypoxia factors module. Such an MF profile could be useful for a subject with a solid cancer (e.g., a melanoma).

In some embodiments, the modules in a MF profile may comprise or consist of: Effector cells (or Effector T cell) module, Natural killer cells (NK cells) module, T cells module, Malignant B cell marker module, M1 signatures module, Th1 signature module, Checkpoint inhibition (or checkpoint molecules) module, Follicular dendritic cells module, Follicular B helper T cells module, Protumor cytokines module, Regulatory T cells (Treg) module, Neutrophil signature model, M2 signature module, Th2 signature module, Complement inhibition module, Fibroblastic reticular cells module, Angiogenesis module, Blood endothelium module, Proliferation rate (or Tumor proliferation rate) module, Oncogenes module, and Tumor suppressors module. The MF profile may additionally include: Major histocompatibility complex I (MHCI) module, Major histocompatibility complex II (MHCII) module, Coactivation molecules module, B cell traffic module, Benign B cells module, Antitumor cytokines module, Treg traffic module, Mast cell signature module, Th17 signature module, Matrix formation (or Matrix) module, Hypoxia factors module, Coagulation module, and Lymphatic endothelium module. Such an MF profile could be useful for a subject with follicular lymphoma. In some embodiments, the gene groups of the modules may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Major histocompatibility complex I (MHCI) module: HLA-A, HLA-B, HLA-C, B2M, TAP1, and TAP2; Major histocompatibility complex II (MHCII) module: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; Coactivation molecules module: CD80, CD86, CD40, CD83, TNFRSF4, ICOSLG, CD28; Effector cells module: IFNG, GZMA, GZMB, PRF1, LCK, GZMK, ZAP70, GNLY, FASLG, TBX21, EOMES, CD8A, and CD8B; Effector T cell module: IFNG, GZMA, GZMB, PRF1, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, EOMES, CLIC3, FGFBP2, KLRF1, and SH2D1B; T cell traffic module: CXCL9, CXCL10, CXCR3, CX3CL1, CCR7, CXCL11, CCL21, CCL2, CCL3, CCL4, and CCL5; T cells module: EOMES, TBX21, ITK, CD3D, CD3E, CD3G, TRAC, TRBC1, TRBC2, LCK, UBASH3A, TRAT1, CD5, and CD28; B cells module: CD19, MS4A1, TNFRSF13C, CD27, CD24, CR2, TNFRSF17, TNFRSF13B, CD22, CD79A, CD79B, BLK, FCRL5, PAX5, and STAP1; B cell traffic module: CXCL13 and CXCR5; Benign B cells module: CD19, MS4A1, TNFRSF13C, CD27, CD24, CR2, TNFRSF17, TNFRSF13B, CD22, CD79A, CD79B, and BLK; Malignant B cell marker module: MME, CD70, CD20, CD22, and PAX5; M1 signatures module: NOS2, IL12A, IL12B, IL23A, TNF, IL1B, and SOCS3; Th1 signature module: IFNG, IL2, CD40LG, IL15, CD27, TBX21, LTA, and IL21; Antitumor cytokines module: HMGB1, TNF, IFNB1, IFNA2, CCL3, TNFSF10, and FASLG; Checkpoint inhibition (or checkpoint molecules) module: PDCD1, CD274, CTLA4, LAG3, PDCD1LG2, BTLA, HAVCR2, and VSIR; Follicular dendritic cells module: CR1, FCGR2A, FCGR2B, FCGR2C, CR2, FCER2, CXCL13, MADCAM1, ICAM1, VCAM1, BST1, LTBR, and TNFRSF1A; Follicular B helper T cells module: CXCR5, B3GAT1, ICOS, CD40LG, CD84, IL21, BCL6, MAF, and SAP; Protumor cytokines module: IL10, TGFB1, TGFB2, TGFB3, IL22, MIF, TNFSF13B, IL6, and IL7; Regulatory T cells (Treg) module: TGFB1, TGFB2, TGFB3, FOXP3, CTLA4, IL10, TNFRSF18, TNFR2, and TNFRSF1B; Treg traffic module: CCL17, CXCL12, CXCR4, CCR4, CCL22, CCL1, CCL2, CCL5, CXCL13, and CCL28; Myeloid-derived suppressor cells (MDSCs) module: IDO1, ARG1, IL4R, IL10, TGFB1, TGFB2, TGFB3, NOS2, CYBB, CXCR4, and CD33; MDSC and TAM traffic module: CXCL1, CXCL5, CCL2, CCL4, CCL8, CCR2, CCL3, CCL5, CSF1, and CXCL8; Granulocytes module: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, MPO, ELANE, PRTN3, CTSG, FCGR3B, CXCR1, CXCR2, CD177, PI3, FFAR2, PGLYRP1, CMA1, TPSAB1, MS4A2, CPA3, IL4, IL5, IL13, and SIGLEC8; Granulocyte traffic module: CXCL8, CXCL2, CXCL1, CCL11, CCL24, KITLG, CCL5, CXCL5, CCR3, and CCL26; Eosinophil signature model: PRG2, EPX, RNASE2, RNASE3, IL5RA, GATA1, SIGLEC8, and PRG3; Neutrophil signature model: MPO, ELANE, PRTN3, CTSG, FCGR3B, CXCR1, CXCR2, CD177, PI3, FFAR2, and PGLYRP1; Mast cell signature module: CMA1, TPSAB1, MS4A2, CPA3, IL4, IL5, IL13, and SIGLEC8; M2 signature module: IL10, VEGFA, TGFB1, IDO1, PTGES, MRC1, CSF1, LRP1, ARG1, PTGS1, MSR1, CD163, and CSF1R; Th2 signature module: IL4, IL5, IL13, IL10, IL25, and GATA3; Th17 signature module: IL17A, IL22, IL26, IL17F, IL21, and RORC; Protumor cytokines module: IL10, TGFB1, TGFB2, TGFB3, IL22, and MIF; Complement inhibition module: CFD, CFI, CD55, CD46, CR1, and CD59; Fibroblastic reticular cells module: DES, VIM, PDGFRA, PDPN, NT5E, THY1, ENG, ACTA2, LTBR, TNFRSF1A, VCAM1, ICAM1, and BST1; Cancer associated fibroblasts (CAFs) module: COL1A1, COL1A2, COL4A1, COL5A1, TGFB1, TGFB2, TGFB3, ACTA2, FGF2, FAP, LRP1, CD248, COL6A1, COL6A2, COL6A3, FBLN1, LUM, MFAP5, LGALS1, and PRELP; Matrix formation (or Matrix) module: MMP9, FN1, COL1A1, COL1A2, COL3A1, COL4A1, CA9, VTN, LGALS7, TIMP1, MMP2, MMP1, MMP3, MMP12, LGALS9, MMP7, and COL5A1; Angiogenesis module: VEGFA, VEGFB, VEGFC, PDGFC, CXCL8, CXCR2, FLT1, PIGF, CXCL5, KDR, ANGPT1, ANGPT2, TEK, VWF, CDH5, NOS3, VCAM1, MMRN1, LDHA, HIF1A, EPAS1, CA9, SPP1, LOX, SLC2A1, and LAMP3; Endothelium module: VEGFA, NOS3, KDR, FLT1, VCAM1, VWF, CDH5, MMRN1, CLEC14A, MMRN2, and ECSCR; Hypoxia factors module: LDHA, HIF1A, EPAS1, CA9, SPP1, LOX, SLC2A1, and LAMP3; Coagulation module: HPSE, SERPINE1, SERPINB2, F3, and ANXA2; Blood endothelium module: VEGFA, NOS3, KDR, FLT1, VCAM1, VWF, CDH5, and MMRN1; Lymphatic endothelium module: CCL21 and CXCL12; Proliferation rate (or Tumor proliferation rate) module: MKI67, ESCO2, CETN3, CDK2, CCND1, CCNE1, AURKA, AURKB, E2F1, MYBL2, BUB1, PLK1, PRC1, CCNB1, MCM2, MCM6, CDK4, and CDK6; Oncogenes module: MDM2, MYC, AKT1, BCL2, MME, and SYK; PI3K/AKT/mTOR signaling module: PIK3CA, PIK3CB, PIK3CG, PIK3CD, AKT1, MTOR, PTEN, PRKCA, AKT2, and AKT3; RAS/RAF/MEK signaling module: BRAF, FNTA, FNTB, MAP2K1, MAP2K2, MKNK1, and MKNK2; Receptor tyrosine kinases expression module: ALK, AXL, KIT, EGFR, ERBB2, FLT3, MET, NTRK1, FGFR1, FGFR2, FGFR3, ERBB4, ERBB3, BCR-ABL, PDGFRA, PDGFRB, and ABL1; Growth Factors module: NGF, CSF3, CSF2, FGF7, IGF1, IGF2, IL7, and FGF2; Tumor suppressors module: TP53, MLL2, CREBBP, EP300, ARID1A, HIST1H1, EBF1, IRF4, IKZF3, KLHL6, PRDM1, CDKN2A, RB1, EPHA7, TNFAIP3, TNFRSF14, FAS, SHP1, SOCS1, SIK1, PTEN, DCN, MTAP, AIM2, and MITF; Metastasis signature module: ESRP1, HOXA1, SMARCA4, TWIST1, NEDD9, PAPPA, CTSL, SNAI2, and HPSE; Antimetastatic factors module: NCAM1, CDH1, KISS1, BRMS1, ADGRG1, TCF21, PCDH10, and MITF; and Mutation status module: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In certain embodiments, two or more genes from any combination of the listed modules may be included in an MF portrait.

In some embodiments, the gene groups of the modules may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Major histocompatibility complex I (MHCI) module: HLA-A, HLA-B, HLA-C, B2M, TAP1, and TAP2; Major histocompatibility complex II (MHCII) module; HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; Coactivation molecules module: CD80, CD86, CD40, CD83, TNFRSF4, ICOSLG, CD28; Effector cells (or Effector T cell) module: IFNG, GZMA, GZMB, PRF1, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GNLY, KIR2DL4, KIR2DS1, KIR2DS2, KIR2DS3, KIR2DS4, KIR2DS5, EOMES, CLIC3, FGFBP2, KLRF1, and SH2D1B; T cells module: TBX21, ITK, CD3D, CD3E, CD3G, TRAC, TRBC1, TRBC2, LCK, UBASH3A, TRAT1, CD5, and CD28; B cells module: CD19, MS4A1, TNFRSF13C, CD27, CD24, CR2, TNFRSF17, TNFRSF13B, CD22, CD79A, CD79B, BLK, FCRL5, PAX5, and STAP1; M1 signatures module: NOS2, IL12A, IL12B, IL23A, TNF, IL1B, and SOCS3; Th1 signature module: IFNG, IL2, CD40LG, IL15, CD27, TBX21, LTA, and IL21; Checkpoint inhibition (or checkpoint molecules) module: PDCD1, CD274, CTLA4, LAG3, PDCD1LG2, BTLA, HAVCR2, and VSIR; Regulatory T cells (Treg) module: TGFB1, TGFB2, TGFB3, FOXP3, CTLA4, IL10, and TNFRSF1B; Myeloid-derived suppressor cells (MDSCs) module: IDO1, ARG1, IL4R, IL10, TGFB1, TGFB2, TGFB3, NOS2, CYBB, CXCR4, and CD33; Neutrophil signature model: MPO, ELANE, PRTN3, CTSG, FCGR3B, CXCR1, CXCR2, CD177, PI3, FFAR2, and PGLYRP1; M2 signature module: IL10, VEGFA, TGFB1, IDO1, PTGES, MRC1, CSF1, LRP1, ARG1, PTGS1, MSR1, CD163, and CSF1R; Th2 signature module: IL4, IL5, IL13, IL10, IL25, and GATA3; Protumor cytokines module: IL10, TGFB1, TGFB2, TGFB3, IL22, and MIF; Complement inhibition module: CFD, CFI, CD55, CD46, and CR1; Cancer associated fibroblasts (CAFs) module: COL1A1, COL1A2, COL4A1, COL5A1, TGFB1, TGFB2, TGFB3, ACTA2, FGF2, FAP, LRP1, CD248, COL6A1, COL6A2, COL6A3, FBLN1, LUM, MFAP5, and PRELP; Angiogenesis module: VEGFA, VEGFB, VEGFC, PDGFC, CXCL8, CXCR2, FLT1, PIGF, CXCL5, KDR, ANGPT1, ANGPT2, TEK, VWF, CDH5, NOS3, VCAM1, and MMRN1; Endothelium module: VEGFA, NOS3, KDR, FLT1, VCAM1, VWF, CDH5, MMRN1, CLEC14A, MMRN2, and ECSCR; Proliferation rate (or Tumor proliferation rate) module: MKI67, ESCO2, CETN3, CDK2, CCND1, CCNE1, AURKA, AURKB, E2F1, MYBL2, BUB1, PLK1, CCNB1, MCM2, MCM6, CDK4, and CDK6; PI3K/AKT/mTOR signaling module: PIK3CA, PIK3CB, PIK3CG, PIK3CD, AKT1, MTOR, PTEN, PRKCA, AKT2, and AKT3; RAS/RAF/MEK signaling module: BRAF, FNTA, FNTB, MAP2K1, MAP2K2, MKNK1, and MKNK2; Receptor tyrosine kinases expression module: ALK, AXL, KIT, EGFR, ERBB2, FLT3, MET, NTRK1, FGFR1, FGFR2, FGFR3, ERBB4, ERBB3, BCR-ABL, PDGFRA, PDGFRB, and ABL1; Growth Factors module: NGF, CSF3, CSF2, FGF7, IGF1, IGF2, IL7, and FGF2; Tumor suppressors module: TP53, SIK1, PTEN, DCN, MTAP, AIM2, RB1, and MITF; Metastasis signature module: ESRP1, HOXA1, SMARCA4, TWIST1, NEDD9, PAPPA, and HPSE; and Antimetastatic factors module: NCAM1, CDH1, KISS1, and BRMS1. In some embodiments, the gene groups of the modules may further comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): T cell traffic module: CXCL9, CXCL10, CXCR3, CX3CL1, CCR7, CXCL11, CCL21, CCL2, CCL3, CCL4, and CCL5; Antitumor cytokines module: HMGB1, TNF, IFNB1, IFNA2, CCL3, TNFSF10, and FASLG; Treg traffic module: CCL17, CXCL12, CXCR4, CCR4, CCL22, CCL1, CCL2, CCL5, CXCL13, and CCL28; MDSC and TAM traffic module: CXCL1, CXCL5, CCL2, CCL4, CCL8, CCR2, CCL3, CCL5, CSF1, and CXCL8; Granulocyte traffic module: CXCL8, CXCL2, CXCL1, CCL11, CCL24, KITLG, CCL5, CXCL5, CCR3, and CCL26; Eosinophil signature model: PRG2, EPX, RNASE2, RNASE3, IL5RA, GATA1, SIGLEC8, and PRG3; Mast cell signature module: CMA1, TPSAB1, MS4A2, CPA3, IL4, IL5, IL13, and SIGLEC8; Th17 signature module: IL17A, IL22, IL26, IL17F, IL21, and RORC; Matrix formation (or Matrix) module: FN1, CA9, MMP1, MMP3, MMP12, LGALS9, MMP7, MMP9, COL1A1, COL1A2, COL4A1, and COL5A1; and Hypoxia factors module: LDHA, HIF1A, EPAS1, CA9, SPP1, LOX, SLC2A1, and LAMP3. In certain embodiments, two or more genes from each of the listed modules are included. Any of the foregoing sets of modules may be used in a MF portrait for a subject with a solid cancer (e.g., melanoma).

In some embodiments, the gene groups of the modules may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Effector T cell module: IFNG, GZMA, GZMB, PRF1, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5; T cells module: EOMES, TBX21, ITK, CD3D, CD3E, CD3G, TRAC, TRBC1, TRBC2, LCK, UBASH3A, and TRAT1; Benign B cells module: CD19, MS4A1, TNFRSF13C, CD27, CD24, CR2, TNFRSF17, TNFRSF13B, CD22, CD79A, CD79B, and BLK; Malignant B cell marker module: MME, CD70, CD20, CD22, and PAX5; M1 signatures module: NOS2, IL12A, IL12B, IL23A, TNF, IL1B, and SOCS3; Th1 signature module: IFNG, IL2, CD40LG, IL15, CD27, TBX21, LTA, and IL21; Checkpoint inhibition (or checkpoint molecules) module: PDCD1, CD274, CTLA4, LAG3, PDCD1LG2, BTLA, and HAVCR2; Follicular dendritic cells module: CR1, FCGR2A, FCGR2B, FCGR2C, CR2, FCER2, CXCL13, MADCAM1, ICAM1, VCAM1, BST1, LTBR, and TNFRSF1A; Follicular B helper T cells module: CXCR5, B3GAT1, ICOS, CD40LG, CD84, IL21, BCL6, MAF, and SAP; Protumor cytokines module: IL10, TGFB1, TGFB2, TGFB3, IL22, MIF, TNFSF13B, IL6, and IL7; Regulatory T cells (Treg) module: TGFB1, TGFB2, TGFB3, FOXP3, CTLA4, IL10, TNFRSF18, and TNFR2; Neutrophil signature model: MPO, ELANE, PRTN3, and CTSG; M2 signature module: IL10, VEGFA, TGFB1, IDO1, PTGES, MRC1, CSF1, LRP1, ARG1, PTGS1, MSR1, CD163, and CSF1R; Th2 signature module: IL4, IL5, IL13, IL10, IL25, and GATA3; Complement inhibition module: CFD, CFI, CD55, CD46, CR1, and CD59; Fibroblastic reticular cells module: DES, VIM, PDGFRA, PDPN, NT5E, THY1, ENG, ACTA2, LTBR, TNFRSF1A, VCAM1, ICAM1, and BST1; Angiogenesis module: VEGFA, VEGFB, VEGFC, PDGFC, CXCL8, CXCR2, FLT1, PIGF, CXCL5, KDR, ANGPT1, ANGPT2, TEK, VWF, and CDH5; Blood endothelium module: VEGFA, NOS3, KDR, FLT1, VCAM1, VWF, CDH5, and MMRN1; Proliferation rate (or Tumor proliferation rate) module: MKI67, ESCO2, CETN3, CDK2, CCND1, CCNE1, AURKA, AURKB, E2F1, MYBL2, BUB1, PLK1, CCNB1, MCM2, and MCM6; Oncogenes module: MDM2, MYC, AKT1, BCL2, MME, and SYK; and Tumor suppressors module: TP53, MLL2, CREBBP, EP300, ARID1A, HIST1H1, EBF1, IRF4, IKZF3, KLHL6, PRDM1, CDKN2A, RB1, EPHA7, TNFAIP3, TNFRSF14, FAS, SHP1, and SOCS1. In some embodiments, the gene groups of the modules may further comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Coactivation molecules module: TNFRSF4 and CD28; B cell traffic module: CXCL13 and CXCR5; Antitumor cytokines module: HMGB1, TNF, IFNB1, IFNA2, CCL3, TNFSF10, FASLG; Treg traffic module: CCL17, CCR4, CCL22, and CXCL13; Eosinophil signature model: PRG2, EPX, RNASE2, RNASE3, IL5RA, GATA1, SIGLEC8, and PRG3; Mast cell signature module: CMA1, TPSAB1, MS4A2, CPA3, IL4, IL5, IL13, and SIGLEC8; Th17 signature module: IL17A, IL22, IL26, IL17F, IL21, and RORC; Matrix formation (or Matrix) module: MMP9, FN1, COL1A1, COL1A2, COL3A1, COL4A1, CA9, VTN, LGALS7, TIMP1, and MMP2; Hypoxia factors module: LDHA, HIF1A, EPAS1, CA9, SPP1, LOX, SLC2A1, and LAMP3; Coagulation module: HPSE, SERPINE1, SERPINB2, F3, and ANXA2; and Lymphatic endothelium module: CCL21 and CXCL12. In certain embodiments, two or more genes from each of the listed modules are included. Any of the foregoing sets of modules may be used in a MF portrait for a subject with a follicular lymphoma.

In some embodiments, the plurality of gene groups (or modules) associated with cancer malignancy is the tumor properties group. In some embodiments, the plurality of gene groups associated with cancer microenvironment are the tumor-promoting immune microenvironment group, the anti-tumor immune microenvironment group, the angiogenesis group, and the fibroblasts group.

In certain embodiments, the plurality of gene groups associated with cancer malignancy comprises at least three genes from the following group (e.g., at least three genes, at least four genes, at least five genes, at least six genes, at least seven genes, at least eight genes, at least nine genes, at least ten genes, or more than ten genes are selected from each group; in some embodiments all of the listed genes are selected from each group): the tumor properties group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In certain embodiments, the plurality of gene groups associated with cancer microenvironment includes at least three genes from each of the following groups (e.g., at least three genes, at least four genes, at least five genes, at least six genes, at least seven genes, at least eight genes, at least nine genes, at least ten genes, or more than ten genes are selected from each group; in some embodiments all of the listed genes are selected from each group): the anti-tumor immune microenvironment group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the tumor-promoting immune microenvironment group: PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDOL ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDOL PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1; the fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; and the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMPS. In some embodiments, an unequal number of genes may be selected from each of the listed groups for use. In specific embodiments, all or almost all of the listed genes are used.

In some embodiments, the plurality of gene groups associated with cancer malignancy are: the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group. In some embodiments, the plurality of gene groups associated with cancer microenvironment are: the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group.

In some embodiments, the plurality of gene groups associated with cancer malignancy comprises at least three genes from each of the following groups (e.g., at least three genes, at least four genes, at least five genes, at least six genes, at least seven genes, at least eight genes, at least nine genes, at least ten genes, or more than ten genes are selected from each group): the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL.

In some embodiments, the plurality of gene groups associated with cancer microenvironment comprises at least three genes from each of the following groups (e.g., at least three genes, at least four genes, at least five genes, at least six genes, at least seven genes, at least eight genes, at least nine genes, at least ten genes, or more than ten genes are selected from each group): the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the antigen presentation group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, and CD28; the cytotoxic T and NK cells group: IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the anti-tumor microenvironment group: NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the checkpoint inhibition group: PDCD1, CD274, CTLA4, LAGS, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDOL ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the tumor-promotive immune group: IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1. In some embodiments, an unequal number of genes may be selected from each of the listed groups for use. In specific embodiments, all or almost all of the listed genes are used.

In some embodiments, the plurality of gene groups associated with cancer malignancy are: the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group. In some embodiments, the plurality of gene groups associated with cancer microenvironment are: the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group.

In some embodiments, the plurality of gene groups associated with cancer malignancy comprises at least three genes from each of the following groups (e.g., at least three genes, at least four genes, at least five genes, at least six genes, at least seven genes, at least eight genes, at least nine genes, at least ten genes, or more than ten genes are selected from each group): the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the growth factors group: NGF, CSF3, CSF2, FGF7, IGF1, IGF2, IL7, and FGF2; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In some embodiments, the plurality of gene groups associated with cancer microenvironment comprises at least three genes from each of the following groups: the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the MHCI group: HLA-A, HLA-B, HLA-C, B2M, TAP1, and TAP2; the MHCII group: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; the coactivation molecules group: CD80, CD86, CD40, CD83, TNFRSF4, ICOSLG, and CD28; the effector cells group: IFNG, GZMA, GZMB, PRF1, LCK, GZMK, ZAP70, GNLY, FASLG, TBX21, EOMES, CD8A, and CD8B; the NK cells group: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5; the T cell traffic group: CXCL9, CXCL10, CXCR3, CX3CL1, CCR7, CXCL11, CCL21, CCL2, CCL3, CCL4, and CCL5; the T cells group: EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the M1 signatures group: NOS2, IL12A, IL12B, IL23A, TNF, IL1B, and SOCS3; the Th1 signature group: IFNG, IL2, CD40LG, IL15, CD27, TBX21, LTA, and IL21; the antitumor cytokines group: HMGB1, TNF, IFNB1, IFNA2, CCL3, TNFSF10, and FASLG; the checkpoint inhibition group: PDCD1, CD274, CTLA4, LAG3, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDOL ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the M2 signature group: IL10, VEGFA, TGFB1, IDO1, PTGES, MRC1, CSF1, LRP1, ARG1, PTGS1, MSR1, CD163, and CSF1R; the Th2 signature group: IL4, IL5, IL13, IL10, IL25, and GATA3; the protumor cytokines group: IL10, TGFB1, TGFB2, TGFB3, IL22, and MIF; and the complement inhibition group: CFD, CFI, CD55, CD46, and CR1. In some embodiments, an unequal number of genes may be selected from each of the listed groups for use. In specific embodiments, all or almost all of the listed genes are used.

MF profiles may depict the intensity (e.g., amount) of a module or gene group using a distinguishing feature (e.g., color, shading or pattern, size, and/or shape). As used herein, "intensity" refers to an amount of a gene group expression level within a MF profile. For example, $2^{nd}$ MF profile type cancers have an intense proliferation rate module indicative of a high proliferation rate of such cancers. Accordingly, in $2^{nd}$ MF profile type cancers, the proliferation rate module is depicted in a larger size as an indication that this module is more abundant in the tumor than other modules. In some embodiments, the MF profile comprises modules of various sizes in which module size is indicative of module intensity. In some embodiments, the MF profile comprises modules of increasing sizes in which increasing module size is indicative of increasing module intensity.

MF profiles may depict a module as a pro-tumor module or anti-tumor module using a distinguishing feature (e.g., color, shading or pattern, size, and/or shape). In some embodiments, the MF profile comprises a pro-tumor module as one color or pattern and an anti-tumor module as another color or pattern. In some embodiments, the MF profile comprises a pro-tumor module as burgundy or a shade thereof and an anti-tumor module as blue or a shade thereof. In some embodiments, the MF profile comprises a pro-tumor module as solid shades without cross-marking and an anti-tumor module as shades with cross-marking.

MF profiles may comprise any number of functional modules. In some embodiments, the MF profile comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or at least 28 modules. In some embodiments, the MF profile comprises up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, or up to 28 modules.

MF Profile Types

The present disclosure is based, in part, on the finding that various cancers (e.g., tumors) can be categorized into four types (i.e., first MF profile type or "$1^{st}$ MF profile," second MF profile type or "$2^{nd}$ MF profile," third MF profile type or "3$^{rd}$ MF profile," and fourth MF profile type or "4$^{th}$ MF profile" cancers) based on certain properties of the cancer or tumor (e.g., expression data).

As used herein, the term "cancer type," "tumor type," or "MF profile type" refers to a cancer (e.g., a tumor) having certain features including certain molecular and cellular compositions, and biological processes.

MF profile type, in some embodiments, may provide information relating to a level of immune cells within and/or surrounding a tumor. For example, an "inflamed" or "hot" MF profile type includes a cancer (e.g., a tumor) that is highly infiltrated by immune cells, a "non-inflamed" or "cold" MF profile type describes a cancer (e.g., a tumor) that is poorly infiltrated by immune cells. In some embodiments, describing a cancer as a 1$^{st}$ MF profile type cancer indicates that the cancer (e.g., a tumor) is inflamed. In some embodiments, describing a cancer as a 2$^{nd}$ MF profile type cancer indicates that the cancer (e.g., a tumor) is inflamed. In some embodiments, describing a cancer as a 3$^{rd}$ MF profile type cancer indicates that the cancer (e.g., a tumor) is non-inflamed. In some embodiments, describing a cancer as a 4$^{th}$ MF profile type cancer indicates that the cancer (e.g., a tumor) is non-inflamed.

MF profile type, in some embodiments, provides information relating to an average ratio of malignant to nonmalignant cells of a tumor (e.g., tumor purity). In some embodiments, the average ratio of malignant to nonmalignant cells increases with MF profile type. For example, 4$^{th}$ MF profile>3$^{rd}$ MF profile>2$^{nd}$ MF profile>1$^{st}$ MF profile with respect to an average ratio of malignant to nonmalignant cells.

In some embodiments, describing a cancer as a 1$^{st}$ MF profile type cancer indicates that the tumor has about 2 times (twice) as many nonmalignant cells as malignant cells. In some embodiments, describing a cancer as a 1$^{st}$ MF profile type cancer indicates that the tumor has an average ratio of malignant to nonmalignant cells of between 0.4 to 0.6. In some embodiments, describing a cancer as a 1$^{st}$ MF profile type cancer indicates that the cancer has an average ratio of malignant to nonmalignant cells of about 0.5.

In some embodiments, describing a cancer as a 2$^{nd}$ MF profile type cancer indicates that the cancer has about 1.5 times as many nonmalignant cells as malignant cells. In some embodiments, describing a cancer as a 2$^{nd}$ MF profile type cancer indicates that the cancer has an average ratio of malignant to nonmalignant cells between 0.6 to 0.7. In some embodiments, describing a cancer as a 2$^{nd}$ MF profile type cancer indicates that the cancer has an average ratio of malignant to nonmalignant cells of about 0.65.

In some embodiments, describing a cancer as a 3$^{rd}$ MF profile type cancer indicates that the cancer has about 1.3 times as many nonmalignant cells as malignant cells. In some embodiments, describing a cancer as a 3$^{rd}$ MF profile type cancer indicates that the cancer has an average ratio of malignant to nonmalignant cells between 0.7 to 0.8. In some embodiments, describing a cancer as a 3$^{rd}$ MF profile type cancer indicates that a tumor has an average ratio of malignant to nonmalignant cells of about 0.8.

In some embodiments, describing a cancer as a 4$^{th}$ MF profile type cancer indicates that the cancer has about 1.1 times as many nonmalignant cells s malignant cells. In some embodiments, describing a cancer as a 4$^{th}$ MF profile type cancer indicates that the cancer has an average ratio of malignant to nonmalignant cells between 0.8 to 0.9. In some embodiments, describing a cancer as a 4$^{th}$ MF profile type cancer indicates that the cancer has an average ratio of malignant to nonmalignant cells of about 0.85.

MF profile type, in some embodiments, provides information relating to tumor vascularization. In some embodiments, describing a cancer as a 1$^{st}$MF profile type cancer indicates that the cancer (e.g., the tumor) is vascularized. In some embodiments, describing a cancer as a 2$^{nd}$ MF profile type cancer indicates that the cancer (e.g., the tumor) is non-vascularized. In some embodiments, describing a cancer as a 3$^{rd}$ MF profile type cancer indicates that the cancer (e.g., the tumor) is vascularized. In some embodiments, describing a cancer as a 4$^{th}$ MF profile type cancer indicates that the cancer (e.g., the tumor) is non-vascularized.

MF profile type, in some embodiments, provides information relating to levels of cancer associated fibroblasts (CAFs) within and/or surrounding a tumor. In some embodiments, describing a cancer as a 1$^{st}$MF profile type cancer indicates that the cancer (e.g., the tumor) comprises CAFs. In some embodiments, describing a cancer as a 2$^{nd}$ MF profile type cancer indicates that the cancer (e.g., the tumor) is devoid of CAFs. In some embodiments, describing a cancer as a 3$^{rd}$ MF profile type cancer indicates that the cancer (e.g., the tumor) comprises CAFs. In some embodiments, describing a cancer as a 4$^{th}$ MF profile type cancer indicates that the cancer (e.g., the tumor) is devoid of CAFs.

MF profile type, in some embodiments, provides information relating to tumor proliferation rates. In some embodiments, describing a cancer as a 1$^{t}$ MF profile type cancer indicates that the cancer (e.g., the tumor) has an average proliferation rate. In some embodiments, describing a cancer as a 2$^{nd}$ MF profile type cancer indicates that the cancer (e.g., the tumor) has a high proliferation rate. In some embodiments, describing a cancer as a 3$^{rd}$ MF profile type cancer indicates that the cancer (e.g., the tumor) has an average proliferation rate. In some embodiments, describing a cancer as a 4$^{th}$ MF profile type cancer indicates that the cancer (e.g., the tumor) has a high proliferation rate.

MF profile type, in some embodiments, provides information relating to patient survival rate. In some embodiments, the patient survival rate increases with MF profile type. For example, 1$^{st}$ MF profile>2$^{nd}$ MF profile>3$^{rd}$ MF profile>4$^{th}$ MF profile with respect to patient survival rate.

In some embodiments, describing a cancer as a 1$^{st}$ MF profile type cancer indicates a good patient survival rate. In some embodiments, describing a cancer as a 2$^{nd}$ MF profile type cancer indicates an optimal patient survival rate. In some embodiments, describing a cancer as a 3$^{rd}$ MF profile type cancer indicates that a poor patient survival rate. In some embodiments, describing a cancer as a 4$^{th}$ MF profile type cancer indicates that a poor patient survival rate.

MF profile type, in some embodiments, provides information relating to patient treatment. In some embodiments, the MF profile type provides information relating to an expected treatment outcome of a therapy. In some embodiments, the MF profile indicates that a specific treatment option is recommended. In some embodiments, the MF profile indicates that a specific treatment option is non-curative. In some embodiments, the MF profile indicates that a specific treatment option is dependent on a certain feature of a tumor, for example, mutational status of the tumor.

In some embodiments, identifying a cancer as a 1$^{st}$ MF profile type cancer indicates that a treatment selected from the group consisting of an angiogenesis inhibitor, a CAFs inhibitor, an immunosuppressive factor inhibitor, a MDSC inhibitor, a Treg inhibitor, a metastatic activity inhibitor, and an immunotherapy should be recommended or used. In some embodiments, identifying a cancer as a 1$^{st}$ MF profile type cancer indicates that treatment using a growth factor inhibitor dependent on a certain feature of a tumor (e.g., mutational status) should be recommended or used.

In some embodiments, identifying a cancer as a $2^{nd}$ MF profile type cancer indicates that a treatment selected from the group consisting of an immunosuppressive factor inhibitor, a MDSC inhibitor, a Treg inhibitor, a metastatic activity inhibitor, a checkpoint inhibitor, and an immunotherapy should be recommended or used. In some embodiments, identifying a cancer as a $2^{nd}$ MF profile type cancer indicates that treatment using a growth factor inhibitor dependent on a certain feature of a tumor (e.g., mutational status) should be recommended or used.

In some embodiments, identifying a cancer as a $3^{rd}$ MF profile type indicates that a treatment selected from the group consisting of an angiogenesis inhibitor, a CAFs inhibitor, an immunosuppressive factor inhibitor, a M2 macrophage inhibitor, a MDSC inhibitor, and a Treg inhibitor should be recommended or used. In some embodiments, identifying a cancer as a $3^{rd}$ MF profile type indicates that a checkpoint inhibitor should be recommended or used.

In some embodiments, identifying a cancer as a $4^{th}$ MF profile type cancer indicates that a treatment such as an angiogenesis inhibitor and/or an immunotherapy should be recommended or used. In some embodiments, identifying a cancer as a $4^{th}$ MF profile type indicates that a non-curative treatment option may be selected from the group consisting of a kinase inhibitor, a radiotherapy, and a chemotherapy.

Visualization of MF Profiles

In some embodiments, a software program may provide a user with a visual representation of a patient's MF profile and/or other information related to a patient's cancer using an interactive graphical user interface (GUI).

In response to being launched, the interactive GUI may provide the user of the software program with initial information related to a patient's cancer. Subsequently, the user may interact with the GUI to obtain additional and/or alternative information related to a patient's cancer. FIGS. 3-37 show illustrative screenshots of the interactive graphical user interface and are described below.

Figure 3:
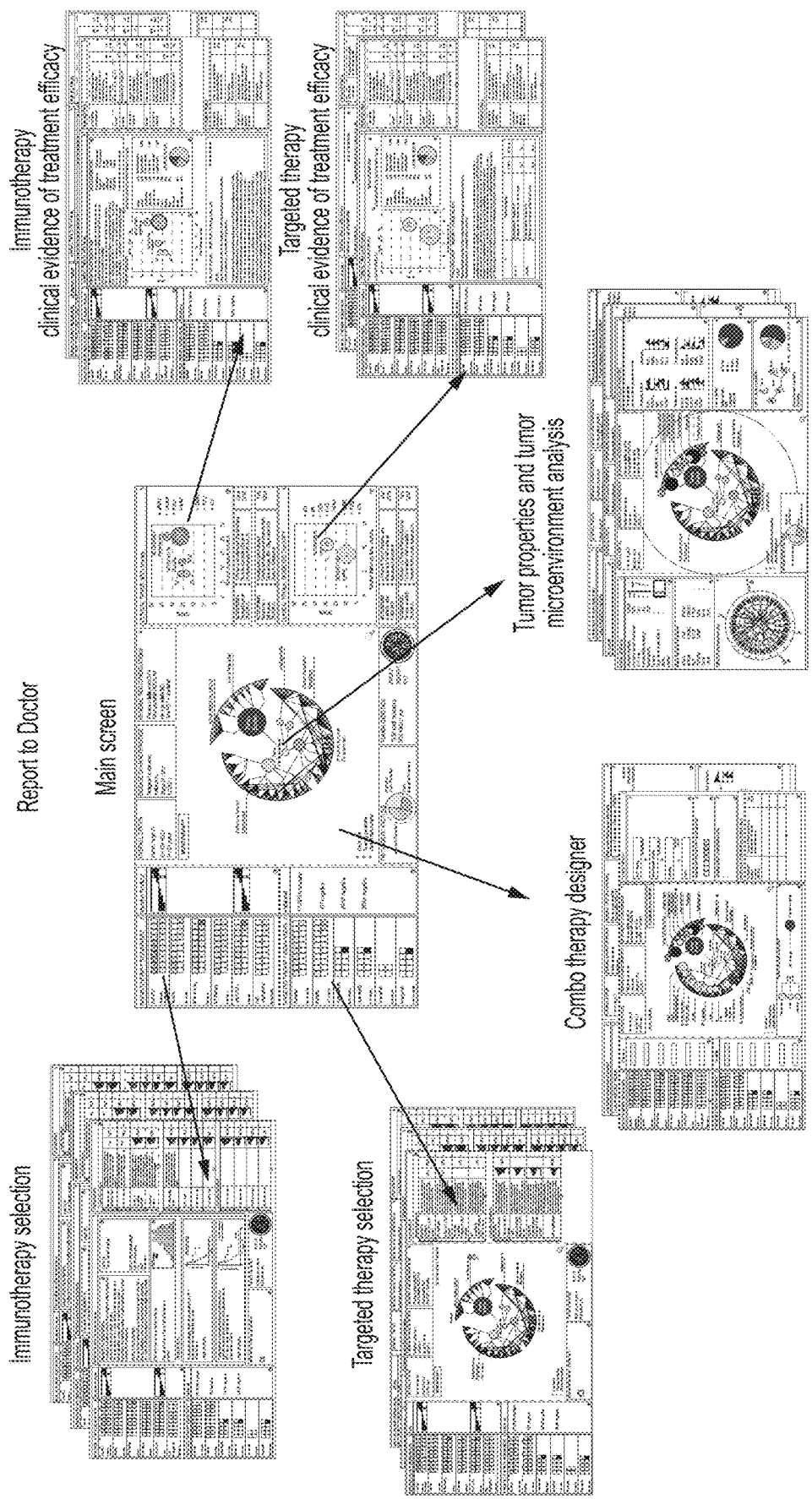
FIG. 3 is a graphic illustrating different types of screens that may be shown to a user of the software program.

FIG. 3 is a graphic illustrating different types of screens that may be shown to a user of the software program. Each of the different screens illustrated in FIG. 3 may be used to present different types of information to the user. A screenshot of a control screen of the software program is shown in the middle of FIG. 3. The control screen includes portions for presenting information relating to treatment selection, tumor properties, and clinical evidence of treatment efficacy and is described further with respect to FIGS. 7-37.

A user may interact with the control screen to obtain additional information about, for example, immunotherapy selection, targeted therapy selection, combination therapy design, tumor properties and tumor microenvironment, clinical evidence of targeted therapy efficacy, and clinical evidence of immunotherapy efficacy. The user may select a portion of the control screen (e.g., the immunotherapy portion) to view one or more additional screens presenting information relating to the selected portion. As shown in FIG. 3, arrows point from a portion of the control screen that may be selected toward the screens presenting additional information related to the selected portion.

For example, the user may select the immunotherapy selection portion of the control screen to view one or more screens presenting information relating to various immunotherapies, biomarkers associated with an immunotherapy (e.g., genetic biomarkers, cellular biomarkers, and expression biomarkers), immune cell properties of the patient's tumor, and clinical trials (e.g., information from and/or regarding published clinical trials and ongoing clinical trials).

In another example, the user may select the targeted therapy selection portion of the control screen to view one or more screens presenting information relating to various targeted therapies, biomarkers associated with targeted therapies (e.g., genetic biomarkers, cellular biomarkers, and/or expression biomarkers), properties of the patient's tumor associated with the targeted therapy, and clinical trials (e.g., published clinical trials and ongoing clinical trials).

In another example, the user may select the molecular-functional portrait (MF profile) portion of the control screen to view one or more screens presenting information relating to the patient's tumor microenvironment. Such information may include information about tumor properties (e.g., proliferation rate), angiogenesis, metastasis, cellular composition, cancer associated fibroblasts, pro-tumor immune environment, and anti-tumor immune environment.

In yet another example, the user may select the clinical evidence of treatment efficacy portion of the control screen to view one or more screens presenting information relating to a therapy (e.g., an immunotherapy or targeted therapy). Such information may include description of the therapy, therapy efficacy, potential adverse effects, related publications, treatment regimen, and patient survival data.

Figure 4:
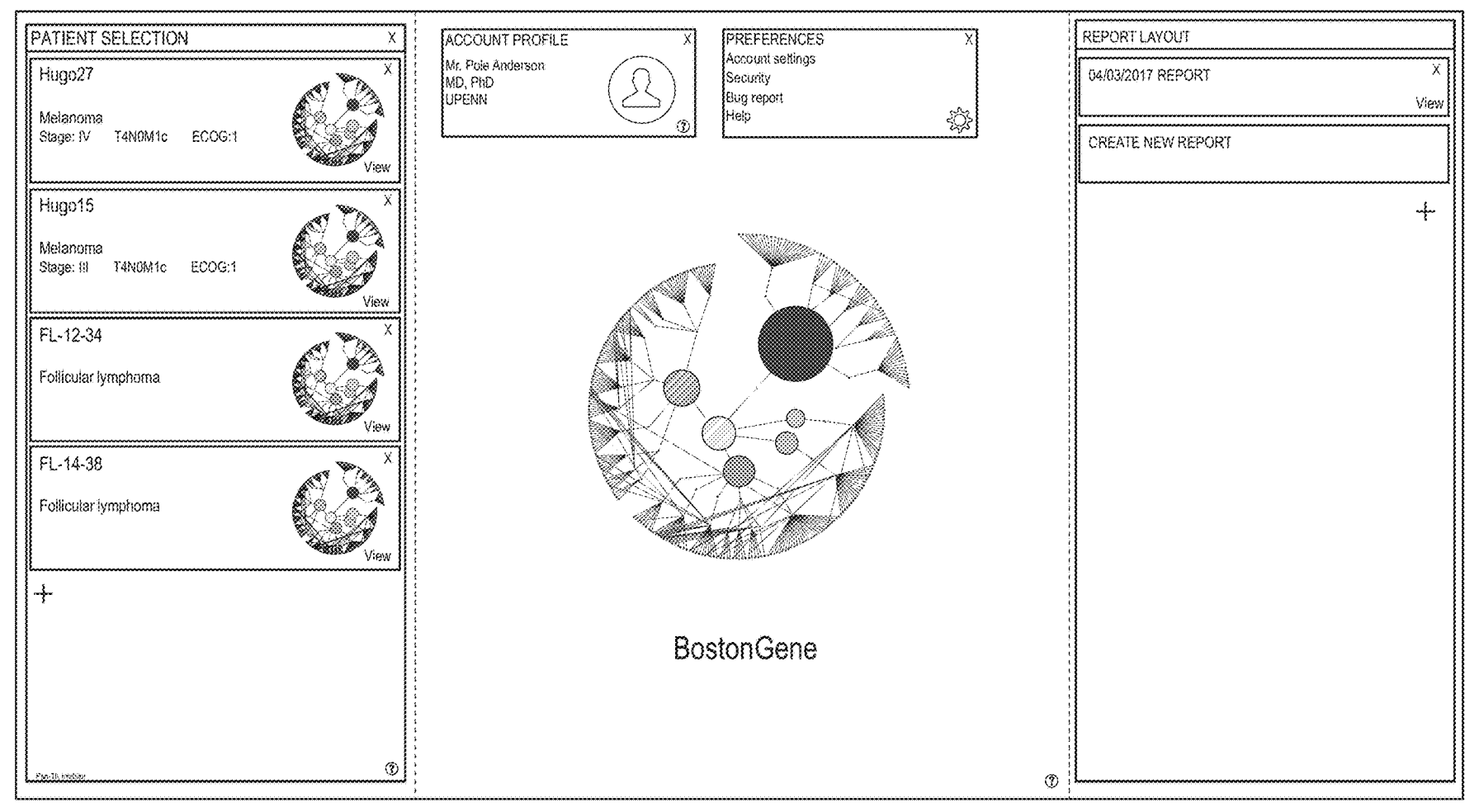

A user of the software program may interact with the GUI to log into the software program. FIG. 4 is a screenshot of the user's account profile screen presented to the user in response to the user logging into the software program. The user's account profile screen may provide information for one or more patients, such as patient identification and diagnosis (e.g., Hugo27, Melanoma, Stage: IV) in a patient selection portion (as shown in the upper left panel). The user's account profile screen may also provide reports generated from the patient's information by the software program in a report layout portion (as shown in the right panel). The report layout portion may provide the user with portions for viewing stored reports that were previously generated by the software program or for creating a new report.

In response to selection by a user, a selected portion of the GUI may be visually highlighted. As a set of non-limiting examples, a "visually highlighted" element may be highlighted through a difference in font (e.g., by italicizing, bolding, and/or underlining), by surrounding the section with a visual object (e.g., a box), by "popping" the element out (e.g., by increasing the zoom for that element), by changing the color of an element, by shading the element, by incorporation of movement into the element (e.g., by causing the element to move), any combination of the foregoing in a portion or the whole of the element, or in any other suitable way.

If a user's account profile screen provides information about one patient, the patient may be selected by the user to view a screen presenting the patient's information. If a user's account profile screen provides information about more than one patient, any one of the patients may be selected by the user to view a screen presenting the selected patient's information. The user may select a stored report to view a screen presenting information relating to the selected report. The user may select the create new report portion to view a screen for creating a new report. For example, the user may select the patient Hugo27, as shown in the upper left panel.

Figure 5:
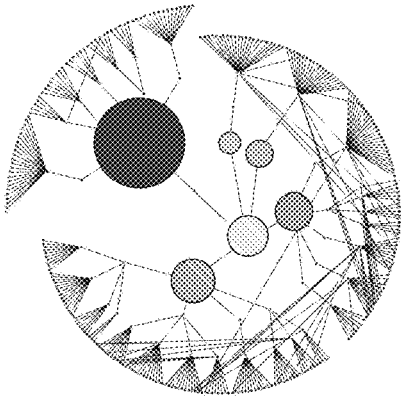
FIG. 5 is a screenshot presenting the selected patient's information provided to the user in response to the user selecting the patient.

FIG. 5 is a screenshot presenting the selected patient's information provided to the user in response to the user selecting the patient. An overview of the patient's information is presented in the patient overview portion (as shown in the left panel) including clinical characteristics of the patient's disease (e.g., histology report). Additional information about the patient or the patient's cancer including overall status, disease characteristics and general recommendations (as shown in the upper middle panel) is provided. Information relating to the selected patient's sequencing data is presented in the Data Files portion (as shown in the right panel) including whole exome sequencing data (WES). The user may use the Upload Data File portion of the screen to upload the patient's tumor biopsy sequencing data.

FIG. 6 is a screenshot presenting that the patient's tumor biopsy sequencing data was downloaded (as shown in the lower right panel). The user may select start in the launch analysis portion of the screen (as shown in the lower middle panel) to view a report created from the patient's sequencing data and other information relating to the patient or the patient's cancer.

Figure 7:
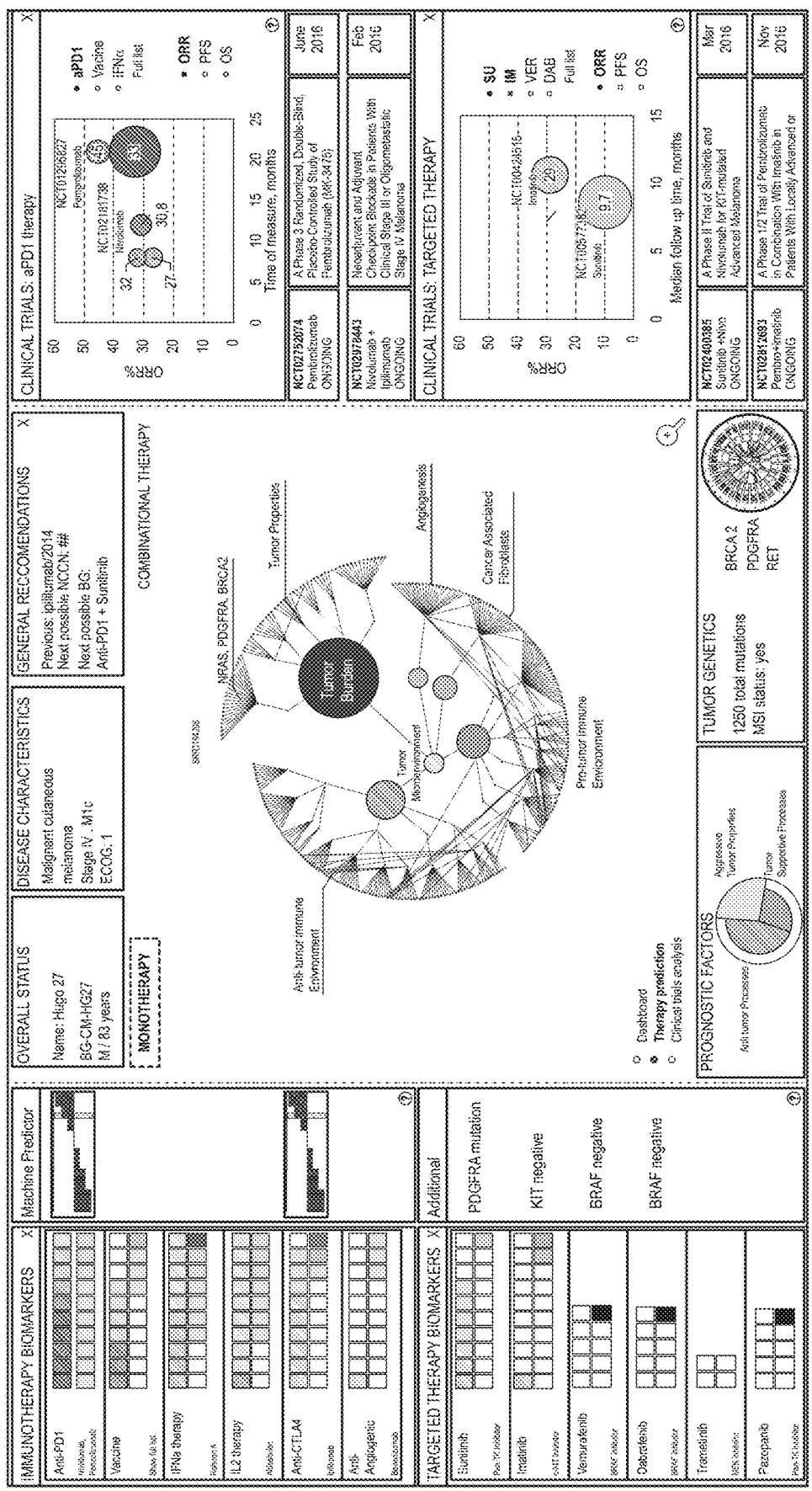
FIG. 7 is a screenshot presenting the selected patient's report including information related to the patient's sequencing data, the patient, and the patient's cancer.

FIG. 7 is a screenshot presenting the selected patient's report including information related to the patient's sequencing data, the patient, and the patient's cancer. The therapy biomarkers portion (as shown in the left panel) presents information related to available therapies (e.g., immunotherapies and targeted therapies) and their predicted efficacy in the selected patient. Additional predictions of the efficacy of a therapy in the patient are provided in the machine predictor portion and additional portion (as shown in the left panel). The MF profile portion presents information relating to the molecular characteristics of a tumor including tumor genetics, pro-tumor microenvironment factors, and anti-tumor immune response factors (as shown in the middle panel). The clinical trials portion provides information relating to clinical trials (as shown in the right panel). The monotherapy or combinational therapy portion (as shown in the middle panel) may be selected by the user to interactively design a personalized treatment for a patient.

A user may select various portions of the screen to view additional information. For example, a user may select anti-PD-1 in the immunotherapy biomarkers portion of the screen (as shown in the left panel) to view information relating to anti-PD-1 treatment including biomarkers associated with anti-PD-1 and tumor cell processes associated with anti-PD-1 treatment.

Figure 8:
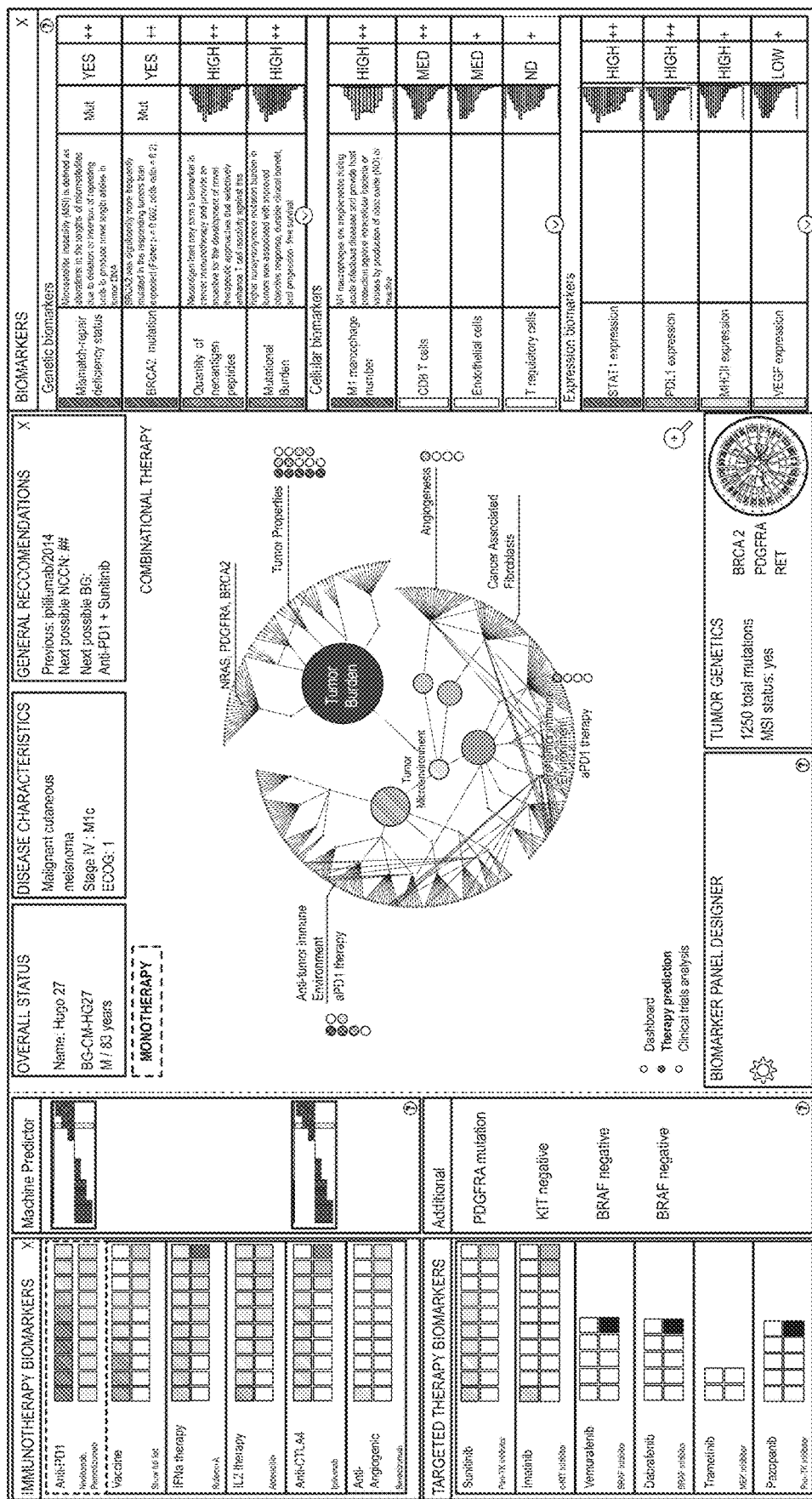
FIG. 8 is a screenshot presenting information related to anti-PD-1 immunotherapy provided in response to selecting anti-PD-1 immunotherapy (as shown by highlighting) in the immunotherapy biomarkers portion of the screen (as shown in the left panel).

FIG. 8 is a screenshot presenting information related to anti-PD-1 immunotherapy provided in response to selecting anti-PD-1 immunotherapy (as shown by highlighting) in the immunotherapy biomarkers portion of the screen (as shown in the left panel). Information relating to biomarkers associated with anti-PD-1 immunotherapy is provided in the biomarkers portion (as shown in the right panel). The biomarkers portion presents genetic biomarkers, cellular biomarkers, and expression biomarkers, as well as patient specific information related to those biomarkers.

The user may select any one of the biomarkers presented in the biomarkers markers portion to view additional information relating to that biomarker including general information about the selected biomarker, patient specific information relating to the selected biomarker, information relating to tumor molecular processes associated with the selected biomarker, and treatment related information associated with the selected biomarker.

Figure 9:
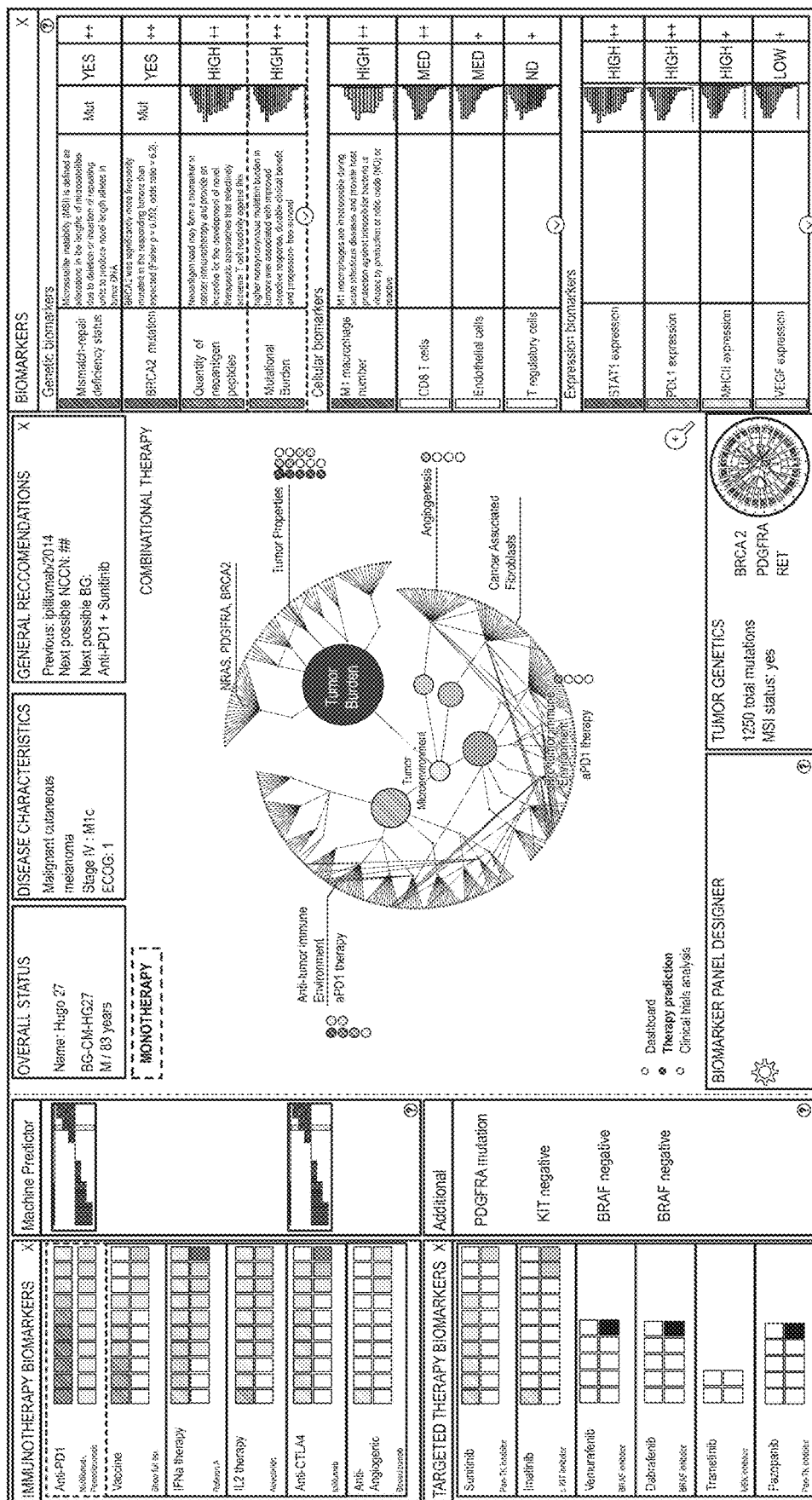
FIG. 9 is a screenshot presenting selection of mutational burden biomarker by a user.

In response to selection by a user, the selected biomarker may be highlighted. FIG. 9 is a screenshot presenting the mutational burden biomarker (as shown by highlighting) was selected by the user. The user may select another portion of the mutational burden biomarker to view a screen presenting information relating to the mutational burden biomarker such as relevant publications.

Figure 10:
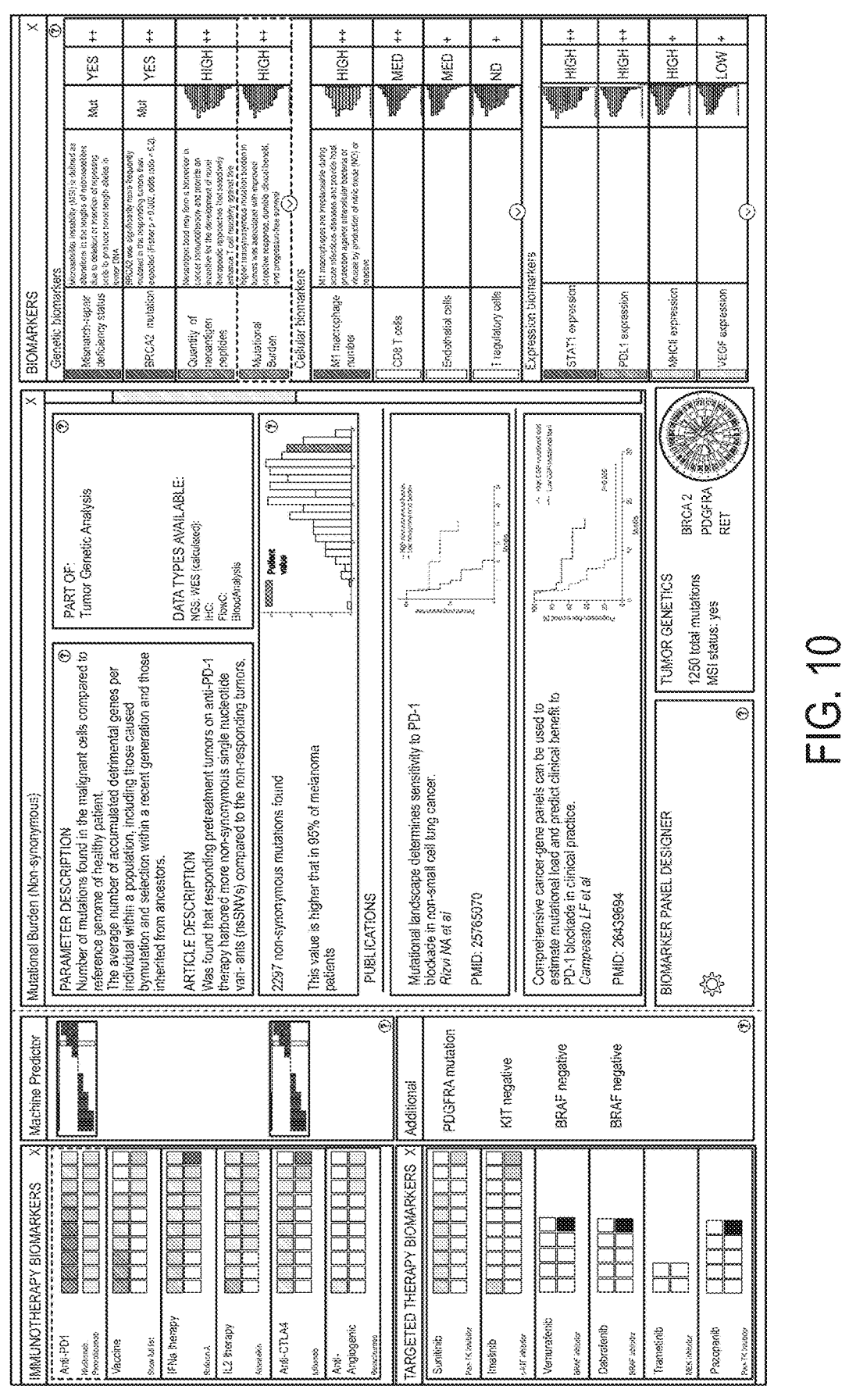

FIG. 10 is a screenshot presenting information relating to the mutational burden biomarker (as shown in the middle panel) provided in response to the user selecting the mutational burden biomarker. The information may include a description of the biomarker, how the biomarker was calculated, the patient's particular biomarker value compared to other patients (as shown in a histogram), and information from publications relating to the selected biomarker.

Biomarkers are indicative of the molecular processes that take place in the tumor microenvironment. Accordingly, a patient's biomarkers provide information specific to the patient's tumor microenvironment. The system allows a user to interactively view biomarker information as it relates to a molecular process in the tumor. Gene groups relating to tumor molecular processes associated with a particular biomarker are highlighted in response to selecting that biomarker.

Figure 11:
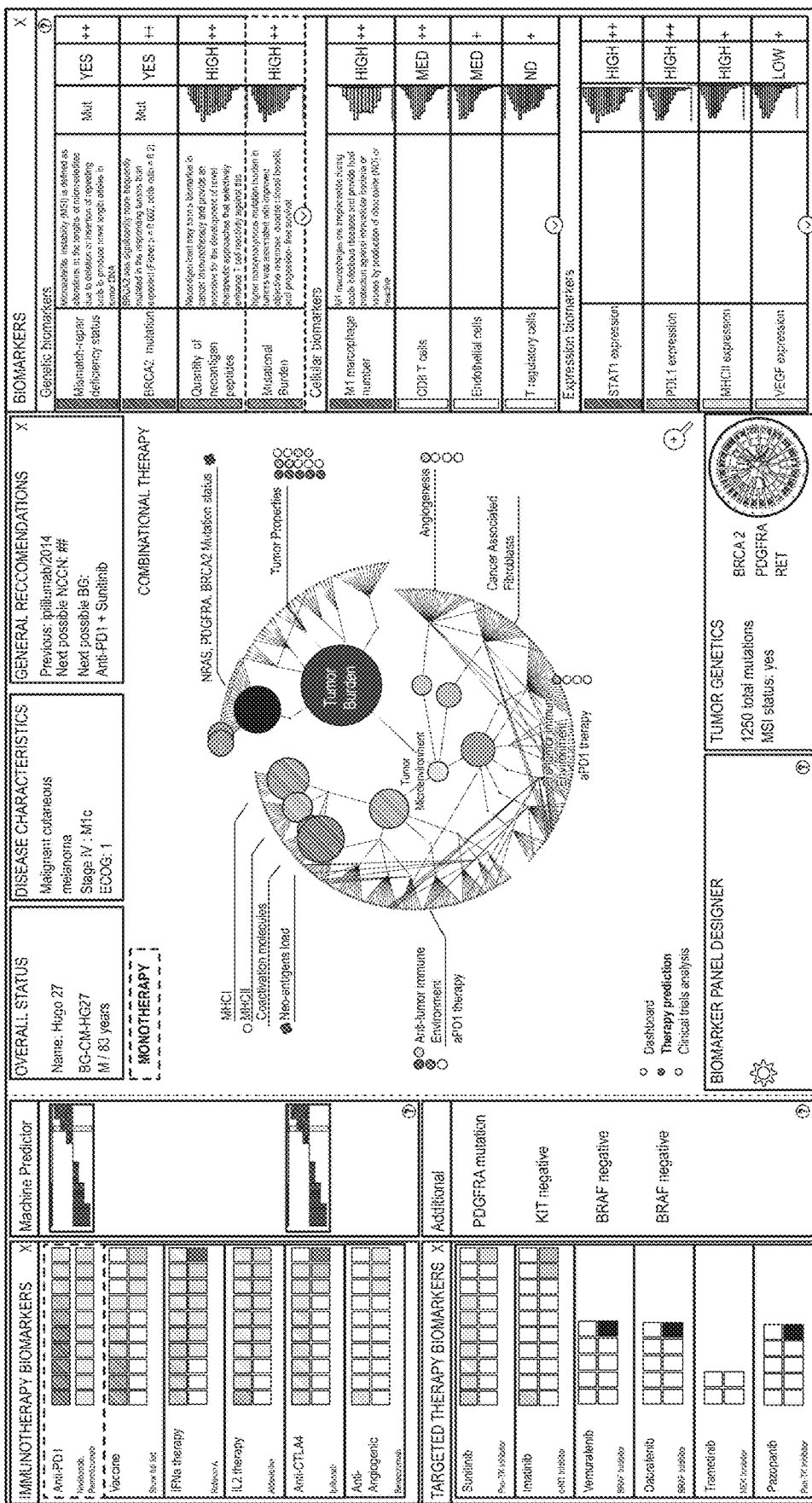
FIG. 11 is a screenshot presenting that the mutational status gene group and neo-antigens load gene group in the MF profile are highlighted in response to the user selecting the mutational burden biomarker (as shown in highlighting).
Figure 12:
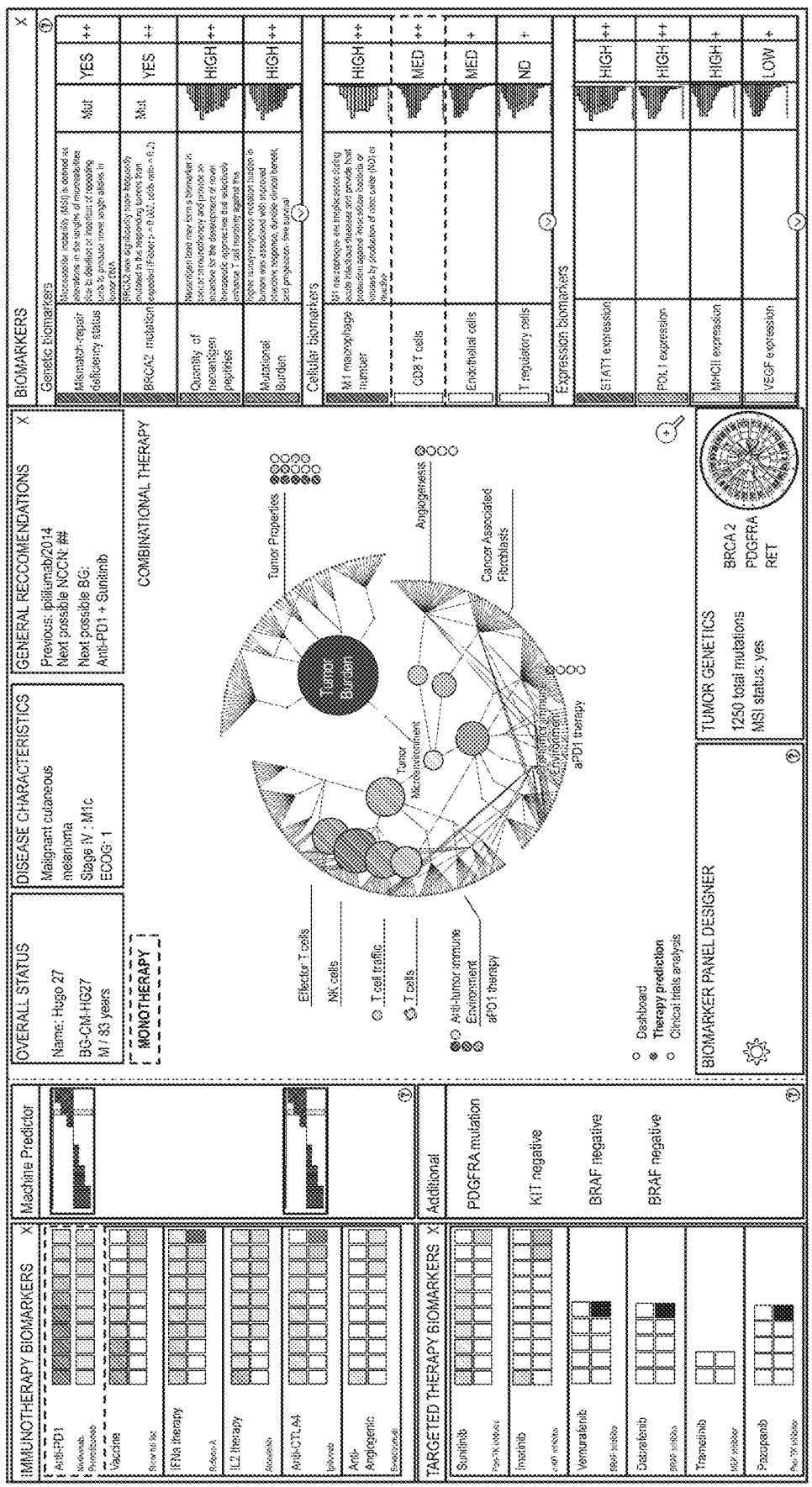
FIG. 12 is a screenshot presenting that the T cells gene group in the MF profile is highlighted in response to the user selecting the CD8 T cell biomarker (as shown in highlighting).
Figure 13:
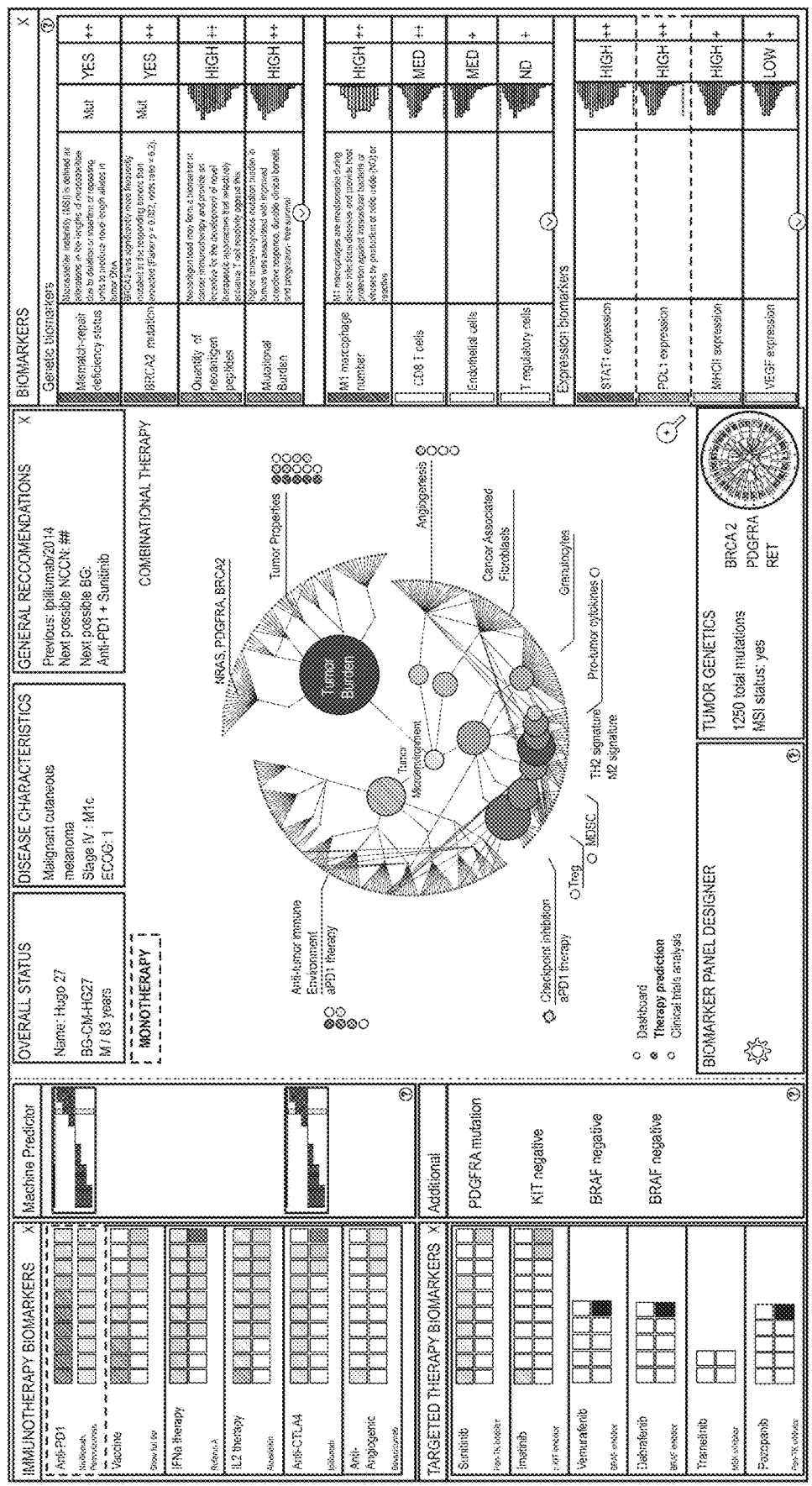
FIG. 13 is a screenshot presenting that the checkpoint inhibition gene group in the MF profile is highlighted in response to the user selecting the PDL1 expression biomarker.

FIGS. 11-13 are screenshots demonstrating that tumor molecular processes gene groups presented in the MF profile that are associated with the selected biomarker are highlighted in response to the user selecting that biomarker.

For example, the user may select the mutational burden biomarker which is associated with the mutational status gene group and the neo-antigens load gene group in the tumor microenvironment. FIG. 11 is a screenshot presenting that the mutational status gene group and neo-antigens load gene group in the MF profile are highlighted in response to the user selecting the mutational burden biomarker (as shown in highlighting).

In another example, the user may select the CD8 T cells biomarker which is associated with the T cells gene group in the tumor microenvironment. FIG. 12 is a screenshot presenting that the T cells gene group in the MF profile is highlighted in response to the user selecting the CD8 T cell biomarker (as shown in highlighting).

In yet another example, the user may select the PDL1 expression biomarker which is associated with the checkpoint inhibition gene group in the tumor microenvironment. FIG. 13 is a screenshot presenting that the checkpoint inhibition gene group in the MF profile is highlighted in response to the user selecting the PDL1 expression biomarker.

The user may select a targeted therapy to view information relating to treatment with the selected targeted therapy including biomarkers associated with the selected therapy and tumor cell processes associated with the selected therapy. For example, the user may select the targeted therapy sunitinib.

Figure 14:
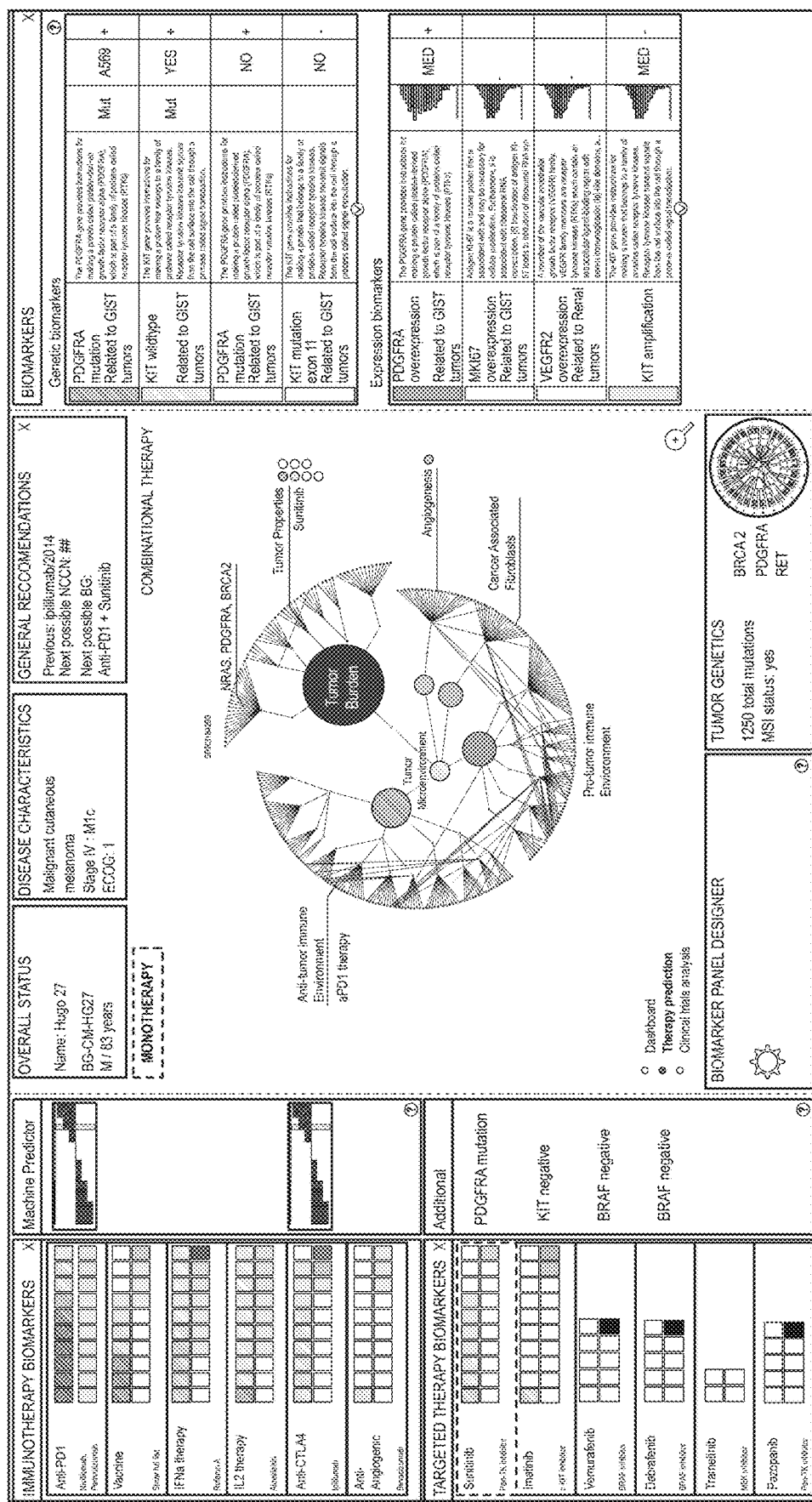
FIG. 14 is a screenshot presenting information related to sunitinib therapy provided in response to selecting sunitinib (as shown by highlighting) in the targeted therapy biomarkers portion of the screen (as shown in the left panel).

FIG. 14 is a screenshot presenting information related to sunitinib therapy provided in response to selecting sunitinib (as shown by highlighting) in the targeted therapy biomarkers portion of the screen (as shown in the left panel). Information relating to biomarkers associated with sunitinib therapy is provided in the biomarkers portion (as shown in the right panel). The biomarkers portion presents genetic biomarkers, cellular biomarkers, and expression biomarkers, as well as patient specific information related to those biomarkers.

Biomarkers are predictive of the efficacy of a therapy. Accordingly, a patient's biomarkers are predictive of the patient's response to a therapy. The system allows a user to interactively view biomarker information as it relates to a predicted response to a therapy. Clinical evidence of treatment efficacy for a therapy (e.g., an immunotherapy or a targeted therapy) may be interactively viewed by the user. FIGS. 15-18 are screenshots demonstrating that a user may select a therapy to view a screen presenting clinical trial data relating to the selected therapy.

Figure 15:
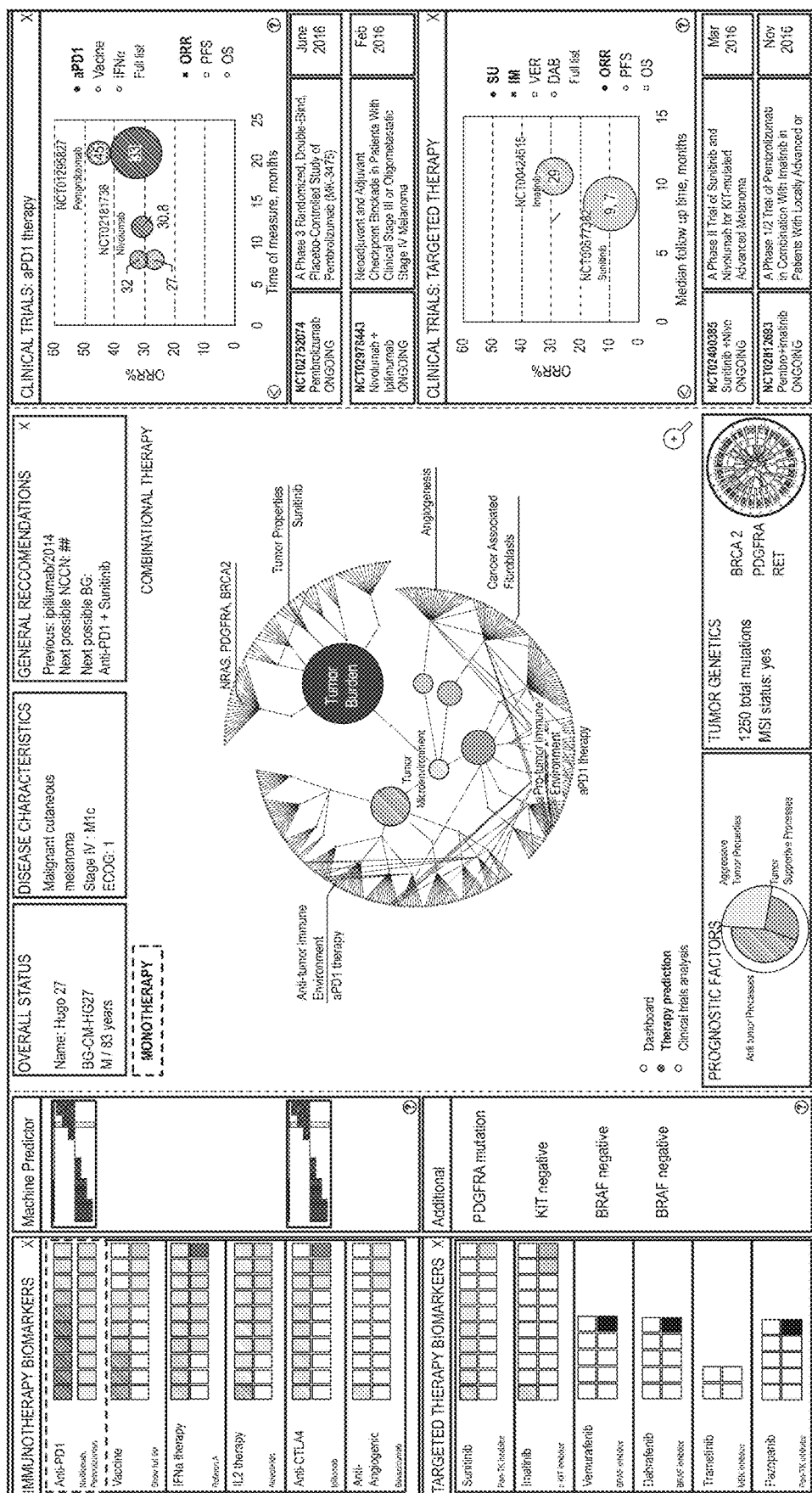
FIG. 15 is a screenshot presenting clinical trial data relating to anti-PD-1 therapy effectivity in patients having stage IV metastatic melanoma (as shown in the right panel) provided in response to the user selecting anti-PD-1 immunotherapy (as shown in the left panel).

For example, the user may select treatment with anti-PD-1 immunotherapy. FIG. 15 is a screenshot presenting clinical trial data relating to anti-PD-1 therapy effectivity in patients having stage IV metastatic melanoma (as shown in the right panel) provided in response to the user selecting anti-PD-1 immunotherapy (as shown in the left panel).

Figure 16:
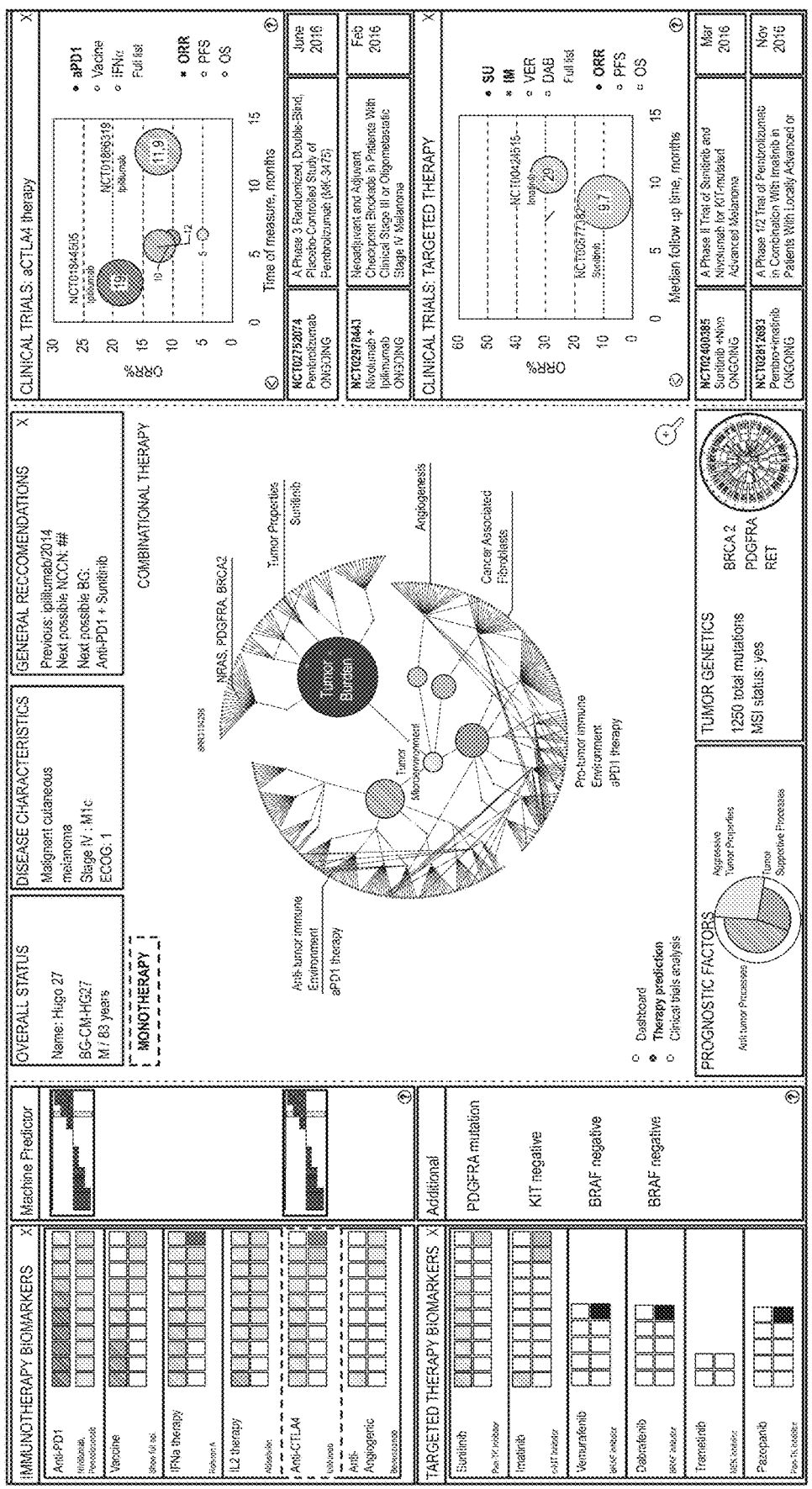
FIG. 16 is a screenshot presenting clinical trial data relating to anti-CTLA4 therapy effectivity in patients having stage IV metastatic melanoma (as shown in the right panel) provided in response to the user selecting anti-CTLA4 immunotherapy (as shown in the left panel).

In another example, the user may select treatment with anti-CTLA4 immunotherapy. FIG. 16 is a screenshot presenting clinical trial data relating to anti-CTLA4 therapy effectivity in patients having stage IV metastatic melanoma (as shown in the right panel) provided in response to the user selecting anti-CTLA4 immunotherapy (as shown in the left panel).

Figure 17:
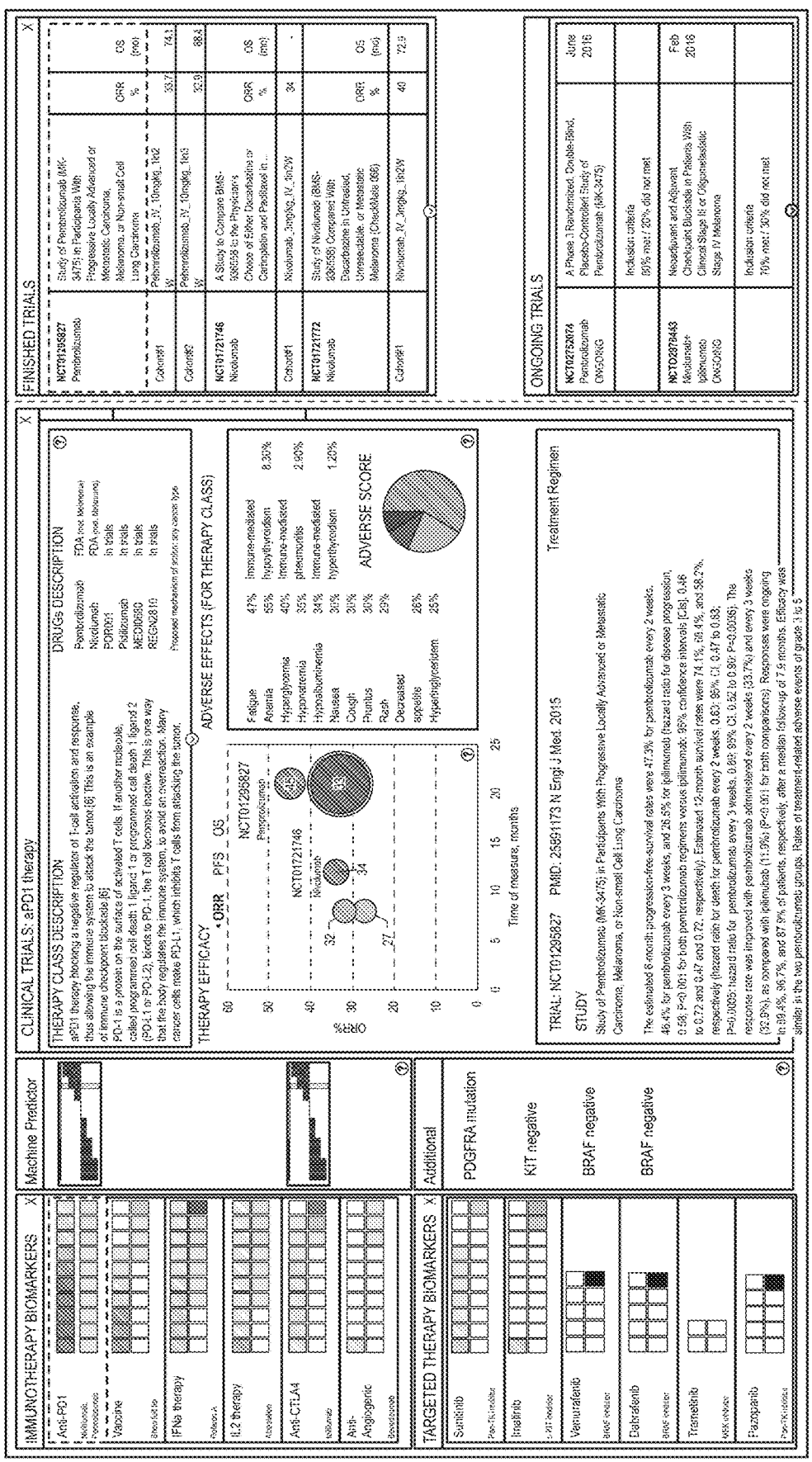
FIG. 17 is a screenshot presenting clinical trial data relating to the NCT01295827 clinical trial of anti-PD-1 treatment (as shown in the middle panel) provided in response to the user selecting the NCT01295827 clinical trial (as shown in the right panel).

A particular clinical trial can be selected to view further information relating to the clinical trial such as therapy efficacy, adverse effects of the therapy, treatment regimen, and published results. FIG. 17 is a screenshot presenting clinical trial data relating to the NCT01295827 clinical trial of anti-PD-1 treatment (as shown in the middle panel) provided in response to the user selecting the NCT01295827 clinical trial (as shown in the right panel).

Figure 18:
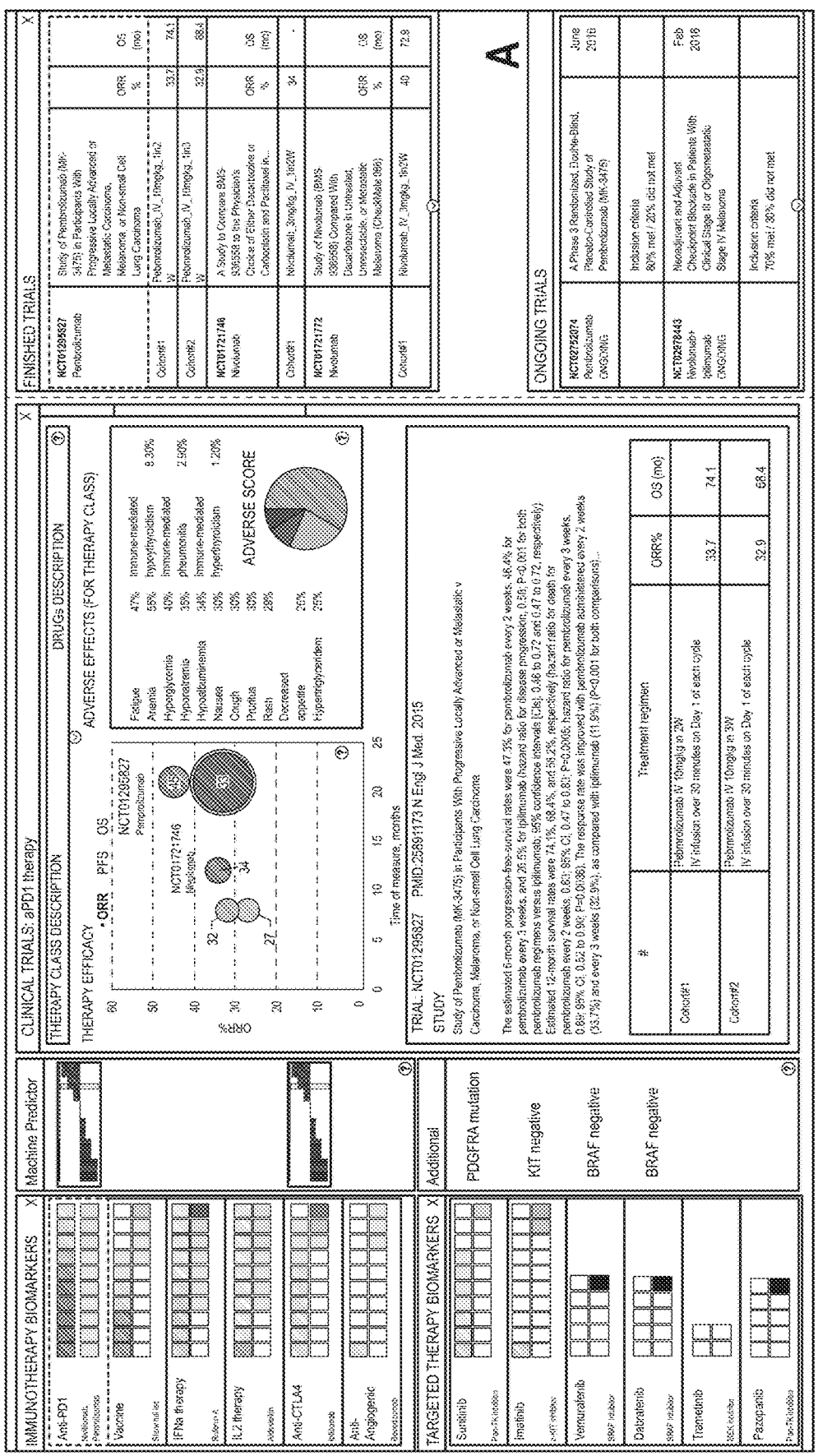
FIG. 18 is a screenshot presenting the treatment regimen of the selected clinical data provided in response to the user minimizing the therapy class description and drug description portions. The screen may also present information relating to ongoing clinical trials (marked by the letter A).

A user can interactively view information relating to the clinical trial. For example, the user can minimize various portions of information to view information in other portions. FIG. 18 is a screenshot presenting the treatment regimen of the selected clinical data provided in response to the user minimizing the therapy class description and drug description portions. The screen may also present information relating to ongoing clinical trials (marked by the letter A).

Information relating to a patient's tumor microenvironment is based on expression of genes within the tumor microenvironment. The MF profile is a visual representation of gene groups within the tumor microenvironment that provide information about tumor properties, tumor processes (e.g., angiogenesis), tumor immune environment, and cellular composition (e.g., cancer associated fibroblasts). FIGS. 19-37 are screenshots demonstrating that a user may select portions of the MF profile to view screens presenting information related to the tumor microenvironment.

Figure 19:
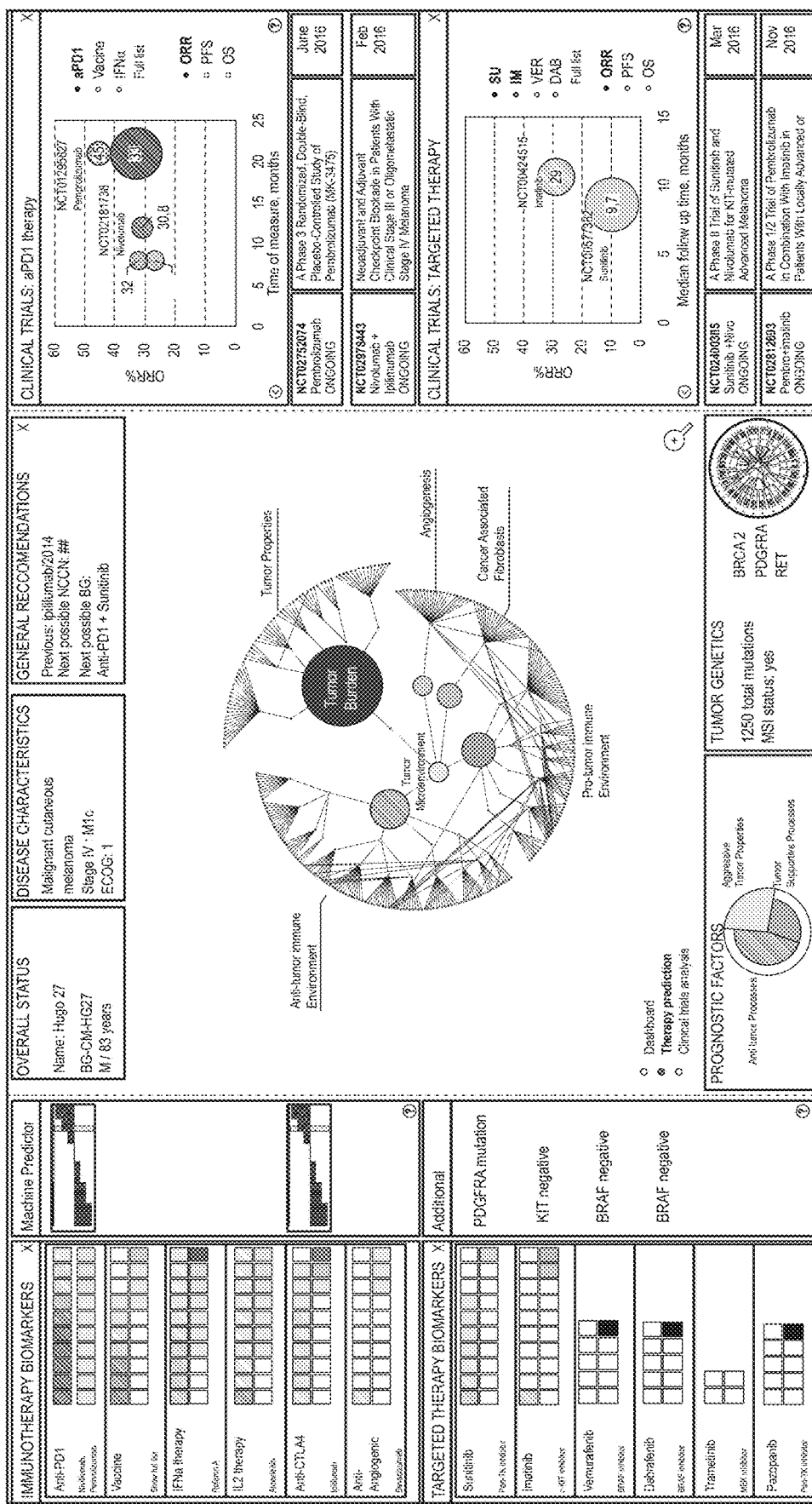
FIG. 19 is a screenshot presenting a patient's MF profile (as shown in the middle panel).

FIG. 19 is a screenshot presenting a patient's MF profile (as shown in the middle panel). The MF profile may present any number of gene groups. As a non-limiting example, FIG. 19 presents five gene groups including the tumor properties gene group, angiogenesis gene group, cancer associated fibroblasts gene group (the fibroblasts group), pro-tumor immune environment gene group (tumor-promoting immune microenvironment group), and anti-tumor immune environment gene group (anti-tumor immune microenvironment group). Any one of these gene groups may be selected to view a screen presenting additional gene groups associated with the selected gene group and information relating to the selected gene group. For example, a user may select the tumor properties gene group of the MF profile to view additional gene groups associated with the tumor properties gene group and information related to particular tumor properties (e.g., tumor genetics and tumor cell properties).

Figure 20:
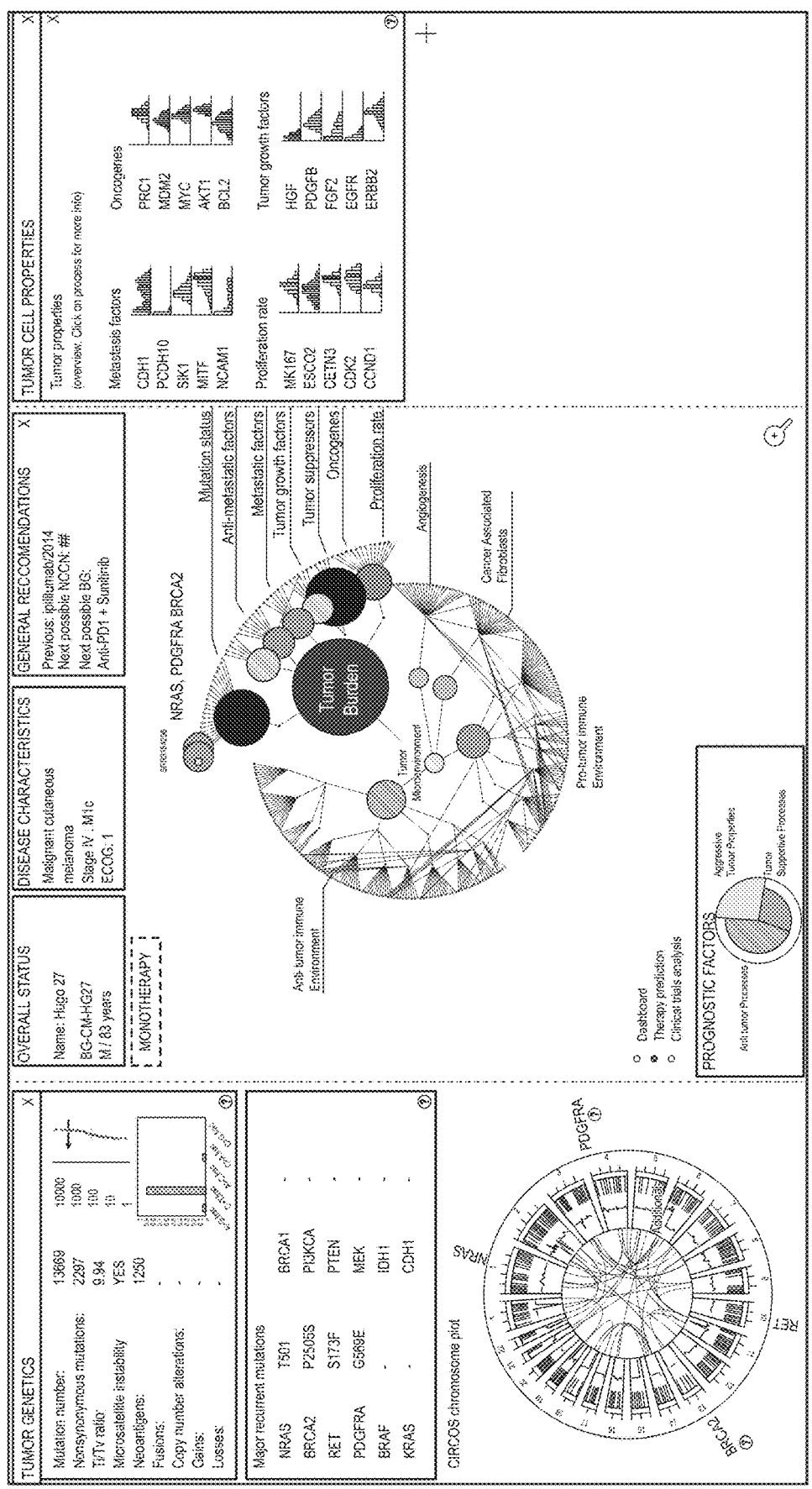
FIG. 20 is a screenshot presenting additional gene groups associated with the tumor properties gene group provided to the user in response to selecting the tumor properties gene group.

FIG. 20 is a screenshot presenting additional gene groups associated with the tumor properties gene group provided to the user in response to selecting the tumor properties gene group. These gene groups include mutational status (mutation status) gene group, anti-metastatic (antimetastatic) factors gene group, metastatic factors (metastasis signature) gene group, tumor growth factors (growth factors) gene group, tumor suppressors gene group, oncogenes gene group (activated signaling pathways; including PI3K/AKT/mTOR signaling, RAS/RAF/MEK signaling, and Receptor tyrosine kinases expression), and proliferation rate gene group. Information relating to tumor genetics (as shown in the left panel) and tumor cell properties (as shown in the right panel) are provided in response to the user selecting the tumor properties gene group. Each of the additional gene groups may be selected to view information relating to the selected gene group. For example, a user may select the proliferation rate gene group in the MF profile.

Figure 21:
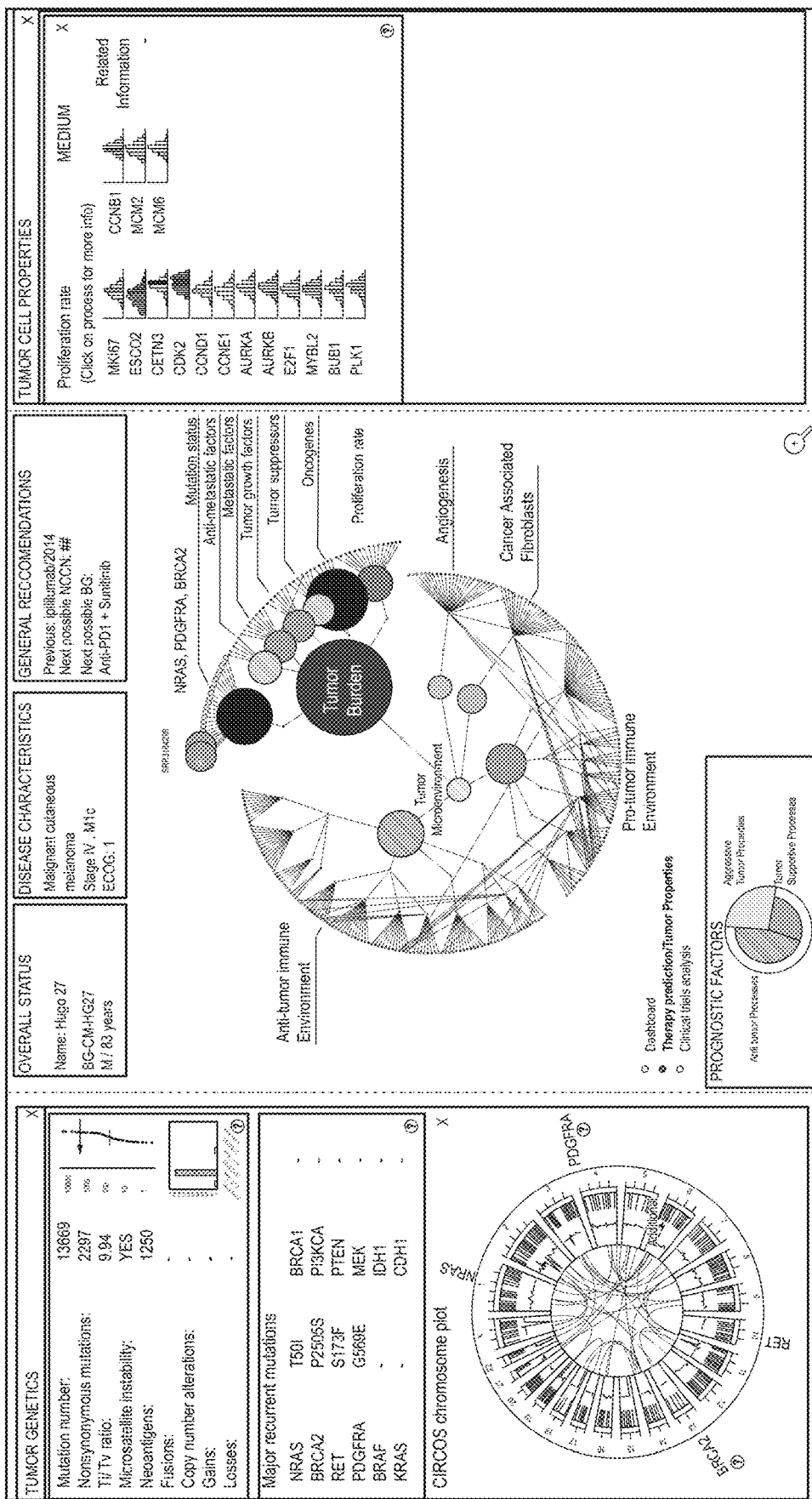
FIG. 21 is a screenshot presenting information relating to the tumor proliferation rate (as shown in the right panel) provided in response to the user selecting the tumor proliferation rate gene group (as shown in highlighting) in the MF profile.

FIG. 21 is a screenshot presenting information relating to the tumor proliferation rate (as shown in the right panel) provided in response to the user selecting the tumor proliferation rate gene group (as shown in highlighting) in the MF profile. The user may also view additional information relating to properties of the patient's tumor.

Figure 22:
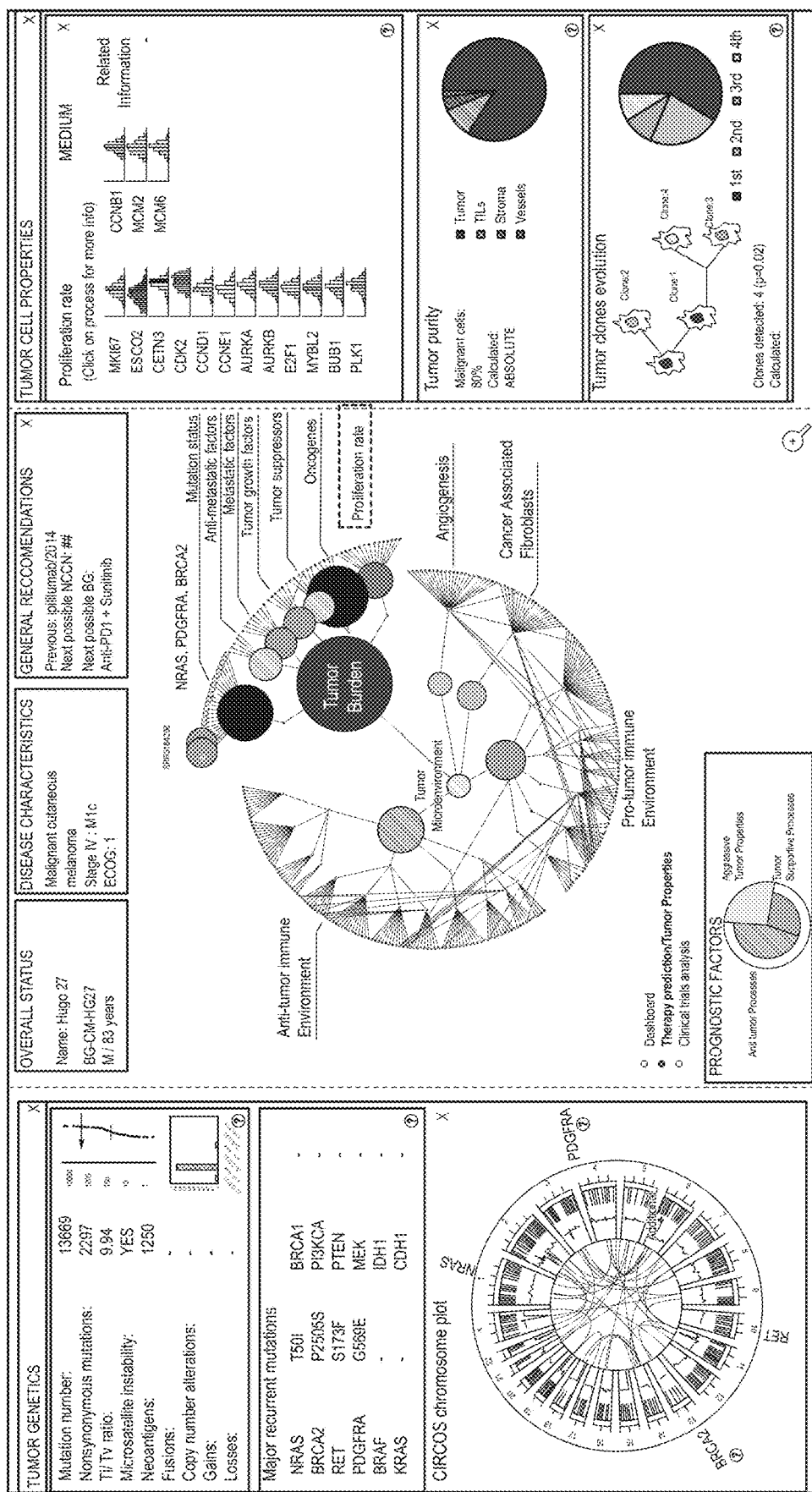
FIG. 22 is a screenshot presenting information relating to the purity of the patient's tumor in the tumor purity portion (as shown in the lower right panel) and information relating to the clonal evolution of the patient's tumor in the tumor clones evolution portion (as shown in the lower right panel).

The user may view different screens presenting information relating to different tumor properties such as a screen presenting information related to tumor purity and tumor clone evolution. FIG. 22 is a screenshot presenting information relating to the purity of the patient's tumor in the tumor purity portion (as shown in the lower right panel) and information relating to the clonal evolution of the patient's tumor in the tumor clones evolution portion (as shown in the lower right panel).

The MF profile provides information relating to the pro-tumor immune environment (tumor-promoting immune microenvironment), and anti-tumor immune environment (anti-tumor immune microenvironment). For example, the user may select the anti-tumor immune environment (anti-tumor immune microenvironment) gene group in the MF profile to view information relating to the anti-tumor immune environment and the user may select the pro-tumor immune environment (tumor-promoting immune microenvironment) gene group in the MF profile to view information relating to the pro-tumor immune environment (tumor-promoting immune microenvironment).

Figure 23:
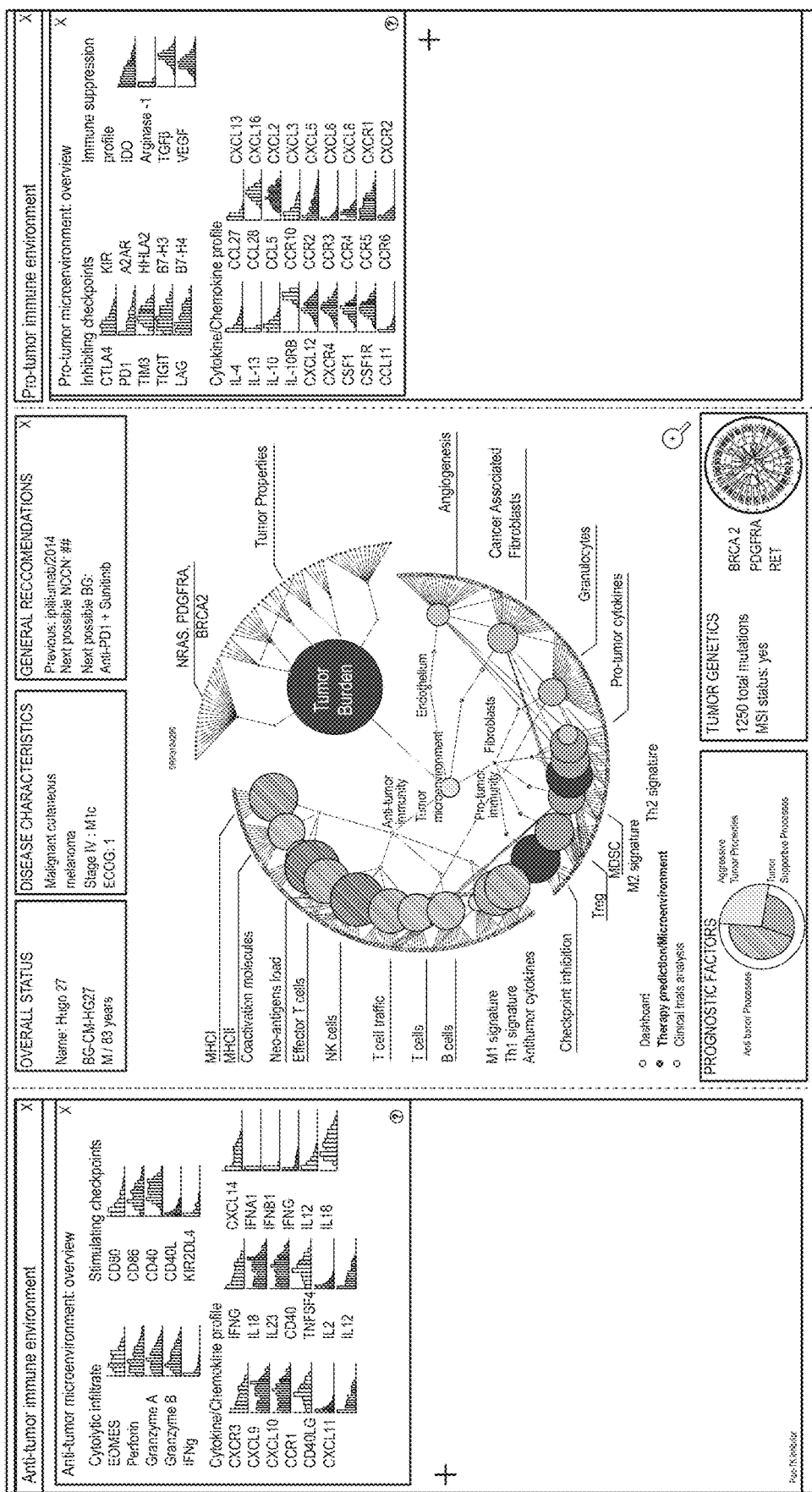
FIG. 23 is a screenshot presenting information relating to the anti-tumor immune environment (as shown in the left panel) provided in response to the user selecting the anti-tumor immune environment gene group and information relating to the pro-tumor immune environment (as shown in the right panel) in response to the user selecting the pro-tumor immune environment gene group.

FIG. 23 is a screenshot presenting information relating to the anti-tumor immune environment (as shown in the left panel; anti-tumor immune microenvironment) provided in response to the user selecting the anti-tumor immune environment (anti-tumor immune microenvironment) gene group and information relating to the pro-tumor immune environment (as shown in the right panel; tumor-promoting immune microenvironment) in response to the user selecting the pro-tumor immune environment (tumor-promoting immune microenvironment) gene group. Additional gene groups relating to the tumor microenvironment are presented in the MF profile in response to selecting the anti-tumor and pro-tumor immune environment (anti-tumor immune microenvironment and tumor-promoting immune microenvironment) gene groups in the MF profile (as shown in the middle panel).

Figure 24:
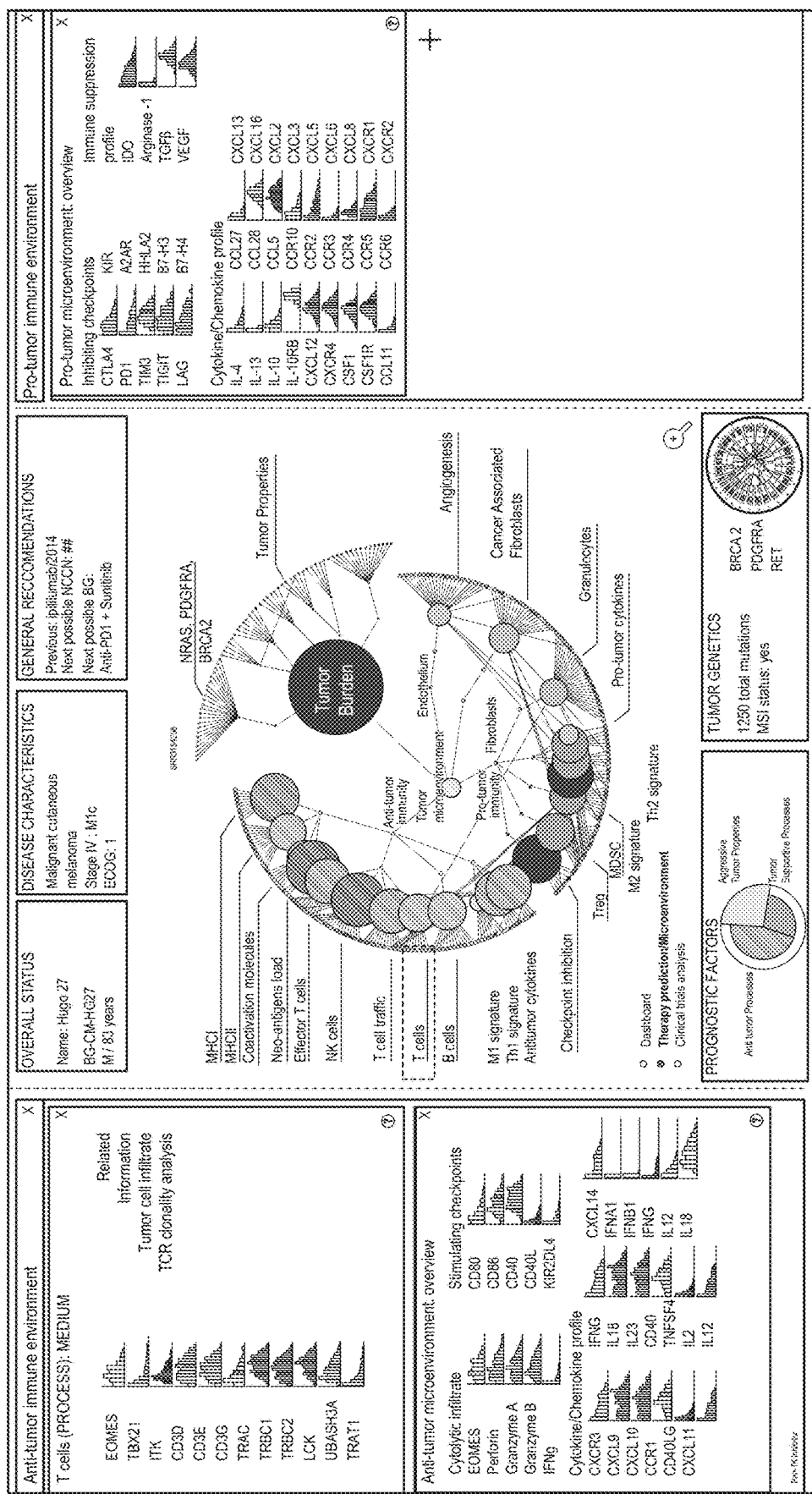
FIG. 24 is a screenshot presenting information relating to expression of genes that determine T cell activity within the tumor in the anti-tumor microenvironment portion (as shown in the lower left panel) provided in response to the user selecting the T cell gene group in the MF profile (as shown by highlighting).

Any one of these additional gene groups in the MF profile may be selected to view information relating to that gene group. For example, the user may select the T cells gene group in the MF profile. FIG. 24 is a screenshot presenting information relating to expression of genes that determine T cell activity within the tumor in the anti-tumor microenvironment portion (as shown in the lower left panel) provided in response to the user selecting the T cell gene group in the MF profile (as shown by highlighting).

Figure 25:
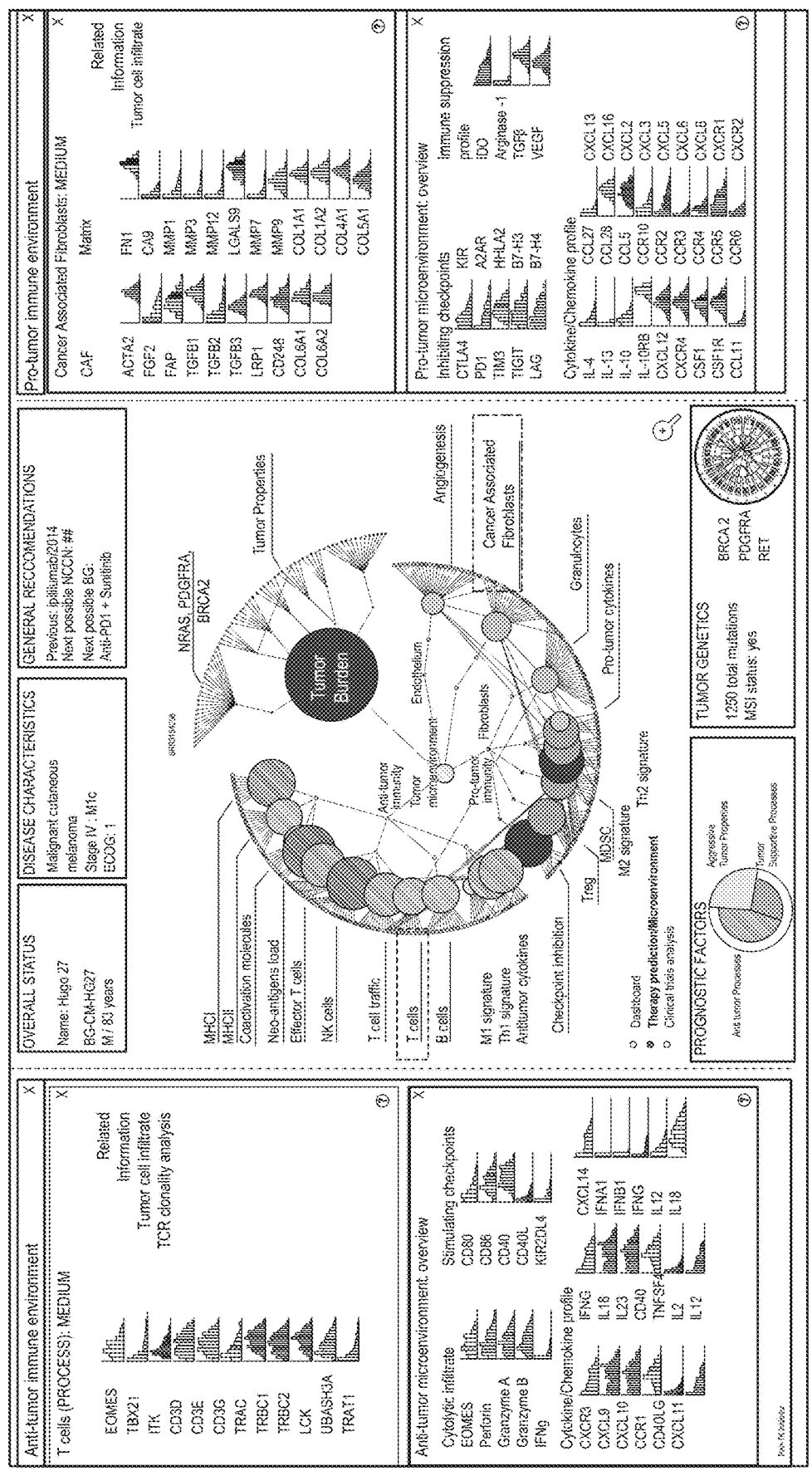
FIG. 25 is a screenshot presenting information relating to expression of genes that determine cancer associated fibroblast activity within the tumor in the pro-tumor microenvironment portion (as shown in the lower right panel) provided in response to the user selecting the cancer associated fibroblast gene group in the MF profile (as shown by highlighting).

FIG. 25 is a screenshot presenting information relating to expression of genes that determine cancer associated fibroblast activity within the tumor in the pro-tumor microenvironment (anti-tumor immune microenvironment) portion (as shown in the lower right panel) provided in response to the user selecting the cancer associated fibroblast (fibroblasts) gene group in the MF profile (as shown by highlighting).

The user may select portions in the anti-tumor immune environment portion (as shown in the left panel; anti-tumor immune microenvironment) and the pro-tumor immune environment portion (as shown in the right panel; tumor-promoting immune microenvironment) to view additional information relating to anti-tumor cells and pro-tumor (or tumor promoting) cells within the tumor microenvironment (anti-tumor immune microenvironment and tumor-promoting immune microenvironment).

Figure 26:
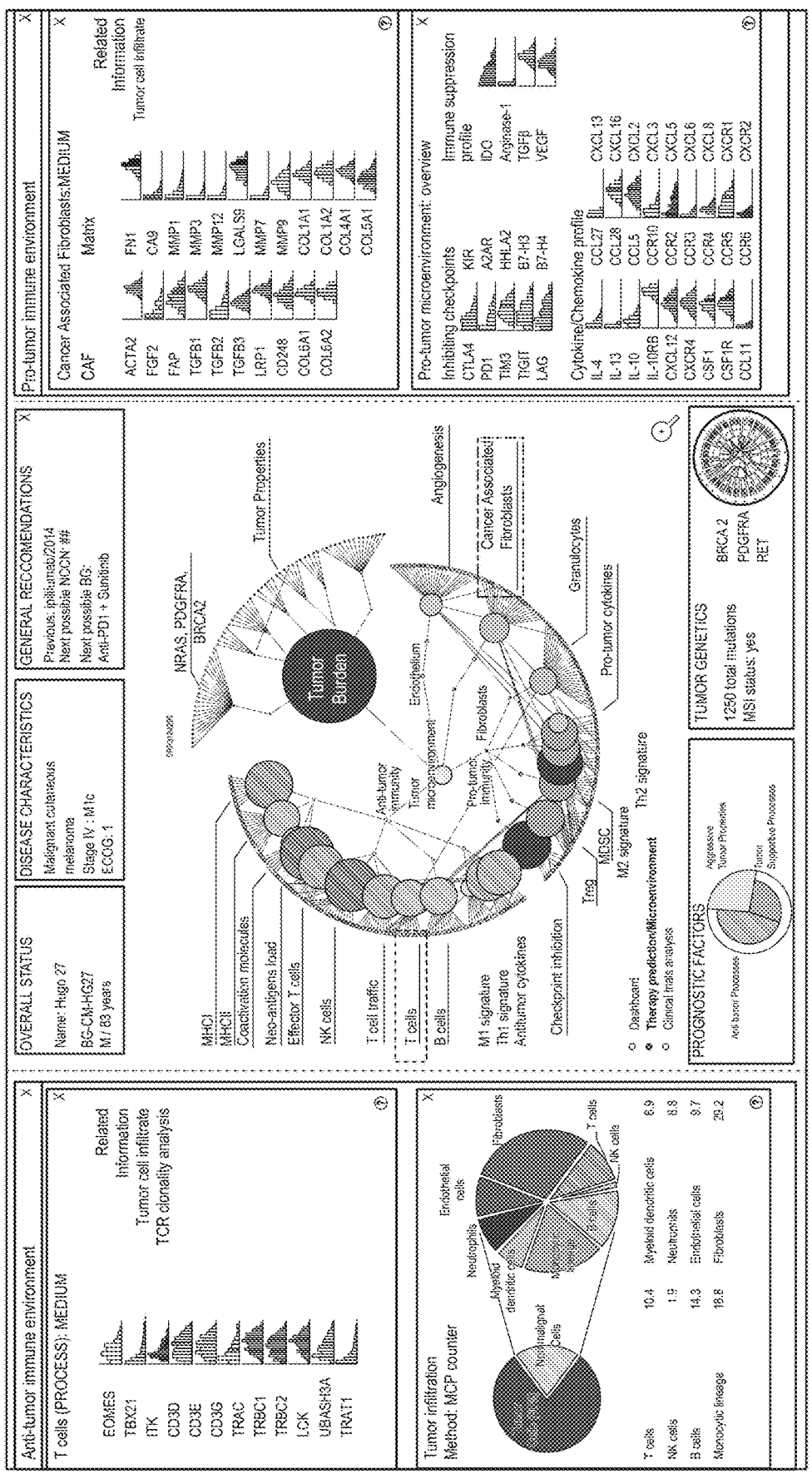
FIG. 26 is a screenshot presenting information relating to the number of non-malignant cells in the patient's tumor (as shown in the lower left panel) provided in response to the user selecting tumor infiltrate in the anti-tumor immune environment portion (as shown in the upper left panel).

FIG. 26 is a screenshot presenting information relating to the number of non-malignant cells in the patient's tumor (as shown in the lower left panel) provided in response to the user selecting tumor infiltrate in the anti-tumor immune environment portion (as shown in the upper left panel).

Figure 27:
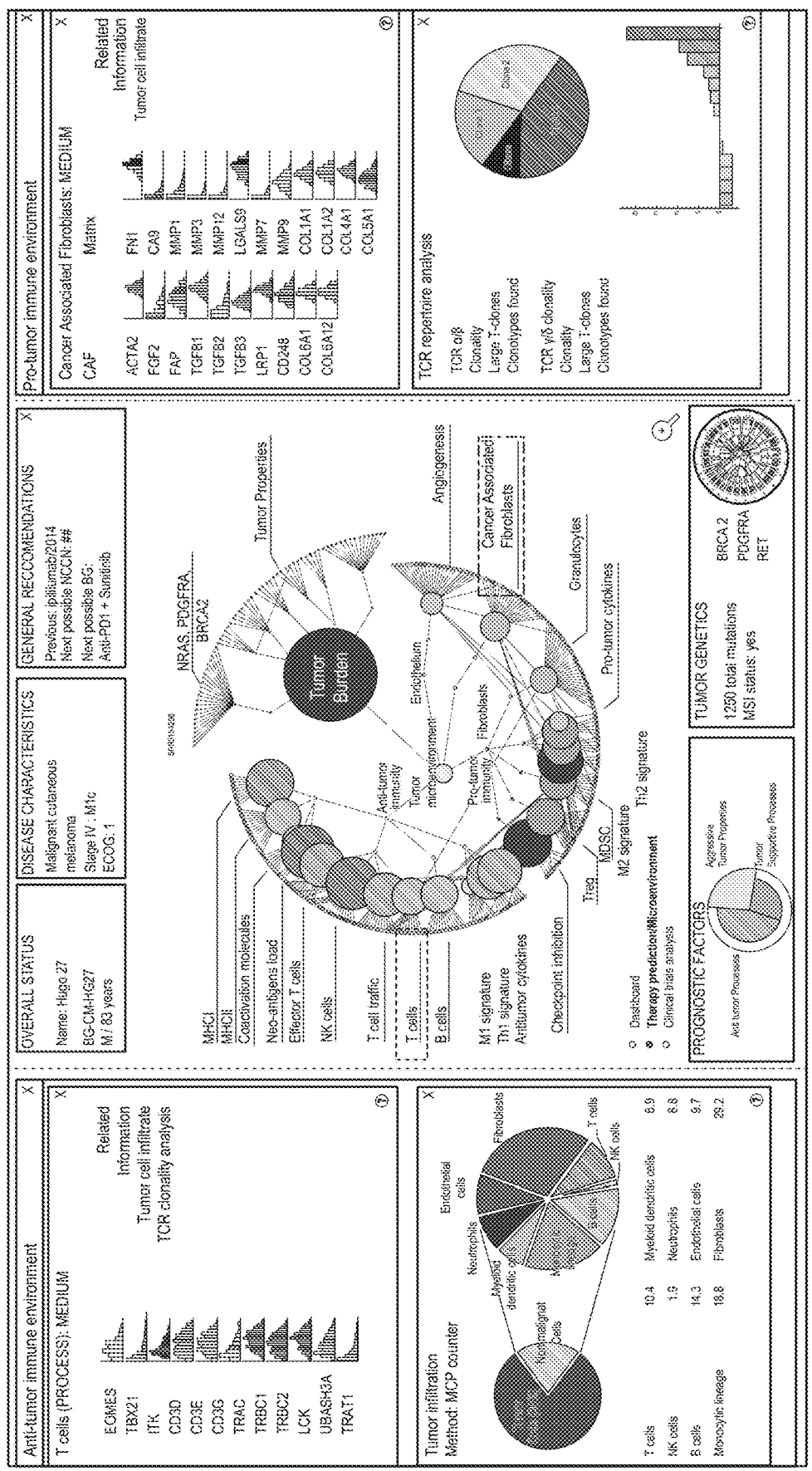
FIG. 27 is a screenshot presenting information relating to the TCR repertoire in the patient's tumor (as shown in the lower right panel) provided in response to the user selecting tumor infiltrate in the pro-tumor immune environment portion (as shown in the upper right panel).

FIG. 27 is a screenshot presenting information relating to the TCR repertoire in the patient's tumor (as shown in the lower right panel) provided in response to the user selecting tumor infiltrate in the pro-tumor immune environment portion (as shown in the upper right panel; tumor-promotive immune infiltrate).

Figure 28:
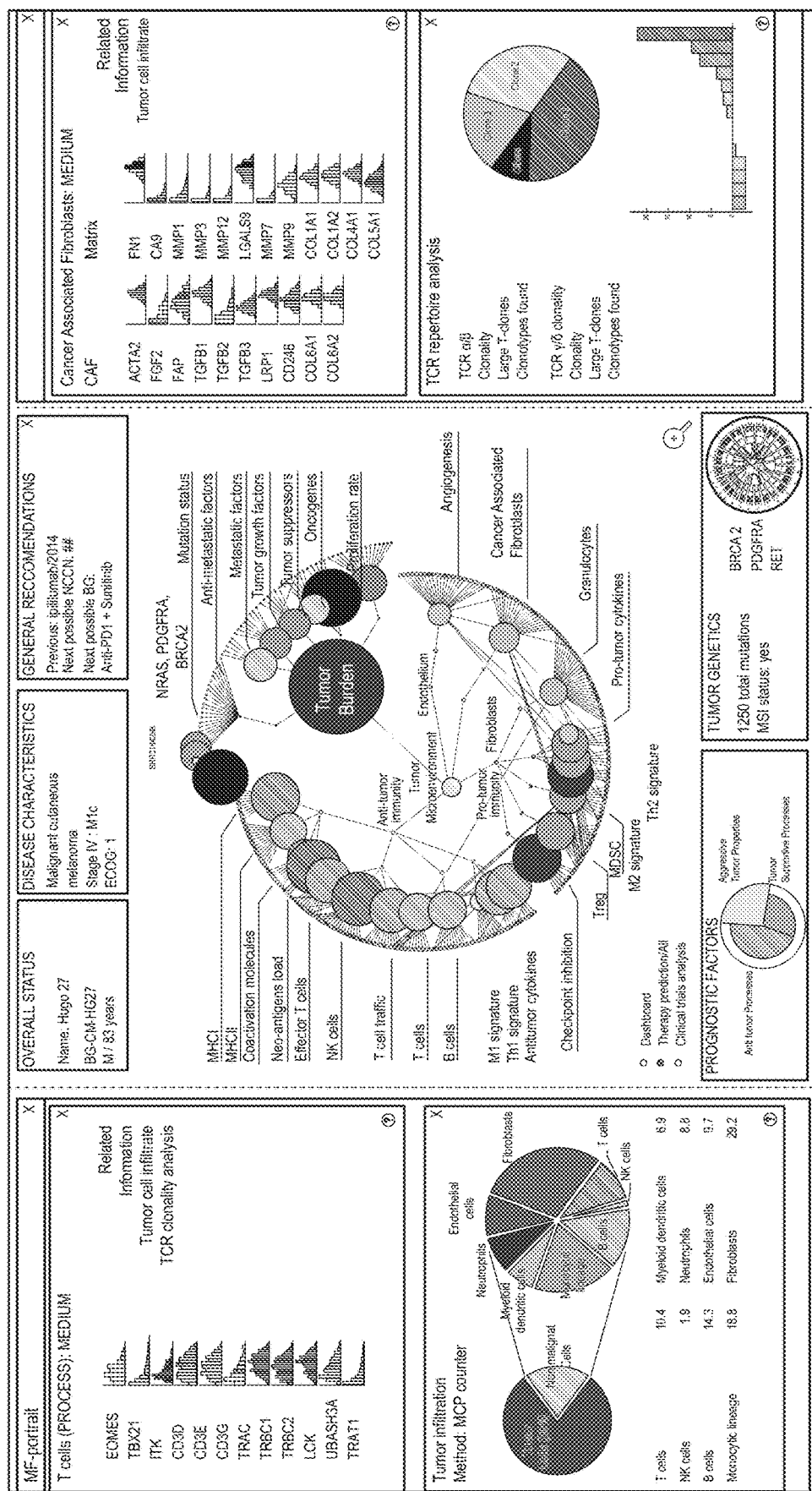
FIG. 28 is a screenshot showing a MF profile presenting twenty-eight gene groups is shown in (as shown in the middle panel).

As disclosed herein, the MF profile may present five gene groups including the tumor properties gene group, angiogenesis gene group, cancer associated fibroblasts gene group (the fibroblasts group), pro-tumor immune environment gene group (tumor-promoting immune microenvironment group), and anti-tumor immune environment gene group (anti-tumor immune microenvironment group). Each of these gene groups may be selected by the user to view associated gene groups. When each of these gene groups is selected, the MF profile may present twenty-eight gene groups. A screen presenting a MF profile presenting twenty-eight gene groups (also described elsewhere herein) is shown in FIG. 28 (as shown in the middle panel).

The "combo therapy" (or "combination therapy") portion can be used to design a combination therapy based on one or more therapies. Combination therapies can be designed to target cancer (e.g., tumor) properties presented in the MF profile. For example, a combination therapy including a treatment to suppress pro-tumor process may be designed for a patient in which the MF profile showed active pro-tumor processes.

The combo therapy portion may present information to the user relating to the selected therapy including a description of the selected therapy, gene groups targeted by the selected therapy, clinical data related to the selected therapy, and predictions of the patient's response to the selected therapy based on information relating to the patient and the patient's cancer. FIGS. 29-37 are screenshots demonstrating that a user may interactively design a combination therapy using the combo therapy portion.

Figure 29:
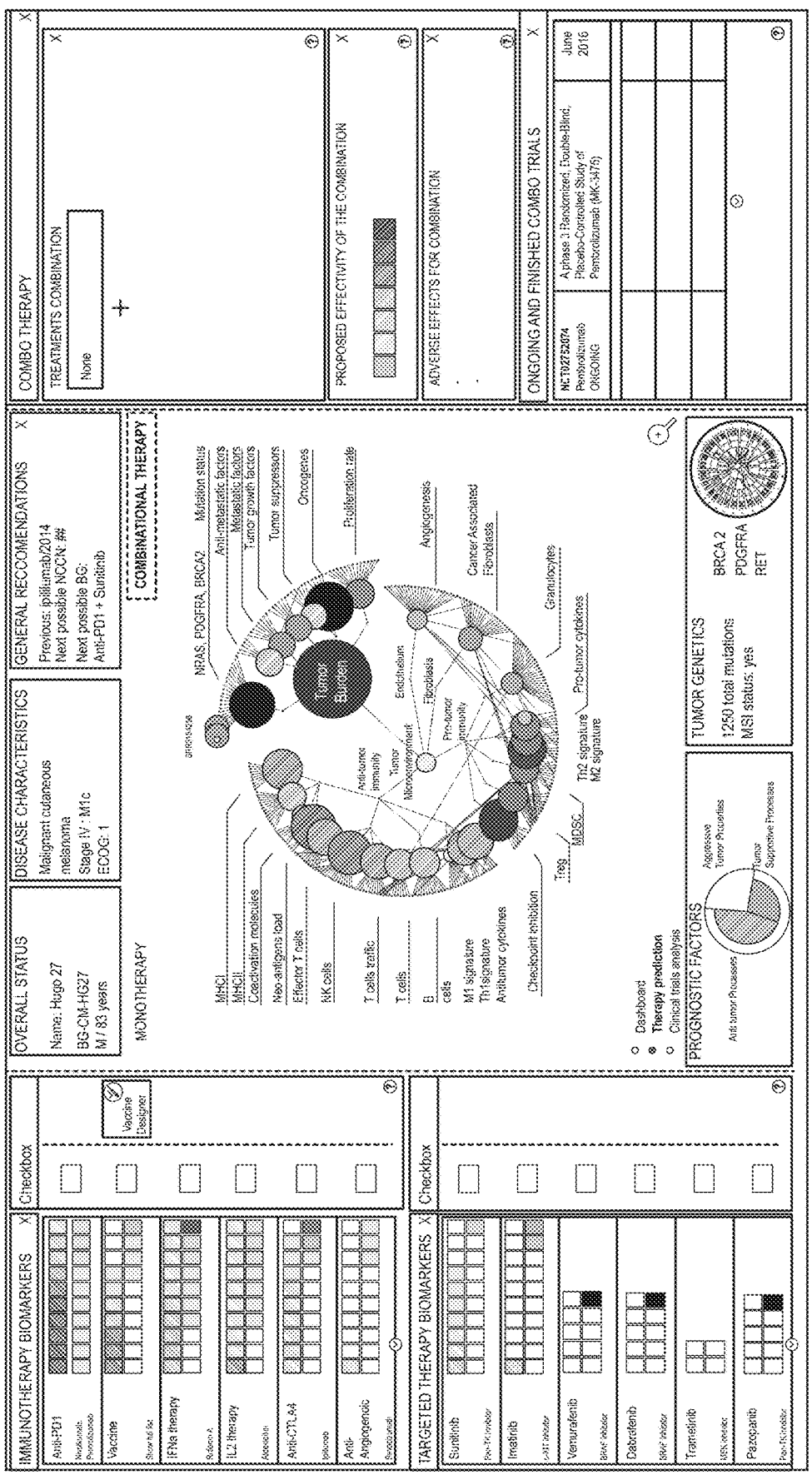
FIG. 29 is a screenshot presenting the combo therapy portion (as shown in the right panel) provided to the user in response to selecting the combinational therapy portion (as shown in the middle panel).

FIG. 29 is a screenshot presenting the combo therapy portion (as shown in the right panel) provided to the user in response to selecting the combinational therapy portion (as shown in the middle panel).

Figure 30:
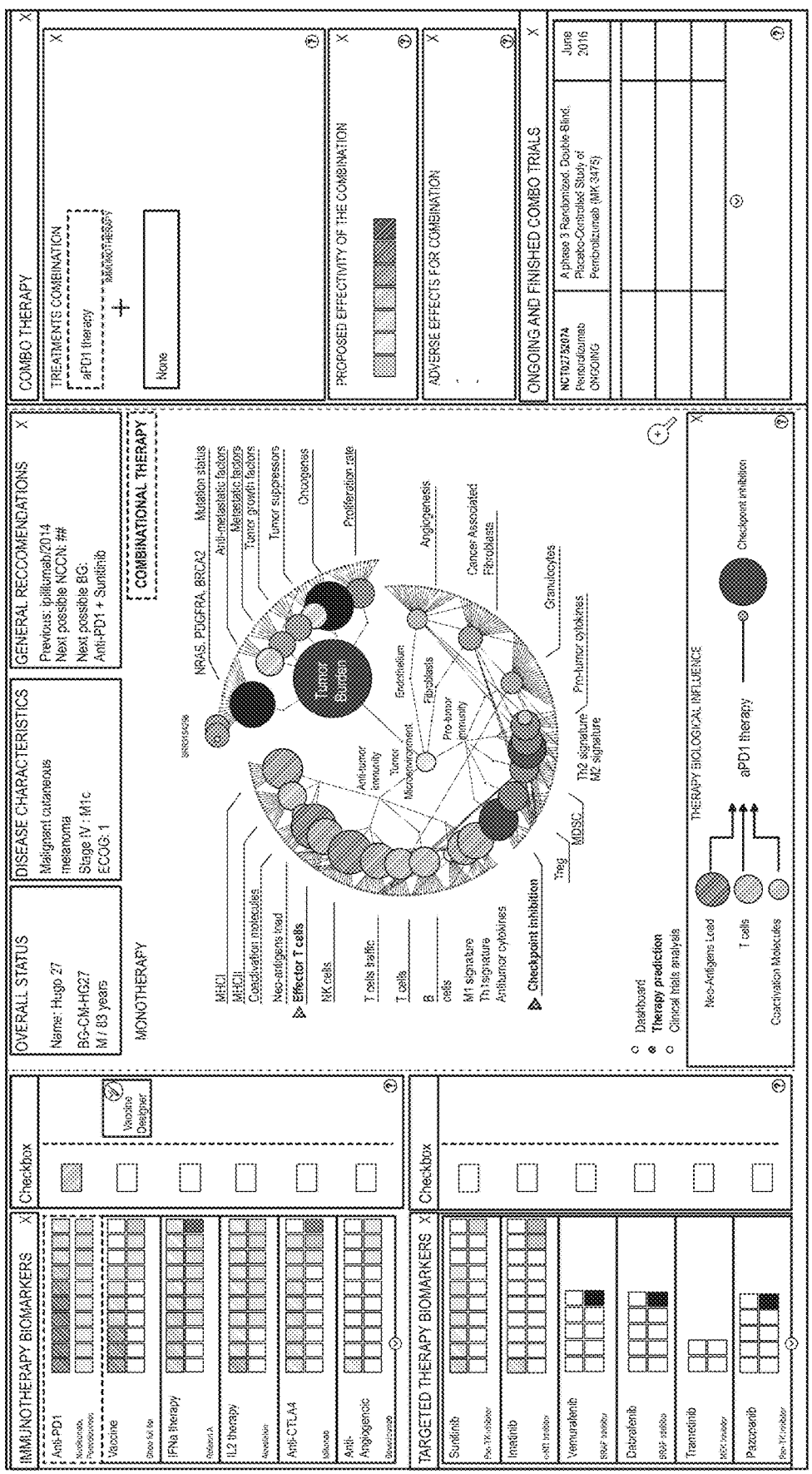
FIG. 30 is a screenshot presenting anti-PD-1 therapy incorporated into the combo therapy portion (as shown in the upper right panel).

FIG. 30 is a screenshot presenting anti-PD-1 therapy incorporated into the combo therapy portion (as shown in the upper right panel). Gene groups targeted by anti-PD-1 therapy in the MF profile are marked with arrows. Information relating to the biological influence of anti-PD-1 therapy is presented in the therapy biological influence portion (as shown in the lower middle panel).

Figure 31:
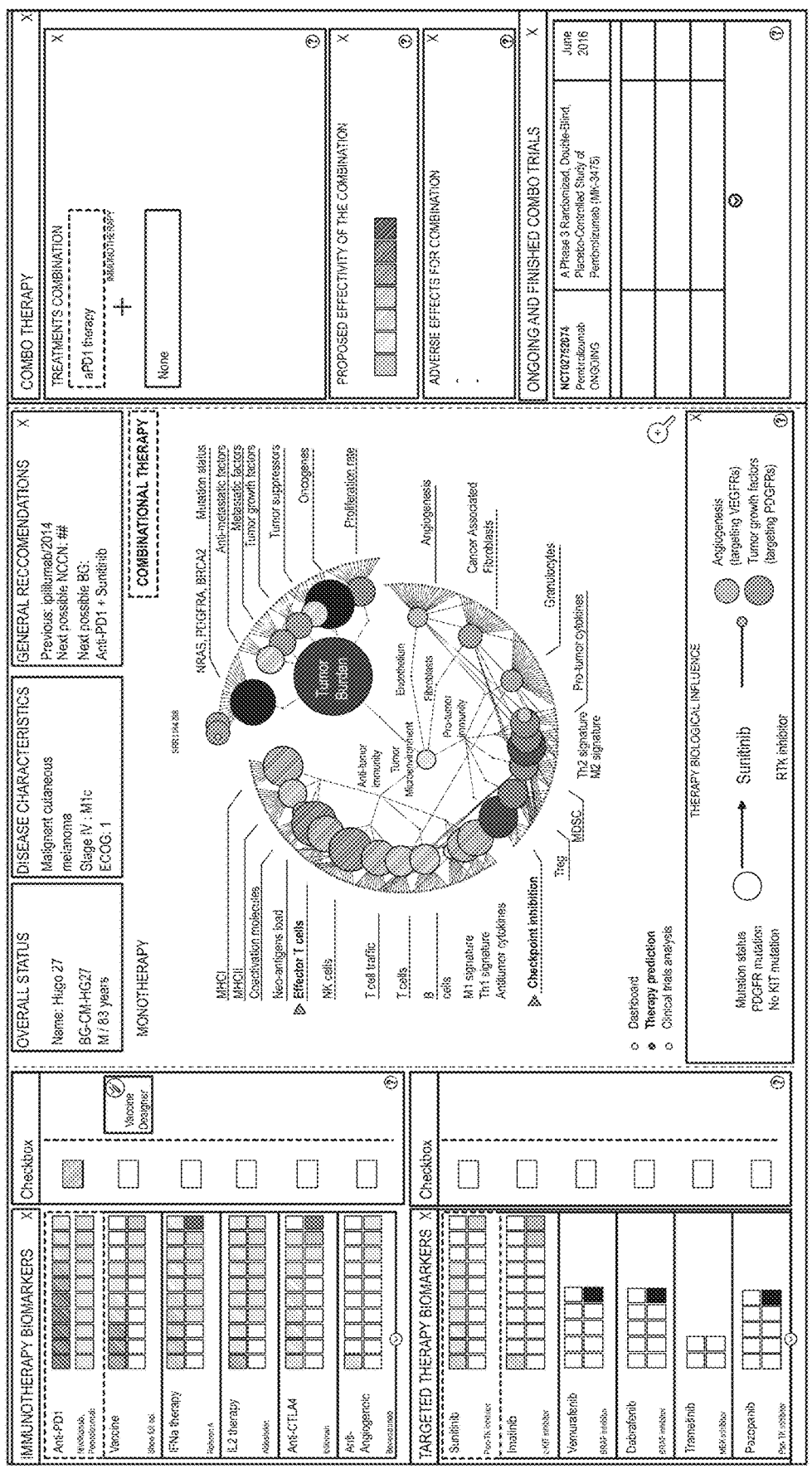
FIG. 31 is a screenshot presenting information related to sunitinib treatment in the therapy biological influence portion (as shown in the lower middle panel) in response to the user selecting sunitinib in the targeted therapy biomarkers portion (as shown by highlighting).

FIG. 31 is a screenshot presenting information related to sunitinib treatment in the therapy biological influence portion (as shown in the lower middle panel) in response to the user selecting sunitinib in the targeted therapy biomarkers portion (as shown by highlighting). The user may determine whether the selected treatment should be incorporated into the combination therapy based on this information.

Figure 32:
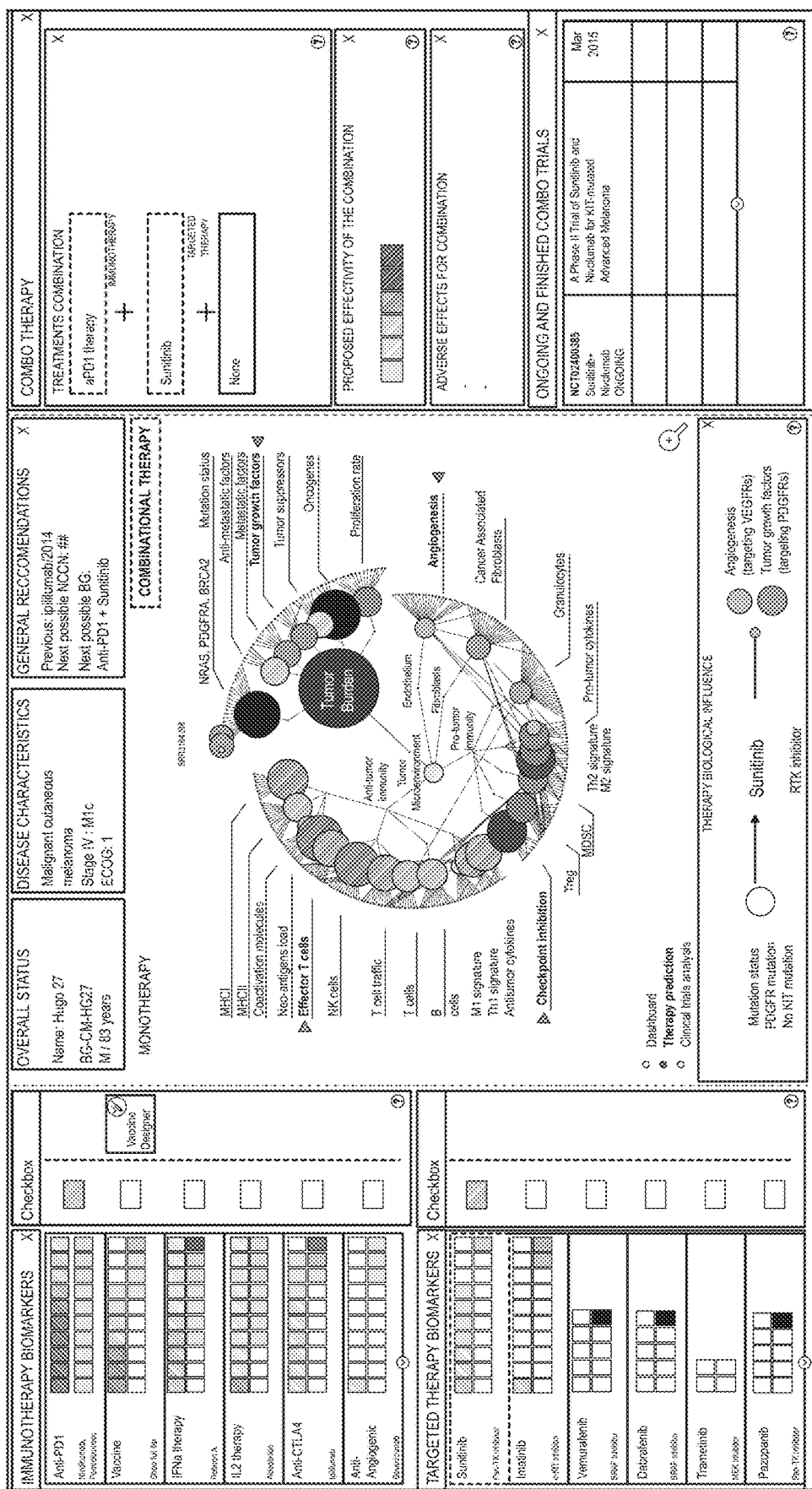
FIG. 32 is a screenshot presenting sunitinib incorporation in the combo therapy portion in response to the user selecting sunitinib.

FIG. 32 is a screenshot presenting sunitinib incorporation in the combo therapy portion in response to the user selecting sunitinib. Gene groups targeted by the anti-PD-1 and sunitinib combination therapy are marked with arrows in the MF profile. Information relating to the combination of anti-PD-1 and sunitinib therapy is presented in the proposed effectivity portion (as shown in the right panel) and in the potential adverse effects portion (as shown in the right panel). Information relating to published and ongoing clinical trials matching the selected combination therapy are presented in the ongoing and finished combo trials portion (as shown in the right panel).

The combination therapy may include more than two therapies. For example, a user may add a vaccine therapy to the anti-PD-1 and sunitinib combination therapy designed by the user.

Figure 33:
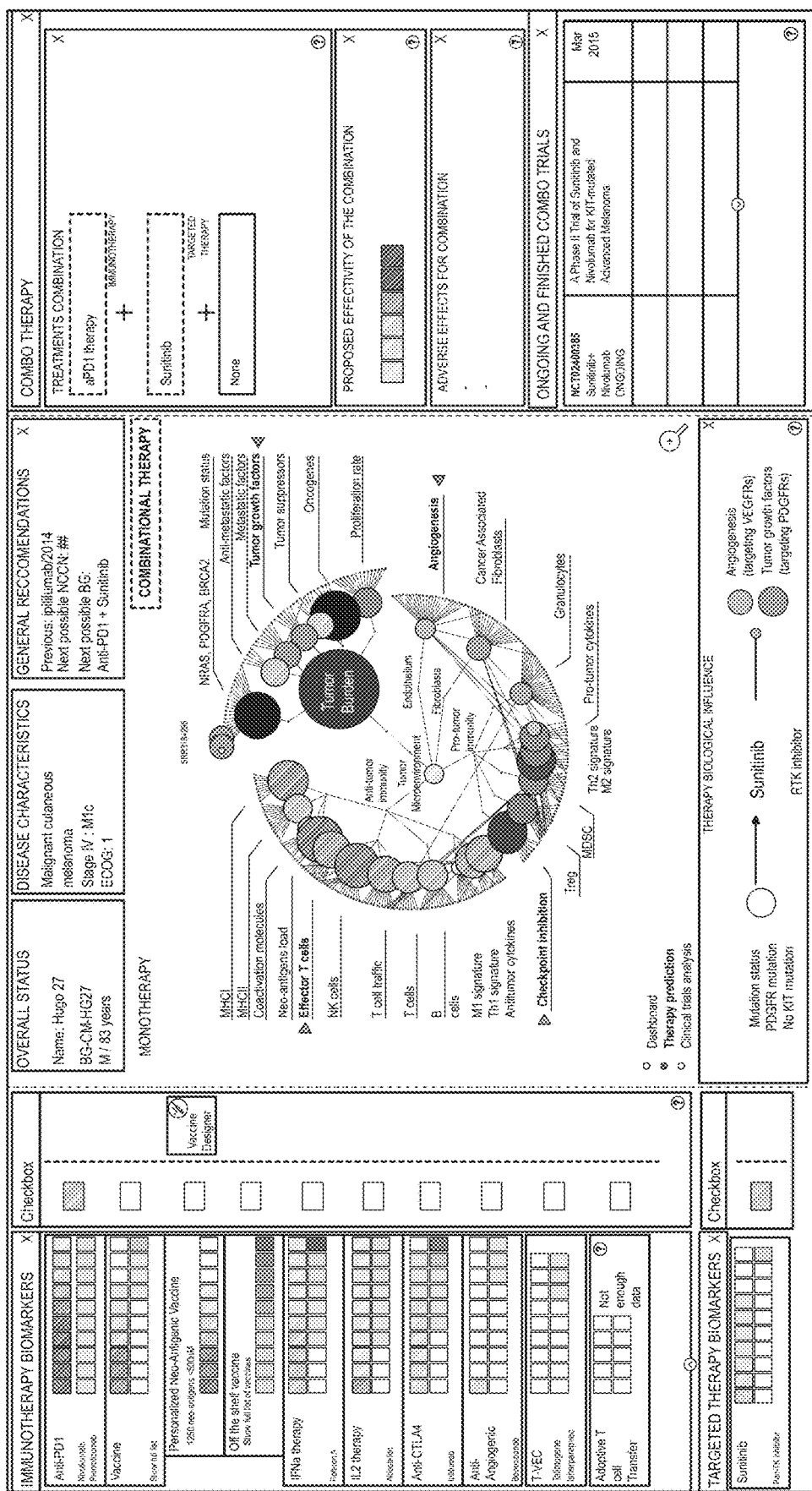
FIG. 33 is a screenshot presenting potential vaccine therapies such as a personalized neo-antigenic vaccine and an off the shelf vaccine provided to the user in response to selecting vaccine in the immunotherapy biomarkers portion (as shown in the left panel).

FIG. 33 is a screenshot presenting potential vaccine therapies such as a personalized neo-antigenic vaccine and an off the shelf vaccine provided to the user in response to selecting vaccine in the immunotherapy biomarkers portion (as shown in the left panel).

Figure 34:
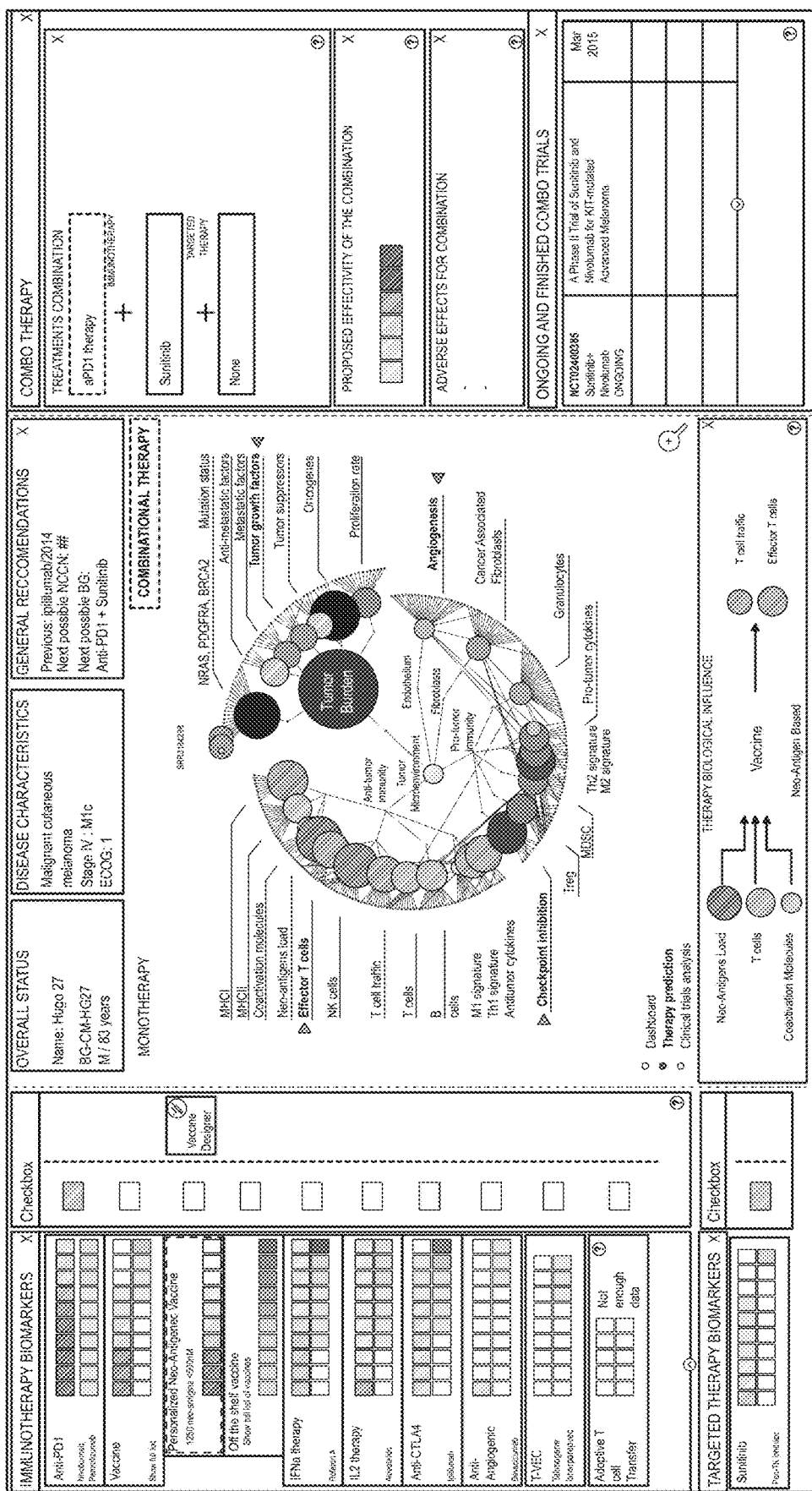
FIG. 34 is a screenshot presenting information relating to treatment with a personalized neo-antigenic vaccine (as shown in the lower middle panel) provided to the user in response to selecting a personalized neo-antigenic vaccine (as shown by highlighting).

FIG. 34 is a screenshot presenting information relating to treatment with a personalized neo-antigenic vaccine (as shown in the lower middle panel) provided to the user in response to selecting a personalized neo-antigenic vaccine (as shown by highlighting).

Figure 35:
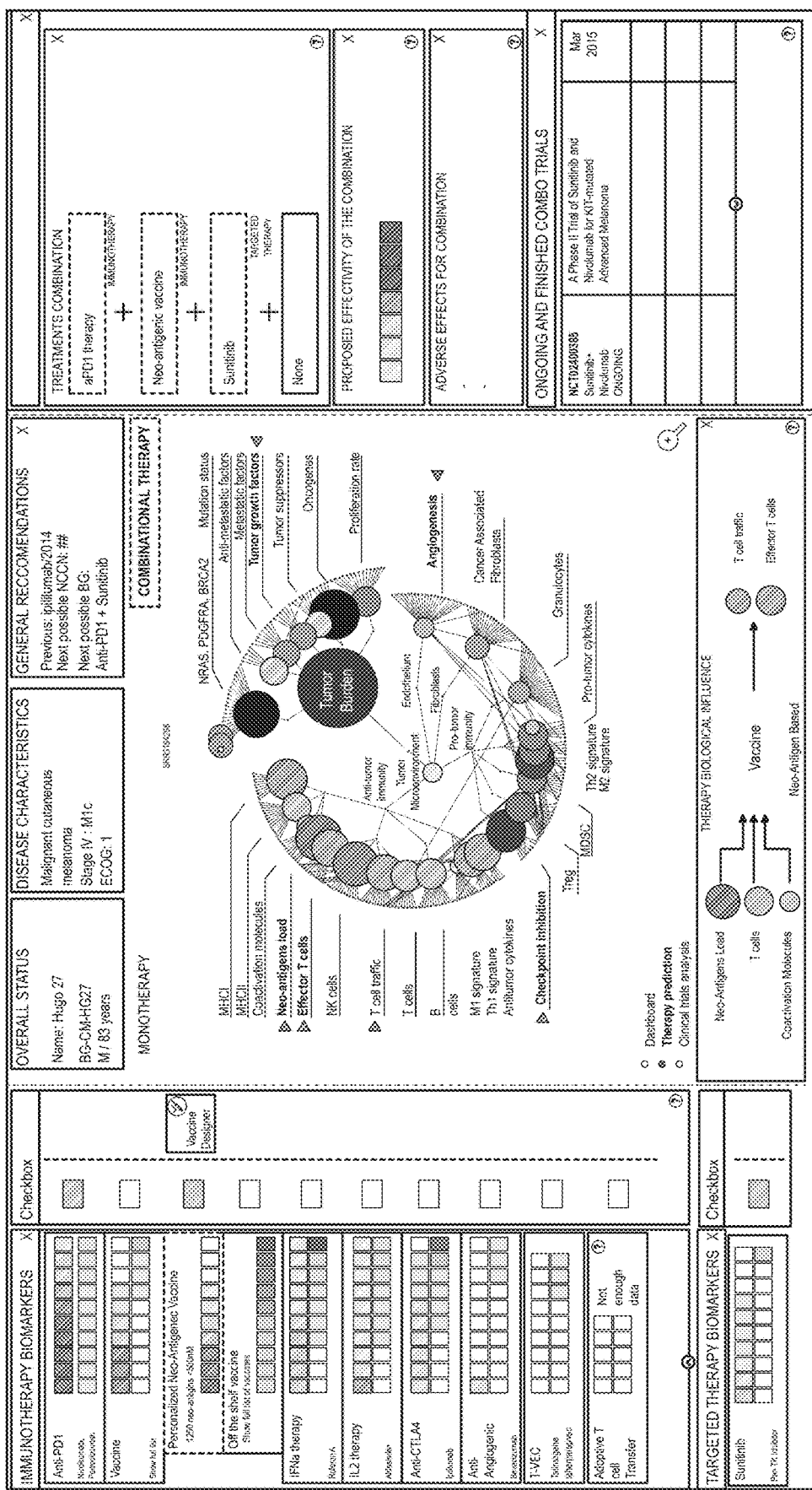
FIG. 35 is a screenshot presenting incorporation of a personalized neo-antigenic vaccine in the combo therapy portion provided to the user in response to the user selecting the personalized neo-antigenic vaccine.

FIG. 35 is a screenshot presenting incorporation of a personalized neo-antigenic vaccine in the combo therapy portion provided to the user in response to the user selecting the personalized neo-antigenic vaccine.

Figure 36:
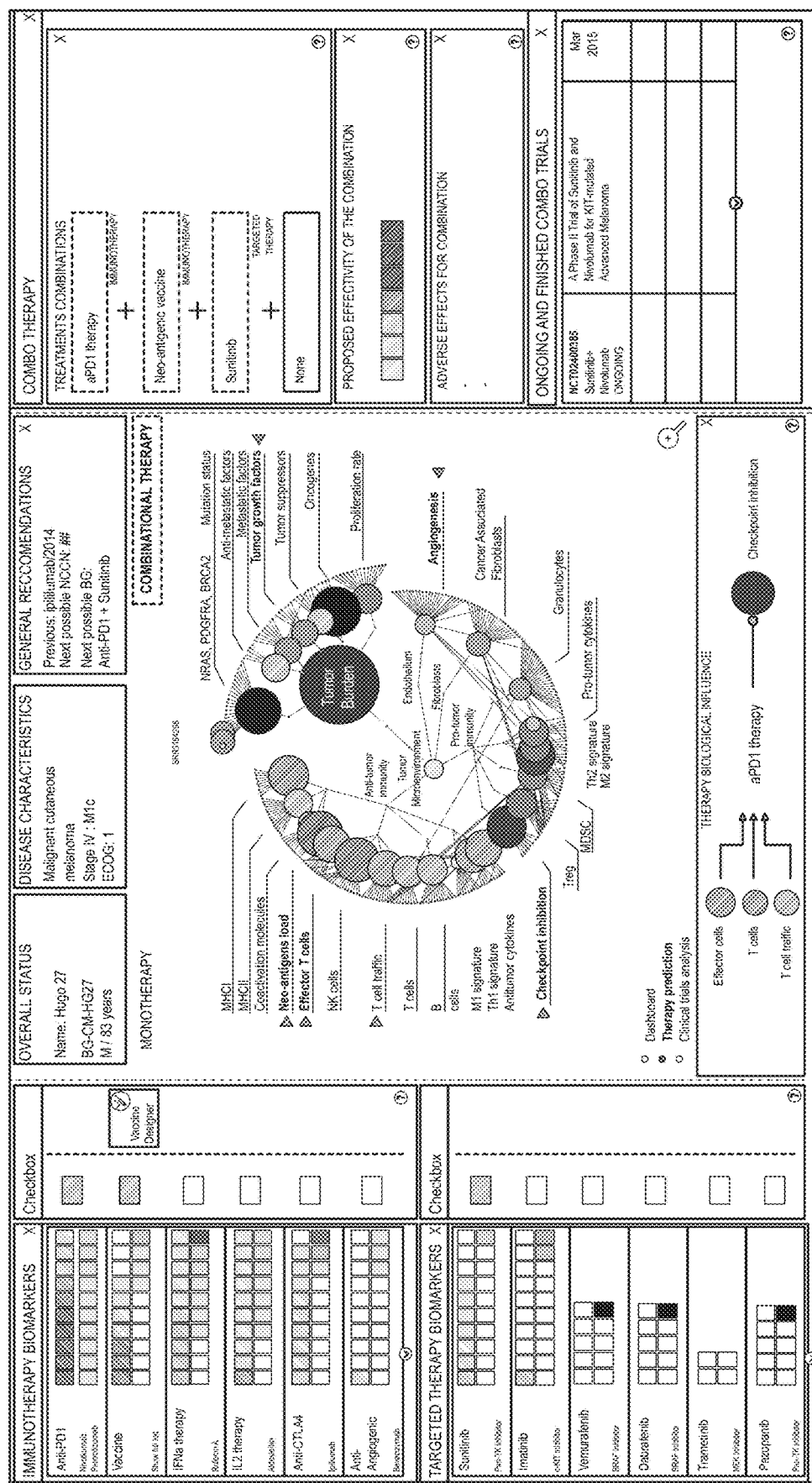
FIG. 36 is a screenshot presenting the personalized neo-antigenic vaccine therapy, anti-PD-1 therapy, and sunitinib therapy in the combo therapy portion provided to the user in response to the user incorporating each of these therapies into the combo therapy portion.

FIG. 36 is a screenshot presenting the personalized neo-antigenic vaccine therapy, anti-PD-1 therapy, and sunitinib therapy in the combo therapy portion provided to the user in response to the user incorporating each of these therapies into the combo therapy portion.

Any one of the therapies in the combination therapy may be substituted for a different therapy. However, a particular combination therapy may be inappropriate for a patient. In response to the user's design of an inappropriate combination therapy, the software will provide an alert to the user indicating that the designed combo therapy is or may be inappropriate for the patient. The user may also receive an alert if the designed combination of therapies has a low effectivity score.

Figure 37:
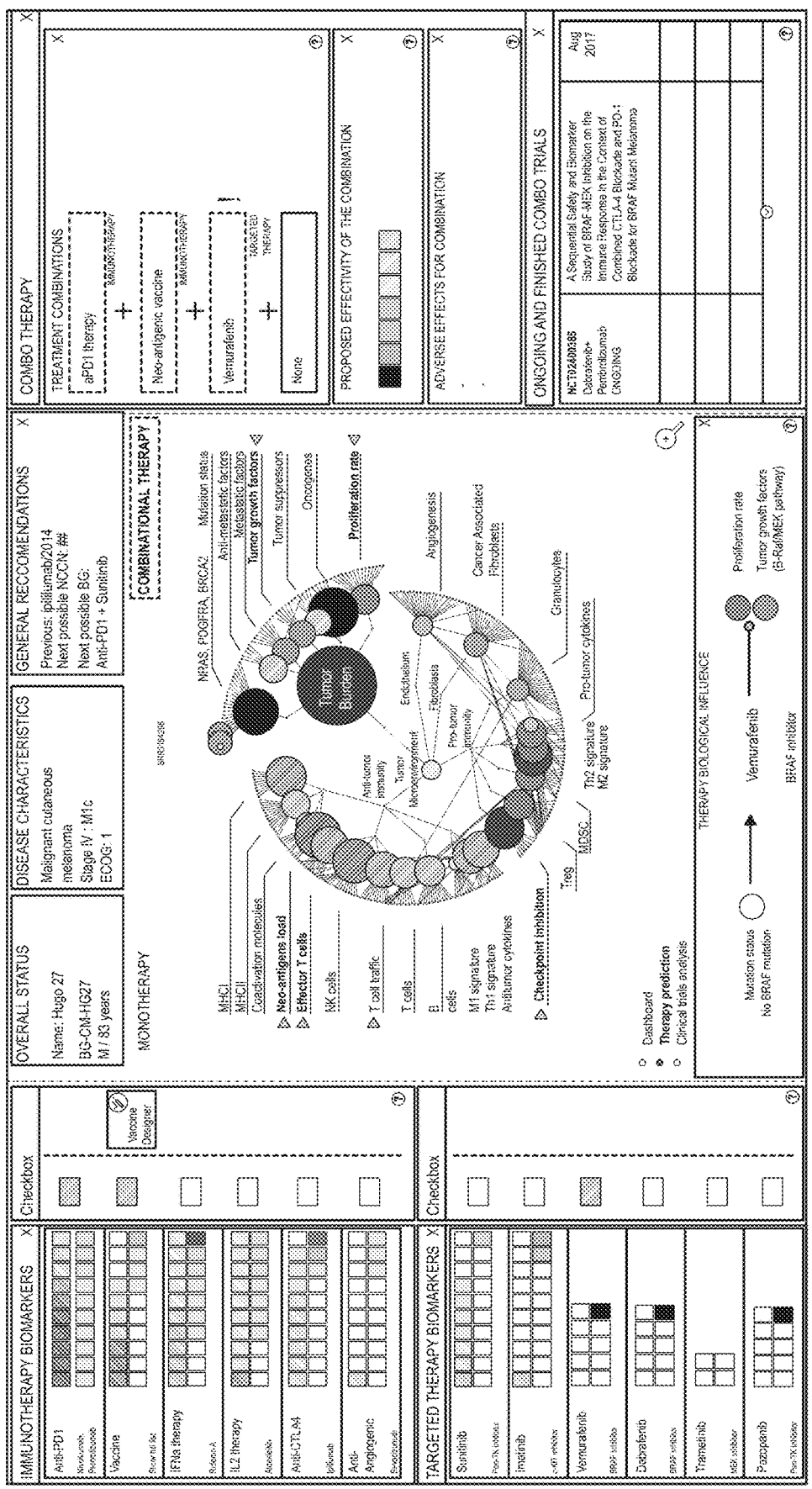
FIG. 37 is a screenshot presenting an alert that substitution of sunitinib therapy with vemurafenib therapy is recognized by the software as an inappropriate combination for the patient.

FIG. 37 is a screenshot presenting an alert that substitution of sunitinib therapy with vemurafenib therapy is recognized by the software as an inappropriate combination for the patient.

Computer Implemented Methods for Generating, Visualizing and Classifying MF Profiles Aspects of the technology described herein provide computer implemented methods for generating, visualizing and classifying molecular-functional (MF) profiles of cancer patients. In some embodiments, a software program may provide a user with a visual representation of a patient's MF profile and/or other information related to a patient's cancer using an interactive graphical user interface (GUI). Such a software program may execute in any suitable computing environment including, but not limited to, a cloud-computing environment, a device co-located with a user (e.g., the user's laptop, desktop, smartphone, etc.), one or more devices remote from the user (e.g., one or more servers), etc.

Figure 2A:
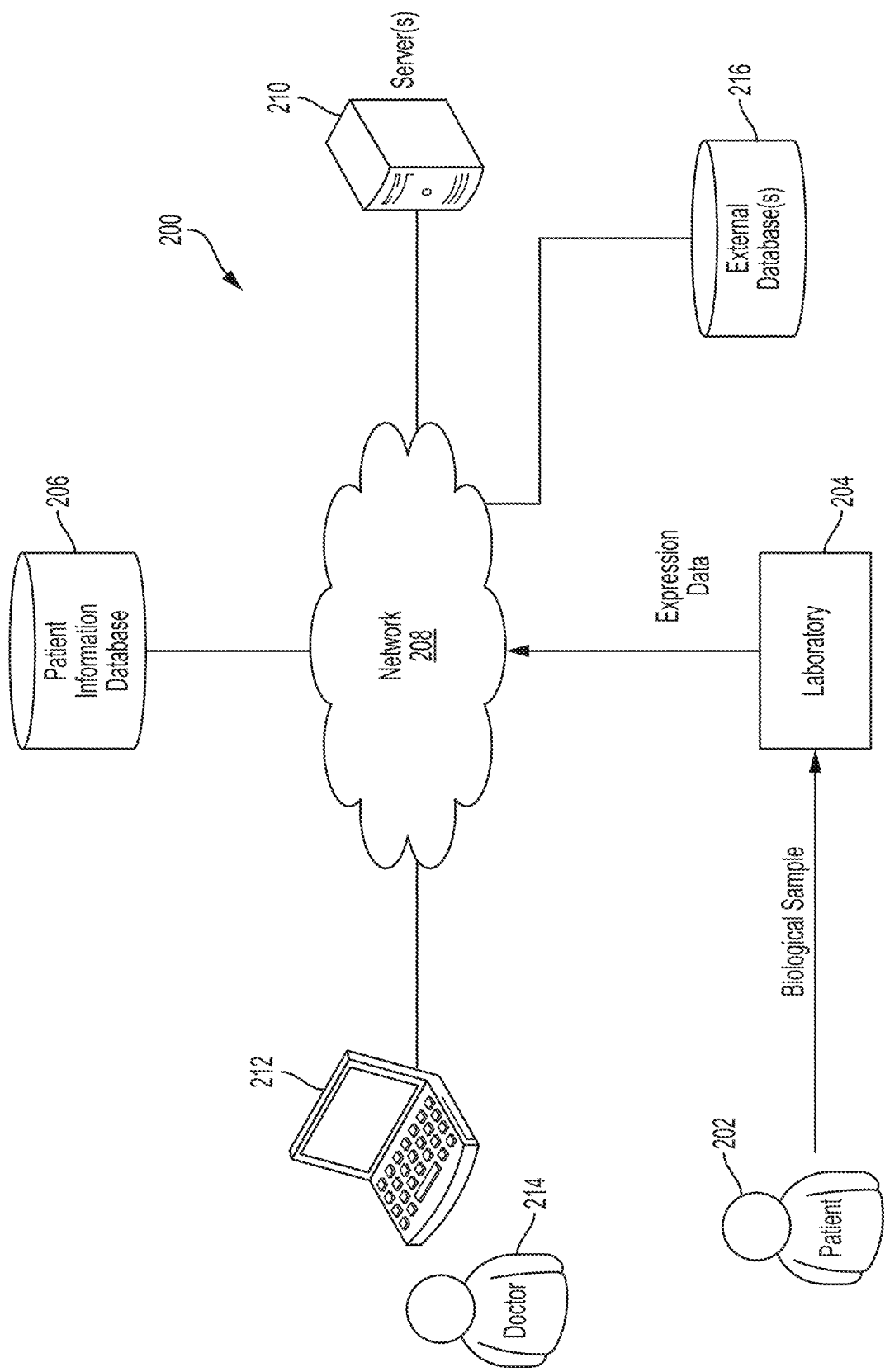
FIG. 2A is a block diagram of an illustrative environment 200 in which some embodiments of the technology described herein may be implemented.

For example, in some embodiments, the techniques described herein may be implemented in the illustrative environment 200 shown in FIG. 2A. As shown in FIG. 2A, within illustrative environment 200, one or more biological samples of a patient 202 may be provided to a laboratory 204. Laboratory 204 may process the biological sample(s) to obtain expression data (e.g., DNA, RNA, and/or protein expression data) and provide it, via network 208, to at least one database 206 that stores information about patient 202.

Network 208 may be a wide area network (e.g., the Internet), a local area network (e.g., a corporate Intranet), and/or any other suitable type of network. Any of the devices shown in FIG. 2A may connect to the network 208 using one or more wired links, one or more wireless links, and/or any suitable combination thereof.

In the illustrated embodiment of FIG. 2A, the at least one database 206 may store expression data for the patient, medical history data for the patient, test result data for the patient, and/or any other suitable information about the patient 202. Examples of stored test result data for the patient include biopsy test results, imaging test results (e.g., MRI results), and blood test results. The information stored in at least one database 206 may be stored in any suitable format and/or using any suitable data structure(s), as aspects of the technology described herein are not limited in this respect. The at least one database 206 may store data in any suitable way (e.g., one or more databases, one or more files). The at least one database 206 may be a single database or multiple databases.

As shown in FIG. 2A, illustrative environment 200 includes one or more external databases 216, which may store information for patients other than patient 202. For example, external databases 216 may store expression data (of any suitable type) for one or more patients, medical history data for one or more patients, test result data (e.g., imaging results, biopsy results, blood test results) for one or more patients, demographic and/or biographic information for one or more patients, and/or any other suitable type of information. In some embodiments, external database(s) 216 may store information available in one or more publically accessible databases such as TCGA (The Cancer Genome Atlas), one or more databases of clinical trial information, and/or one or more databases maintained by commercial sequencing suppliers. The external database(s) 216 may store such information in any suitable way using any suitable hardware, as aspects of the technology described herein are not limited in this respect. In some embodiments, the at least one database 206 and the external database(s) 216 may be the same database, may be part of the same database system, or may be physically co-located, as aspects of the technology described herein are not limited in this respect.

In some embodiments, information stored in patient information database 206 and/or in external database(s) 216 may be used to perform any of the techniques described herein related to determining whether a subject is likely to respond positively or not likely to respond positively to an immune checkpoint blockade therapy. For example, the information stored in the database(s) 206 and/or 216 may be accessed, via network 208, by software executing on server(s) 210 to perform any one or more of the techniques described herein including with reference to FIGS. 39A, 39B, 39C, 39D, 40A and 40B. For example, in some embodiments, server(s) 210 may access information stored in database(s) 206 and/or 216 and use this information to perform process 3900, described with reference to FIG. 39A, for identifying a MF profile cluster with which to associate an MF profile for a subject.

As another example, in some embodiments, server(s) 210 may access information stored in database(s) 206 and/or 216 and use this information to perform process 3920, described with reference to FIG. 39B, for generating MF profile clusters using RNA expression data obtained from subjects having a particular type of cancer.

As another example, in some embodiments, server(s) 210 may access information stored in database(s) 206 and/or 216 and use this information to perform process 3940, described with reference to FIG. 39C, for identifying an MF profile cluster with which to associate an MF profile determined for a subject at least in part by determining the subject's expression levels for multiple gene groups.

As another example, in some embodiments, server(s) 210 may access information stored in database(s) 206 and/or 216 and use this information to perform process 3960, described with reference to FIG. 39D, for generating MF profile clusters using RNA expression data obtained from subjects having a particular type of cancer, and associating a subject with one of the generated MF clusters based on the subject's MF profile.

As another example, in some embodiments, server(s) 210 may access information stored in database(s) 206 and/or 216 and use this information to perform process 4000, described with reference to FIG. 40A, for generating an MF profile for a subject and generating an MF portrait for visualizing the MF profile in a graphical user interface.

As another example, in some embodiments, server(s) 210 may access information stored in database(s) 206 and/or 216 and use this information to perform process 4020, described with reference to FIG. 40B, for presenting a generated personalized graphical user interface (GUI) to a user.

In some embodiments, server(s) 210 may include one or multiple computing devices. When server(s) 210 include multiple computing devices, the device(s) may be physically co-located (e.g., in a single room) or distributed across multi-physical locations. In some embodiments, server(s) 210 may be part of a cloud computing infrastructure. In some embodiments, one or more server(s) 210 may be co-located in a facility operated by an entity (e.g., a hospital, research institution) with which doctor 214 is affiliated. In such embodiments, it may be easier to allow server(s) 210 to access private medical data for the patient 202.

As shown in FIG. 2A, in some embodiments, the results of the analysis performed by server(s) 210 may be provided to doctor 214 through a computing device 214 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 2A, the results are provided to a doctor, in other embodiments, the results of the analysis may be provided to patient 202 or a caretaker of patient 202, a healthcare provider such as a nurse, or a person involved with a clinical trial.

In some embodiments, the results may be part of a graphical user interface (GUI) presented to the doctor 214 via the computing device 212. In some embodiments, the GUI may be presented to the user as part of a webpage displayed by a web browser executing on the computing device 212. In some embodiments, the GUI may be presented to the user using an application program (different from a web-browser) executing on the computing device 212. For example, in some embodiments, the computing device 212 may be a mobile device (e.g., a smartphone) and the GUI may be presented to the user via an application program (e.g., "an app") executing on the mobile device.

The GUI presented on computing device 212 provides a wide range of oncological data relating to both the patient and the patient's cancer in a new way that is compact and highly informative. Previously, oncological data was obtained from multiple sources of data and at multiple times making the process of obtaining such information costly from both a time and financial perspective. Using the techniques and graphical user interfaces illustrated herein, a user can access the same amount of information at once with less demand on the user and with less demand on the computing resources needed to provide such information. Low demand on the user serves to reduce clinician errors associated with searching various sources of information. Low demand on the computing resources serves to reduce processor power, network bandwidth, and memory needed to provide a wide range of oncological data, which is an improvement in computing technology.

Figure 2B:
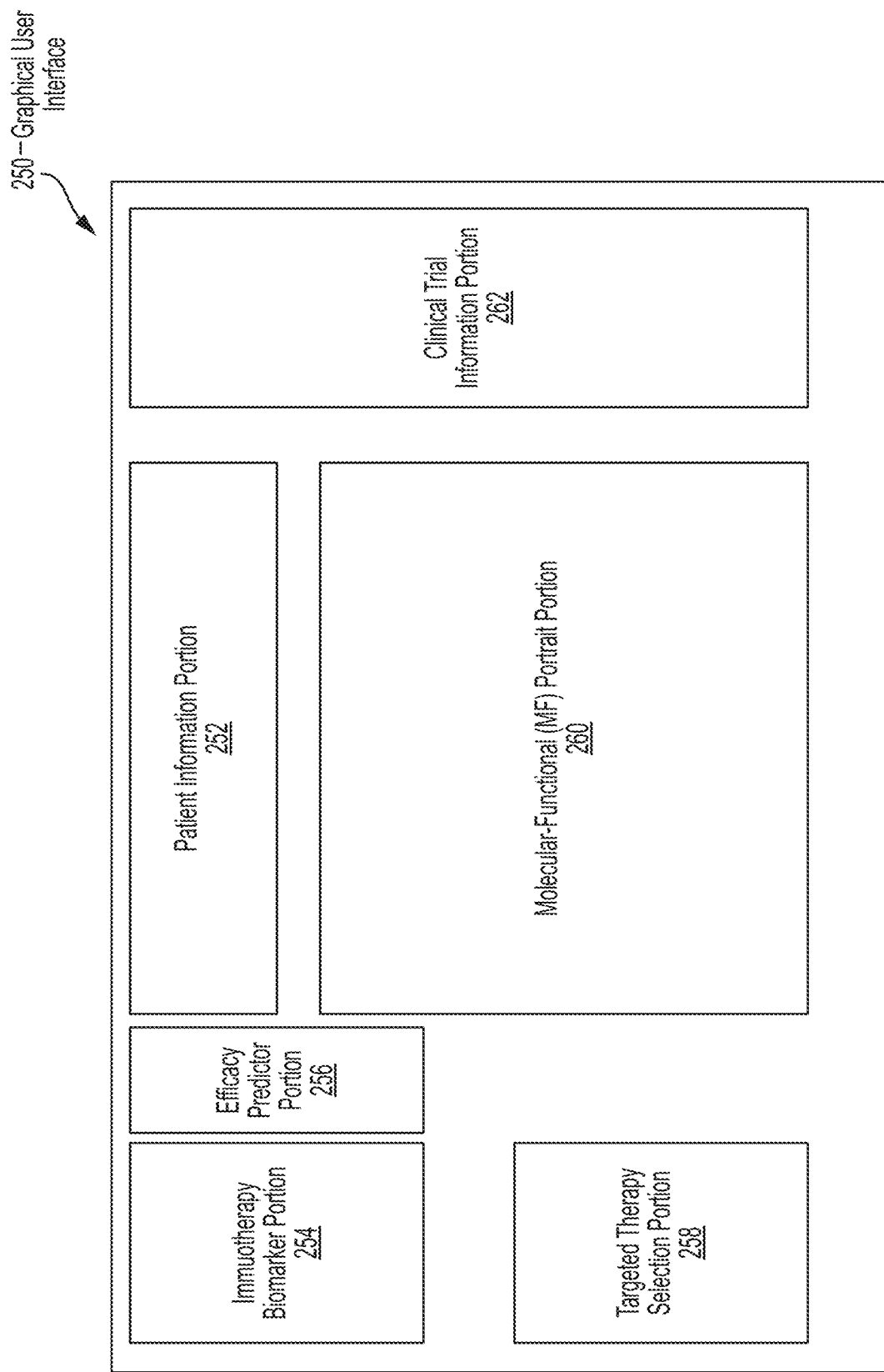
FIG. 2B is a block diagram of an illustrative graphical user interface 250 including patient data that may be presented to a user (e.g., a doctor), in accordance with some embodiments of the technology described herein.

FIG. 2B shows a block diagram of an illustrative GUI 250 containing information about patient 202. GUI 250 may include separate portions providing different types of information about patient 202. Illustrative GUI 150 includes the following portions: Patient Information Portion 252, Molecular-Functional (MF) Portrait Portion 260, Clinical Trial Information Portion 262, Immunotherapy Portion 254, Efficacy Predictor Portion 256, and Targeted Therapy Selection Portion 258.

Patient Information Portion 252 may provide general information about the patient and the patient's cancer. General information about the patient may include such information as the patient's name and date of birth, the patient's insurance provider, and contact information for the patient such as address and phone number. General information about the patient's cancer may include the patient's diagnosis, the patient's history of relapse and/or remission, and information relating to stage of the patient's cancer. Patient Information Portion 252 may also provide information relating to potential treatment options for the patient and/or previously administered treatments.

Molecular-Functional (MF) Portrait Portion 260 may include a molecular functional tumor portrait (MF profile) which refers to a graphical depiction of a tumor with regard to its molecular and cellular composition, and biological processes that are present within and/or surrounding the tumor. Further aspects relating to a patient's MF profile are provided herein.

Clinical Trial Information Portion 262 may include information relating to a clinical trial for a therapy that may be and/or will be administered to the patient. Clinical Trial Information Portion 262 may provide information about an ongoing clinical trial or a completed clinical trial. Information that may be provided in Clinical Trial Information Portion 262 may include information related to a therapy used in the clinical trial such as dosage and dosage regimen, number and diagnosis of patients participating in the clinical trial, and patient outcomes.

Immunotherapy Portion 254 may include patient specific information as it relates to an immunotherapy. Immunotherapy Portion 254 may provide such information for different immunotherapies, for example, immune checkpoint blockade therapies, anti-cancer vaccine therapies, and T cell therapies. Patient specific information relating to an immunotherapy may include information about the patient such as the patient's biomarkers associated with an immunotherapy and/or information about the patient's cancer such as composition of immune cells in the patient's tumor.

Efficacy Predictor Portion 256 may include information indicative of the patient's predicted response to an immunotherapy based on patient specific information presented in Immunotherapy Portion 254. Efficacy Predictor Portion 256 may provide predicted efficacy of an immunotherapy determined, in some embodiments, using a patient's biomarkers as described in International patent application number PCT/US18/37008, entitled "Systems and Methods for Identifying Cancer Treatments from Normalized Biomarker Scores," filed Jun. 12, 2018, the entire contents of which are incorporated herein by reference. Additionally or alternatively, Efficacy Predictor Portion 256 may provide predicted efficacy of an immune checkpoint blockade therapy determined using patient specific information such as gene expression data as described in International patent application number PCT/US18/37018, entitled "Systems and Methods for Identifying Responders and Non-Responders to Immune Checkpoint Blockade Therapy," filed Jun. 12, 2018, the entire contents of which are incorporated herein by reference. Targeted Therapy Selection Portion 258 may include patient specific information as it relates to a targeted therapy. Targeted Therapy Selection Portion 258 may provide such information for different targeted therapies, for example, a kinase inhibitor therapy, a chemotherapy, and anti-cancer antibody therapy. Patient specific information relating to an a targeted therapy may include information about the patient such as the patient's biomarkers associated with a targeted therapy and/or information about the patient's cancer such as whether a mutation is present in the patient's tumor.

Figure 2C:
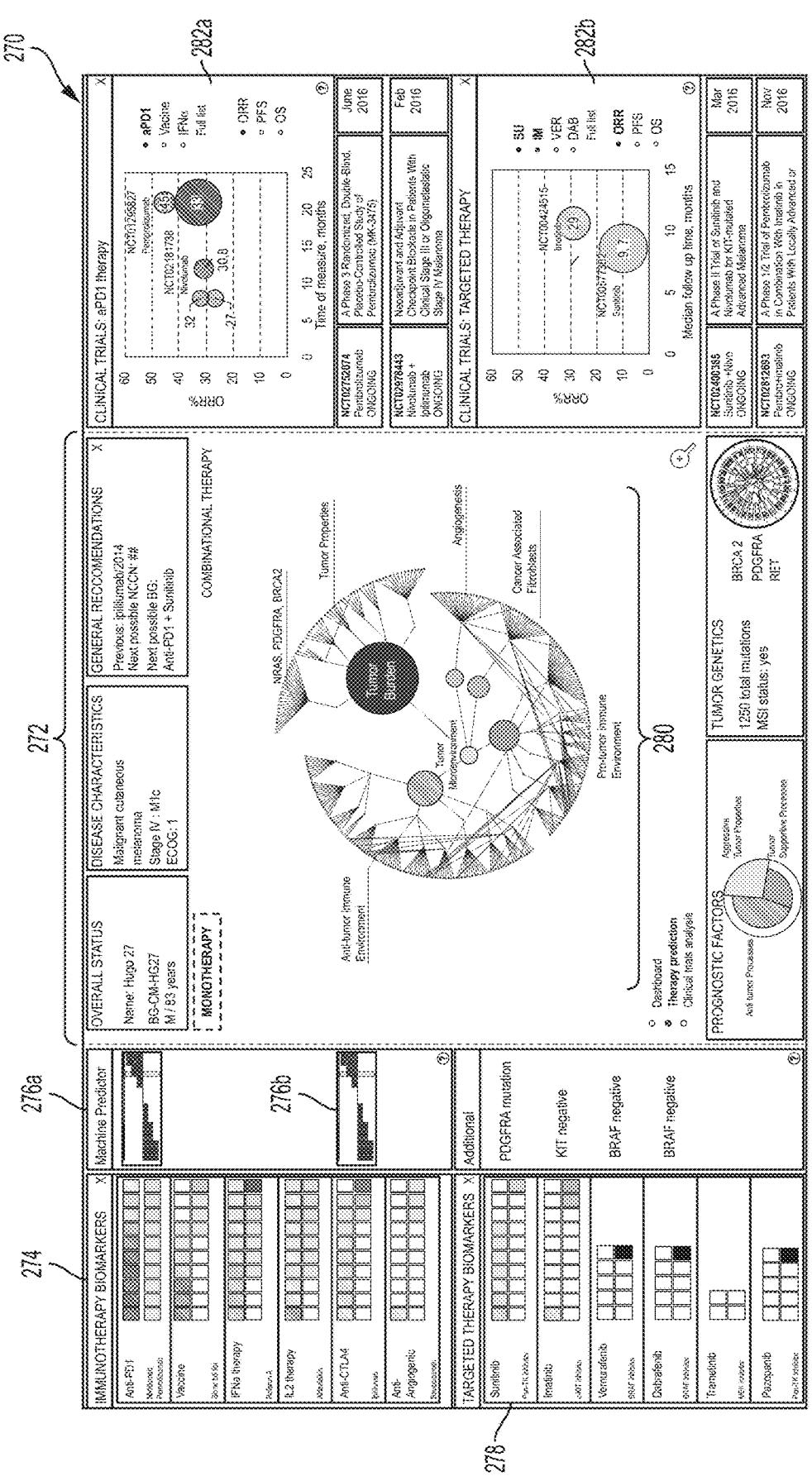
FIG. 2C is an illustrative example of the graphical user interface 250 of FIG. 2B, in accordance with some embodiments of the technology described herein.

An illustrative example of the graphical user interface 250 of FIG. 2B is shown as graphical user interface 270 of FIG. 2C. As shown in FIG. 2C, Patient Information Portion 272 may provide different information in different panels, for example, Overall Status panel, Disease Characteristics panel, and General Recommendations panel. Overall Status panel, in some embodiments, may provide general information about the patient such as patient name and patient age. Disease Characteristics panel, in some embodiments, may provide information about the patient's cancer such as type of cancer and stage of cancer. General Recommendations panel, in some embodiments, may provide previous treatments and possible treatment options for the patient.

Clinical Trial Information Portion 282a provides information relating to a clinical trial for anti-PD-1 therapy. Clinical Trial Information Portion 282a (as shown in the upper portion) shows a graph providing patient overall response rate (ORR) for anti-PD-1 therapy and other therapies such as vaccine or IFNα therapies. A user may select portions of the Clinical Trial Information Portion 282a to access information related to patient progression-free survival (PFS) and/or patient overall survival (OS). Clinical Trial Information Portion 282a (as shown in the lower portion) provides information relating to different clinical trials that may be presented to a user including a brief description of the clinical trial.

Clinical Trial Information Portion 282b provides information relating to a clinical trial for different targeted therapies. Clinical Trial Information Portion 282b (as shown in the upper portion) shows a graph providing patient overall response rate (ORR) for different targeted therapies including sunitinib (SU), imatinib (IM), vemurafenib (VER) and dabrafenib (DAB). A user may select portions of the Clinical Trial Information Portion 282b to access information related to patient progression-free survival (PFS) and/or patient overall survival (OS). Clinical Trial Information Portion 282b (as shown in the lower portion) provides information relating to different clinical trials that may be presented to a user including a brief description of the clinical trial.

Immunotherapy Portion 274 provides patient specific information associated with an immunotherapy and information indicative of the patient's predicted response to that immunotherapy. Immunotherapy Portion 274 provides such information for anti-PD-1 therapy, a therapeutic cancer vaccine, IFNα therapy, IL2 therapy, anti-CTLA4 therapy, and anti-angiogenic therapy. Patient specific information shown in Immunotherapy Portion 274 includes the patient's biomarker information relating to various immunotherapies and the patient's therapy scores calculated from their biomarkers.

Efficacy Predictor Portion 276a provides information indicative of the patient's predicted response to anti-PD-1 therapy based on patient specific information presented in Immunotherapy Portion 274. Efficacy Predictor Portion 276b provides information indicative of the patient's predicted response to anti-CTLA4 therapy based on patient specific information presented in Immunotherapy Portion 274.

Targeted Therapy Selection Portion 278 provides patient specific information associated with a targeted therapy and information indicative of the patient's predicted response to the targeted therapy. Targeted Therapy Selection Portion 278 provides such information for sunitinib (SU), imatinib (IM), vemurafenib (VER), dabrafenib (DAB), trametinib, and pazopanib. Patient specific information shown in Targeted Therapy Selection Portion 278 includes a patient's biomarker information relating to various targeted therapies and the patient's therapy scores calculated from their biomarkers.

Figure 38:
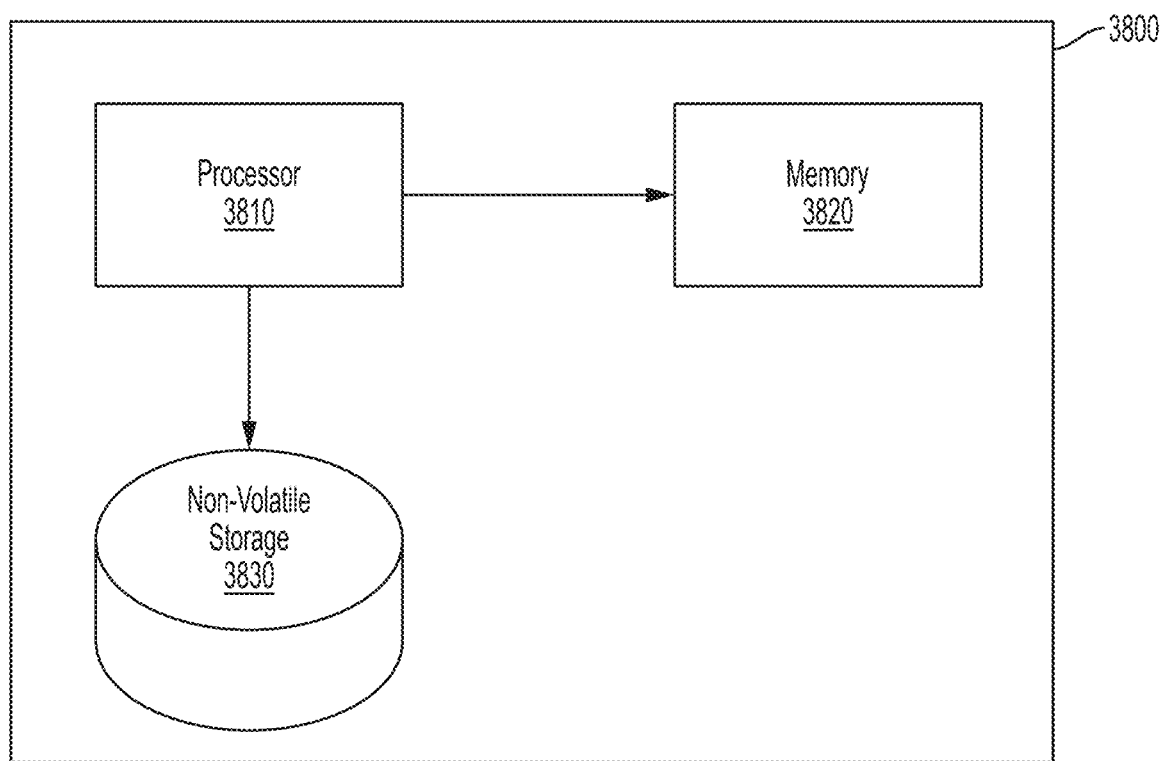
FIG. 38 is a block diagram of an illustrative computer system that may be used in implementing some embodiments of the technology described herein.

An illustrative implementation of a computer system 3800 that may be used in connection with any of the embodiments of the technology described herein is shown in FIG. 38. The computer system 600 may include one or more computer hardware processors 3800 and one or more articles of manufacture that comprise non-transitory computer-readable storage media (e.g., memory 3820 and one or more non-volatile storage devices 3830). The processor(s) 3810 may control writing data to and reading data from the memory 3820 and the non-volatile storage device(s) 3830 in any suitable manner. To perform any of the functionality described herein, the processor(s) 3810 may execute one or more processor-executable instructions stored in one or more non-transitory computer-readable storage media (e.g., the memory 3820), which may serve as non-transitory computer-readable storage media storing processor-executable instructions for execution by the processor(s) 3810.

Systems and methods described herein provide for calculating an MF profile of a subject and associating the MF profile with an existing MF profile cluster. For example, computer-implemented processes for calculating a MF profile of a subject and associating the calculated MF profile with an existing MF profile cluster are described with reference to FIGS. 39A and 39C.

Figure 39A:
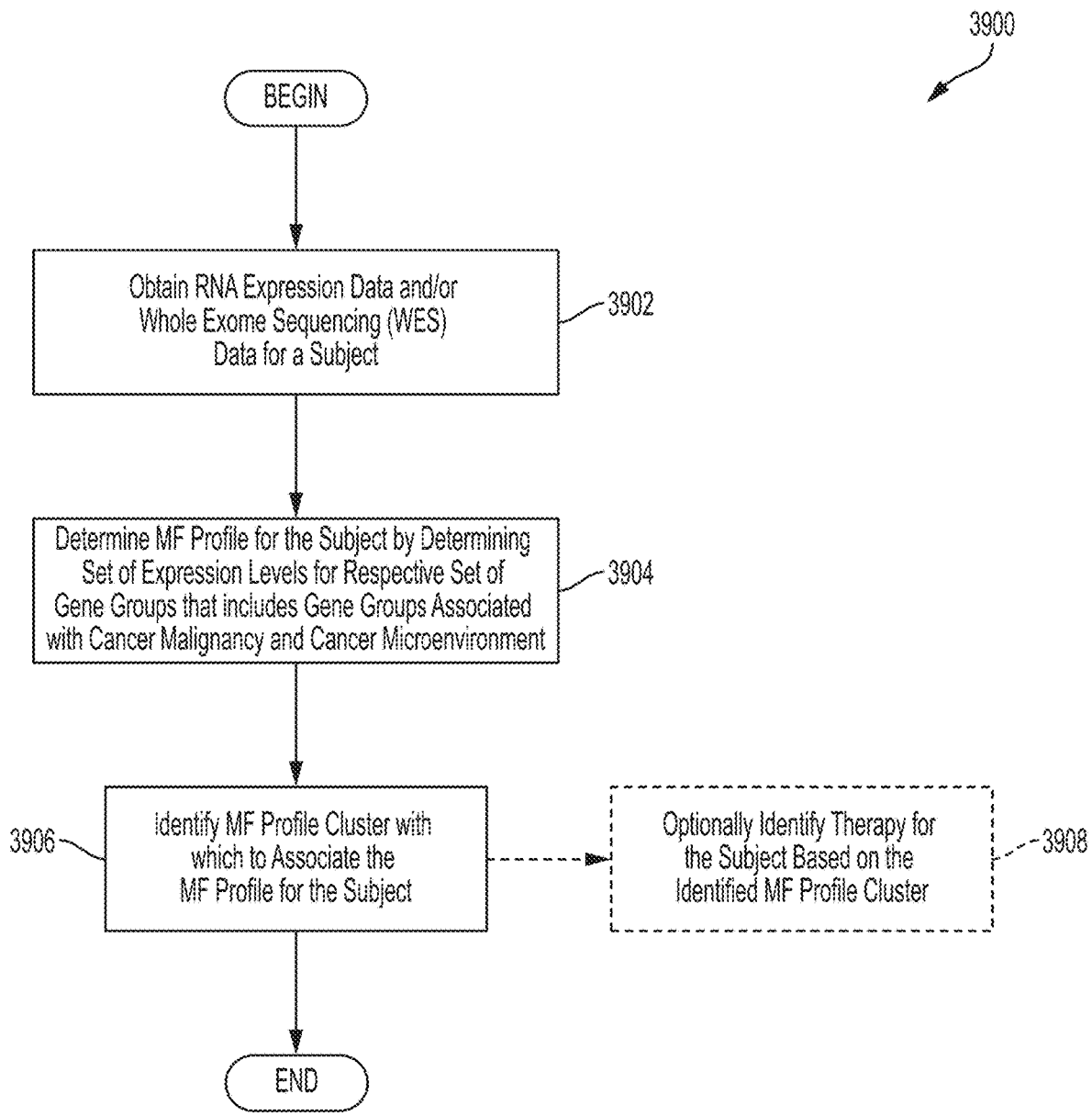
FIG. 39A is a flowchart of an illustrative process 3900 for identifying an MF profile cluster with which to associate an MF profile for a subject, in accordance with some embodiments of the technology described herein.

FIG. 39A is a flowchart of an illustrative computer-implemented process 3900 for identifying a MF profile cluster with which to associate an MF profile for a subject (e.g., a cancer patient), in accordance with some embodiments of the technology described herein. Process 3900 may be performed by any suitable computing device(s). For example, may be performed by a laptop computer, a desktop computer, one or more servers, in a cloud computing environment, or in any other suitable way.

Process 3900 begins at act 3902, where RNA expression data and/or whole exome sequencing (WES) data for a subject is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section titled "Obtaining Expression Data".

Next, process 3900 proceeds to act 3904, where the MF profile for the subject is determined by determining a set of expression levels for a respective set of gene groups that includes gene groups associated with cancer malignancy and cancer microenvironment. The MF profile may be determined for a subject having any type of cancer, including any of the types described herein. The MF profile may be determined using any number of gene groups that relate to compositions and processes present within and/or surrounding the subject's tumor. Gene group expression levels, in some embodiments, may be calculated as a gene set enrichment (GSEA) score for the gene group. Further aspects relating to determining MF profiles are provided in section titled "MF Profiles".

Next, process 3900 proceeds to act 3906, where a MF profile cluster with which to associate the MF profile of the subject is identified. The MF profile of the subject may be associated with any of the types of MF profile clusters types described herein. A subject's MF profile may be associated with one or multiple of the MF profile clusters in any suitable way. For example, an MF profile may be associated with one of the MF profile clusters using a similarity metric (e.g., by associating the MF profile with the MF profile cluster whose centroid is closest to the MF profile according to the similarity metric). As another example, a statistical classifier (e.g., k-means classifier or any other suitable type of statistical classifier) may be trained to classify the MF profile as belonging to one or multiple of the MF clusters. Further aspects relating to determining MF profiles are provided in section "MF Profiles".

Optionally, process 3900 proceeds to act 3908, where a therapy for the subject is identified based on the identified MF profile cluster. The identified therapy may be any type of anti-cancer therapy depending on the patient's cancer and their identified MF profile cluster. A single anti-cancer therapy or a combination of anti-cancer therapies may be identified in act 3908. Identifying a therapy based on the MF profile cluster includes excluding those therapies that may be ineffective or harmful to the subject in order to identify a suitable therapy for the subject. Further aspects related to using a patient's identified MF profile cluster for clinical purposes are provided in section "Applications".

The MF profile of the subject may be output to a user, in some embodiments, by displaying the MF profile to the user in a graphical user interface (GUI), including the information about the MF profile in a report, sending an email to the user, and/or in any other suitable way. For example, the MF profile of the subject and other patient related information may be provided to a user in a GUI as shown in FIGS. 3-37.

In this way, a patient's MF profile can be identified and used for various clinical purposes including assessing the efficacy of a treatment for cancer and/or evaluating suitability of a patient for participating in a clinical trial.

Figure 39B:
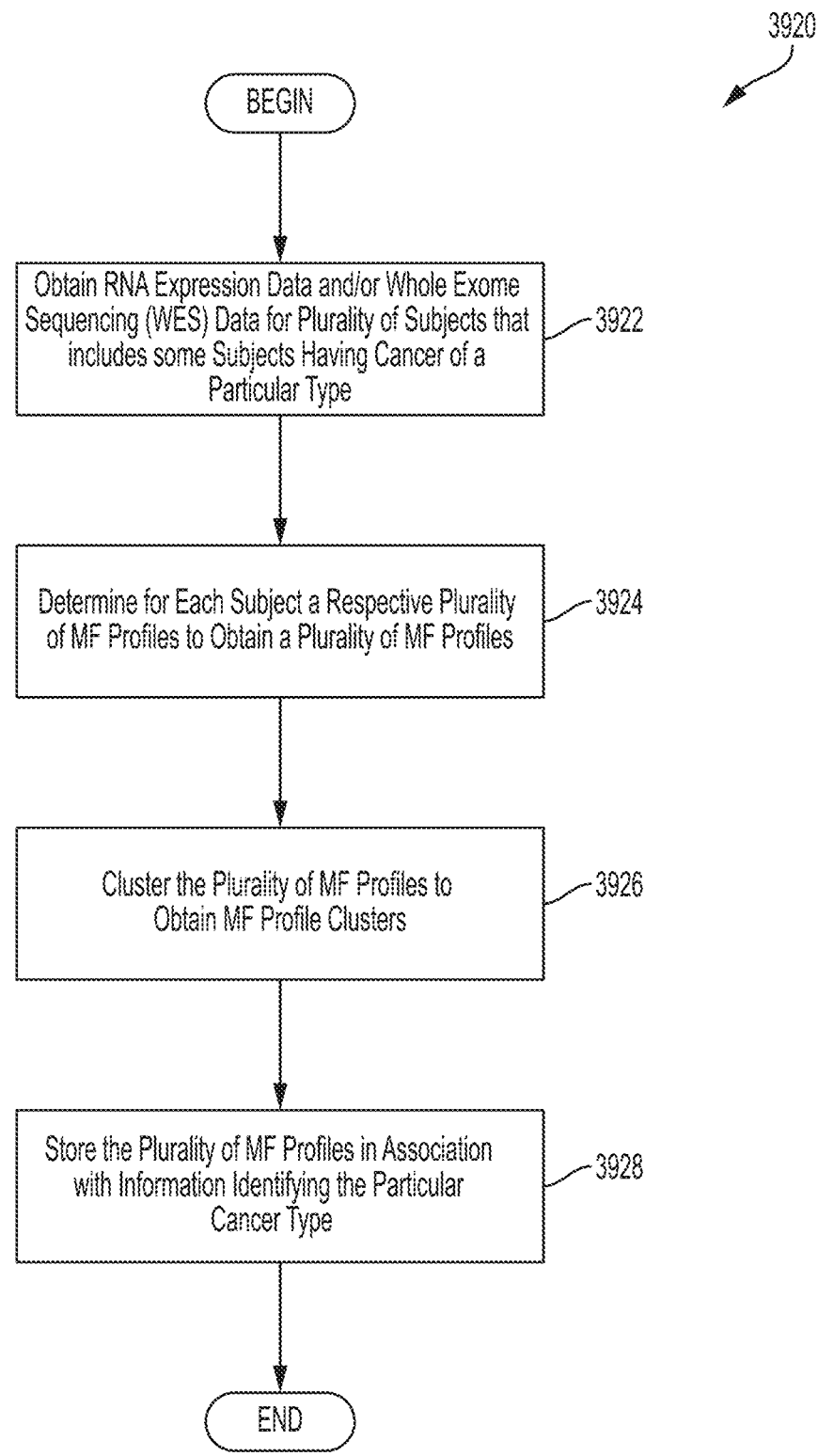
FIG. 39B is a flowchart of an illustrative process 3920 for generating MF profile clusters using RNA expression data obtained from subjects having a particular type of cancer, in accordance with some embodiments of the technology described herein.
Figure 39C:
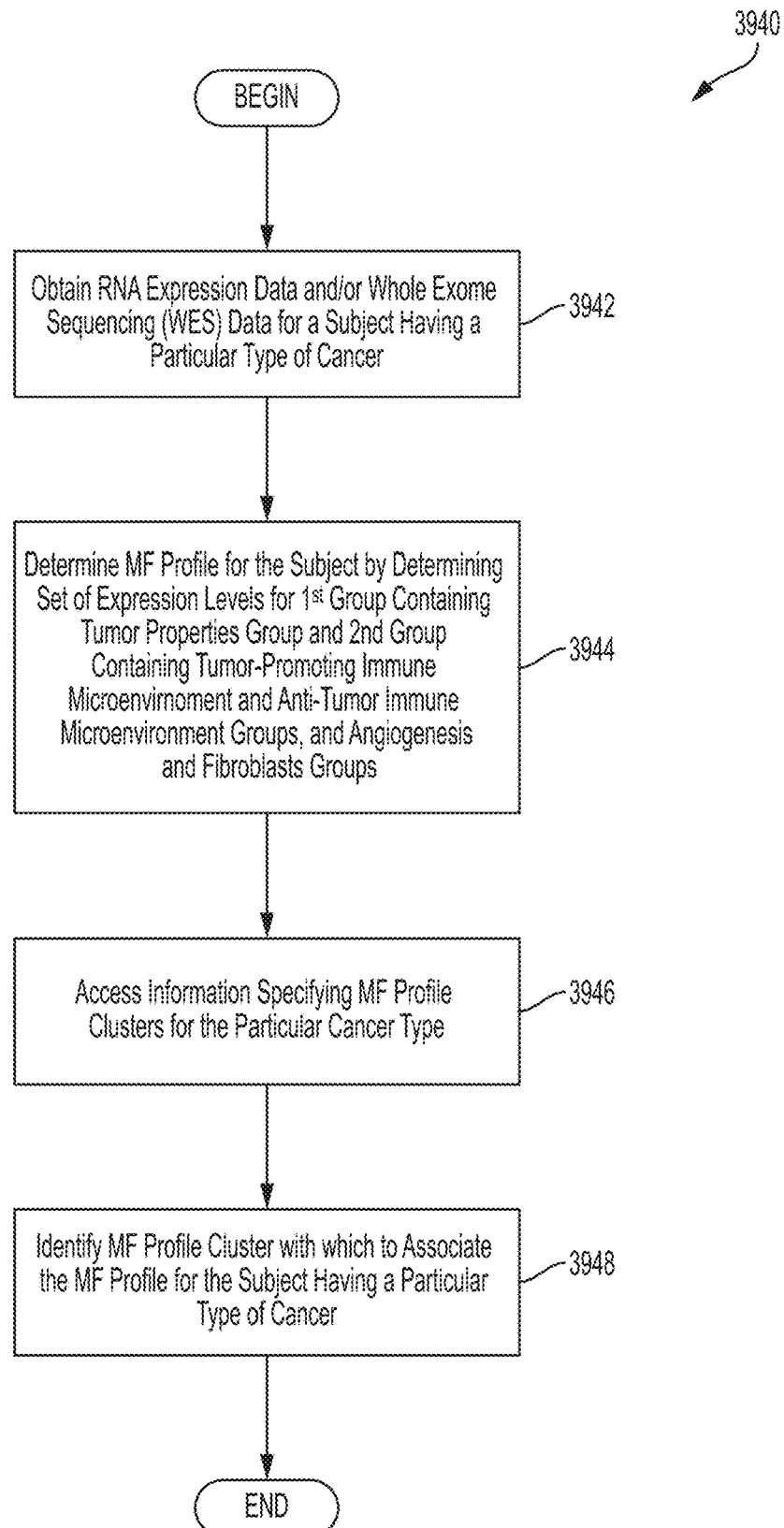
FIG. 39C is a flowchart of an illustrative process 3940 for identifying an MF profile cluster with which to associate an MF profile determined for a subject at least in part by determining the subject's expression levels for multiple gene groups, in accordance with some embodiments of the technology described herein.

FIG. 39C is a flowchart of an illustrative computer-implemented process 3940 for identifying an existing MF profile cluster with which to associate a MF profile for a subject (e.g., a cancer patient), in accordance with some embodiments of the technology described herein. Process 3940 may be performed by any suitable computing device (s). For example, may be performed by a laptop computer, a desktop computer, one or more servers, in a cloud computing environment, or in any other suitable way.

Process 3940 begins at act 3942, where RNA expression data and/or whole exome sequencing (WES) data for a subject having a particular type of cancer is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data".

Next, process 3940 proceeds to act 3944, where the MF profile for the subject is determined by determining a set of expression levels for a respective set of gene groups that includes at least one gene group associated with cancer malignancy and at least four gene groups associated with cancer microenvironment. The at least one gene group associated with cancer malignancy, in some embodiments, consists of a tumor properties gene group. The at least four gene groups associated with cancer microenvironment, in some embodiments, consists of tumor-promoting immune microenvironment group, anti-tumor immune microenvironment group, angiogenesis group, and fibroblasts group.

It should be appreciated that act 3944 may be performed using any number of gene groups associated with cancer malignancy and cancer microenvironment. For example, MF profiles may be determined using set of gene groups that includes 19 gene groups where the gene groups associated with cancer malignancy consists of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group, and the gene groups associated with cancer microenvironment consists of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group.

In another example, MF profiles may be determined using set of gene groups that includes 30 gene groups where the gene groups associated with cancer malignancy consists of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group, and the gene groups associated with cancer microenvironment consists of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group.

The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "MF Profiles".

Next, process 3940 proceeds to act 3946, where information specifying MF profile clusters for the particular cancer type are accessed. Different MF profile clusters are accessed for different cancers. For example, MF profile clusters associated with lung cancer are accessed when process 3940 is performed for a patient having lung cancer and MF profile clusters associated with melanoma are accessed when process 3940 is performed for a patient having melanoma. Any number of MF profile clusters for the particular cancer may be accessed including at least two, at least 5, at least 10 or at least 20. The number of accessed MF profiles, in some embodiments, may be between 2-20, between 2-10, or between 15-20. The number of accessed MF profile clusters may vary depending on the particular cancer with which the MF profile clusters are associated. For example, 5 MF profile clusters may be accessed when the particular cancer type is lung cancer and 12 MF profile clusters may be accessed when the particular cancer is melanoma. Accessing information specifying MF profile clusters for the particular cancer may include accessing information from a variety of sources and/or a variety of databases.

Next, process 3940 proceeds to act 3948, where a MF profile cluster with which to associate the MF profile of the subject is identified. The MF profile of the subject may be associated with any of the types of MF profile clusters types described herein. A subject's MF profile may be associated with one or multiple of the MF profile clusters in any suitable way. For example, an MF profile may be associated with one of the MF profile clusters using a similarity metric (e.g., by associating the MF profile with the MF profile cluster whose centroid is closest to the MF profile according to the similarity metric). As another example, a statistical classifier (e.g., k-means classifier or any other suitable type of statistical classifier) may be trained to classify the MF profile as belonging to one or multiple of the MF clusters. Further aspects relating to determining MF profiles are provided in section "MF Profiles".

The MF profile of the subject may be output to a user, in some embodiments, by displaying the MF profile to the user in a graphical user interface (GUI), including the information about the MF profile in a report, sending an email to the user, and/or in any other suitable way. For example, the MF profile of the subject and other patient related information may be provided to a user in a GUI as shown in FIGS. 3-37.

In this way, a patient's MF profile can be identified and used for various clinical purposes including assessing the efficacy of a treatment for cancer and/or evaluating suitability of a patient for participating in a clinical trial.

Systems and methods described herein provide for generating MF profile clusters and for generating a MF profile for a patient and associating that MF profile to a generated MF cluster. For example, a computer-implemented process 3920 for generating MF profile clusters using RNA expression data obtained from subjects having a particular type of cancer is described with reference to FIG. 39B. As another example, a computer-implemented process 3960 for generating MF profile clusters using RNA expression data obtained from subjects having a particular type of cancer, and associating a subject with one of the generated MF clusters based on the subject's MF profile is described with reference to FIG. 39D.

FIG. 39B is a flowchart of an illustrative computer-implemented process 3920 for generating MF profile clusters using expression data obtained from subjects having a particular type of cancer, in accordance with some embodiments of the technology described herein. MF profile clusters may be generated for any cancer using expression data obtained from patients having that type of cancer. For example MF profile clusters associated with melanoma may be generated using expression data from melanoma patients. In another example MF profile clusters associated with lung cancer may be generated using expression data from lung cancer patients.

Process 3920 begins at act 3922, where RNA expression data and/or whole exome sequencing (WES) data for a plurality of subjects having a particular cancer are obtained. The plurality of subjects for which expression data is obtained may comprise any number of patients having a particular cancer. For example, expression data may be obtained for a plurality of melanoma patients, for example, 100 melanoma patients, 1000 melanoma patients, or any number of melanoma patients as the technology is not so limited. RNA expression data may be acquired using any method known in the art, e.g., whole transcriptome sequencing, total RNA sequencing, and mRNA sequencing. Further aspects relating to obtaining expression data are provided in section "Obtaining Expression Data".

Next, process 3920 proceeds to act 3924, where the MF profile for each subject in the plurality of subject is determined by determining a set of expression levels for a respective set of gene groups that includes gene groups associated with cancer malignancy and cancer microenvironment. MF profiles may be determined using any number of gene groups that relate to compositions and processes present within and/or surrounding the subject's tumor. Gene group expression levels, in some embodiments, may be calculated as a gene set enrichment (GSEA) score for the gene group. Further aspects relating to determining MF profiles are provided in section titled "MF Profiles".

Next, process 3920 proceeds to act 3926, where the plurality of MF profiles are clustered to obtain MF profile clusters. MF profiles may be clustered using any of the techniques described herein including, for example, community detection clustering, dense clustering, k-means clustering, or hierarchical clustering. MF profiles may be clustered for any type of cancer using MF profiles generated for patients having that type of cancer. MF profile clusters, in some embodiments, comprises a $1^{st}$ MF profile cluster, a $2^{nd}$ MF profile cluster, a $3^{rd}$ MF profile, and a $4^{th}$ MF profile. The relative sizes of $1^{st}$-$4^{th}$ MF clusters may vary among cancer types. For example, the size of the $3^{rd}$ MF profile cluster (shown as C) was larger for ACC (adrenocortical carcinoma) than that of BLCA (bladder urothelial carcinoma. MF profiles were clustered for different cancers as shown in Example 4. Further aspects relating to MF profile clusters are provided in section titled "MF profiles".

Next, process 3920 proceeds to act 3928, where the plurality of MF profiles in association with information identifying the particular cancer type are stored. MF profiles may be stored in a database in any suitable format and/or using any suitable data structure(s), as aspects of the technology described herein are not limited in this respect. The database may store data in any suitable way, for example, one or more databases and/or one or more files. The database may be a single database or multiple databases.

In this way, MF profile clusters can be stored and used as existing MF profile clusters with which a patient's MF profile can be associated. Existing MF profiles clusters, in some embodiments, may be associated with a patient's MF profile generated using five gene groups, 19 gene groups, or 30 gene groups as described with respect to FIG. 39C.

Figure 39D:
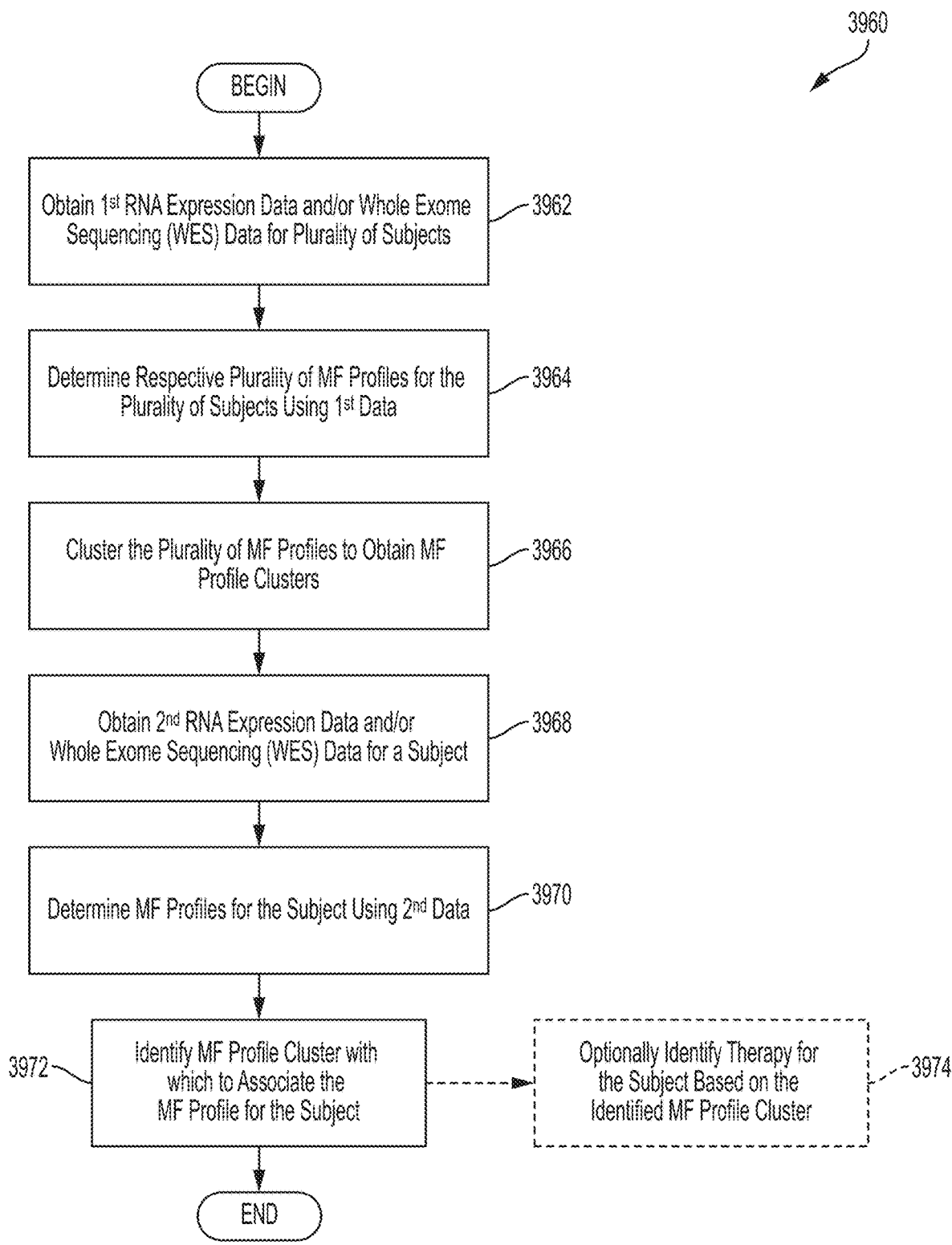
FIG. 39D is a flowchart of an illustrative process 3960 for generating MF profile clusters using RNA expression data obtained from subjects having a particular type of cancer, and associating a subject with one of the generated MF clusters based on the subject's MF profile, in accordance with some embodiments of the technology described herein.

FIG. 39D is a flowchart of an illustrative computer-implemented process 3960 for generating MF profile clusters using expression data obtained from subjects having a particular type of cancer, and associating a subject with one of the generated MF clusters based on the subject's MF profile, in accordance with some embodiments of the technology described herein. Process 3960 may be performed by any suitable computing device(s). For example, may be performed by a laptop computer, a desktop computer, one or more servers, in a cloud computing environment, or in any other suitable way.

Process 3960 begins at act 3962, where RNA expression data and/or whole exome sequencing (WES) data for each subject in a plurality of subjects having a particular type of cancer is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data".

Next, process 3960 proceeds to act 3964, where the MF profile for each subject in the plurality of subjects is determined by determining a set of expression levels for a respective set of gene groups that includes at least one gene group associated with cancer malignancy and at least four gene groups associated with cancer microenvironment. The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "MF Profiles".

Next, process 3960 proceeds to act 3966, where the plurality of MF profiles are clustered to obtain MF profile clusters. MF profiles may be clustered using any of the techniques described herein including, for example, community detection clustering, dense clustering, k-means clustering, or hierarchical clustering. MF profiles may be clustered for any type of cancer using MF profiles generated for patients having that type of cancer. MF profile clusters, in some embodiments, comprises a $1^{st}$ MF profile cluster, a $2^{nd}$ MF profile cluster, a $3^{rd}$ MF profile, and a $4^{th}$ MF profile. The relative sizes of $1^{st}$-$4^{th}$ MF clusters may vary among cancer types. For example, the size of the $3^{rd}$ MF profile cluster (shown as C) was larger for ACC (adrenocortical carcinoma) than that of BLCA (bladder urothelial carcinoma. MF profiles were clustered for different cancers as shown in Example 4. Further aspects relating to MF profile clusters are provided in section titled "MF profiles".

Next, process 3960 proceeds to act 3968, where RNA expression data and/or whole exome sequencing (WES) data for an additional subject is obtained. Expression data for an additional subject may be obtained by any suitable means as described in further detail in section "Obtaining Expression Data". Expression data for the additional subject may be obtained in the same manner used for obtaining expression data of the plurality of subjects. Alternatively or in addition to, expression data for the additional subject may be obtained in a manner different from that used to obtain expression data of the plurality of subjects. Further aspects relating to obtaining expression data are provided in section "Obtaining Expression Data".

Next, process 3960 proceeds to act 3970, where MF profiles for the additional subject are determined using the additional subject's expression data. The MF profile for the additional subject is determined by determining a set of expression levels for a respective set of gene groups that includes at least one gene group associated with cancer malignancy and at least four gene groups associated with cancer microenvironment. The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "MF Profiles".

Next, process 3960 proceeds to act 3972, where a MF profile cluster with which to associate the MF profile of the subject is identified. The MF profile of the subject may be associated with any of the types of MF profile clusters determined in act 3966. A subject's MF profile may be associated with one or multiple of the MF profile clusters in any suitable way. For example, an MF profile may be associated with one of the MF profile clusters using a similarity metric (e.g., by associating the MF profile with the MF profile cluster whose centroid is closest to the MF profile according to the similarity metric). As another example, a statistical classifier (e.g., k-means classifier or any other suitable type of statistical classifier) may be trained to classify the MF profile as belonging to one or multiple of the MF clusters. Further aspects relating to determining MF profiles are provided in section "MF Profiles".

Optionally, process 3960 proceeds to act 3974, where a therapy for the subject is identified based on the identified MF profile cluster. The identified therapy may be any type of anti-cancer therapy depending on the patient's cancer and their identified MF profile cluster. A single anti-cancer therapy or a combination of anti-cancer therapies may be identified in act 3974. Identifying a therapy based on the MF profile cluster includes excluding those therapies that may be ineffective or harmful to the subject in order to identify a suitable therapy for the subject. Further aspects related to using a patient's identified MF profile cluster for clinical purposes are provided in section "Applications".

The MF profile of the subject may be output to a user, in some embodiments, by displaying the MF profile to the user in a graphical user interface (GUI), including the information about the MF profile in a report, sending an email to the user, and/or in any other suitable way. For example, the MF profile of the subject and other patient related information may be provided to a user in a GUI as shown in FIGS. 3-37.

In this way, a patient's MF profile can be identified and used for various clinical purposes including assessing the efficacy of a treatment for cancer and/or evaluating suitability of a patient for participating in a clinical trial.

Systems and methods described herein provide for generating a MF profile for a patient and generating a visualization of the generated MF profile as a MF portrait. For example, a computer-implemented process for generating a MF profile and an associated MF portrait is shown in FIG. 40A, and a computer-implemented process for generating a MF profile using five gene groups and an associated MF portrait is shown in FIG. 40B.

Figure 40A:
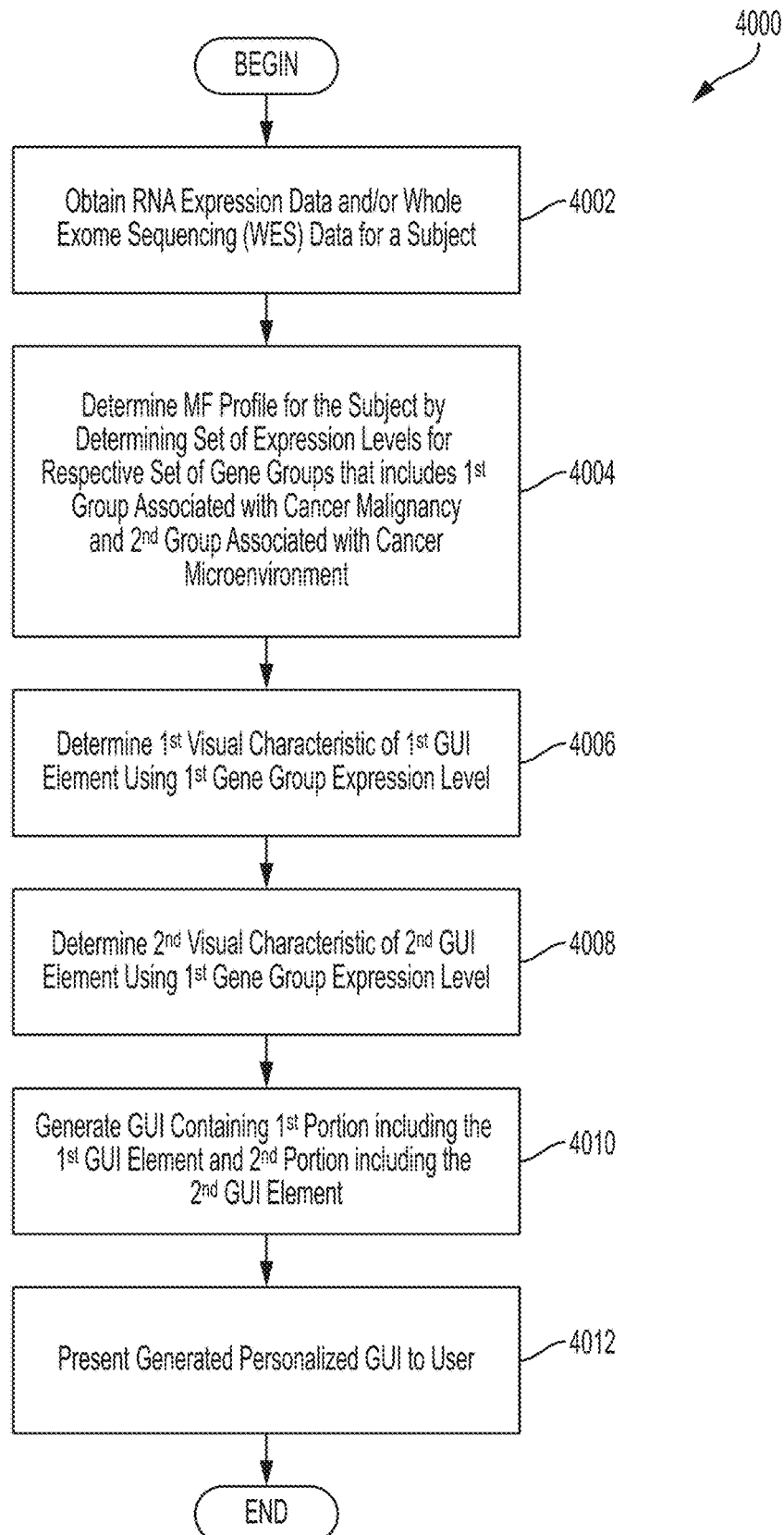
FIG. 40A is a flowchart of an illustrative process 4000 for generating an MF profile and generating an MF portrait for visualizing the MF profile in a graphical user interface (GUI), in accordance with some embodiments of the technology described herein.

FIG. 40A is a flowchart of an illustrative computer-implemented process 4000 for generating a MF profile and an associated MF portrait, in accordance with some embodiments of the technology described herein. Process 4000 may be performed by any suitable computing device(s). For example, may be performed by a laptop computer, a desktop computer, one or more servers, in a cloud computing environment, or in any other suitable way.

Process 4000 begins at act 4002, where RNA expression data and/or whole exome sequencing (WES) data for a subject having a particular type of cancer is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data".

Next, process 4000 proceeds to act 4004, where the MF profile for the subject is determined by determining a set of expression levels for a respective set of gene groups that includes gene groups associated with cancer malignancy and gene groups associated with cancer microenvironment. The MF profile may be determined for a subject having any type of cancer, including any of the types described herein. The MF profile may be determined using any number of gene groups (or functional modules) that relate to compositions and processes present within and/or surrounding the subject's tumor. Gene group expression levels, in some embodiments, are calculated as a gene set enrichment (GSEA) score for the gene group. Further aspects relating to determining MF profiles are provided in section "MF Profiles".

Next, process 4000 proceeds to act 4006, where a first set of visual characteristics for a first plurality of GUI elements using the first gene group expression levels are determined. Examples of visual characteristics for a GUI element include color, shading or pattern, size, and/or shape. A set of visual characteristics may contain any number of visual characteristics. GUI elements, for example, include genes, gene groups, biomarkers, and biomarker information. A plurality of GUI elements may contain any number of GUI elements. Further aspects of visual characteristics and GUI elements are shown in and/or described with reference to FIGS. 3-37.

Next, process 4000 proceeds to act 4008, where a second set of visual characteristics for a second plurality of GUI elements using the second gene group expression levels are determined. Examples of visual characteristics for a GUI element include color, shading or pattern, size, and/or shape. A set of visual characteristics may contain any number of visual characteristics. GUI elements, for example, include genes, gene groups, biomarkers, and biomarker information. A plurality of GUI elements may contain any number of GUI elements. Further aspects of visual characteristics and GUI elements are shown in and/or described with reference to FIGS. 3-37.

Next, process 4000 proceeds to act 4010, where a GUI containing a first portion including the first GUI element and a second portion including the second GUI element is generated. For example, the MF profile of the subject and other patient related information may be provided to a user in a GUI as shown in FIGS. 3-37. Further aspects relating to the GUI as shown in FIGS. 3-37 are provided in section "Visualization of MF Profiles".

Next, process 4000 proceeds to act 4012, where the generated personalized GUI is presented to a user. In some embodiments, the GUI may be presented to the user as part of a webpage displayed by a web browser. In some embodiments, the GUI may be presented to the user using an application program (different from a web-browser). For example, in some embodiments, the GUI may be presented to the user via an application program (e.g., "an app") executing on a mobile device.

Figure 40B:
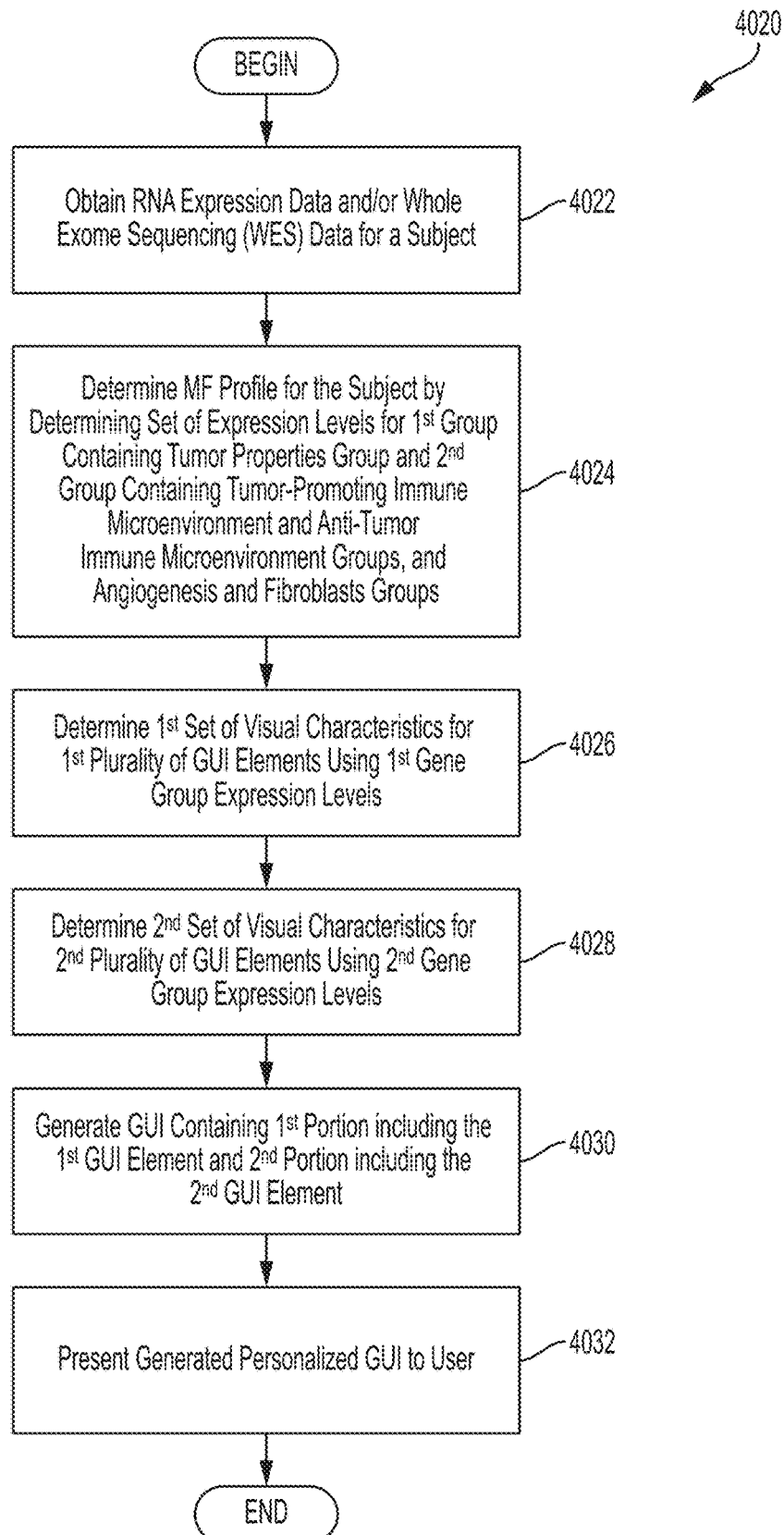
FIG. 40B is a flowchart of an illustrative process 4020 for generating an MF profile by determining expression levels for multiple gene groups and generating an MF portrait for visualizing the MF profile in a graphical user interface (GUI), in accordance with some embodiments of the technology described herein.

FIG. 40B is a flowchart of an illustrative computer-implemented process 4020 for generating a MF profile using at least one gene group associated with cancer malignancy and at least four gene groups associated with cancer microenvironment, and an associated MF portrait, in accordance with some embodiments of the technology described herein. Process 4020 may be performed by any suitable computing device(s). For example, may be performed by a laptop computer, a desktop computer, one or more servers, in a cloud computing environment, or in any other suitable way.

Process 4020 begins at act 4022, where RNA expression data and/or whole exome sequencing (WES) data for a subject having a particular type of cancer is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data".

Next, process 4020 proceeds to act 4024, where the MF profile for the subject is determined by determining a set of expression levels for a respective set of gene groups that includes at least one gene group associated with cancer malignancy and at least four gene groups associated with cancer microenvironment. The at least one gene group associated with cancer malignancy, in some embodiments, consists of a tumor properties gene group. The at least four gene groups associated with cancer microenvironment, in some embodiments, consists of tumor-promoting immune microenvironment group, anti-tumor immune microenvironment group, angiogenesis group, and fibroblasts group.

It should be appreciated that act 4024 may be performed using any number of gene groups associated with cancer malignancy and cancer microenvironment. For example, MF profiles may be determined using set of gene groups that includes 19 gene groups where the gene groups associated with cancer malignancy consists of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group, and the gene groups associated with cancer microenvironment consists of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group.

In another example, MF profiles may be determined using set of gene groups that includes 30 gene groups where the gene groups associated with cancer malignancy consists of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group, and the gene groups associated with cancer microenvironment consists of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group.

The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "MF Profiles".

Next, process 4020 proceeds to act 4026, where a first set of visual characteristics for a first plurality of GUI elements using the first gene group expression levels are determined. Examples of visual characteristics for a GUI element include color, shading or pattern, size, and/or shape. A set of visual characteristics may contain any number of visual characteristics. GUI elements, for example, include genes, gene groups, biomarkers, and biomarker information. A plurality of GUI elements may contain any number of GUI elements. Further aspects of visual characteristics and GUI elements are shown in and/or described with reference to FIGS. 3-37.

Next, process 4020 proceeds to act 4028, where a second set of visual characteristics for a second plurality of GUI elements using the second gene group expression levels are determined. Examples of visual characteristics for a GUI element include color, shading or pattern, size, and/or shape. A set of visual characteristics may contain any number of visual characteristics. GUI elements, for example, include genes, gene groups, biomarkers, and biomarker information. A plurality of GUI elements may contain any number of GUI elements. Further aspects of visual characteristics and GUI elements are shown in and/or described with reference to FIGS. 3-37.

Next, process 4020 proceeds to act 4030, where a GUI containing a first portion including the first GUI element and a second portion including the second GUI element is generated. For example, the MF profile of the subject and other patient related information may be provided to a user in a GUI as shown in FIGS. 3-37. Further aspects relating to the GUI as shown in FIGS. 3-37 are provided in section "Visualization of MF Profiles".

Next, process 4020 proceeds to act 4032, where the generated personalized GUI is presented to a user. In some embodiments, the GUI may be presented to the user as part of a webpage displayed by a web browser. In some embodiments, the GUI may be presented to the user using an application program (different from a web-browser). For example, in some embodiments, the GUI may be presented to the user via an application program (e.g., "an app") executing on a mobile device.

Such MF portraits provided in the GUI can used for various clinical purposes described herein including assessing the efficacy of a treatment for cancer and/or evaluating suitability of a patient for participating in a clinical trial.

Applications

Methods and compositions for tumor type characterization as described herein may be used for various clinical purposes including, but not limited to, monitoring the progress of cancer in a subject, assessing the efficacy of a treatment for cancer, identifying patients suitable for a particular treatment, evaluating suitability of a patient for participating in a clinical trial and/or predicting relapse in a subject. Accordingly, described herein are diagnostic and prognostic methods for cancer treatment based on tumor type described herein.

Methods and compositions described herein can be used to evaluate the efficacy of a cancer treatment, such as those described herein, given the correlation between cancer type (e.g., tumor types) and cancer prognosis. For example, multiple biological samples, such as those described herein, can be collected from a subject to whom a treatment is performed either before and after the treatment or during the course of the treatment. The cancer type (e.g., the tumor type) in the biological sample from the subject can be determined using any of the methods described herein. For example, if the cancer type indicates that the subject has a poor prognosis and the cancer type changes to a cancer type indicative of a favorable prognosis after the treatment or over the course of treatment (e.g., $1^{st}$ MF profile cancer type in a later collected sample when compared to $4^{th}$ MF profile cancer type in an earlier collected sample), it indicates that the treatment is effective.

If the subject is identified as not responsive to the treatment based on cancer type (e.g., no change in cancer type is identified in response to treatment), a higher dose and/or greater frequency of dosage of the anti-cancer therapeutic agent may be administered to the identified subject. Alternatively, an alternative treatment can be administered to a subject who is found to not be responsive to a first or subsequent treatment. In some embodiments, the dosage or frequency of dosage of the therapeutic agent is maintained, lowered, or ceased in a subject identified as responsive to the treatment or not in need of further treatment. In certain embodiments, the dosage or frequency of dosage of the therapeutic agent is increased in a subject identified as non-responsive to the treatment. In some embodiments, a first therapeutic agent is halted and a new (second) therapeutic is used to treat the subject; or (alternatively) an additional (second) therapeutic is added in a subject identified as non-responsive to the first therapeutic agent.

In some embodiments, cancer types can also be used to identify a cancer that may be treatable using a specific anti-cancer therapeutic agent (e.g., a chemotherapy). To practice this method, the cancer type in a sample (e.g., a tumor biopsy) collected from a subject having cancer can be determined using methods described herein. If the cancer type is identified as being susceptible to treatment with an anti-cancer therapeutic agent, the method may further comprise administering to the subject having the cancer an effective amount of the anti-cancer therapeutic agent.

In some embodiments, the methods and compositions for cancer type characterization as described herein may be relied on in the development of new therapeutics for cancer. In some embodiments, the cancer type may indicate or predict the efficacy of a new therapeutic or the progression of cancer in a subject prior to, during, or after the administration of the new therapy.

In some embodiments, methods and compositions for cancer type characterization as described herein may be used to evaluate suitability of a patient for participating in a clinicial trial. In some embodiments, the cancer type may be used to include patients in a clinical trial. In some embodiments, patients having a specified cancer type (e.g., type A, or $1^{st}$ MF profile) are included in a clinical trial. Herein, cancer types A-D correspond to the $1^{st}$-$4^{th}$ MF profile types, respectively. In some embodiments, patients having any one of two specified cancer types (e.g., $1^{st}$ MF profile or $4^{th}$ MF profile) are included in a clinical trial. In some embodiments, patients having any one of three specified cancer types (e.g., patients having a $1^{st}$ MF profile, a $2^{nd}$ MF profile, or a $3^{rd}$ MF profile) are included in a clinical trial. In some embodiments, patients having any one of four specified cancer types (e.g., patients having a $1^{st}$MF profile, a $2^{nd}$ MF profile, a $3^{rd}$ MF profile, or a $4^{th}$ MF profile) are included in a clinical trial.

In some embodiments, the cancer type may be used to exclude patients in a clinical trial. In some embodiments, patients having a specified cancer type (e.g., $1^{st}$MF profile) are excluded from a clinical trial. In some embodiments, patients having any one of two specified cancer types (e.g., $1^{st}$ MF profile or $4^{th}$ MF profile) are excluded from a clinical trial. In some embodiments, patients having any one of three specified cancer types (e.g., patients having a $1^{st}$ MF profile, a $2^{nd}$ MF profile, or a $3^{rd}$ MF profile) are excluded from a clinical trial. In some embodiments, patients having any one of four specified cancer types (e.g., patients having a $1^{st}$ MF profile, a $2^{nd}$ MF profile, a $3^{rd}$ MF profile, or a $4^{th}$ MF profile) are excluded from a clinical trial.

Further, methods and compositions for tumor type characterization as described herein may be applied for non-clinical uses including, for example, for research purposes. In some embodiments, the methods described herein may be used to study cancer cell function. For example, the methods described herein may be used to evaluate a tumor process (e.g., tumor metastasis), which can be used for various purposes including identifying targets that specifically effect the tumor process being evaluated.

Methods of Treatment In certain methods described herein, an effective amount of anti-cancer therapy described herein may be administered or recommended for administration to a subject (e.g., a human) in need of the treatment via a suitable route (e.g., intravenous administration).

The subject to be treated by the methods described herein may be a human patient having, suspected of having, or at risk for a cancer. Examples of a cancer include, but are not limited to, melanoma, lung cancer, brain cancer, breast cancer, colorectal cancer, pancreatic cancer, liver cancer, prostate cancer, skin cancer, kidney cancer, bladder cancer, or prostate cancer. The subject to be treated by the methods described herein may be a mammal (e.g., may be a human). Mammals include, but are not limited to: farm animals (e.g., livestock), sport animals, laboratory animals, pets, primates, horses, dogs, cats, mice, and rats.

A subject having a cancer may be identified by routine medical examination, e.g., laboratory tests, biopsy, PET scans, CT scans, or ultrasounds. A subject suspected of having a cancer might show one or more symptoms of the disorder, e.g., unexplained weight loss, fever, fatigue, cough, pain, skin changes, unusual bleeding or discharge, and/or thickening or lumps in parts of the body. A subject at risk for a cancer may be a subject having one or more of the risk factors for that disorder. For example, risk factors associated with cancer include, but are not limited to, (a) viral infection (e.g., herpes virus infection), (b) age, (c) family history, (d) heavy alcohol consumption, (e) obesity, and (f) tobacco use.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons, or for virtually any other reasons.

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an anti-cancer therapeutic agent may be appropriate. Various formulations and devices for achieving sustained release are known in the art.

In some embodiments, dosages for an anti-cancer therapeutic agent as described herein may be determined empirically in individuals who have been administered one or more doses of the anti-cancer therapeutic agent. Individuals may be administered incremental dosages of the anti-cancer therapeutic agent. To assess efficacy of an administered anti-cancer therapeutic agent, one or more aspects of a cancer (e.g., tumor formation, tumor growth, or cancer or tumor Type A-D) may be analyzed.

Generally, for administration of any of the anti-cancer antibodies described herein, an initial candidate dosage may be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 µg/mg to about 2 mg/kg (such as about 3 µg/mg, about 10 µg/mg, about 30 mg/kg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy may be monitored by conventional techniques and assays and/or by monitoring cancer Types A-D ($1^{st}$-$4^{th}$ MF profile clusters, respectively) as described herein. The dosing regimen (including the therapeutic used) may vary over time.

When the anti-cancer therapeutic agent is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an anti-cancer therapeutic agent will depend on the specific anti-cancer therapeutic agent(s) (or compositions thereof) employed, the type and severity of cancer, whether the anti-cancer therapeutic agent is administered for preventive or therapeutic purposes, previous therapy, the patient's clinical history and response to the anti-cancer therapeutic agent, and the discretion of the attending physician. Typically the clinician will administer an anti-cancer therapeutic agent, such as an antibody, until a dosage is reached that achieves the desired result.

Administration of an anti-cancer therapeutic agent can be continuous or intermittent, depending, for example, upon the recipient's physiological condition, whether the purpose of the administration is therapeutic or prophylactic, and other factors known to skilled practitioners. The administration of an anti-cancer therapeutic agent (e.g., an anti-cancer antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward a cancer.

Alleviating a cancer includes delaying the development or progression of the disease, or reducing disease severity. Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. Alternatively or in addition to the clinical techniques known in the art, development of the disease may be detectable and assessed based on the cancer types ($1^{st}$-$4^{th}$ MF profile types) described herein. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the anti-cancer therapeutic agent (e.g., an antibody) described herein is administered to a subject in need of the treatment at an amount sufficient to reduce cancer (e.g., tumor) growth by at least 10% (e.g., 20%, 30%, 40%, 50%, 60%, 70%, 80%, 90% or greater). In some embodiments, the anti-cancer therapeutic agent (e.g., an antibody) described herein is administered to a subject in need of the treatment at an amount sufficient to reduce cancer cell number or tumor size by at least 10% (e.g., 20%, 30%, 40%, 50%, 60%, 70%, 80%, 90% or more). In other embodiments, the anti-cancer therapeutic agent is administered in an amount effective in altering cancer type (e.g., from cancer Type D to cancer Type A). Alternatively, the anti-cancer therapeutic agent is administered in an amount effective in reducing tumor formation or metastasis.

Conventional methods, known to those of ordinary skill in the art of medicine, may be used to administer the anti-cancer therapeutic agent to the subject, depending upon the type of disease to be treated or the site of the disease. The anti-cancer therapeutic agent can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, an anti-cancer therapeutic agent may be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (e.g., glycerol, propylene glycol, liquid polyethylene glycol, and the like). For intravenous injection, water soluble anti-cancer therapeutic agents can be administered by the drip method, whereby a pharmaceutical formulation containing the antibody and a physiologically acceptable excipients is infused. Physiologically acceptable excipients may include, for example, 5% dextrose, 0.9% saline, Ringer's solution, and/or other suitable excipients. Intramuscular preparations, e.g., a sterile formulation of a suitable soluble salt form of the anti-cancer therapeutic agent, can be dissolved and administered in a pharmaceutical excipient such as Water-for-Injection, 0.9% saline, and/or 5% glucose solution.

In one embodiment, an anti-cancer therapeutic agent is administered via site-specific or targeted local delivery techniques. Examples of site-specific or targeted local delivery techniques include various implantable depot sources of the agent or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568, the contents of each of which are incorporated by reference herein for this purpose.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., *Gene Therapeutics: Methods And Applications Of Direct Gene Transfer* (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. The contents of each of the foregoing are incorporated by reference herein for this purpose.

Therapeutic compositions containing a polynucleotide may be administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

Therapeutic polynucleotides and polypeptides can be delivered using gene delivery vehicles. The gene delivery vehicle can be of viral or non-viral origin (e.g., Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). The contents of each of the foregoing are incorporated by reference herein for this purpose. Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. The contents of each of the foregoing are incorporated by reference herein for this purpose.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:

16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581. The contents of each of the foregoing are incorporated by reference herein for this purpose.

It is also apparent that an expression vector can be used to direct expression of any of the protein-based anti-cancer therapeutic agents (e.g., anti-cancer antibody). For example, peptide inhibitors that are capable of blocking (from partial to complete blocking) a cancer causing biological activity are known in the art.

In some embodiments, more than one anti-cancer therapeutic agent, such as an antibody and a small molecule inhibitory compound, may be administered to a subject in need of the treatment. The agents may be of the same type or different types from each other. At least one, at least two, at least three, at least four, or at least five different agents may be co-administered. Generally anti-cancer agents for administration have complementary activities that do not adversely affect each other. Anti-cancer therapeutic agents may also be used in conjunction with other agents that serve to enhance and/or complement the effectiveness of the agents.

Treatment efficacy can be assessed by methods well-known in the art, e.g., monitoring tumor growth or formation in a patient subjected to the treatment. Alternatively or in addition to, treatment efficacy can be assessed by monitoring tumor type over the course of treatment (e.g., before, during, and after treatment). See, e.g., Example 5 below.

Combination Therapy

Compared to monotherapies, combinations of treatment approaches showed higher efficacy in many studies, but the choice of remedies to be combined and designing the combination therapy regimen remain speculative. Given that the number of possible combinations is now extremely high, there is great need for a tool that would help to select drugs and combinations of remedies based on objective information about a particular patient. Use of cancer MF profiles for designing or electing a specific combination therapy establishes a scientific basis for choosing the optimal combination of preparations.

When using MF profiles for designing a combination therapy one can define a rational level of portrait detail. It is advisable to create a portrait of the modules with known therapeutic effectors, while modules that currently can't be influenced using medical approaches could be excluded. At the same time, there may be modules that are important to the outcome of the disease, having no effectors embodied in drugs or other therapies (e.g., radiation, cell therapy, oncolytic viruses, etc.). Such modules may have scientific value and their preservation is reasonable in portraits intended for research work.

As noted above, also provided herein are methods of treating a cancer or recommending treating a cancer using any combination of anti-cancer therapeutic agents or one or more anti-cancer therapeutic agents and one or more additional therapies (e.g., surgery and/or radiotherapy). The term combination therapy, as used herein, embraces administration of more than one treatment (e.g., an antibody and a small molecule or an antibody and radiotherapy) in a sequential manner, that is, wherein each therapeutic agent is administered at a different time, as well as administration of these therapeutic agents, or at least two of the agents or therapies, in a substantially simultaneous manner.

Sequential or substantially simultaneous administration of each agent or therapy can be affected by any appropriate route including, but not limited to, oral routes, intravenous routes, intramuscular, subcutaneous routes, and direct absorption through mucous membrane tissues. The agents or therapies can be administered by the same route or by different routes. For example, a first agent (e.g., a small molecule) can be administered orally, and a second agent (e.g., an antibody) can be administered intravenously.

As used herein, the term "sequential" means, unless otherwise specified, characterized by a regular sequence or order, e.g., if a dosage regimen includes the administration of an antibody and a small molecule, a sequential dosage regimen could include administration of the antibody before, simultaneously, substantially simultaneously, or after administration of the small molecule, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents or therapies described herein.

Combination therapy can also embrace the administration of the anti-cancer therapeutic agent (e.g., an antibody) in further combination with other biologically active ingredients (e.g., a vitamin) and non-drug therapies (e.g., surgery or radiotherapy).

It should be appreciated that any combination of anti-cancer therapeutic agents may be used in any sequence for treating a cancer. The combinations described herein may be selected on the basis of a number of factors, which include but are not limited to the effectiveness of altering identified tumor type (e.g., Type A-D), reducing tumor formation or tumor growth, and/or alleviating at least one symptom associated with the cancer, or the effectiveness for mitigating the side effects of another agent of the combination. For example, a combined therapy as provided herein may reduce any of the side effects associated with each individual members of the combination, for example, a side effect associated with an administered anti-cancer agent.

In some embodiments, an anti-cancer therapeutic agent is an antibody, an immunotherapy, a radiation therapy, a surgical therapy, and/or a chemotherapy.

Examples of the antibody anti-cancer agents include, but are not limited to, alemtuzumab (Campath), trastuzumab (Herceptin), Ibritumomab tiuxetan (Zevalin), Brentuximab vedotin (Adcetris), Ado-trastuzumab emtansine (Kadcyla), blinatumomab (Blincyto), Bevacizumab (Avastin), Cetuximab (Erbitux), ipilimumab (Yervoy), nivolumab (Opdivo), pembrolizumab (Keytruda), atezolizumab (Tecentriq), avelumab (Bavencio), durvalumab (Imfinzi), and panitumumab (Vectibix).

Examples of an immunotherapy include, but are not limited to, a PD-1 inhibitor or a PD-L1 inhibitor, a CTLA-4 inhibitor, adoptive cell transfer, therapeutic cancer vaccines, oncolytic virus therapy, T-cell therapy, and immune checkpoint inhibitors.

Examples of radiation therapy include, but are not limited to, ionizing radiation, gamma-radiation, neutron beam radiotherapy, electron beam radiotherapy, proton therapy, brachytherapy, systemic radioactive isotopes, and radiosensitizers.

Examples of a surgical therapy include, but are not limited to, a curative surgery (e.g., tumor removal surgery), a preventive surgery, a laparoscopic surgery, and a laser surgery.

Examples of the chemotherapeutic agents include, but are not limited to, Carboplatin or Cisplatin, Docetaxel, Gemcitabine, Nab-Paclitaxel, Paclitaxel, Pemetrexed, and Vinorelbine.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin hydrochloride, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives or derivatives thereof); Purine antagonists (Thioguanine, Fludarabine, Cladribine, 6-Mercaptopurine, Pentostatin, clofarabine, and relatives or derivatives thereof) and Pyrimidine antagonists (Cytarabine, Floxuridine, Azacitidine, Tegafur, Carmofur, Capacitabine, Gemcitabine, hydroxyurea, 5-Fluorouracil (5FU), and relatives or derivatives thereof); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives or derivatives thereof); nitrosoureas (e.g., Carmustine, Lomustine, Semustine, Fotemustine, Nimustine, Ranimustine, Streptozocin, and relatives or derivatives thereof); Triazenes (e.g., Dacarbazine, Altretamine, Temozolomide, and relatives or derivatives thereof); Alkyl sulphonates (e.g., Busulfan, Mannosulfan, Treosulfan, and relatives or derivatives thereof); Procarbazine; Mitobronitol, and Aziridines (e.g., Carboquone, Triaziquone, ThioTEPA, triethylenemalamine, and relatives or derivatives thereof); Antibiotics, such as Hydroxyurea, Anthracyclines (e.g., doxorubicin agent, daunorubicin, epirubicin and relatives or derivatives thereof); Anthracenediones (e.g., Mitoxantrone and relatives or derivatives thereof); Streptomyces family antibiotics (e.g., Bleomycin, Mitomycin C, Actinomycin, and Plicamycin); and ultraviolet light.

EXAMPLES

In order that the invention described herein may be more fully understood, the following examples are set forth. The examples described in this application are offered to illustrate the methods, compositions, and systems provided herein and are not to be construed in any way as limiting their scope.

Example 1

Methods

Molecular and Clinical Data

Genomic, transcriptomic and clinical data for 23 solid tumors from The Cancer Genome Atlas (TCGA) were downloaded via the TCGA data portal (https://tcga-data.nci.nih.gov). Mutations were obtained out of corresponding TCGA MAF files. RNA-sequencing data were downloaded and processed in FPKM units. Tumor samples were used.

Creating Biologically Relevant Gene Sets to Evaluate Processes in a Tumor Microenvironment To visualize the composition of a patient's tumor microenvironment and the immune system processes occurring within the tumor, an approach based on analysis of signature gene lists was used. The analysis required associating target gene expression with biological processes and/or cell functions. The signatures used in the analysis comprised a diverse set of adaptive and innate immune cell types, as well as tumor tissue functioning and growth associated processes. The latter included tumor-supporting components of microenvironment: cancer-associated fibroblasts, tumor vasculature abundance and angiogenesis-inducing processes. Tumor purity (cellularity) indicating percentage of malignant cells in a tumor was also included in the visualization of the patient's cancer-immune portrait to represent size of the malignant compartment. The immune-related gene expression signatures comprised 327 genes. Genes highly specific to the functional process they describe were selected.

The list of gene set annotations is shown in Table 2. The created gene sets were compared to The Molecular Signatures Database (MSigDB), a publicly available collection of annotated gene sets. The similarity between proposed gene sets and the MSigDB collection was calculated using a hypergeometric test (FDR<0.05). Each gene was scientifically validated to represent its true influence on the process for which it was designated. Gene annotations were confirmed using scientific publications.

TABLE 2

List of Gene Set Annotations.

| Level 1 | Level 2 | Level 3 | GMT | | |
|---|---|---|---|---|---|
| Anti-tumor immune infiltrate | Antigen presentation | MHCI | HLA-A | HLA-C | TAP1 |
| | | | HLA-B | B2M | TAP2 |
| | | MHCII | HLA-DRA | HLA-DOA | HLA-DQA1 |
| | | | HLA-DRB1 | HLA-DPA1 | HLA-DRB5 |
| | | | HLA-DOB | HLA-DPB1 | HLA-DQA2 |
| | | | HLA-DPB2 | HLA-DMB | HLA-DQB2 |
| | | | HLA-DMA | HLA-DQB1 | HLA-DRB6 |

TABLE 2-continued

List of Gene Set Annotations.

| Level 1 | Level 2 | Level 3 | GMT | | |
|---|---|---|---|---|---|
| | | Coactivation molecules | CD80<br>CD40<br>CD28 | TNFRSF4<br>CD86 | CD83<br>COSLG |
| | Cytotoxic T and NK cells | Effector cells | IFNG<br>PRF1<br>ZAP70<br>GZMA<br>EOMES | LCK<br>GNLY<br>GZMB<br>GZMK | FASLG<br>TBX21<br>CD8A<br>CD8B |
| | | NK cells | NKG7<br>KLRK1<br>KIR2DL4<br>CD160<br>CD226<br>KIR2DS5 | KIR2DS1<br>CD244<br>GZMH<br>KIR2DS2<br>NCR1 | GNLY<br>KIR2DS3<br>KLRC2<br>IFNG<br>KIR2DS4 |
| | | T cell traffic | CXCL9<br>CXCL10<br>CXCR3<br>CX3CL1 | CCR7<br>CXCL11<br>CCL21<br>CCL2 | CCL3<br>CCL4<br>CCL5 |
| | | T cells | EOMES<br>CD3E<br>TRBC2<br>TBX21 | CD3G<br>LCK<br>ITK<br>TRAC | UBASH3A<br>CD3D<br>TRBC1<br>TRAT1 |
| | B cells | B cells | CD19<br>CD24<br>CD22<br>MS4A1 | CR2<br>CD79A<br>TNFRSF13C<br>TNFRSF17 | CD79B<br>CD27<br>NFRSF13B<br>BLK |
| | Anti-tumor microenvironment | M1 signatures | NOS2<br>IL12B<br>SOCS3 | TNF<br>IL12A | IL23A<br>IL1B |
| | | Th1 signature | IFNG<br>CD40LG<br>LTA | CD27<br>IL2 | IL15<br>TBX21 |
| | | Antitumor cytokines | HMGB1<br>IFNB1<br>CCL3 | TNF<br>IFNA2 | NFSF10<br>FASLG |
| Tumor-promoting immune infiltrate | Checkpoint inhibition | Checkpoint inhibition | PDCD1<br>CTLA4<br>PDCD1LG2<br>CXCL12 | CD274<br>LAG3<br>BTLA<br>IL10 | HAVCR2<br>VSIR |
| | Treg | Treg | TGFB1<br>TGFB2<br>TGFB3<br>FOXP3 | TNFRSF1B<br>CCL17<br>CXCR4<br>CCR4 | CCL1<br>CCL2<br>CCL5<br>CXCL13 |
| | MDSC | MDSC | CTLA4<br>IDO1<br>ARG1<br>IL4R<br>IL10<br>TGFB1<br>TGFB2<br>TGFB3 | CCL22<br>NOS2<br>CYBB<br>CXCR4<br>CD33<br>CXCL1<br>CXCL5<br>CCL2 | CCL28<br>CCL4<br>CCL8<br>CCR2<br>CCL3<br>CCL5<br>CSF1<br>CXCL8 |
| | Granulocytes | Granulocytes | CXCL8<br>CXCL2<br>CXCL1<br>CCL11<br>CCL24<br>KITLG<br>CCL5<br>CXCL5<br>CCR3<br>CCL26 | PRG2<br>EPX<br>RNASE2<br>RNASE3<br>IL5RA<br>GATA1<br>SIGLEC8<br>PRG3<br>CMA1<br>TPSAB1 | MS4A2<br>CPA3<br>IL4<br>IL5<br>IL13<br>SIGLEC8<br>MPO<br>ELANE<br>PRTN3<br>CTSG |
| | Tumor-promoting immune infiltrate | M2 signature | IL10<br>VEGFA<br>TGFB1<br>IDO1<br>PTGES | MRC1<br>CSF1<br>LRP1<br>ARG1 | MSR1<br>CD163<br>CSF1R<br>PTGS1 |
| | | Th2 signature | IL4<br>IL5 | IL13<br>IL10 | IL25<br>GATA3 |
| | | Protumor cytokines | IL10<br>TGFB1 | TGFB2<br>TGFB3 | IL22<br>MIF |
| | | Complement inhibition | CFD<br>CFI | CD55<br>CD46 | CR1 |

TABLE 2-continued

List of Gene Set Annotations.

| Level 1 | Level 2 | Level 3 | GMT | | |
|---|---|---|---|---|---|
| Fibroblasts | CAF | CAF | LGALS1 | TGFB1 | FAP |
| | | | COL1A1 | TGFB2 | LRP1 |
| | | | COL1A2 | TGFB3 | CD248 |
| | | | COL4A1 | ACTA2 | COL6A1 |
| | | | COL5A1 | FGF2 | COL6A2 |
| | | | COL6A3 | | |
| Angiogenesis | Angiogenesis | Angiogenesis | VEGFA | KDR | MMRN1 |
| | | | VEGFB | ANGPT1 | LDHA |
| | | | VEGFC | ANGPT2 | HIF1A |
| | | | PDGFC | TEK | EPAS1 |
| | | | CXCL8 | VWF | CA9 |
| | | | CXCR2 | CDH5 | SPP1 |
| | | | FLT1 | NOS3 | LOX |
| | | | PIGF | KDR | SLC2A1 |
| | | | CXCL5 | VCAM1 | LAMP3 |
| Tumor Properties | Proliferation rate | Proliferation rate | MKI67 | AURKA | MYBL2 |
| | | | ESCO2 | AURKB | BUB1 |
| | | | CETN3 | CDK4 | PLK1 |
| | | | CDK2 | CDK6 | CCNB1 |
| | | | CCND1 | PRC1 | MCM2 |
| | | | CCNE1 | E2F1 | MCM6 |
| | Activated signaling pathways | PI3K/AKT/mTOR signaling | PIK3CA | AKT1 | PRKCA |
| | | | PIK3CB | MTOR | AKT2 |
| | | | PIK3CG | PTEN | AKT3 |
| | | | PIK3CD | | |
| | | RAS/RAF/MEK signaling | BRAF | MAP2K1 | MKNK1 |
| | | | FNTA | MAP2K2 | MKNK2 |
| | | | FNTB | | |
| | | Receptor tyrosine kinases expression | ALK | MET | ERBB4 |
| | | | AXL | NTRK1 | ERBB3 |
| | | | KIT | FGFR1 | BCR-ABL |
| | | | EGFR | FGFR2 | PDGFRA |
| | | | ERBB2 | FGFR3 | PDGFRB |
| | | | FLT3 | | |
| | | Growth Factors | NGF | FGF7 | IL7 |
| | | | CSF3 | IGF1 | FGF2 |
| | | | CSF2 | IGF2 | |
| | Tumor suppressors | Tumor suppressors | TP53 | DCN | AIM2 |
| | | | SIK1 | MTAP | RB1 |
| | | | PTEN | | |
| | Metastasis signature | Metastasis signature | ESRP1 | SMARCA4 | NEDD9 |
| | | | CTSL | SNAI2 | PAPPA |
| | | | HOXA1 | TWIST1 | HPSE |
| | Antimetastatic factors | Antimetastatic factors | KISS1 | TCF21 | NCAM1 |
| | | | ADGRG1 | CDH1 | MITF |
| | | | BRMS1 | PCDH10 | |
| | Mutation status | Mutation status | Major Recurrent Mutations | | |
| Additional modules | | | | | Purity |
| Malignant cells | | | | | |
| Non-malignant microenvironment | | | | | 1-Purity |

Quantification of Process Intensity ssGSEA enrichment scores (ES) were calculated using the GSVA R package with default parameters (gsea method with type="ssgsea"; normalized=True). ES were then transformed into z-scores and clipped to the range [−4, 4] for each functional process in each dataset.

For tumor purity estimation, CPE metric values obtained from Aran et al. Systematic pan-cancer analysis of tumour purity. Nat Commun. Nature Publishing Group; 2015; 6:8971 were used. Tumor infiltration cell number (nonmalignant cell number) was calculated as 1—tumor purity.

Mutation data including presence of driver mutations and total number of nonsynonymous mutations for the "Mutation status" node was obtained from TCGA MAF files.

Quantification of Tumor Microenvironment with Deconvolution Methods

Cell type deconvolution was performed using CIBERSORT with LM22 matrix and MCP-counter, capable of estimating the abundance of tissue-infiltrating immune and stromal cell populations according to gene expression. In addition, single-sample GSEA (ssGSEA), an extension of Gene Set Enrichment Analysis (GSEA), was performed on widely used gene signatures of immune infiltrate.

Hierarchical Organization of Processes

Biological properties describing the tumor microenvironment and tumor processes were hierarchically organized according to their associated biology. A clustered graph structure was created from descriptions from the highest to the lowest granularity including genes, biological processes including high-level and low-level processes, and biological categories. The high-level processes were chosen as follows: tumor (as tumor burden or tumor purity), tumor nonmalignant microenvironment comprised of the angiogenesis module, cancer-associated fibroblasts, tumor-promoting, and anti-tumor immune infiltrates. As a non-limiting example, CD80 genes were made part of a "co-activation molecules"

process, which was a part of an "antigen presentation" process, which in turn was part of an "anti-tumor immune infiltration" module. Gene annotations for each high- or low-level process are presented in Table 2. Using the determined hierarchical organization of the tumor processes, a cancer-immune portrait was visualized at different levels of detail.

Visualization of the Cancer-Immune Portrait

Portraits were visualized as a graph based structure using Mathematica 11 standard packages (Wolfram Research, USA). A node size that described an intensity of a process in a particular patient was taken according to a normalized score calculated for process intensity. A distribution of ssGSEA enrichment scores for each process was mapped to the range of (0,1), by a cumulative distribution function (CDF) within the corresponding TCGA cohort. Driver mutations influencing therapeutic and prognostic outcomes were depicted in the tumor properties group as the "Mutation status" node representing a total number of nonsynonymous mutations found in the patient tumor, while the upper genes arising from this node demonstrated recurrent mutations. The "mutation status" node size was also transformed to the range of (0,1) by CDF from the corresponding cohort distribution.

All the processes were labeled either anti-tumor or pro-tumor. Anti-tumor processes were colored in a blue gradient, pro-tumor processes were colored in a burgundy gradient. The intensity (i.e., intensity of the shade or darkness/lightness) represented process intensity. Gene nodes were accorded a fixed size and color using the same method as the processes. The size of the "Malignant cells", as well as the "Non-malignant microenvironment" nodes were visualized based on the tumor purity. The same visualization principles were applied to the molecular functional portraits with different levels of detail.

Survival Analysis

Survival curves were calculated according to the Kaplan-Meier method, and differences between curves were assessed using the log-rank test.

Dense Clustering

Edges that represent <40% samples correlation were removed to get connected graphs with <1% node connectivity (~0.6% for pan-cancer and SKCM). Node connectivity was calculated using the NetworkX python package. All edges with weight >50 were removed, leading to graph connectivity break.

The similarity of tumor samples was measured using the Pearson correlation [−1, 1] between process intensities (ssGSEA enrichment scores). Similarities in the space of 28 processes were calculated using python pandas and SciPy. Distance matrix was converted into a NetworkX graph as follows: each sample formed a node; two nodes formed an edge with weight equal to their Pearson correlation. Later edges with weight <0.4 were removed. The Louvain community detection algorithm was applied to calculate graph partitioning into clusters using python-louvain with default parameters. Final partitions were labeled as Types A-D ($1^{st}$-$4^{th}$ MF profile clusters, respectively).

Dense clusters were visualized in Cytoscape (v3.4.0). Nodes were organized using "Perfuse force directed layout" (default spring coefficient=1e-5, number of iterations=100). Node size represents the number of its neighbors (adjacent edges). Node color corresponds to tumor subtype (A-D) unless otherwise specified.

K-Means Clustering 28 functional processes were organized into four clusters using GENE-E k-means algorithm with 20,000 iterations using the Pearson correlation as a distance metric.

Comparison of Clusters by the Process Values

Comparison of each process activity between cluster pairs was performed by t-test. Per-cluster prevalence and deficiency of mutations in the driver genes were analyzed by the Fisher exact test.

Heatmaps

Python-matplotlib (v1.5.1) or python-seaborn (v0.7.1) or GENE-E were used to create heatmaps. The Pearson correlation was used as the default similarity metric (unless otherwise mentioned) for correlation matrixes. Hierarchical clustering was performed using complete linkage and euclidean distance for correlation matrixes clustering.

tSNE tSNE analysis was performed by Rtsne (v0.13) package in R and visualized by R plot function.

Validating Prevalent (Dominant) Molecular-Functional Types of Cancers

In order to validate the proposed molecular-functional types of cancer organization, additional analysis was performed. The additional analysis showed the dominant clusters of MF profiles in 20 epithelial cancers. The additional analysis further showed that the quantified melanoma microenvironment activity by functional process scores formed explicit clusters, but that the underlying expressions of the 10,000 most expressed genes did not, due to the increased noise generated from the addition of multiple unnecessary and unrelated genes. In that sense, expression profiles of 298 genes composing functional processes showed a fuzzier structure with less distinct clusters than expression profiles of functional process scores. Pan-cancer patient correlation analysis also confirmed the formation of distinct types of cancer molecular-functional portraits.

Prevalent Types Analysis

MCP-counter, CIBERSORT, and cell deconvolution algorithms were applied to the RNA-Seq data of 470 melanoma patients. This analysis demonstrated that Type A, B, C and D clusters ($1^{st}$-$4^{th}$ MF profile clusters, respectively) were segregated using the MCP-counter but not with CIBERSORT. Notably, the MCP-counter revealed the main types of leukocytes and lymphocytes, tumor-associated fibroblasts, and endothelial cells.

CIBERSORT with LM22 matrix provided a composition of leukocyte/lymphocyte infiltrate, but did not take into account endothelial cells and CAFs. However, Types A and B (first and second MF profile clusters, respectively) melanomas displaying dominant CD8 T cells were segregated from Types C and D (third and fourth MF profile clusters, respectively) displaying dominant tumor-associated macrophages (e.g., M2 macrophages) using CIBERSORT/LM22.

Deconvolution methods based on gene sets proposed by Senbabaoglu et al. were analyzed. See Senbabaoglu et al. Tumor immune microenvironment characterization in clear cell renal cell carcinoma identifies prognostic and immunotherapeutically relevant messenger RNA signatures; Genome Biology (2016) 17:231, which is herein incorporated by reference for this purpose. However, this analysis was unable to differentiate between the four tumor cell clusters corresponding to Types A-D ($1^{st}$-$4^{th}$ MF profile clusters, respectively). Driver mutations are thought to be key factors of tumorigenesis. In order to analyze whether driver mutations are associated with any of the prevalent four types of melanomas, the abundance of such mutations in each cluster along with their enrichment or deficiency in the cluster was computed. Fisher's exact test was used to evaluate the cluster's enrichment with samples containing mutations in any given gene. However, after correction for multiple testing, no driver genes showed significant (FDR<0.05) enrichment. The APC gene (FDR=0.084) had almost reached a significant cutoff as being overrepresented (incidence ratio 2.38) in Type D melanomas.

Results for 38 driver mutations found in different melanoma types are provided in Table 3. Values that were statistically significant in single tests (p-value<0.05) are marked. Mutation-rich melanoma types (underlined) had a relative abundance over 1.0, and mutation-deficient melanoma types (bold) had a relative abundance under 1.0.

1) Calculated TCGA X cancer cohort processes values using ssGSEA. Calculated mean and standard of each process. Obtained Z-score TCGA X cancer cohort.

$$ZscoredSampleProcess_x = \frac{SampleProcess_x - mean(TCGACohortProcess_x)}{std(TCGACohortProcess_x)}$$

TABLE 3

Percent of patients with indicated mutations and relative abundance of these mutations in the melanoma cohort (470 patients).

| | Patients with indicated mutation in the given melanoma type | | | | Relative abundance of mutation compared to the whole melanoma cohort | | | |
|---|---|---|---|---|---|---|---|---|
| | A | B | C | D | A | B | C | D |
| APC | 5.1% | 8.6% | 2.9% | 17.7% | 0.68 | 1.16 | 0.39 | 2.38 |
| ARID1A | 2.2% | 5.2% | 5.8% | 3.8% | 0.51 | 1.22 | 1.37 | 0.89 |
| ATM | 3.6% | 5.2% | 5.8% | 3.8% | 0.78 | 1.11 | 1.24 | 0.81 |
| ATRX | 4.3% | 6.0% | 7.2% | 2.5% | 0.82 | 1.14 | 1.37 | 0.48 |
| BAP1 | 0.7% | 2.6% | 0.7% | 2.5% | 0.49 | 1.74 | 0.49 | 1.70 |
| BRAF | 50.7% | 50.0% | 57.2% | 32.9% | 1.03 | 1.01 | 1.16 | 0.67 |
| BRCA2 | 5.1% | 4.3% | 8.0% | 7.6% | 0.82 | 0.70 | 1.29 | 1.23 |
| CDH1 | 0.0% | 1.7% | 2.2% | 2.5% | 0.00 | 1.16 | 1.46 | 1.70 |
| CDKN2A | 6.5% | 12.1% | 7.2% | 11.4% | 0.73 | 1.35 | 0.81 | 1.28 |
| CTCF | 0.0% | 0.0% | 1.4% | 1.3% | 0.00 | 0.00 | 2.28 | 1.99 |
| CTNNB1 | 4.3% | 5.2% | 4.3% | 5.1% | 0.93 | 1.11 | 0.93 | 1.08 |
| DNMT3 | 2.2% | 3.4% | 1.4% | 3.8% | 0.85 | 1.35 | 0.57 | 1.49 |
| EGFR | 7.2% | 1.7% | 3.6% | 13.9% | 1.22 | 0.29 | 0.61 | 2.34 |
| FBXW7 | 1.4% | 1.7% | 4.3% | 5.1% | 0.49 | 0.58 | 1.46 | 1.70 |
| FLT3 | 4.3% | 12.9% | 8.0% | 11.4% | 0.50 | 1.49 | 0.92 | 1.31 |
| GATA3 | 1.4% | 2.6% | 0.0% | 6.3% | 0.68 | 1.22 | 0.00 | 2.98 |
| HRAS | 0.7% | 1.7% | 1.4% | 0.0% | 0.68 | 1.62 | 1.37 | 0.00 |
| IDH1 | 3.6% | 6.9% | 2.2% | 6.3% | 0.81 | 1.55 | 0.49 | 1.42 |
| KRAS | 1.4% | 2.6% | 2.2% | 2.5% | 0.68 | 1.22 | 1.02 | 1.19 |
| MAP3K1 | 1.4% | 0.9% | 0.7% | 0.0% | 1.71 | 1.02 | 0.85 | 0.00 |
| MTOR | 3.6% | 6.9% | 5.1% | 7.6% | 0.66 | 1.25 | 0.92 | 1.38 |
| NAV3 | 5.1% | 12.9% | 12.3% | 11.4% | 0.50 | 1.27 | 1.21 | 1.12 |
| NCOR1 | 0.7% | 4.3% | 7.2% | 12.7% | 0.13 | 0.78 | 1.31 | 2.29 |
| NF1 | 7.2% | 13.8% | 8.7% | 20.3% | 0.63 | 1.20 | 0.76 | 1.77 |
| NOTCH1 | 2.2% | 2.6% | 2.2% | 5.1% | 0.79 | 0.94 | 0.79 | 1.83 |
| NPM1 | 0.0% | 0.9% | 1.4% | 1.3% | 0.00 | 1.02 | 1.71 | 1.49 |
| NRAS | 18.1% | 30.2% | 23.9% | 41.8% | 0.68 | 1.13 | 0.89 | 1.56 |
| PBRM1 | 3.6% | 4.3% | 4.3% | 6.3% | 0.81 | 0.97 | 0.98 | 1.42 |
| PIK3CA | 2.2% | 1.7% | 2.2% | 2.5% | 1.02 | 0.81 | 1.02 | 1.19 |
| PIK3R1 | 2.2% | 0.9% | 1.4% | 0.0% | 1.71 | 0.68 | 1.14 | 0.00 |
| PTEN | 2.9% | 6.9% | 8.7% | 1.3% | 0.55 | 1.30 | 1.64 | 0.24 |
| RB1 | 2.9% | 2.6% | 1.4% | 1.3% | 1.37 | 1.22 | 0.68 | 0.60 |
| RUNX1 | 1.4% | 0.0% | 0.0% | 0.0% | 3.41 | 0.00 | 0.00 | 0.00 |
| SETD2 | 1.4% | 9.5% | 3.6% | 7.6% | 0.28 | 1.86 | 0.71 | 1.49 |
| STAG2 | 0.7% | 3.4% | 2.2% | 0.0% | 0.43 | 2.03 | 1.28 | 0.00 |
| TAF1 | 0.7% | 6.0% | 2.2% | 3.8% | 0.24 | 2.03 | 0.73 | 1.28 |
| TP53 | 10.1% | 14.7% | 7.2% | 17.7% | 0.87 | 1.26 | 0.62 | 1.52 |
| VHL | 0.0% | 0.0% | 0.7% | 1.3% | 0.00 | 0.00 | 1.71 | 2.98 |

Prevalent melanoma types appeared to be enriched or deficient in distinct sets of driver mutations. It appeared that key MAPK pathway genes varied according to the mutation rate among four melanoma types. In addition, no single factor explicitly defined a melanoma type to a specific mutation. Taken together, these results suggested that mutations are associated with but do not determine the molecular-functional types of these cancers (i.e., cancer Types A-D; $1^{st}$-$4^{th}$ MF profile clusters, respectively).

Classification of Tumor Organization into Four Prevalent Types

The following procedure was used for preprocessing data from TCGA:

2) Calculated patient's processes values using ssGSEA. Obtained Z-score patients processes values using mean and standard from previous step cancer cohort.

$$ZscoredPatentProcess_x = \frac{PatentsProcess_x - mean(TCGACohortProcess_x)}{std(TCGACohortProcess_x)}$$

3) Patient's sample was classified according to MF profile type with the closest (smallest) distance from patient's processes z-scored vector to MFP cancer cohort centroids.

4) Distance was calculated as Euclidean distance in z-scored processes space or (1-pearson/spearman correlation).
5) 1-distance to the each of MF profile types was treated as a similarity measure in the case of intermediate cases (if, for example, a patient's sample was very close to 2 prevalent types resulting in mixed features from both types).

The following procedure was used for preprocessing other data types (e.g., data from DNA microarrays, other references, outlying patient data from TCGA X cancer cohort PCA projection into 2-dimm space):
1) Calculated TCGA X cancer cohort processes values using ssGSEA, Z-score TCGA X cancer cohort.
2) Obtained a cohortA of patients with X cancer, processed them similarly as the patient (>40 samples). Calculated cohortA processes values using ssGSEA.
3) Calculated patient's processes values using ssGSEA. Obtained Z-score for combined cohortA and the patient.
4) If z-scored TCGA X cancer cohort and z-scored cohortA admixed on combined PCA 2-dimm projection, the procedure continued with step 3 described herein.

Example 2

Creating a Molecular Functional (MF) Portrait of a Tumor

A bioinformatics pipeline was constructed to determine tumor properties (e.g., malignant properties, non-malignant properties), and depict the tumor properties in a Molecular Functional Portrait (MF profile). The MF profile was designed to depict tumor cell composition and functional activities, and to facilitate the practical use of such information in cancer therapy. An exemplary bioinformatics pipeline for constructing a tumor portrait is shown in FIG. 1A. An exemplary MF profile is shown in FIG. 1B.

In brief, the bioinformatics pipeline was used to (i) evaluate the intrinsic properties of tumor cells such as oncogenic pathways, proliferation rate, epithelial-mesenchymal transition (EMT), and metastatic capacities; (ii) reconstruct the comprehensive immune, stromal and vascular networks of the tumor microenvironment; (iii) quantify the functional activities of different tumor associated cell types; and (iv) determine the intensity of processes that collectively either stimulated or inhibited progressive tumor growth.

Tumor cell composition was reconstructed from RNA-Seq and Exome-Seq data of tumor and normal tissue using in silico methods for inferring tumor purity and through deconvolution of the expression profiles for assessing functional subsets of both infiltrating hematopoietic cells and stromal cells. RNA-Seq data also provided a measure of certain cellular processes based on the expression of specific gene signatures associated with defined biological functions distributed among different cell types, such as antigen presentation, metastasis and inflammation.

A comprehensive cancer model was formulated by analysis of more than 373 publications, and yielded 28 functional modules listed in Table 2. The intensity of the "Mutation status" module was evaluated through quantitating mutations in 38 driver genes. The intensities of the remaining 27 modules were evaluated by gene set enrichment analysis (ssGSEA) on custom built signatures, which enabled estimation of the activity of different intratumoral processes. Taken together, these modules inherently reflected the relative content of the main cell types in a tumor tissue.

The qualitative and quantitative functional properties as the intensities of processes in 28 functional modules were graphically depicted in FIG. 1B. Module size corresponds to its ssGSEA enrichment score (or mutation counts) normalized within the same TCGA cohort. Colors reflect the module pro- or anti-cancer activity. Solid shades without cross-marking were assigned to the modules that promote tumor growth, while shades with cross-marking were assigned to those having anti-cancer activity. The coloration of the modules was also dependent on the ssGSEA score.

Example 3

Figure 41A:
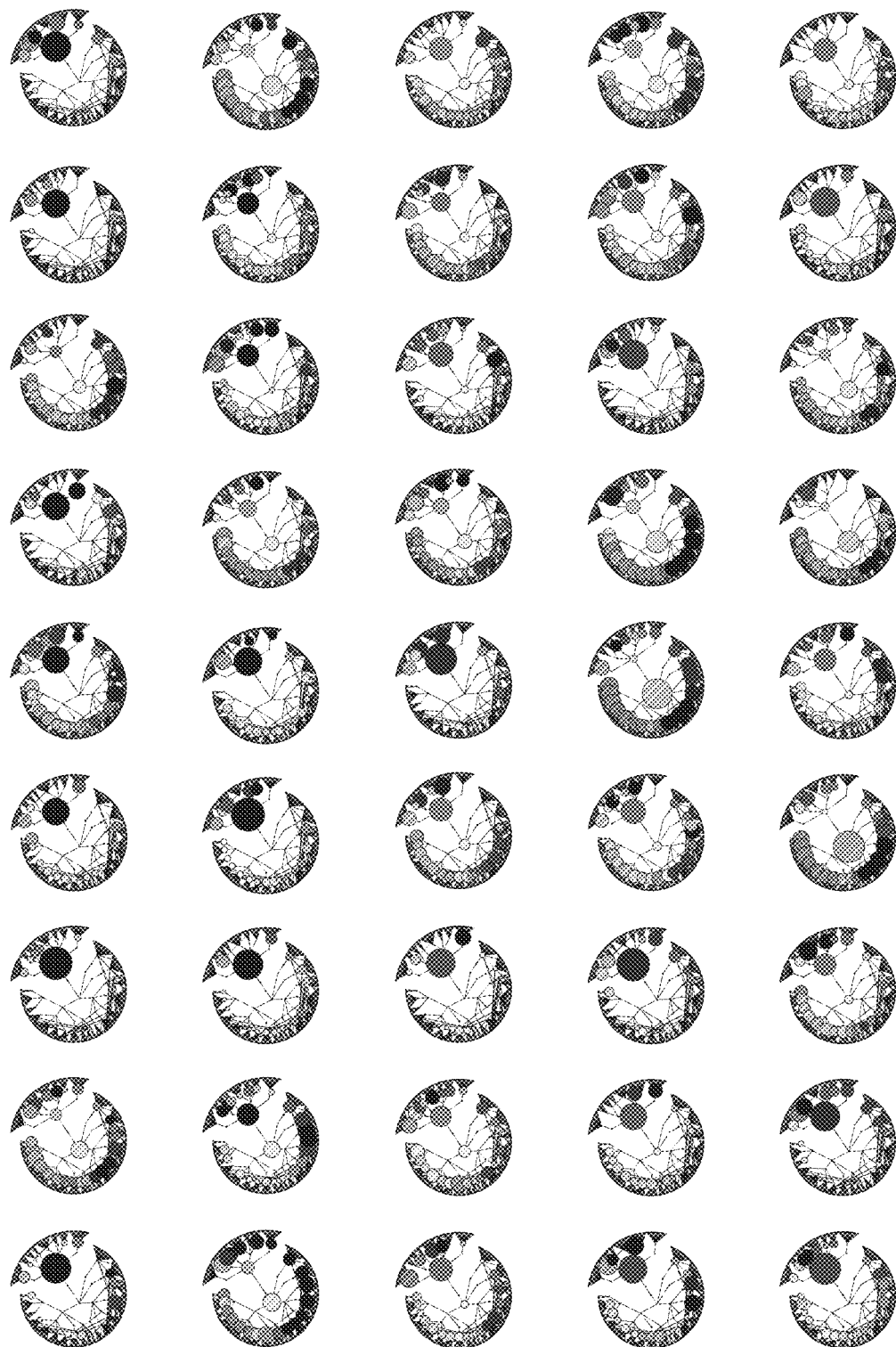
FIG. 41A shows a series of MF profiles of melanoma patients (n=45) chosen randomly, in accordance with some embodiments of the technology described herein.

Prevalent Types of Melanoma According to their Structural-Functional Organization Revealed Via an MF Profile The visualization method described herein enables a user to study the structural and functional composition of a particular patient's tumor, as well as to compare tumors from different patients. MF profiles for 470 patient human skin cutaneous melanoma (SKCM) tumors were constructed using data available from TCGA. The MF profile of each particular patient tumor was unique, yet the model clearly revealed a similarity of tumor MF profiles among different patients (FIG. 41A).

Figure 41B:
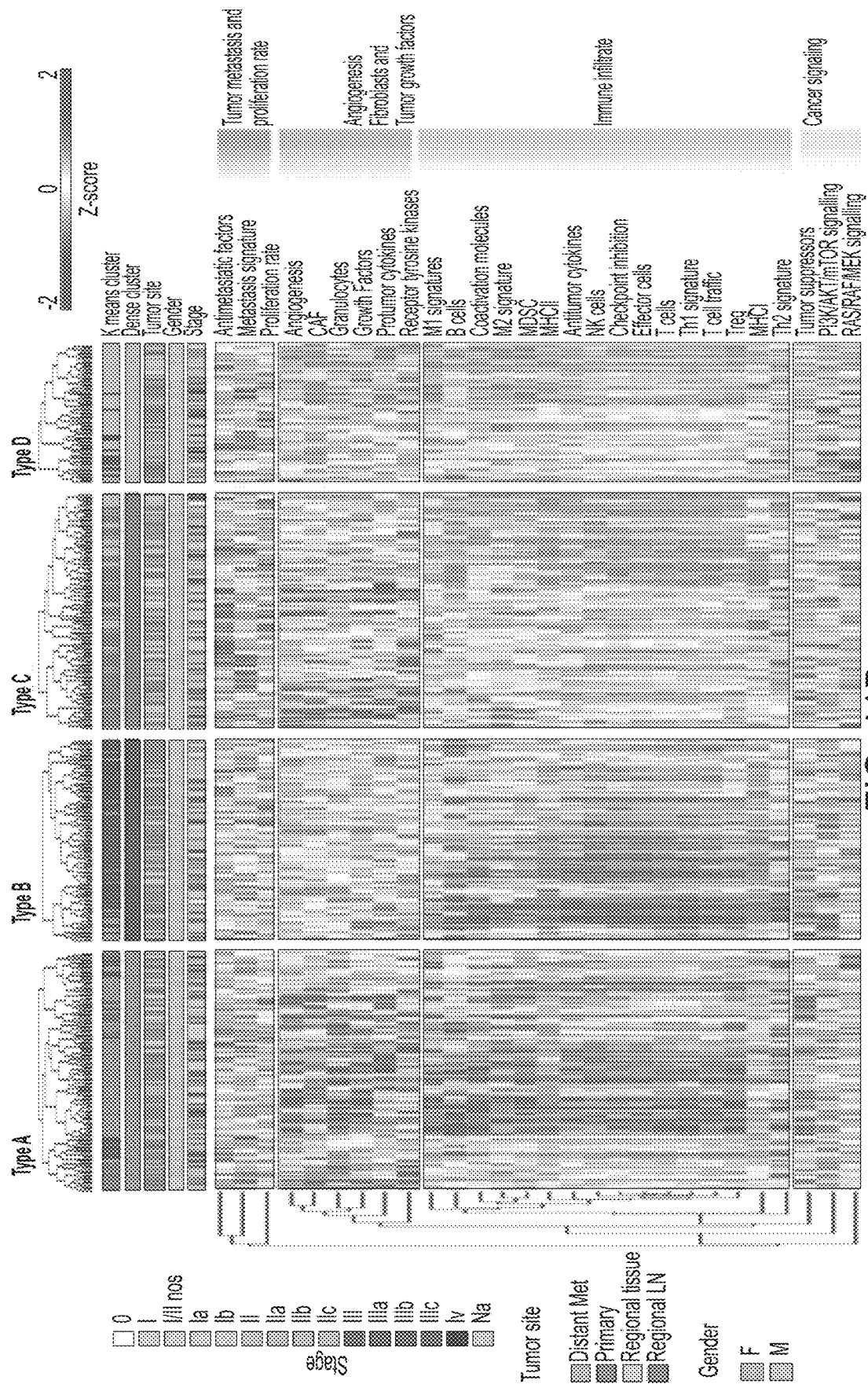
FIG. 41B shows data from an unsupervised dense subgraph network cluster analysis of tumor functional processes calculated from RNA-Seq data of patient melanoma tumors (n=470 patients), in accordance with some embodiments of the technology described herein. The determined clusters were labeled Types A-D ($1^{st}$-$4^{th}$ MF profile clusters, respectively).
Figure 41C:
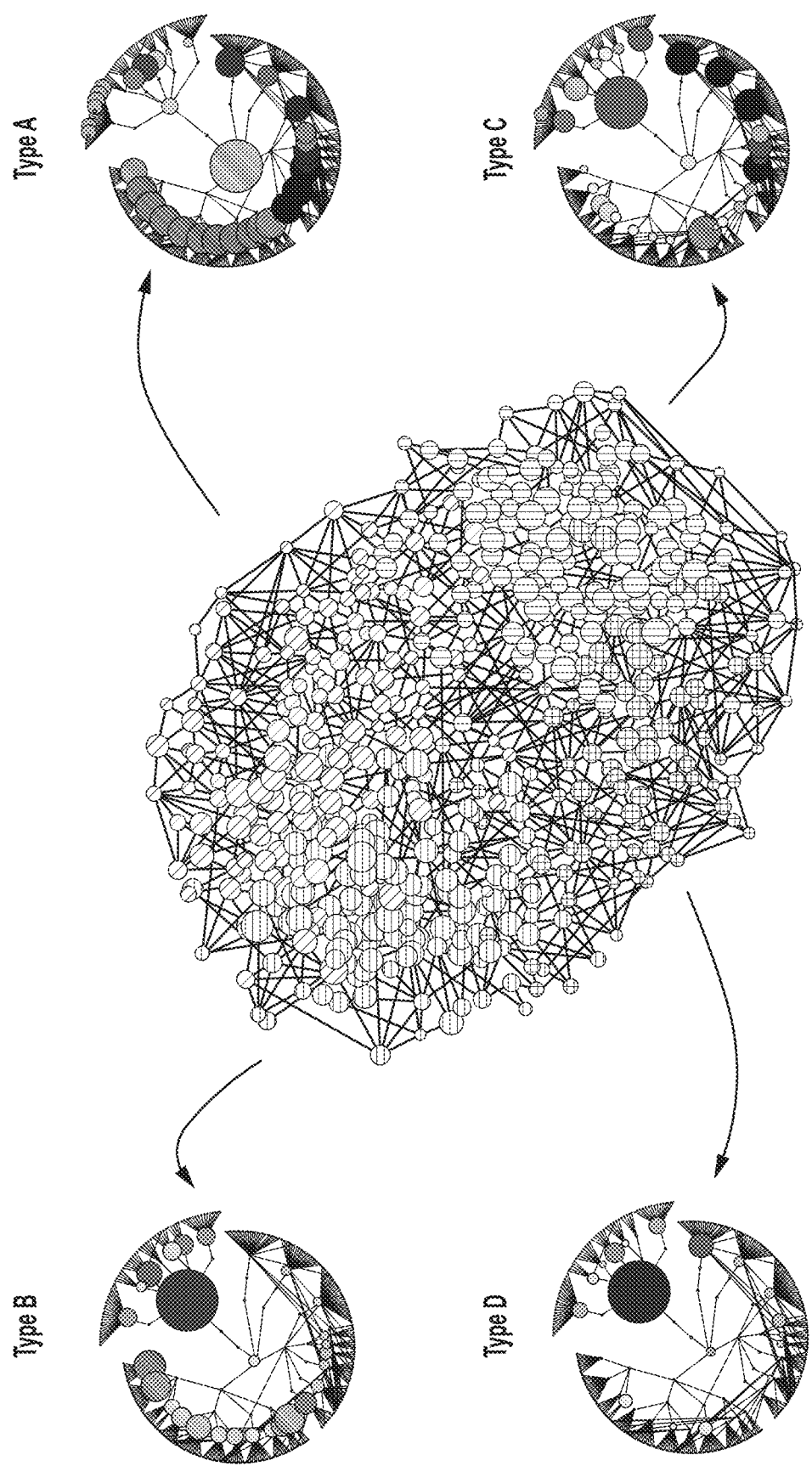
FIG. 41C is a graphical representation of a correlation-based graph network of patients showing determined clusters, in accordance with some embodiments of the technology described herein. Each dot represents an individual melanoma patient, who is connected to other patients with a weight corresponding to its correlation value. The size of the dot corresponds to the vertex degree.

The prevalent types of melanoma tumors were further revealed using unsupervised dense clustering analysis based on detection of the tightly connected networks of similar patients within the patients' correlation graph (FIG. 41B). This analysis revealed that the graph contained four distinct dense subpopulations (FIG. 41C). These four tumor types were labeled as Types A, B, C and D ($1^{st}$-$4^{th}$ MF profile clusters, respectively). Analysis of tumor type abundance demonstrated that Type A, B, C, and D tumors were present in 22%, 28%, 24%, and 24% of melanoma patients, respectively. In other words, 98% of melanoma patients could be determined to have one of the four prevalent tumor types.

Figure 41D:
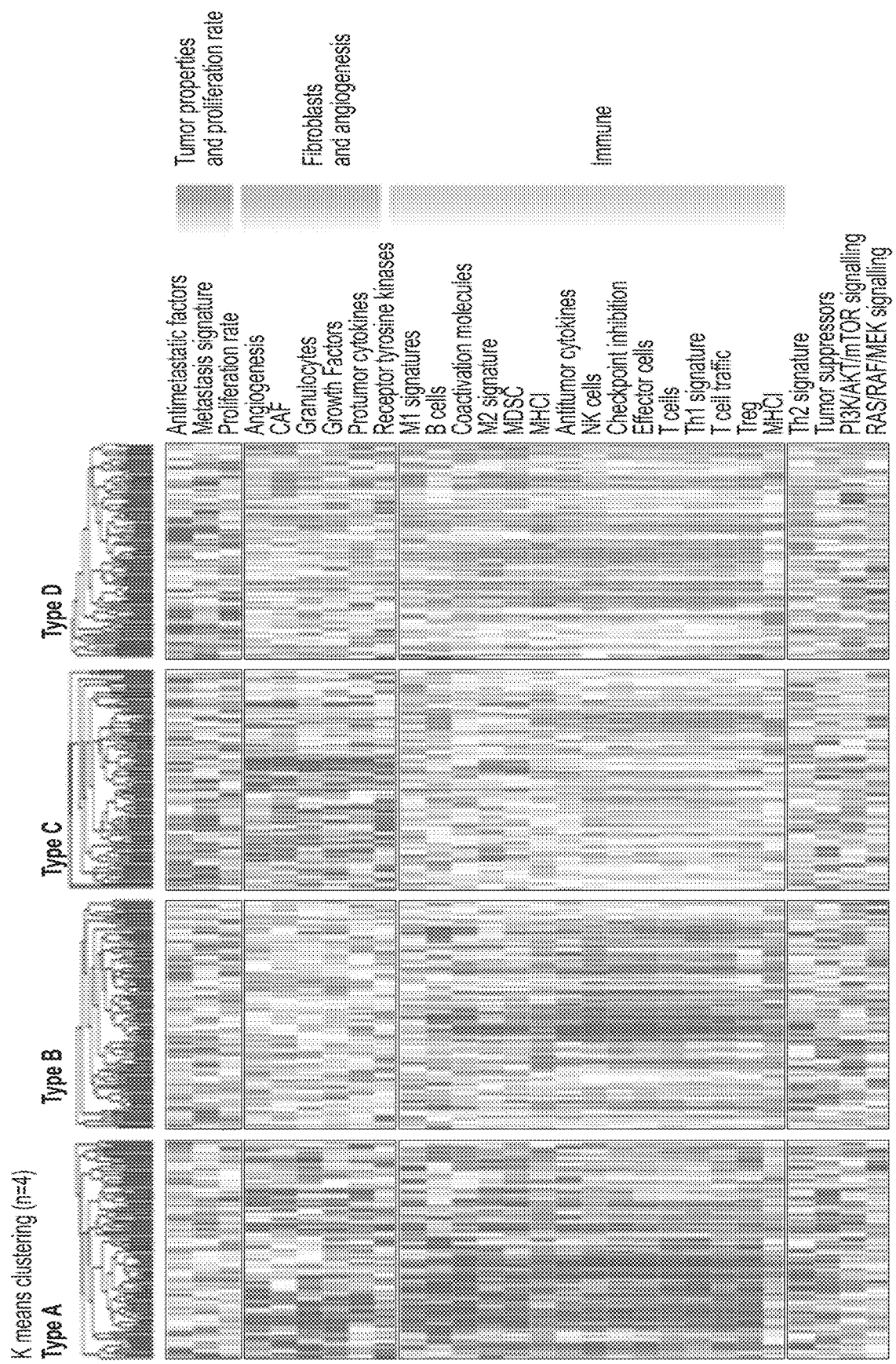
FIG. 41D shows data from a k-means clustering analysis of tumor functional processes calculated from RNA-Seq data of melanoma tumors (n=470 patient tumors), in accordance with some embodiments of the technology described herein. The determined clusters were labeled Types A-D ($1^{st}$-$4^{th}$ MF profile clusters, respectively).
Figure 41E:
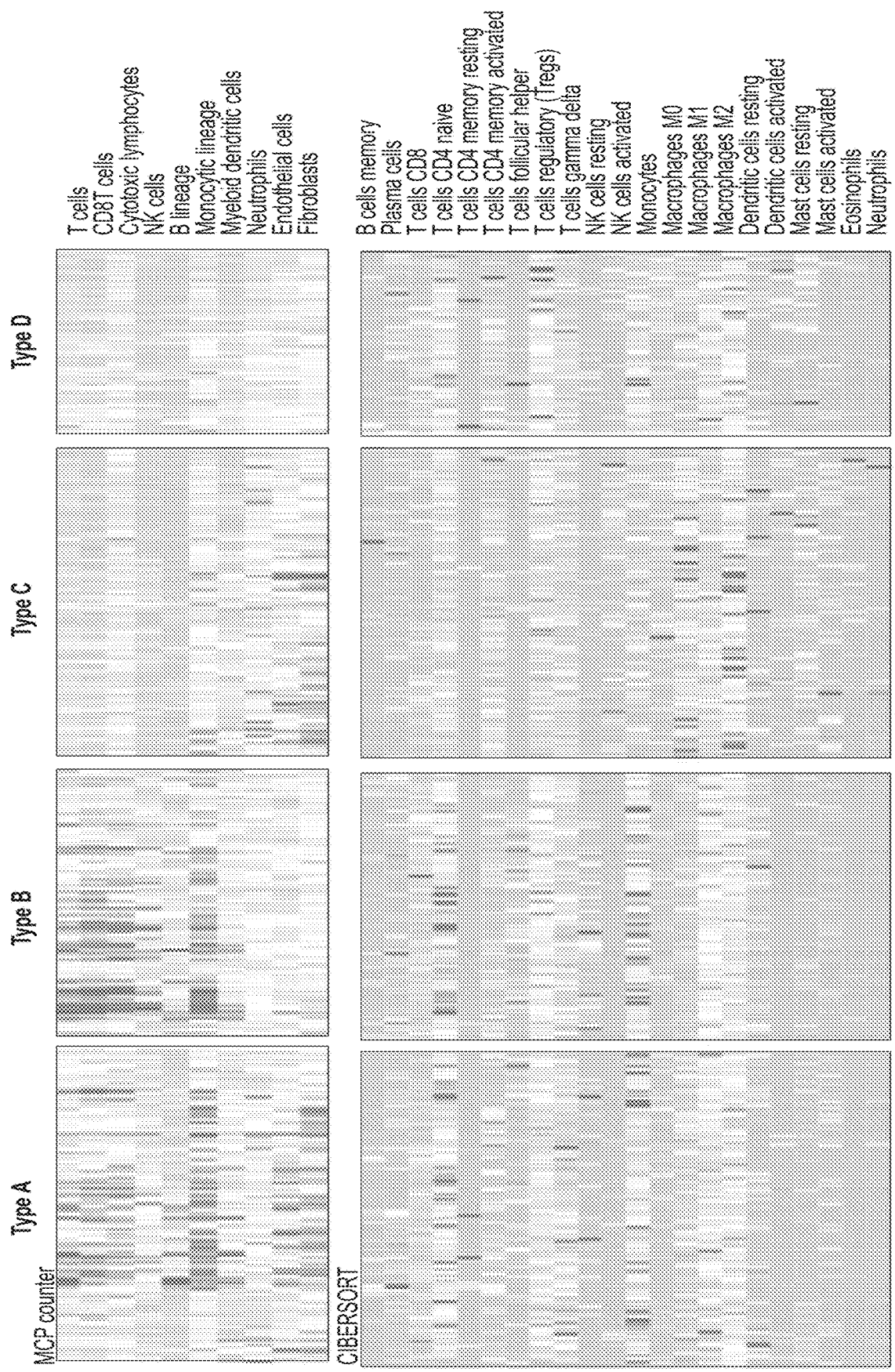
FIG. 41E shows data from a cell composition analysis of melanoma tumors grouped into determined cluster Types A-D ($1^{st}$-$4^{th}$ MF profile clusters, respectively) using MCP-counter and CIBERSORT, in accordance with some embodiments of the technology described herein.
Figure 41F:
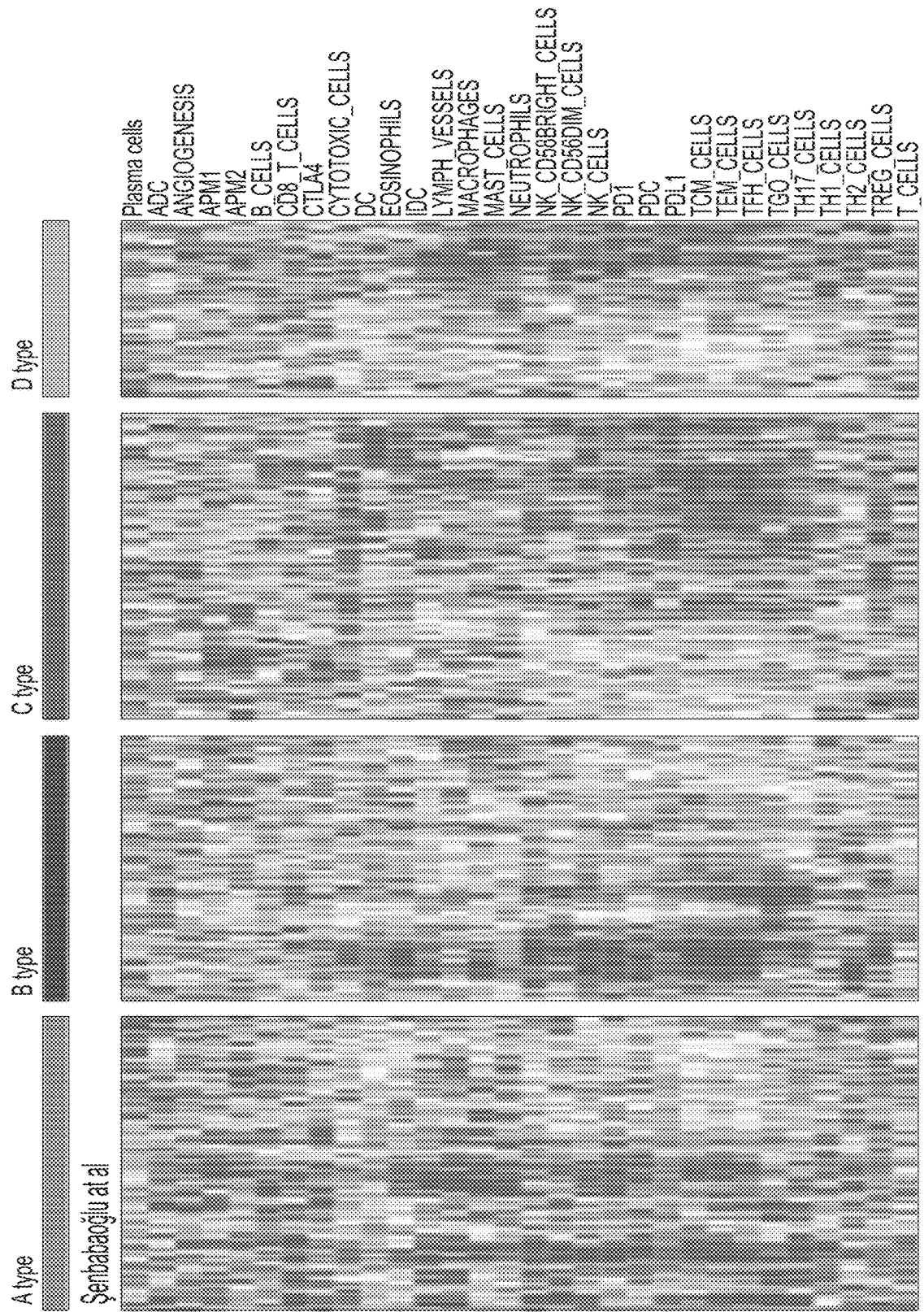
FIG. 41F shows data from a gene set enrichment analysis of melanoma tumors grouped into determined cluster Types A-D ($1^{st}$-$4^{th}$ MF profile clusters, respectively), in accordance with some embodiments of the technology described herein.

As an alternative approach, k-means clustering was applied, which gave rise to nearly the same clusters of patients as the unsupervised dense clustering approach (FIG. 41D). These clusters were also supported by tumor dissection using MCP-counter cell (FIG. 41E), CIBERSORT deconvolution algorithm (FIG. 41E), and by dissection based on phenotype-specific gene signatures (FIG. 41F).

Figure 41G:
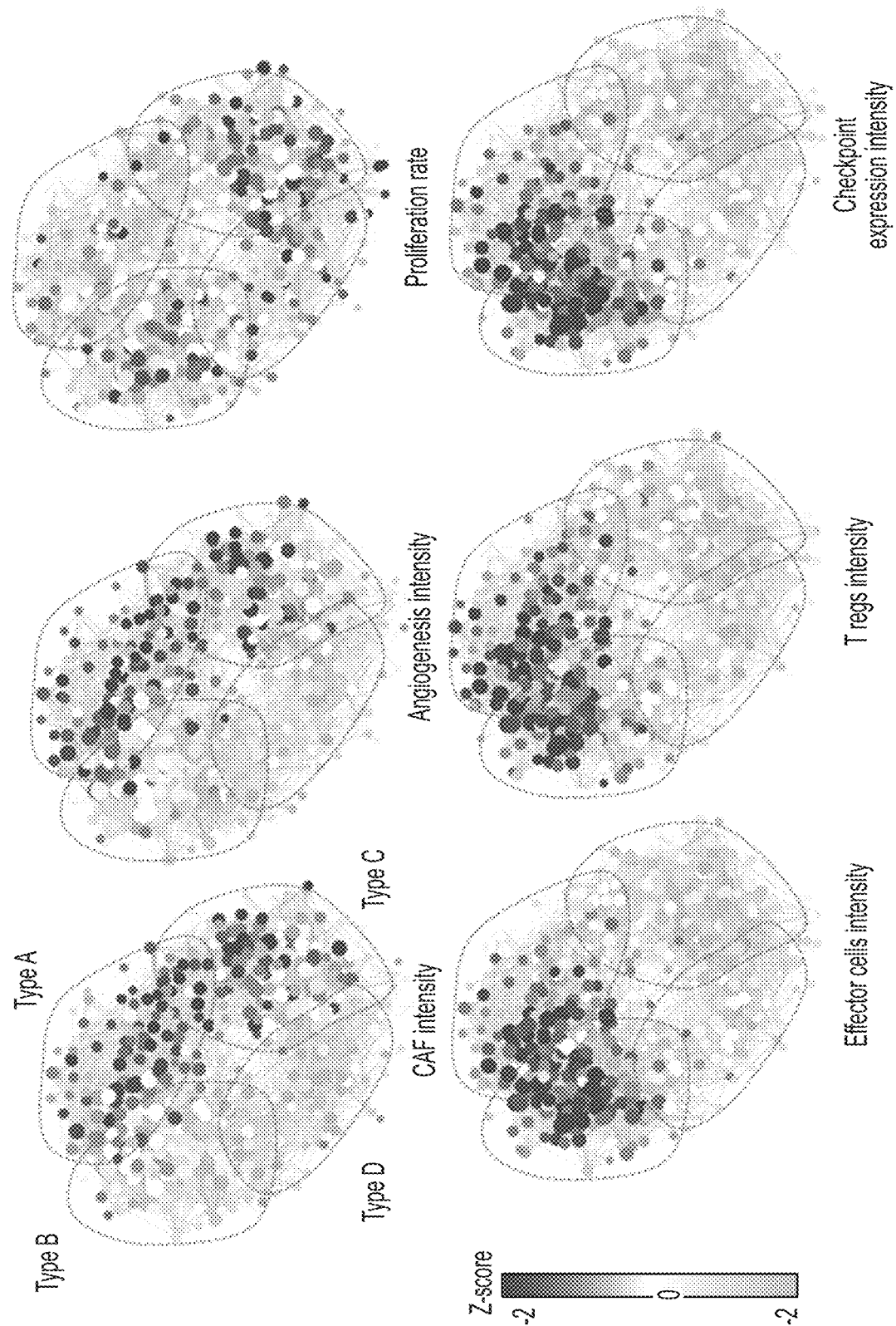
FIG. 41G is a graphical representation of functional process intensity associated with tumor growth (e.g., CAF, Angiogenesis, or Proliferation rate) or intratumoral immune infiltrate (e.g., effector cells or regulatory T cells (Tregs)) layered on cancers of determined cluster Types A-D ($1^{st}$-$4^{th}$ MF profile clusters, respectively), in accordance with some embodiments of the technology described herein.
Figure 41H:
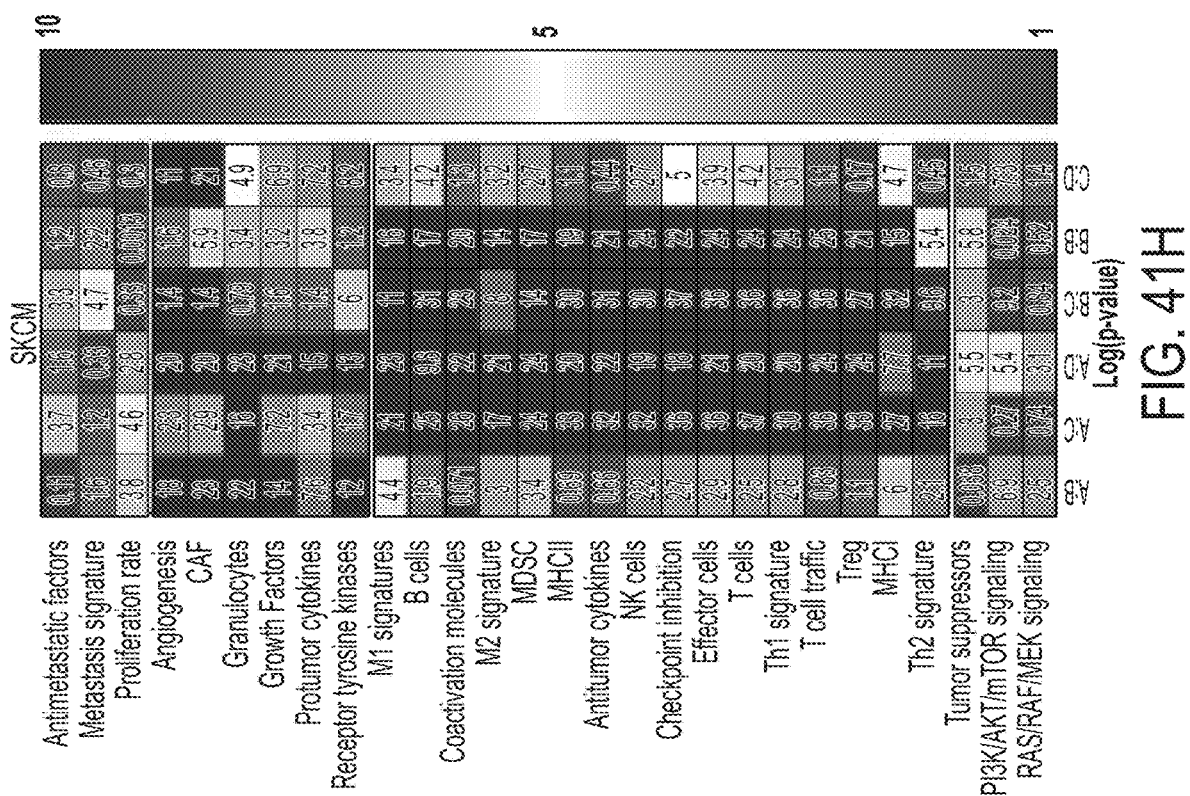
FIG. 41H shows data from a log(p-value) t-test difference in process activity (enrichment score) between cancers of determined cluster Types A-D ($1^{st}$-$4^{th}$ MF profile clusters, respectively), in accordance with some embodiments of the technology described herein.

These four types of MF profiles are significantly different according to the activity of 28 functional modules. Inter-cluster analysis revealed that the differences between the clusters resides in the activity of their underlying processes (FIG. 41G). Process activity between the cluster pairs were compared using the t-test. Each pair of clusters differed by the activity of at least six processes with a p-value<$10^{-7}$ (FIG. 41H).

Figure 41J:
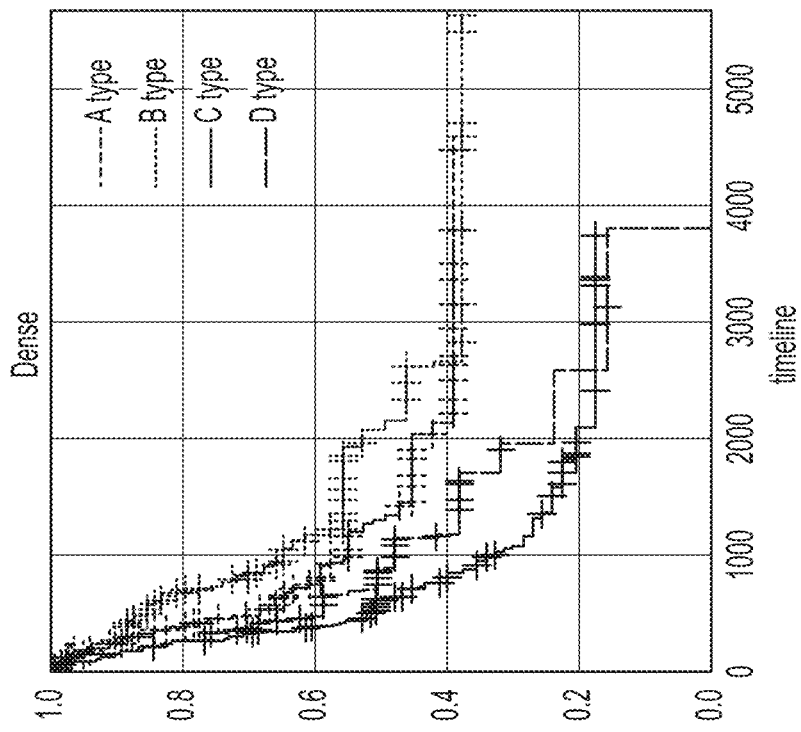
FIG. 41J shows Kaplan-Meier survival curves for melanoma patients split into cohorts according to the their MF profile determined cluster types (Types A-D; which are equivalent to the $1^{st}$-$4^{th}$ types of portraits described herein, respectively) using k-means clustering, in accordance with some embodiments of the technology described herein.
Figure 41I:
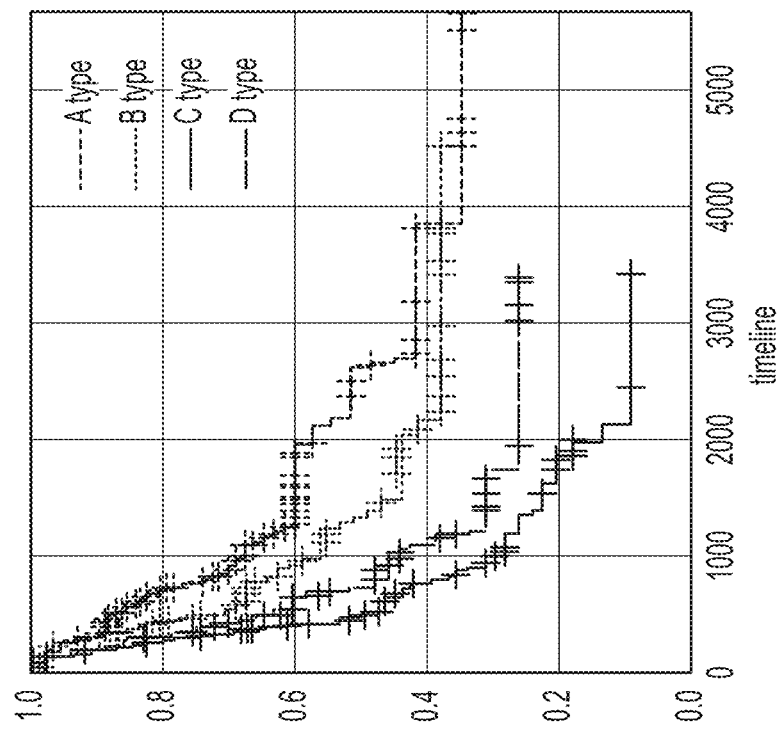
FIG. 41I shows Kaplan-Meier survival curves for melanoma patients split into cohorts according to the their MF profile determined cluster types (Types A-D; which are equivalent to the $1^{st}$-$4^{th}$ types of portraits described herein, respectively) using unsupervised dense subgraph network clustering, in accordance with some embodiments of the technology described herein.
Figure 41K:
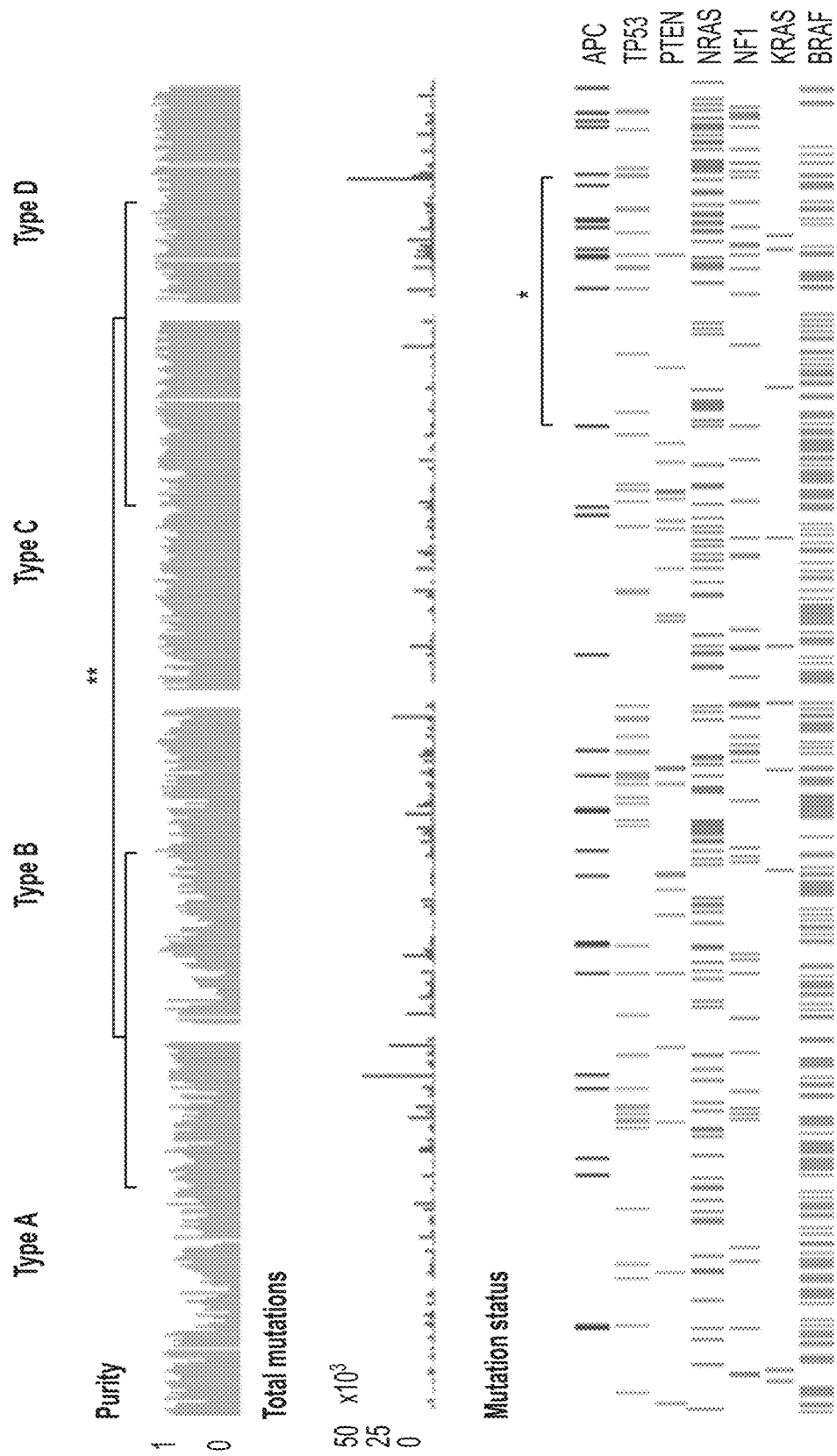
FIG. 41K shows data from a purity, mutational load and mutational status analysis of melanoma tumors grouped according to their determined cluster Types A-D (which are equivalent to the $1^{st}$-$4^{th}$ types of portraits described herein, respectively), in accordance with some embodiments of the technology described herein.

The four tumor types were characterized in terms of patient prognosis and abundance of driver mutations. Patients having Types A and B (first and second MF profile clusters, respectively) melanomas had significantly longer survival time as compared to patients with Types C and D melanomas (third and fourth MF profile clusters, respectively) (FIGS. 41I and 41J). The four prevalent melanoma types appeared to be enriched or deficient in distinct sets of driver mutations, yet it was revealed that mutations are associated but do not determine molecular-functional types of melanoma tumors (FIG. 41K).

Detailed MF profiles representative for Types A-D melanomas ($1^{st}$-$4^{th}$ MF profile clusters, respectively) are shown in FIGS. 42A-42D. Types A and B (first and second MF profile clusters, respectively) were characterized as "inflamed" tumors, and types C and D (third and fourth MF profile clusters, respectively) were characterized as "noninflamed" tumors. "Inflamed" tumors are characterized by excessive infiltration with immune cells. "Noninflamed" tumors are poorly infiltrated by hematopoietic cells.

Human skin cutaneous melanomas characterized as MF profile type A were characterized by abundant infiltration of immune cells and the presence of factors necessary for antigen presentation to T cells and their activation (e.g., MHC class I and II, CD80, CD86, CD40, etc.). An average ratio of malignant to nonmalignant cells (tumor purity) in this type of melanoma was 0.57. Type A cancers have pronounced signs of tumor infiltration by immune cells known to possess anticancer effector activity (e.g., cytotoxic T, NK cells, Th1 and M1 cells). Balanced against anti-cancer (e.g., anti-tumor) processes, Type A tumors also demonstrated active expression of checkpoint inhibitor molecules and recruitment of suppressor cells (e.g., MDSC and Treg), as well as other types of cells that support tumor growth (e.g., M2 and Th2). Type A tumors had a highly developed network of blood vessels and an increased concentration of cancer-associated fibroblasts, which promote epithelial-mesenchymal transition and malignant cell metastatic spread. Taken together, the analysis revealed that Type A tumors are characterized by high intensities of both anticancer and pro-cancer immune processes.

Type B melanoma tumors had similar features to Type A melanoma tumors except that Type B tumors demonstrated a lower intensity of tumor immune/inflammatory infiltration and lacked extensive angiogenesis and CAF networks. Type B melanoma tumors had 0.64 tumor purity on average.

Type C melanoma tumors and Type D melanoma tumors were demonstrated to have poor or no leukocyte/lymphocyte infiltration. Type C melanoma tumors had extensive vascularization and increased levels of CAFs. By contrast, excessive angiogenesis and CAF networks were not found in Type D melanoma tumors. Average tumor purities for Type C melanoma tumors and Type D melanoma tumors were 0.81 and 0.85, respectively, reflecting the predominance of malignant cells.

Type B melanoma tumors and Type D melanoma tumors were characterized by high tumor proliferation rates, and a lack of intensive angiogenesis and CAF networks.

In sum, highly prevalent MF profiles revealed in a large cohort (n=470) of melanoma patients suggested that melanoma tumors comprised a restricted number of principal variants in terms of their functional organization, which includes a pro-tumor microenvironment in dynamic equilibrium with an anti-tumor immune microenvironment.

Characteristics of melanoma tumor Types A-D ($1^{st}$-$4^{th}$ MF profile clusters, respectively) were correlated with patient survival, intensity of cell infiltration (e.g., immune cells, stromal cells, and inflammatory cells), and tumor vascularization to provide a brief description of the four melanoma MF profiles. The brief description of the identified MF profiles in terms of a treatment perspective (e.g., good, optimal, poor) and cellular infiltrate (e.g., immune, vascular, fibrotic) were:

A—good (immune, vascular, fibrotic);
B—optimal (immune);
C—poor (immunosuppressive, vascular, fibrotic); and
D—poor (immune "desert").

Example 4

Four General Types of MF Profiles were Revealed Throughout Different Cancers

Figure 43A:
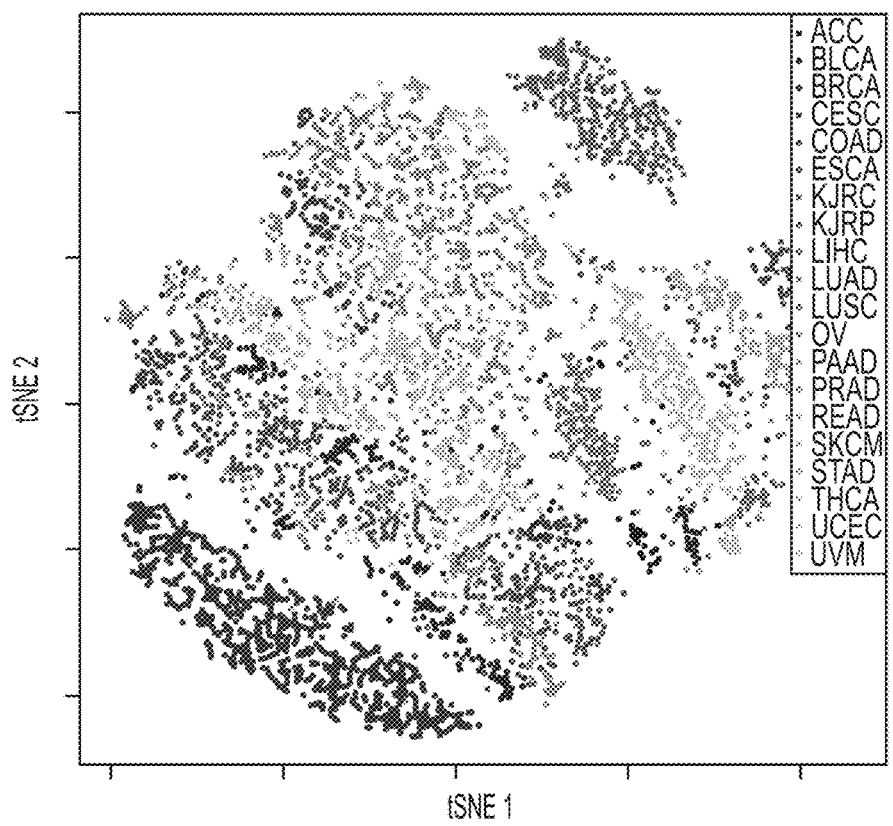
FIG. 43A shows data from a tSNE analysis over non-normalized process enrichment scores, in accordance with some embodiments of the technology described herein. Each data point corresponds to an individual analyzed tumor sample. Different datasets (e.g., cancer types) are indicated by various grayscale intensities.
Figure 43B:
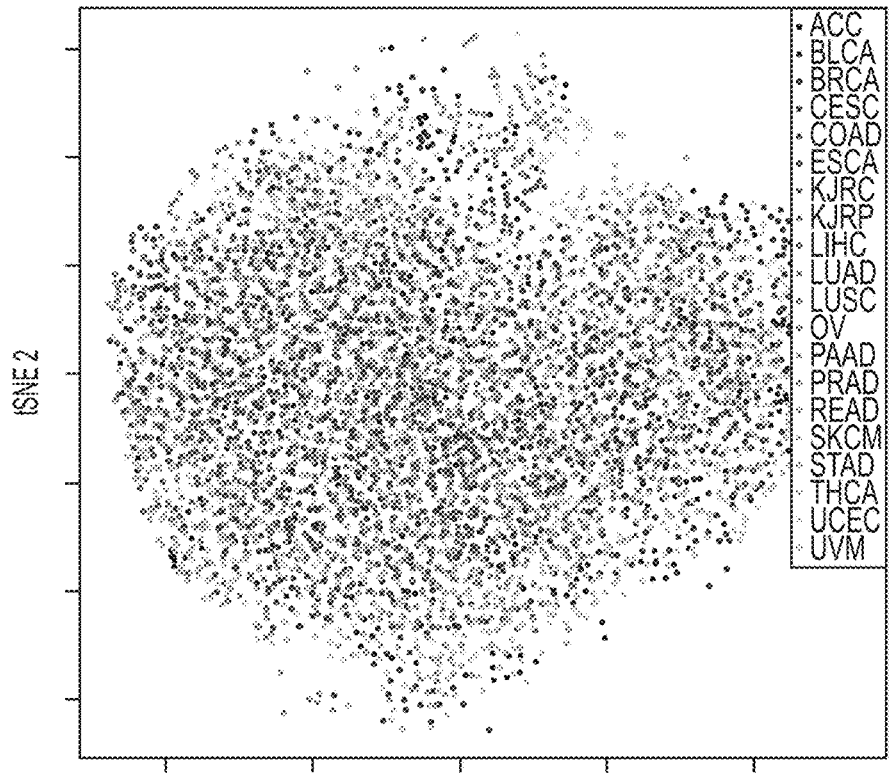
FIG. 43B shows data from a tSNE analysis over process enrichment scores normalized within specific cancer types, in accordance with some embodiments of the technology described herein. Each data point corresponds to an individual tumor sample analyzed. Different datasets (e.g., cancer types) are indicated by various grayscale intensities.

To determine whether the MF profile classification method displayed tissue-specificity, t-distributed stochastic neighbor embedding (tSNE) analysis was performed on 20 epithelial cancers (n=7920, TCGA) over process activity values (ES scores). This analysis showed that process activity values formed distinct tissue of origin specific sample subsets (FIG. 43A). A common cluster for colon (COAD) and rectal (READ) cancers was coherent with the current view that they have similar molecular and cellular origins. In order to minimize cancer specificity, process activity values were normalized by Z-score transformation within each cancer type. Following such normalization the MF profiles formed a uniform single set in tSNE analysis (FIG. 43B).

Figure 43C:
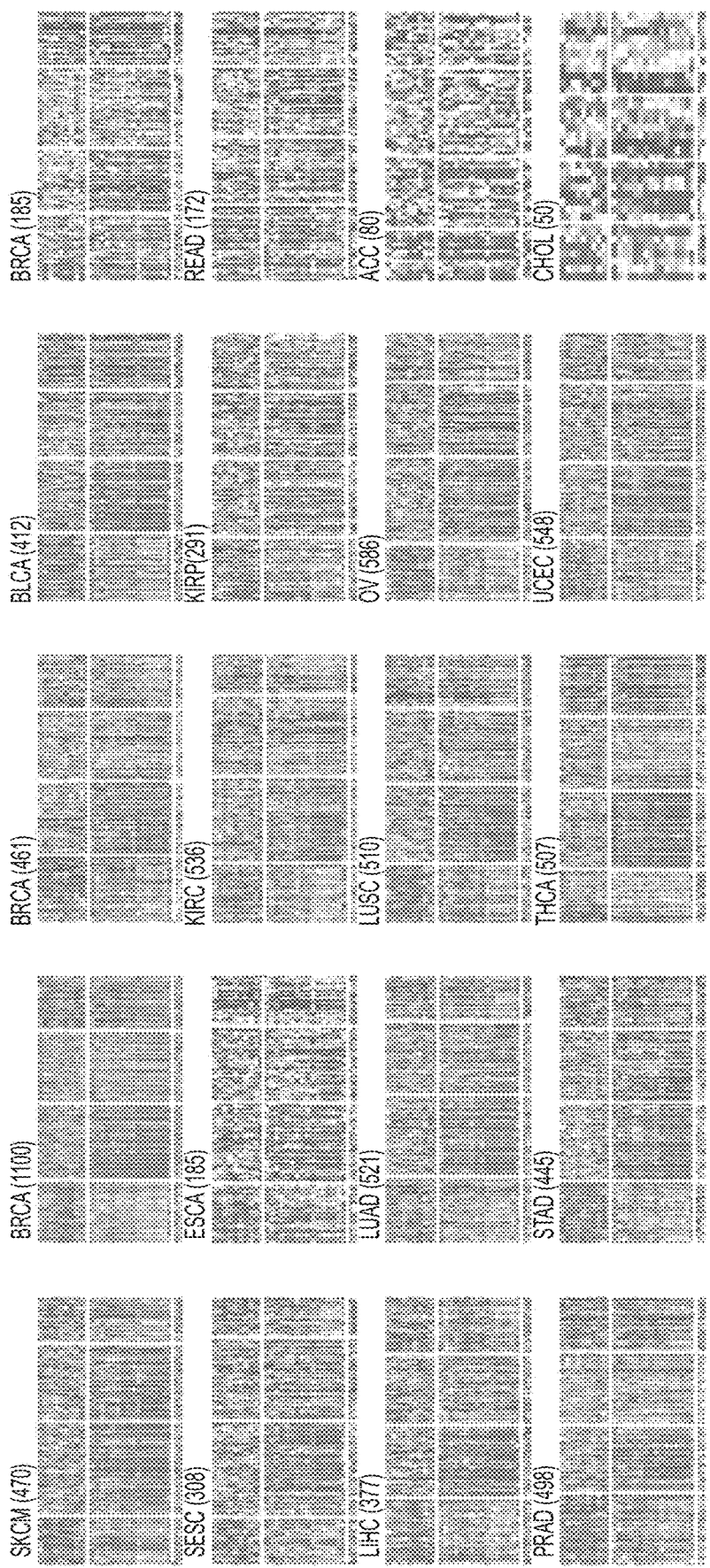
FIG. 43C shows data from an unsupervised dense subgraph network cluster analysis of tumor functional processes calculated from RNA-Seq data of different patient tumors. The following cancers were analyzed using TCGA data (listed n values indicate the numbers of individual patients): ACC—adrenocortical carcinoma (n=80), BLCA—bladder urothelial carcinoma (n=412), BRCA—breast invasive carcinoma (n=1100), CESC—cervical squamous cell carcinoma and endocervical adenocarcinoma (n=308), COAD—colon adenocarcinoma (n=461), ESCA—esophageal carcinoma (n=185), KIRC—kidney renal clear cell carcinoma (n=536), KIRP—kidney renal papillary cell carcinoma (n=291), LIHC—liver hepatocellular carcinoma (n=377), LUAD—lung adenocarcinoma (n=521), LUSC—lung squamous cell carcinoma (n=510), OV—ovarian serous cystadenocarcinoma (n=586), PAAD—pancreatic adenocarcinoma (n=185), PRAD—prostate adenocarcinoma (n=498), READ—rectal adenocarcinoma (n=172), SKCM—skin cutaneous melanoma (n=470), STAD—stomach adenocarcinoma (n=445), THCA—thyroid carcinoma (n=507), UCEC—uterine corpus endometrial carcinoma (n=548), CHOL—Cholangiocarcinoma—(n=36).
Figure 43D:
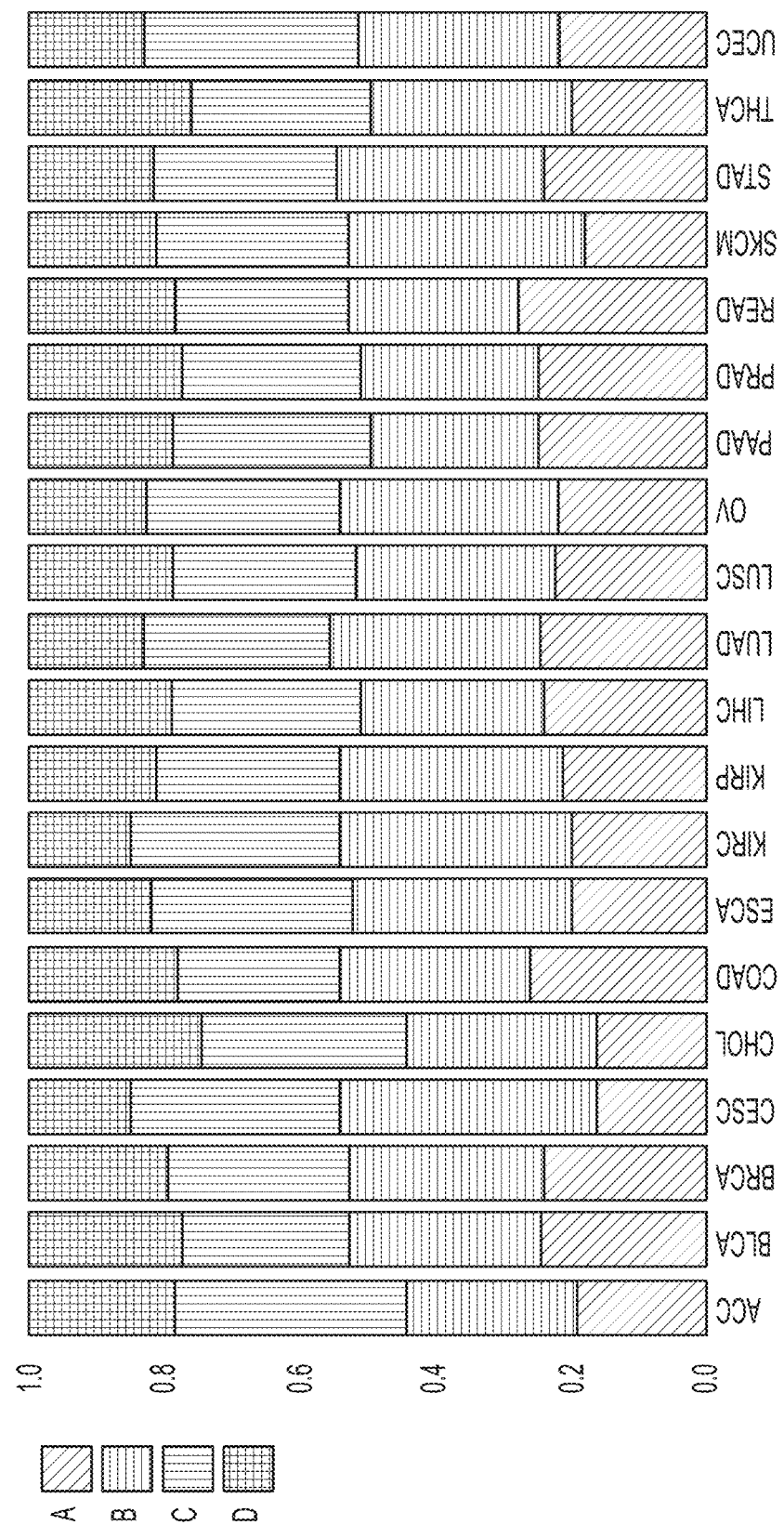
FIG. 43D shows the frequency of determined cancer cluster Types A-D ($1^{st}$-$4^{th}$ MF profile clusters, respectively) in patients having different malignant neoplasms, in accordance with some embodiments of the technology described herein.
Figure 43E:
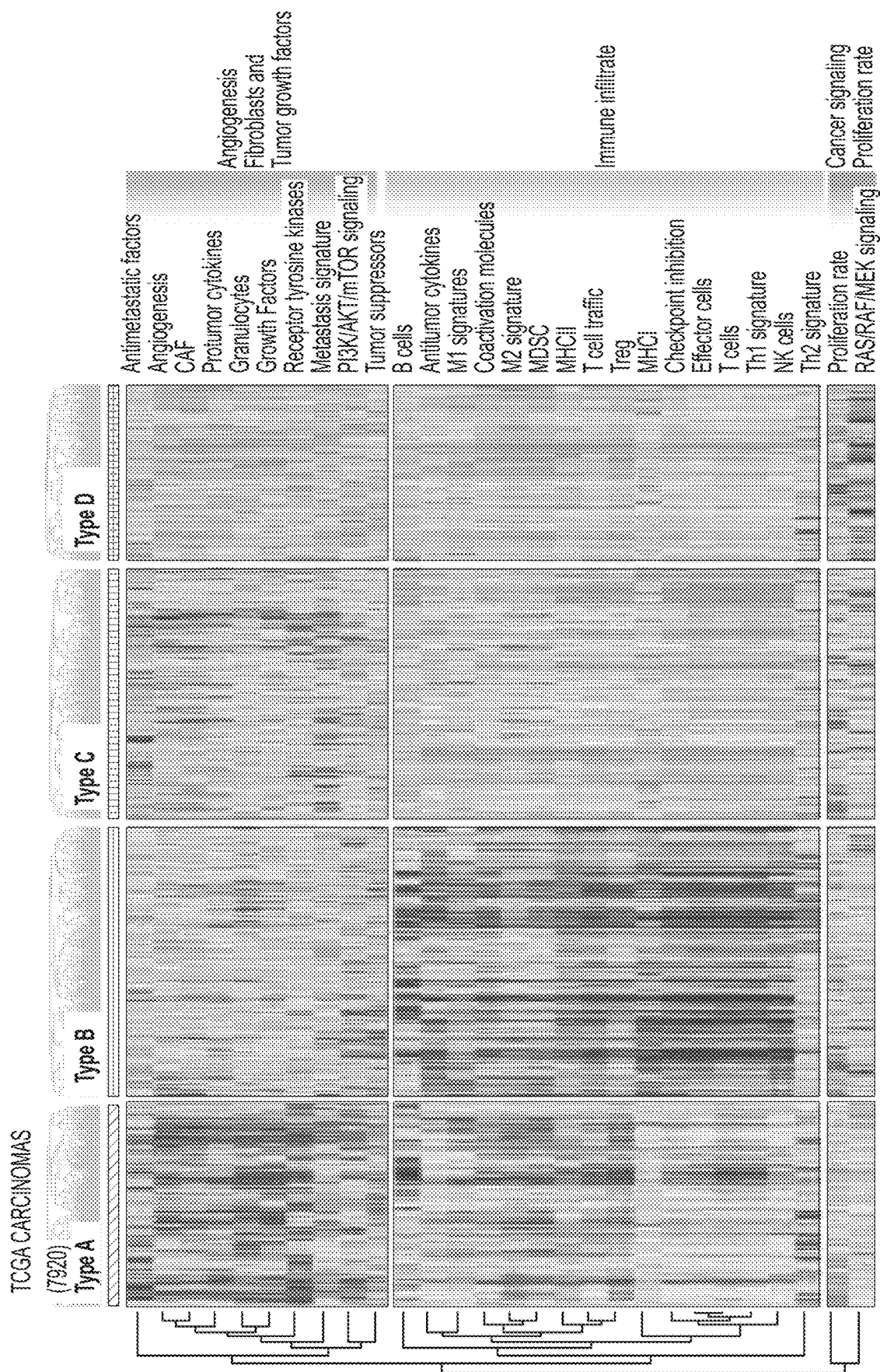
FIG. 43E shows data from an unsupervised dense subgraph network cluster analysis of tumor functional processes calculated from RNA-Seq data of patient having different malignant neoplasms, in accordance with some embodiments of the technology described herein. The determined clusters were labeled Types A-D ($1^{st}$-$4^{th}$ MF profile clusters, respectively).

Methods of building tumor MF profiles as described herein were applied to carcinomas of different tissue origins. Using NGS data of cancer patients available from TCGA, unsupervised dense subgraph clustering analysis was performed and tumor MF profiles for 7920 patients with 20 different epithelial cancers were reconstructed. Among the different carcinoma patients studied, four prevalent types of molecular-functional organization were identified that were strikingly similar to the organization of MF profiles for melanoma. The relative sizes of A, B, C and D clusters varied among cancer types (FIG. 43C). The four MF profile types were also clearly evident in the analysis of the combined dataset of 20 cancer types (FIG. 43E). Similar results were obtained by the k-means pan-cancer clustering algorithm (FIGS. 44A-44G).

Figure 43F:
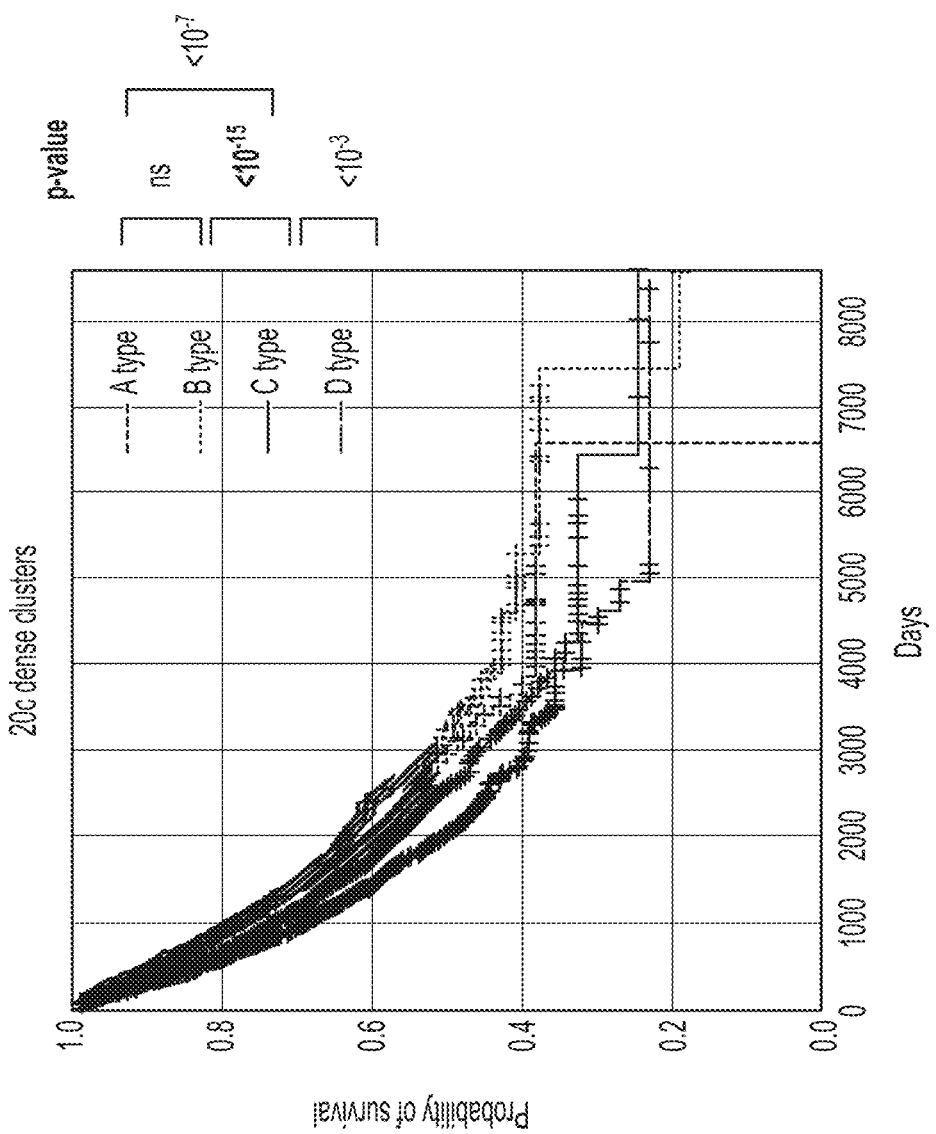
FIG. 43F shows Kaplan-Meier survival curves for patients having different malignant neoplasms split into cohorts according to the their determined cancer cluster Types A-D ($1^{st}$-$4^{th}$ MF profile clusters, respectively), in accordance with some embodiments of the technology described herein.
Figure 44A:
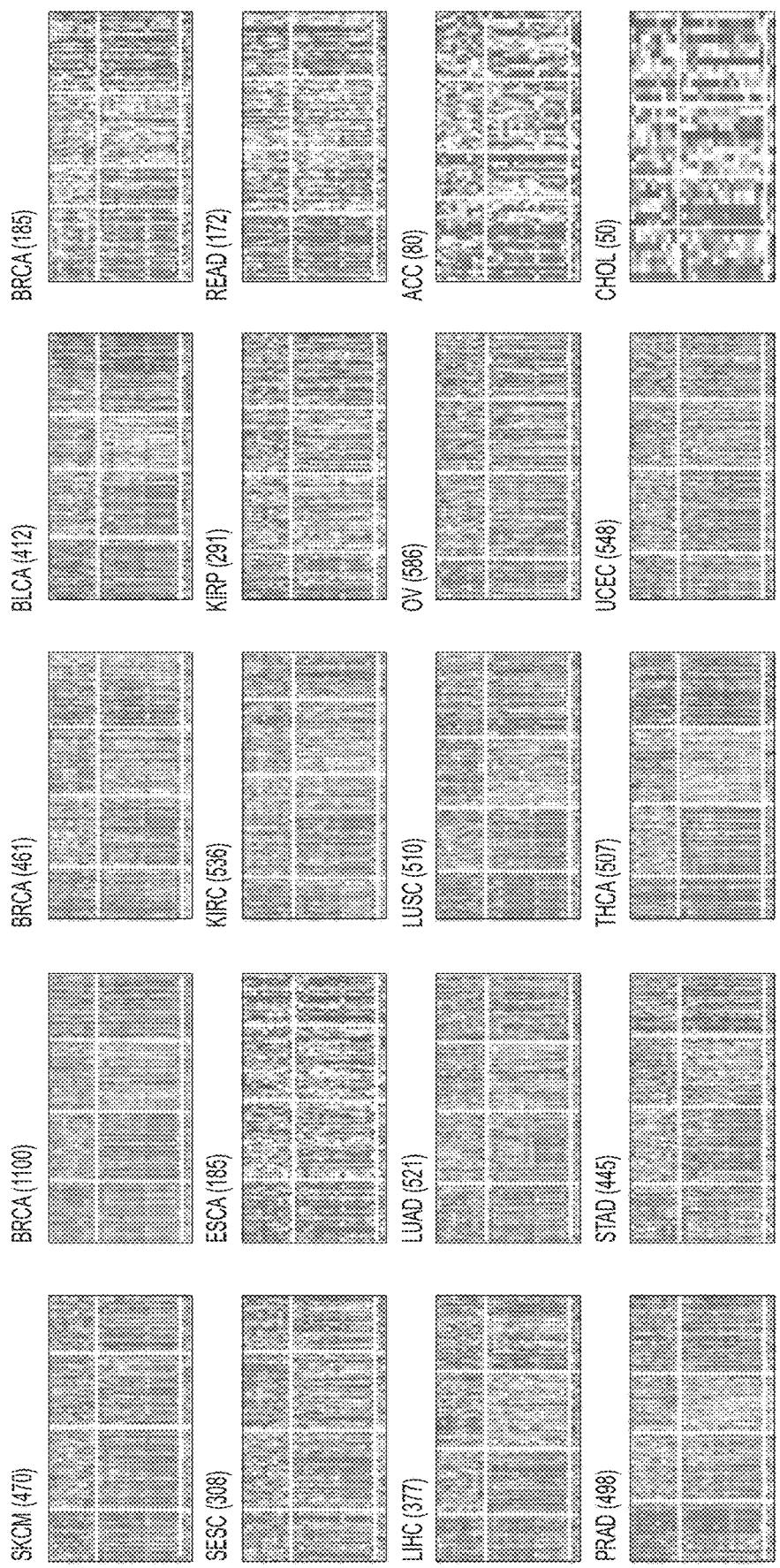
FIG. 44A shows data from a k-means clustering analysis of tumor functional processes calculated from RNA-Seq data for each cancer sample, in accordance with some embodiments of the technology described herein. The determined clusters were labeled Types A-D ($1^{st}$-$4^{th}$ MF profile clusters, respectively).
Figure 44B:
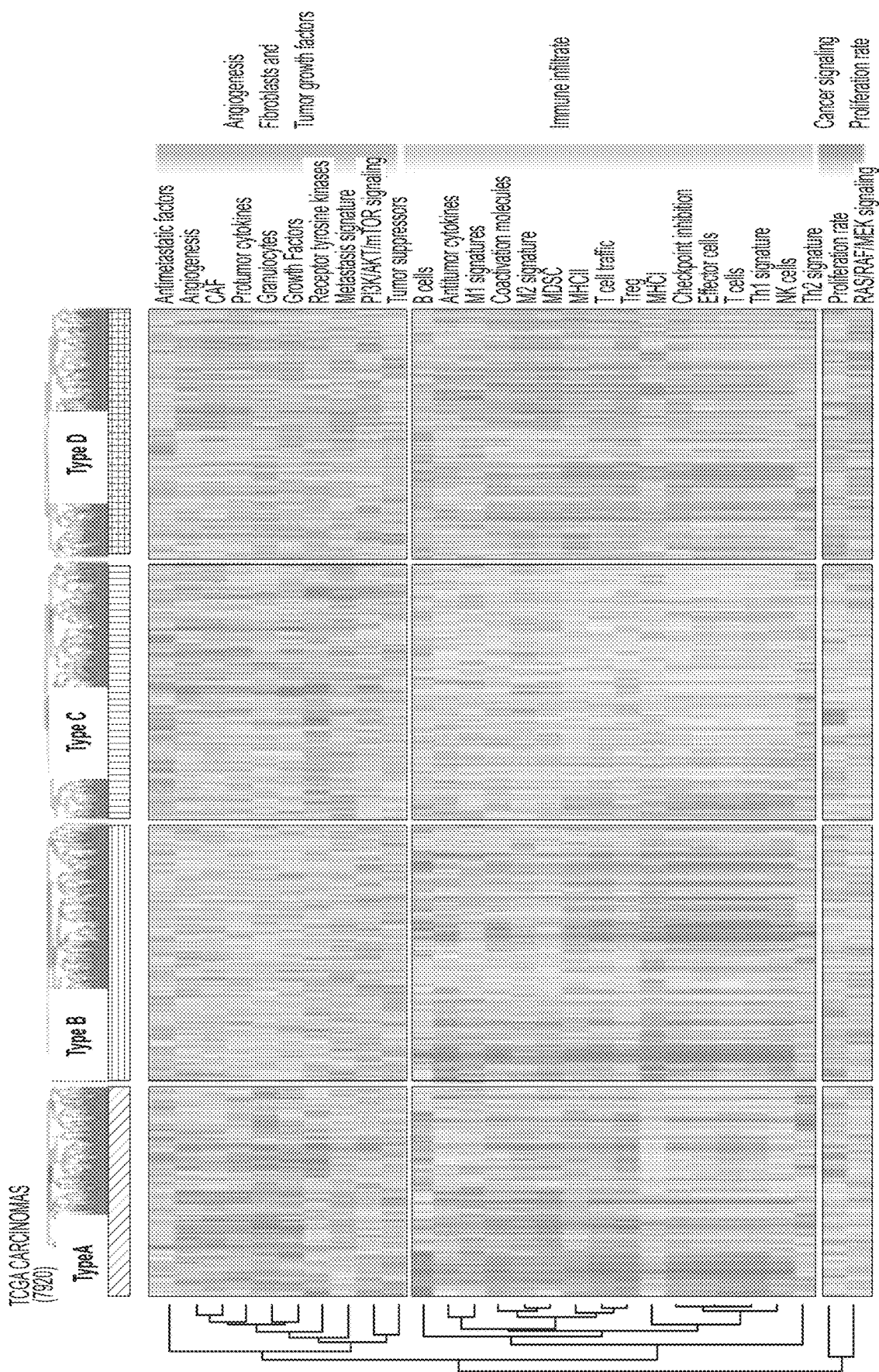
FIG. 44B shows data from a k-means clustering analysis of tumor functional processes calculated from RNA-Seq data for merged pan-cancer tumors, in accordance with some embodiments of the technology described herein. The determined clusters were labeled Types A-D ($1^{st}$-$4^{th}$ MF profile clusters, respectively).
Figure 44C:
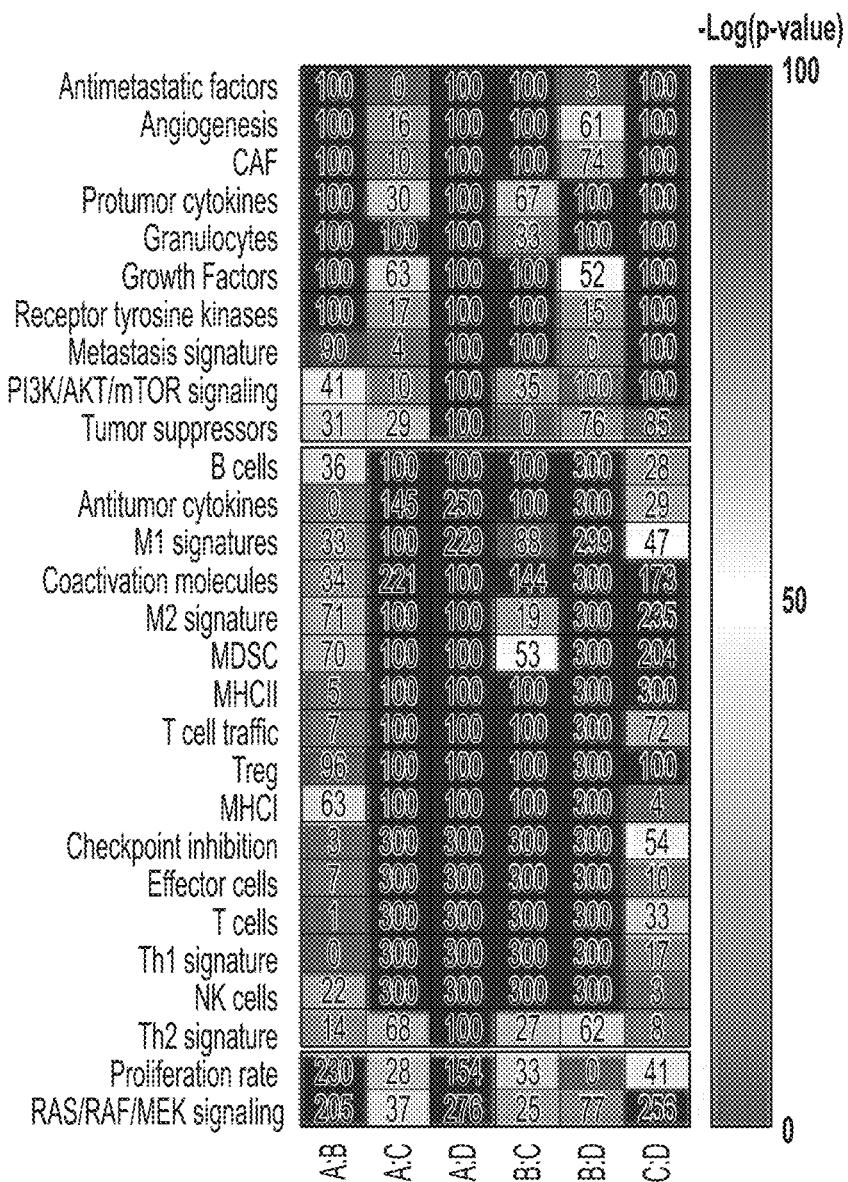
FIG. 44C shows data from a log(p-value) t-test difference in process activity enrichment scores between determined cancer cluster Types A-D ($1^{st}$-$4^{th}$ MF profile clusters, respectively) for merged pan-cancer tumors, in accordance with some embodiments of the technology described herein.
Figure 44E:
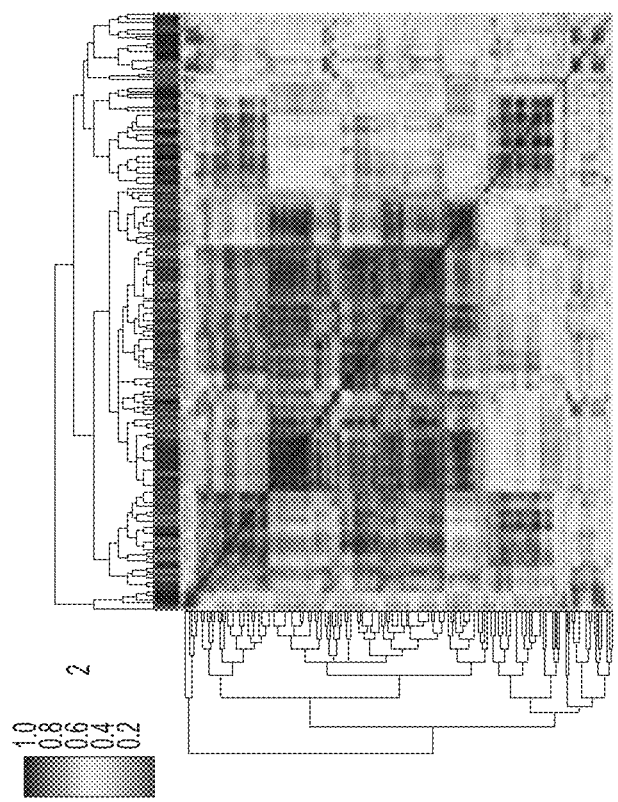
FIG. 44E shows a heatmap of correlation between melanoma samples (n=470) and to 298 genes constituting the functional processes, in accordance with some embodiments of the technology described herein.
Figure 44D:
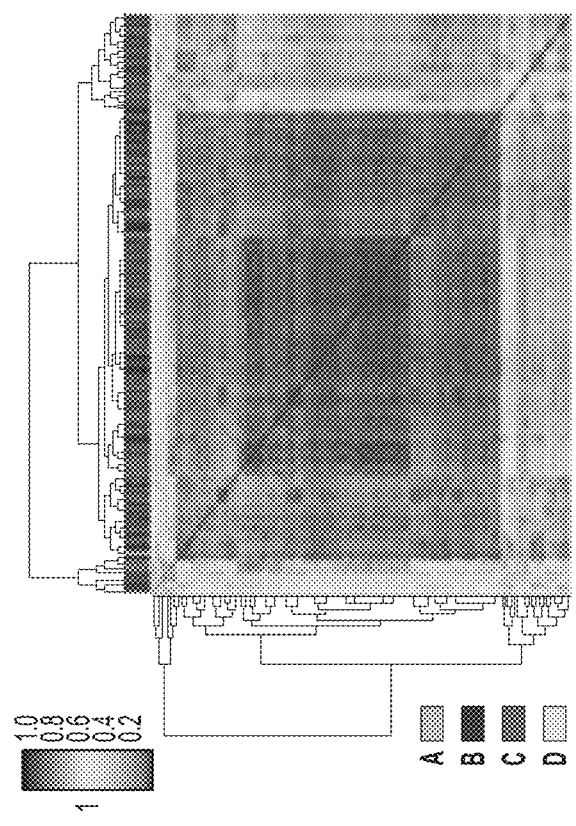
FIG. 44D shows a heatmap of correlation between melanoma samples (n=470) and the 10,000 most expressed genes, in accordance with some embodiments of the technology described herein. Pearson correlation matrices were clustered using Euclidean distance measured by the complete linkage method. Dense clusters are highlighted in column bar.
Figure 44F:
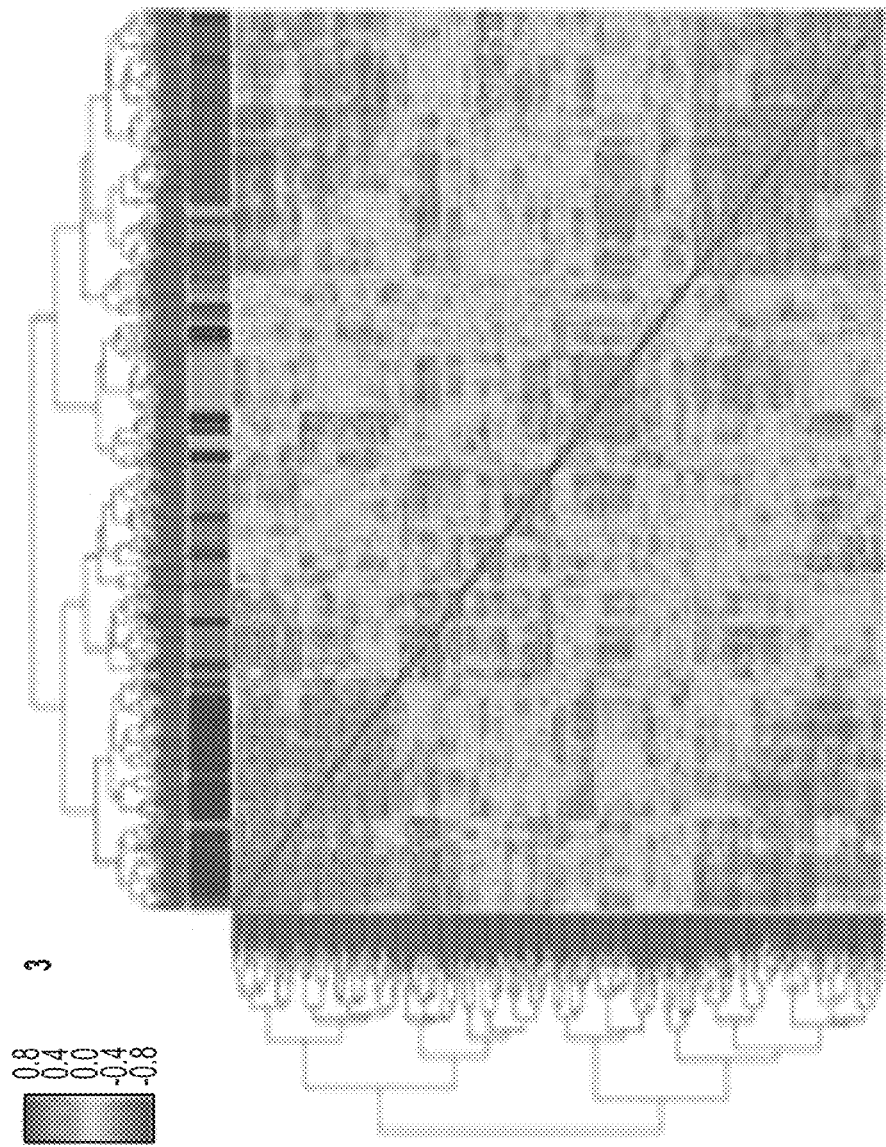
FIG. 44F shows a heatmap of correlation between melanoma samples (n=470) and to 28 functional process scores, in accordance with some embodiments of the technology described herein.
Figure 44G:
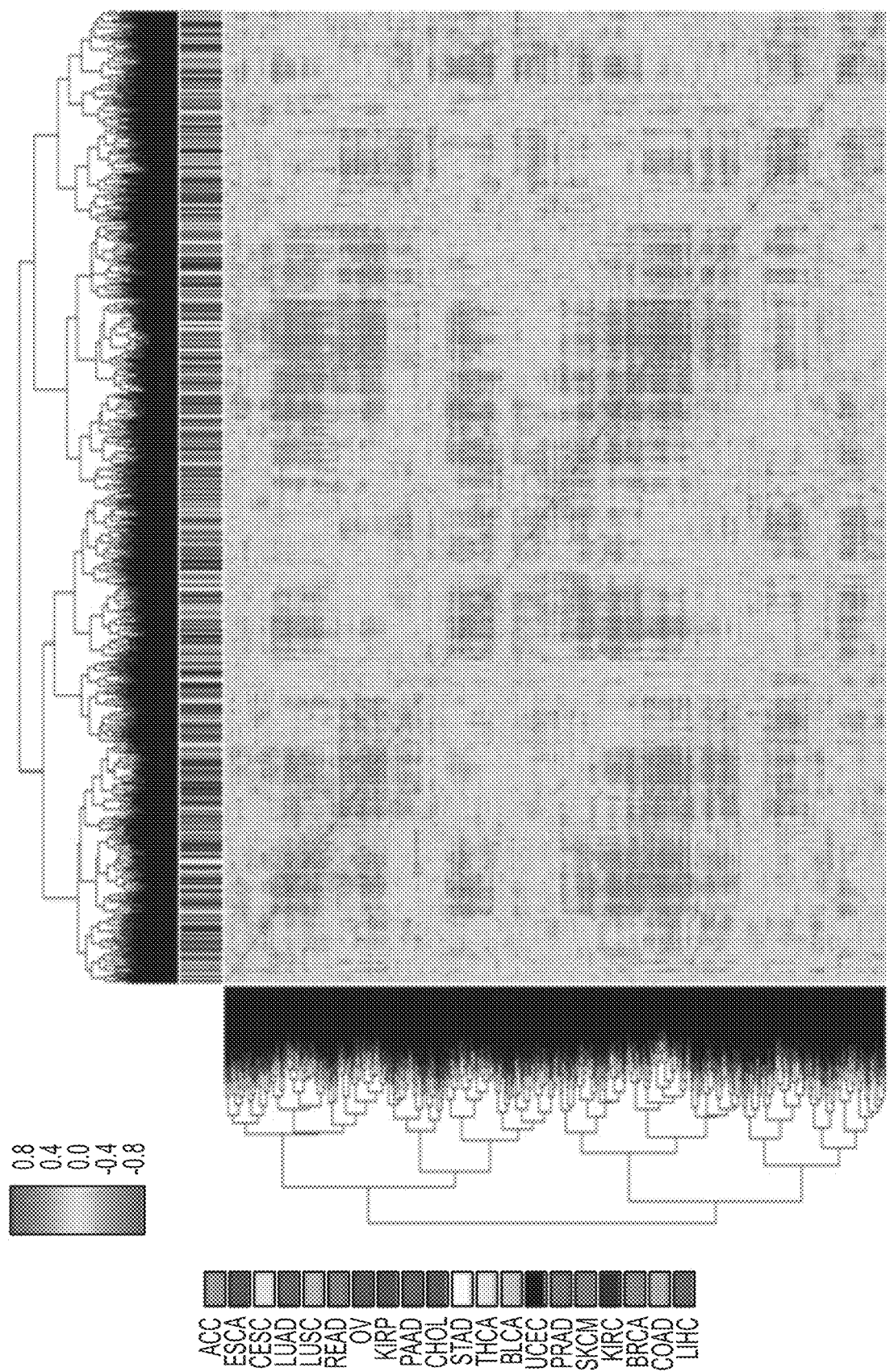
FIG. 44G shows a heatmap of correlation between 20 different carcinoma tumors, in accordance with some embodiments of the technology described herein. Panel (1) shows correlation with the 10,000 most expressed genes; panel (2) shows correlation with 298 genes constituting the functional processes; and panel (3) shows correlation with the 28 functional process scores. Pearson correlation matrices were clustered using Euclidean distance measured by the complete linkage method. Dense clusters are highlighted in column bar.

MF profile types for the different cancers and patient survival were evaluated. The Type C (e.g., immunosuppression, vascular, fibrotic) cluster of carcinoma patients was linked with the poorest overall survival, while the Type B (e.g., immune) cluster had the best prognosis (FIG. 43F). These results were similar to what was seen in the melanoma cohort.

Figure 45A:
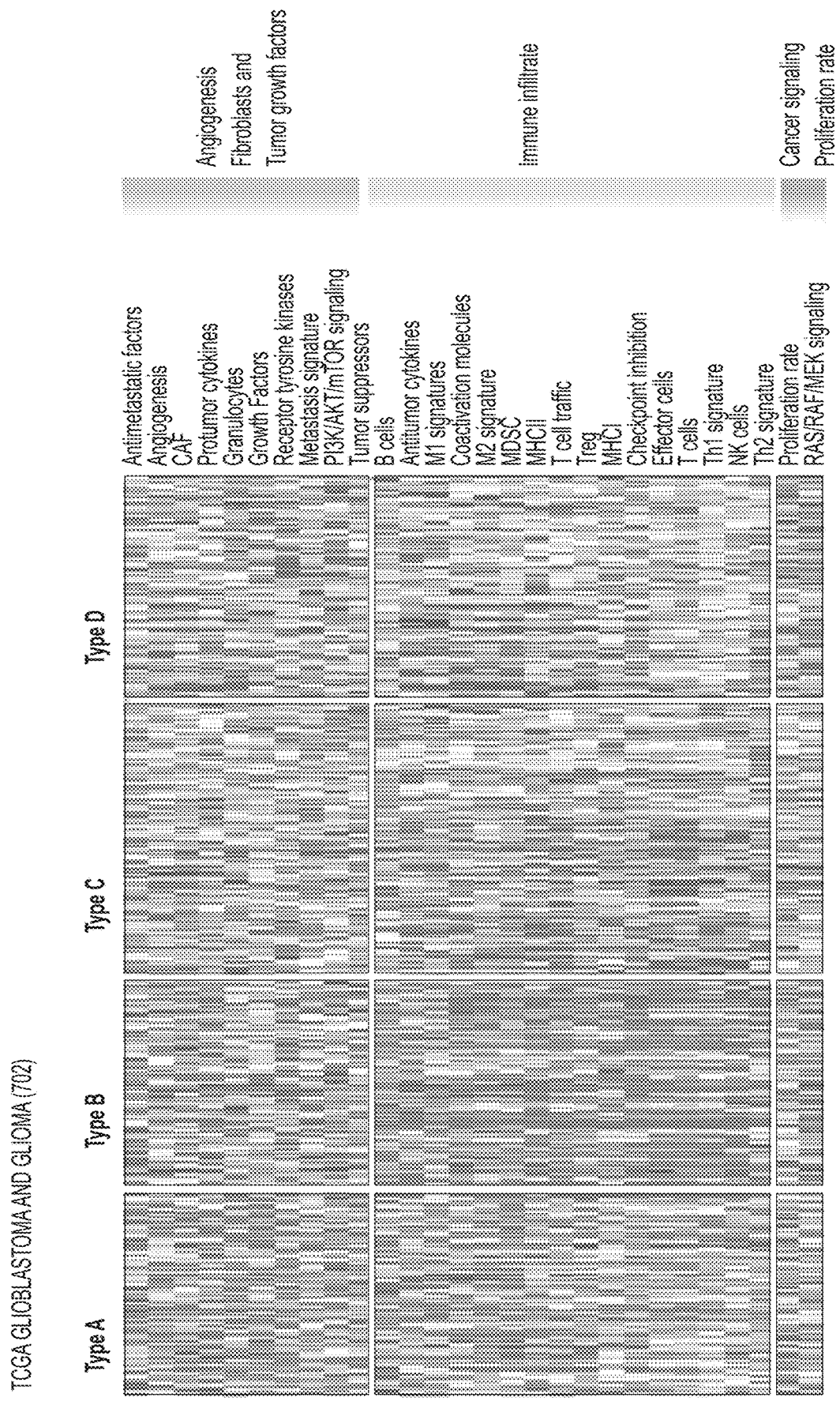
FIG. 45A shows data from an unsupervised dense subgraph network cluster analysis of tumor functional processes calculated from RNA-Seq data of patient glioblastoma tumors (n=159) and glioma tumors (n=516), in accordance with some embodiments of the technology described herein. The determined clusters were labeled Types A-D ($1^{st}$-$4^{th}$ MF profile clusters, respectively).
Figure 45B:
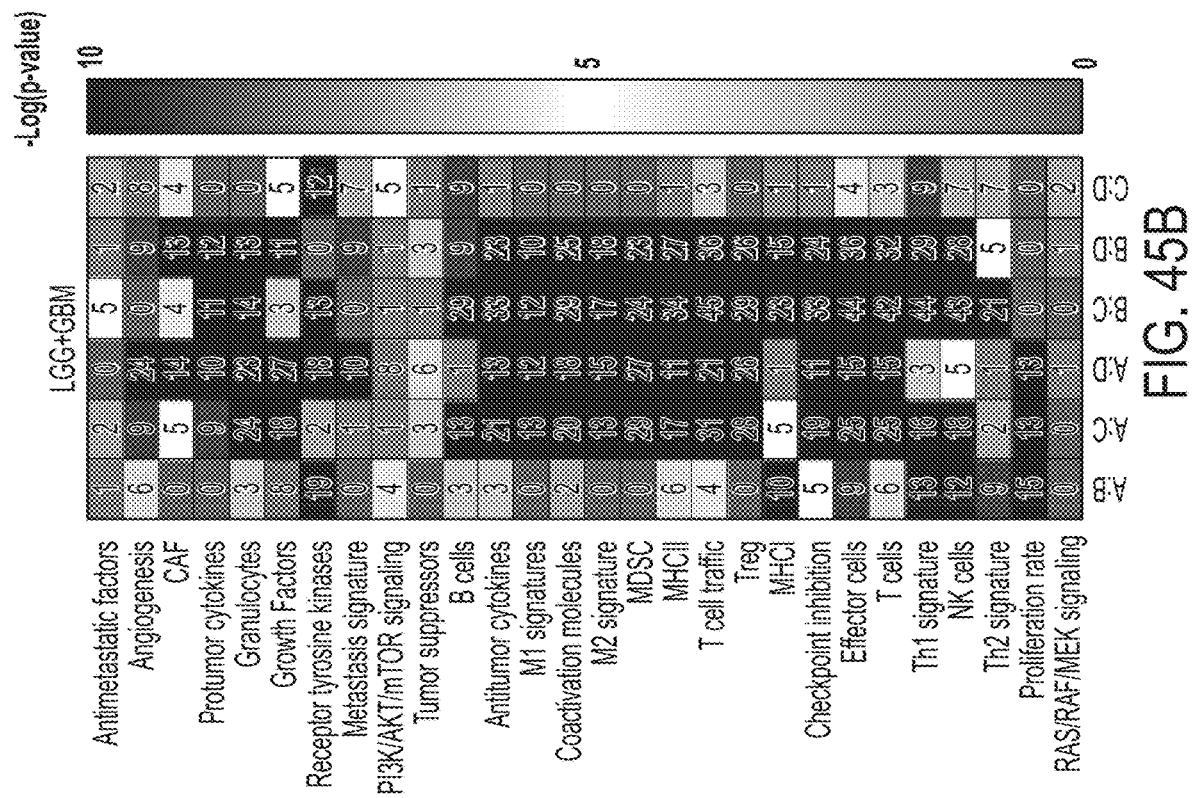
FIG. 45B shows data from a log(p-value) t-test difference in process activity enrichment scores between brain tumors determined to fall within cluster Types A-D ($1^{st}$-$4^{th}$ MF profile clusters, respectively), in accordance with some embodiments of the technology described herein.
Figure 45C:
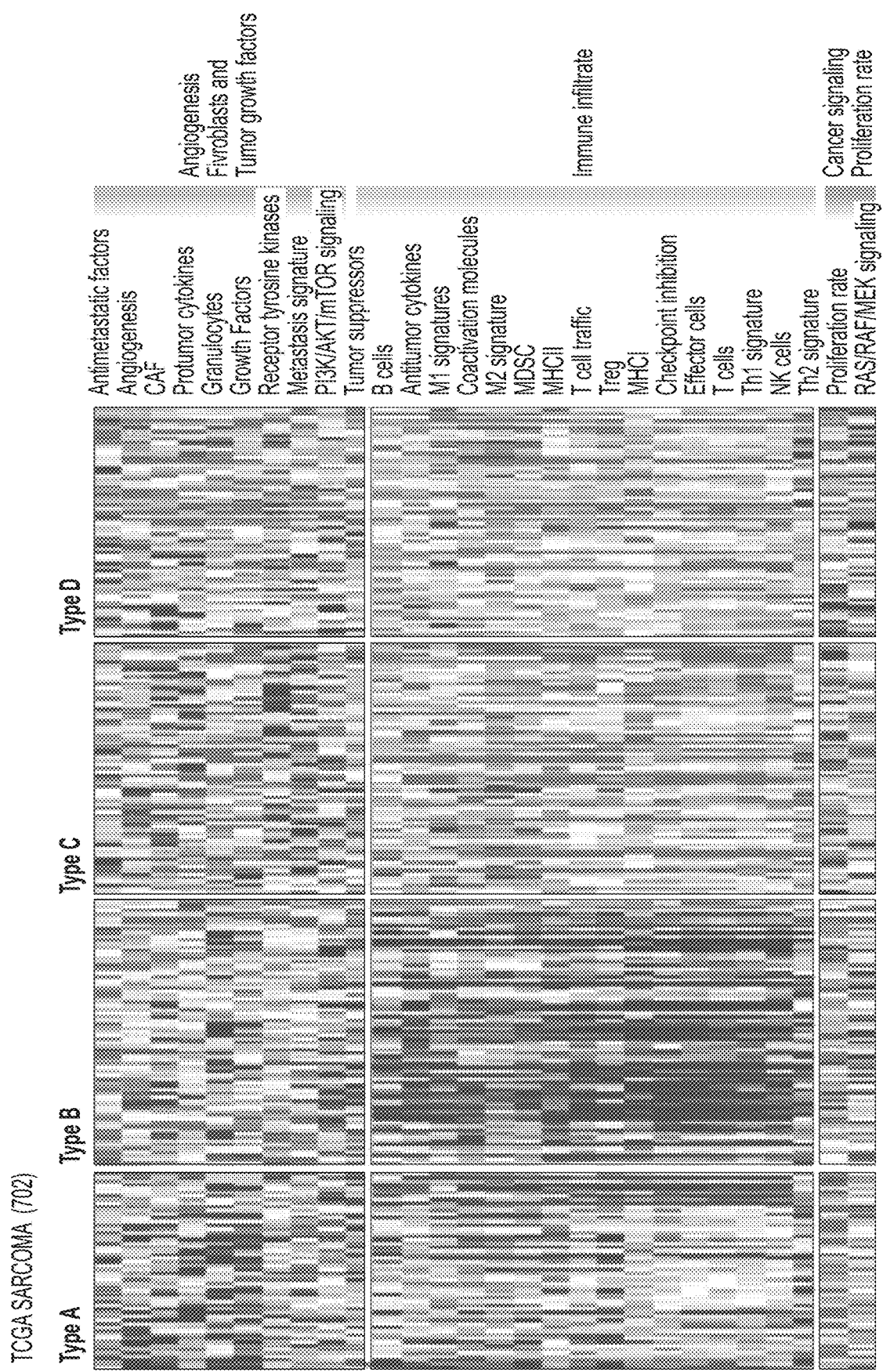
FIG. 45C shows data from an unsupervised dense subgraph network cluster analysis of tumor functional processes calculated from RNA-Seq data of patient sarcoma tumors (n=261), in accordance with some embodiments of the technology described herein. The determined clusters were labeled Types A-D ($1^{st}$-$4^{th}$ MF profile clusters, respectively).
Figure 45D:
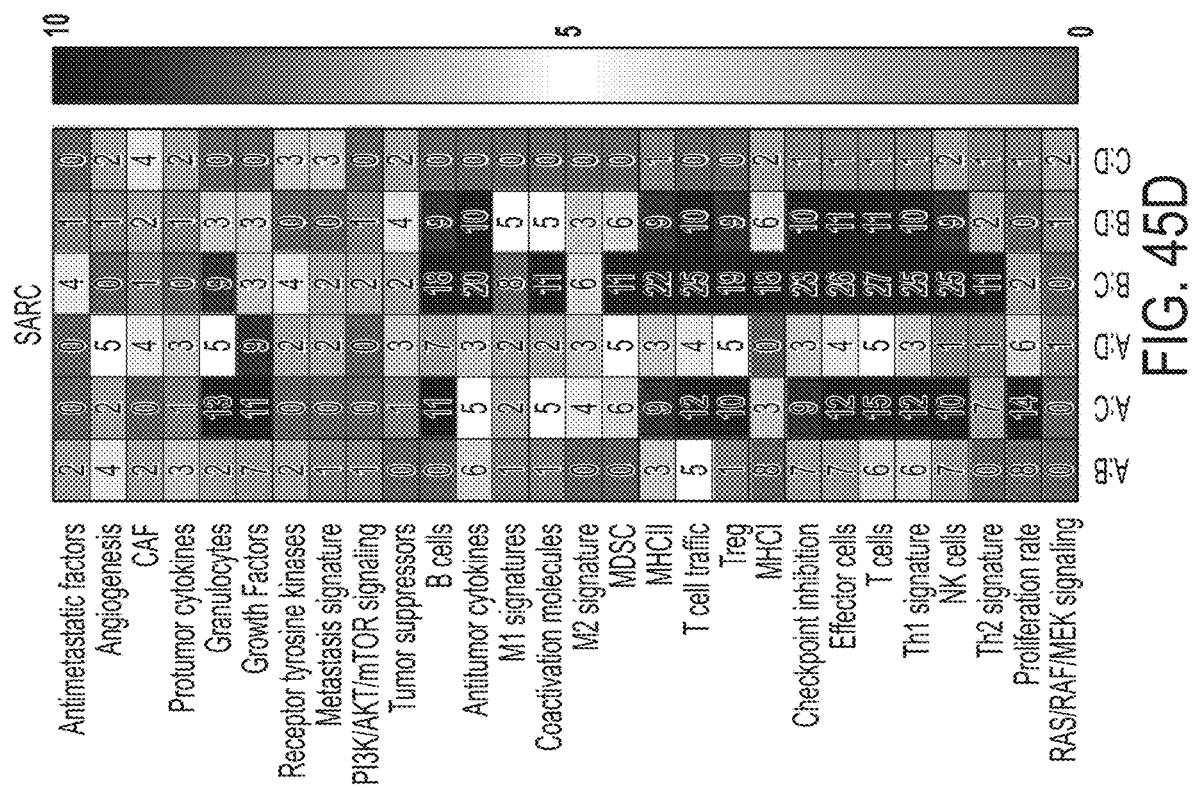
FIG. 45D shows data from a log(p-value) t-test difference in process activity enrichment scores between sarcoma tumors determined to fall within cluster Types A-D ($1^{st}$-$4^{th}$ MF profile clusters, respectively), in accordance with some embodiments of the technology described herein.

The molecular-functional organization of non-epithelial neoplasms including sarcoma, glioblastoma and glioma were analyzed. This analysis revealed that glioblastoma and glioma (FIGS. 45A-45B), and sarcoma (FIGS. 45C-45D) types can be classified in a manner that is similar to carcinomas. However, Types A-D ($1^{st}$-$4^{th}$ MF profile clusters, respectively) of the analyzed non-epithelial cancers demonstrated a set of distinct molecular processes discriminating one type from another (FIGS. 45B and 45D).

Example 5

Tumor Type as a Basis for Response to Immune and Targeted Therapies

An MF profile was created to be a personalized picture of patient's tumor microenvironment. Therefore, it could be used as a basis to understand the influence of microenvironment on the efficacy of different therapies.

To examine whether the four prevalent types of tumor organization are indicative of a patient's response to certain therapies, the link between a patient's MF profile and response to therapy was analyzed.

Figure 46A:
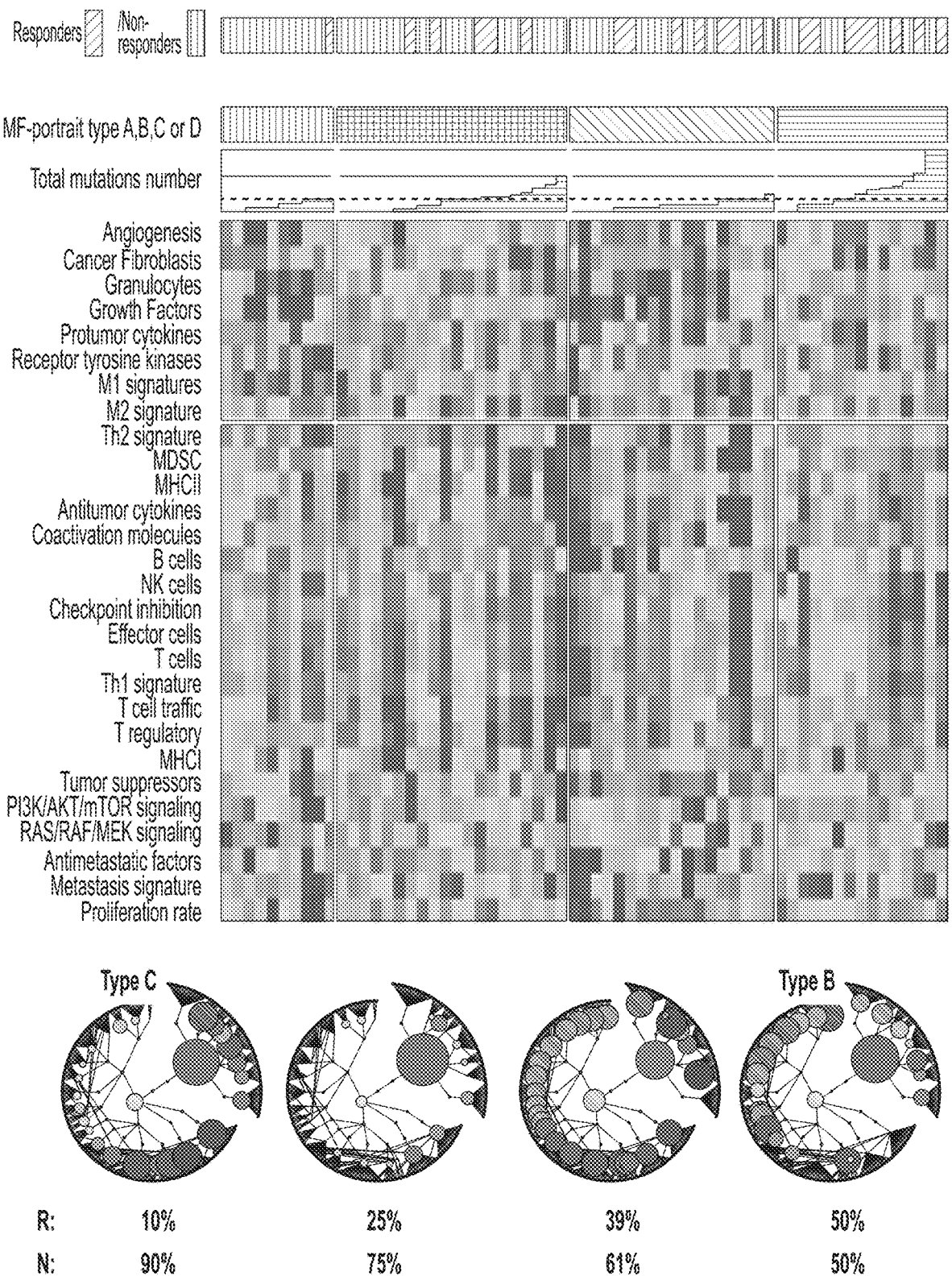
FIG. 46A shows a heatmap showing processes of tumor MF profiles of melanoma patients treated with anti-CTLA4 therapy, in accordance with some embodiments of the technology described herein. Annotation of responders and non-responders, MF profile classification of determined cluster Types A-D ($1^{st}$-$4^{th}$ MF profile clusters, respectively), and total number of mutations is shown above the heatmap. The average MF profiles corresponding to patients from the heatmap and percent responders (R) and non-responders (N) for patients having the indicated tumor type are shown under the heatmap.

Efficacy of immune checkpoint blockage therapy (e.g., anti-CTLA-4 and anti-PD-1) is dependent on the amount of active immune infiltrate in the tumor microenvironment and tumor antigenicity. The expression levels of immune checkpoint inhibitor molecules cannot predict the efficacy of check point blockade therapy on their own. On the concatenated datasets of patients treated with anti-CTLA-4 (Nathanson et al., 2016; Van Allen et al., 2015) it was determined that patients with tumor MF-types A and B (first and second MF profile clusters, respectively) having high intratumoral immune content and high mutational burden were more likely to respond to therapy (FIG. 46A). However, patients with immune suppressive fibrotic MF-type C tumors (the third MF profile cluster) appeared to be completely non-responsive, regardless of mutation load in their tumors. See Nathanson T et al. Somatic Mutations and Neoepitope Homology in Melanomas Treated with CTLA-4 Blockade. Cancer Immunol Res. 2017 January; 5(1):84-91. See also Van Allen E M et al. Genomic correlates of response to CTLA-4 blockade in metastatic melanoma. Science. 2015 Oct. 9; 350(6257):207-211. Each of the foregoing references are incorporated herein by reference in their entirety.

Figure 46B:
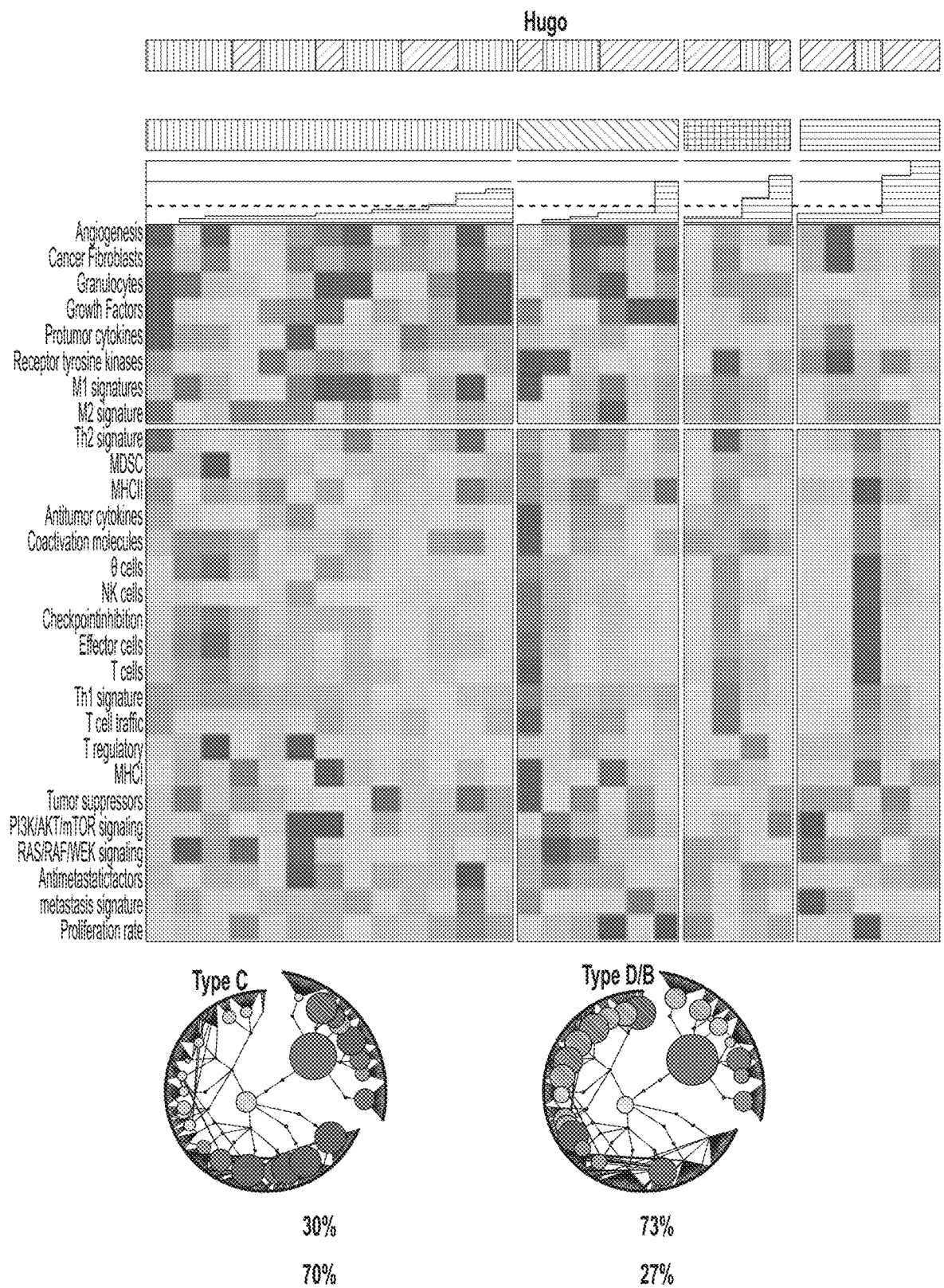
FIG. 46B shows a heatmap showing processes of tumor MF profiles of melanoma patients treated with anti-PD-1 therapy, in accordance with some embodiments of the technology described herein.

Analysis of the cohort of patients treated by anti-PD-1 (Hugo et al.) yielded similar results. See Hugo W et al. Genomic and Transcriptomic Features of Response to Anti-PD-1 Therapy in Metastatic Melanoma. Cell. 2016 Mar. 24; 165(1):35-44, which is hereby incorporated by reference in its entirety. Patients having tumor type C did not respond to therapy (FIG. 46B). MF profile B patients responded to immunotherapy independently of their tumor mutation status (FIG. 46B), which is consistent with the characterization of Type B tumors as having low levels of pro-tumor angiogenic and fibrotic activities. However, the analysis revealed that type A tumors which have increased levels of both immune and fibrotic processes need to possess high mutational burden to increase the probability of response. It is determined that tumors with high immune content (e.g., type A) may also contain many highly suppressive cancer-associated fibroblasts that suppress T cell activation independently of T-cell checkpoint inhibition mechanisms.

Figure 46C:
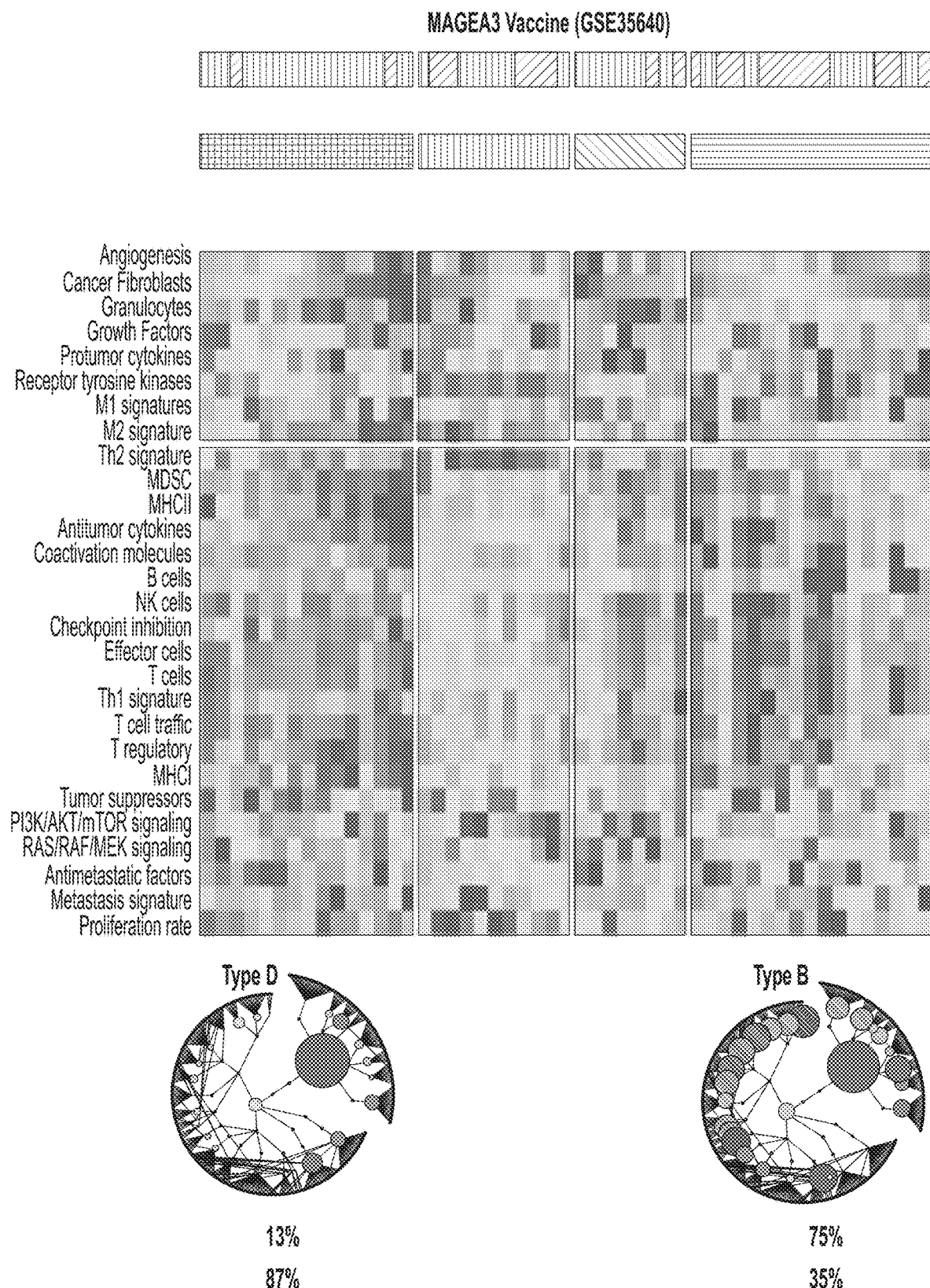
FIG. 46C shows a heatmap showing processes of tumor MF profiles of melanoma patients treated with MAGE-A3 vaccine, in accordance with some embodiments of the technology described herein.
Figure 46D:
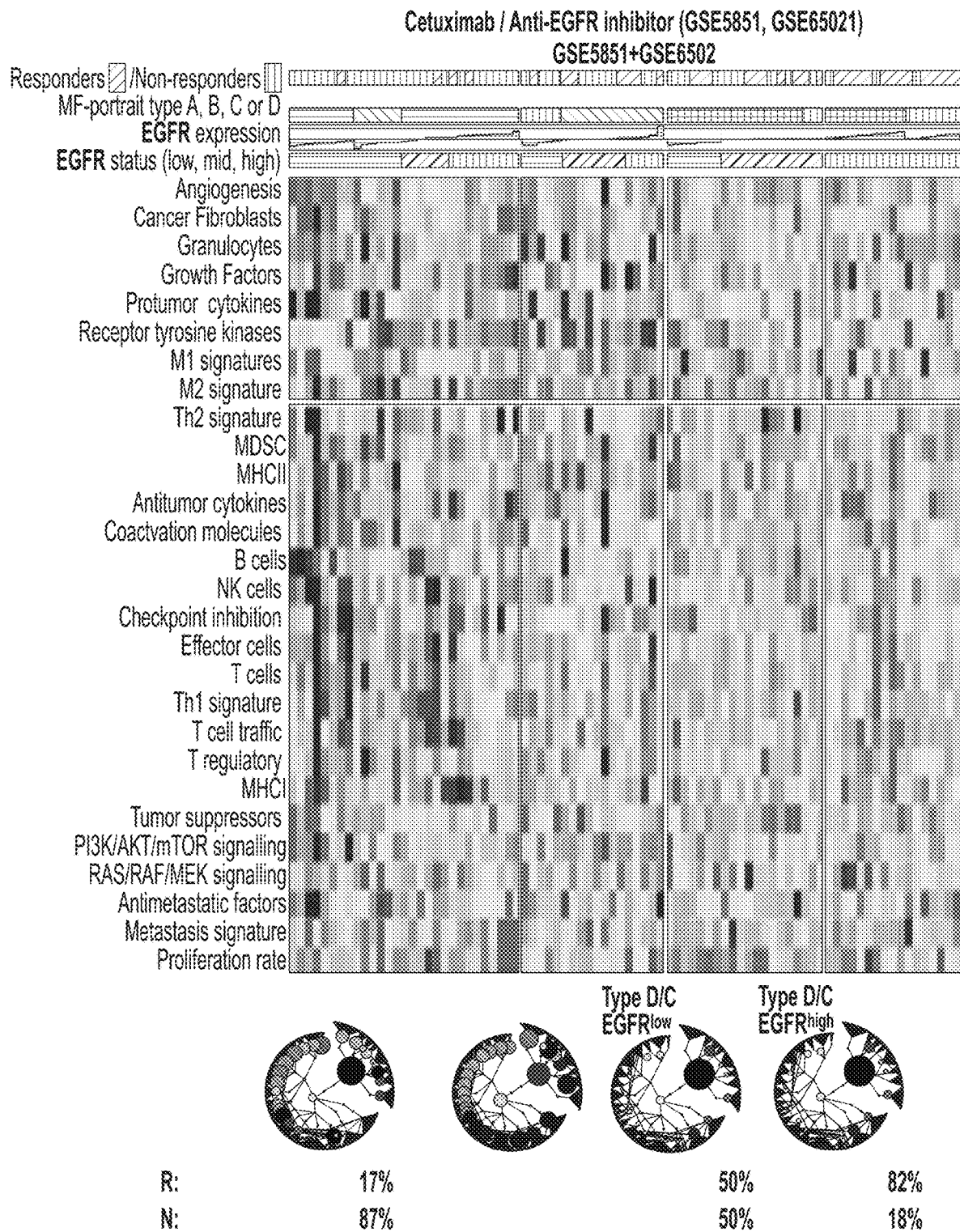
FIG. 46D shows a heatmap showing processes of tumor MF profiles of mCRC patients from GSE5851 and HNSCC patients from GSE65021 treated with cetuximab, in accordance with some embodiments of the technology described herein. EGFR expression status is also indicated.
Figure 46E:
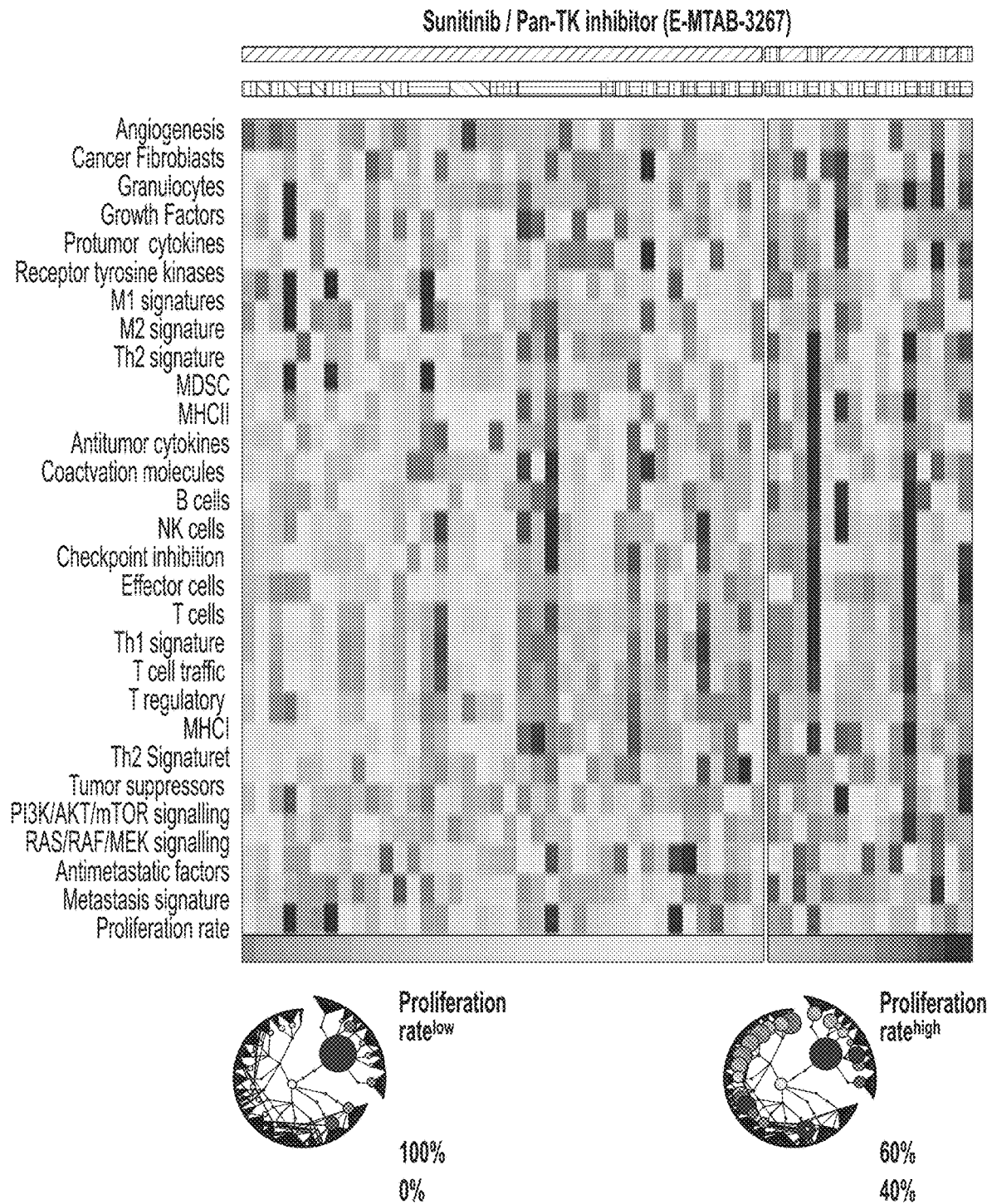
FIG. 46E shows a heatmap showing processes of tumor MF profiles of ccRCC patients treated with sunitinib, in accordance with some embodiments of the technology described herein.
Figure 46F:
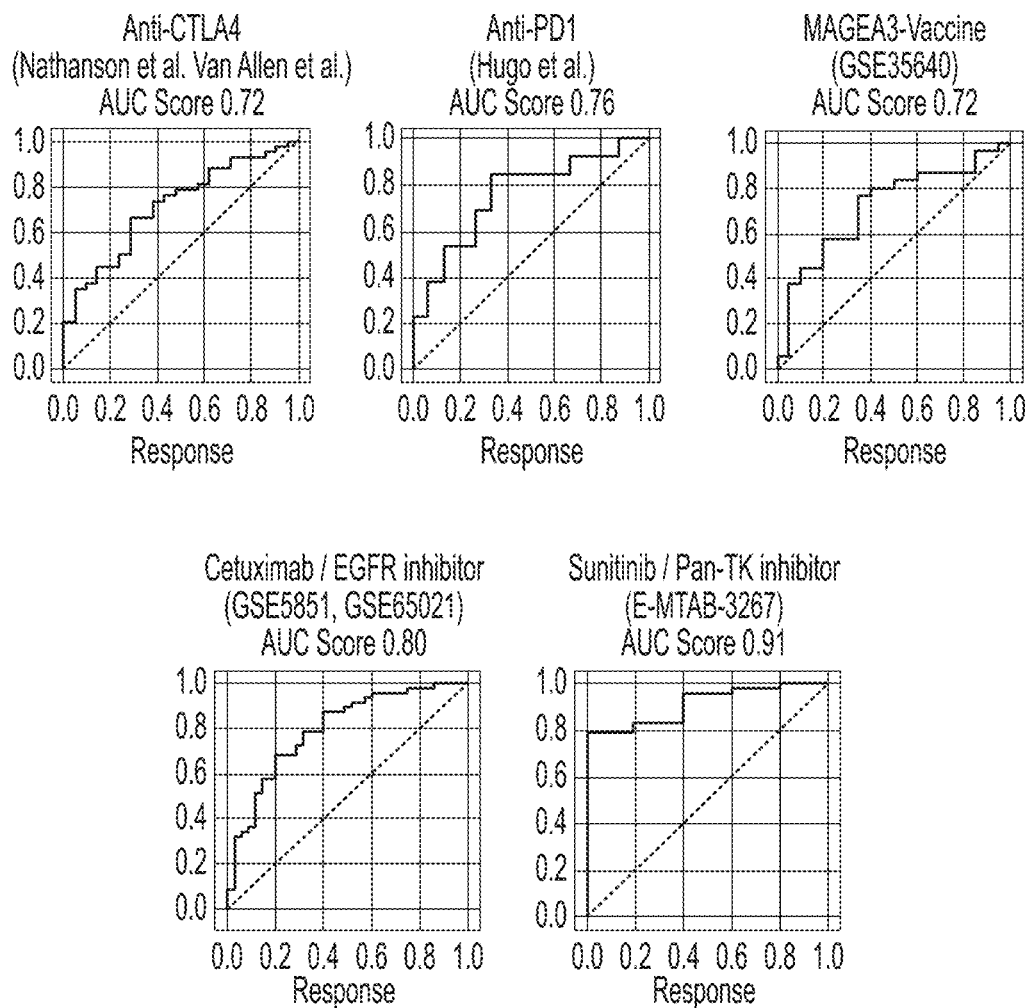
FIG. 46F shows data of receiver operating characteristics for therapy response prediction based on MF profile type and AUC scores, in accordance with some embodiments of the technology described herein.
Figure 46H:
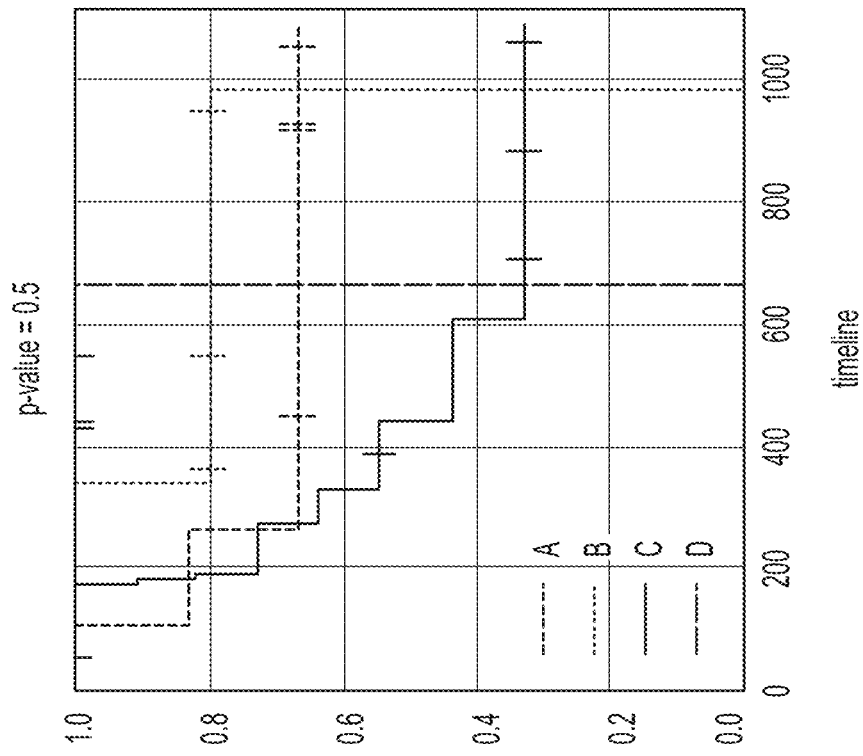
FIG. 46H shows Kaplan-Meier survival curves for melanoma patients treated with anti-PD-1 therapy split into cohorts according to the their determined MF profile type (Types A-D; $1^{st}$-$4^{th}$ MF profile clusters, respectively), in accordance with some embodiments of the technology described herein.
Figure 46G:
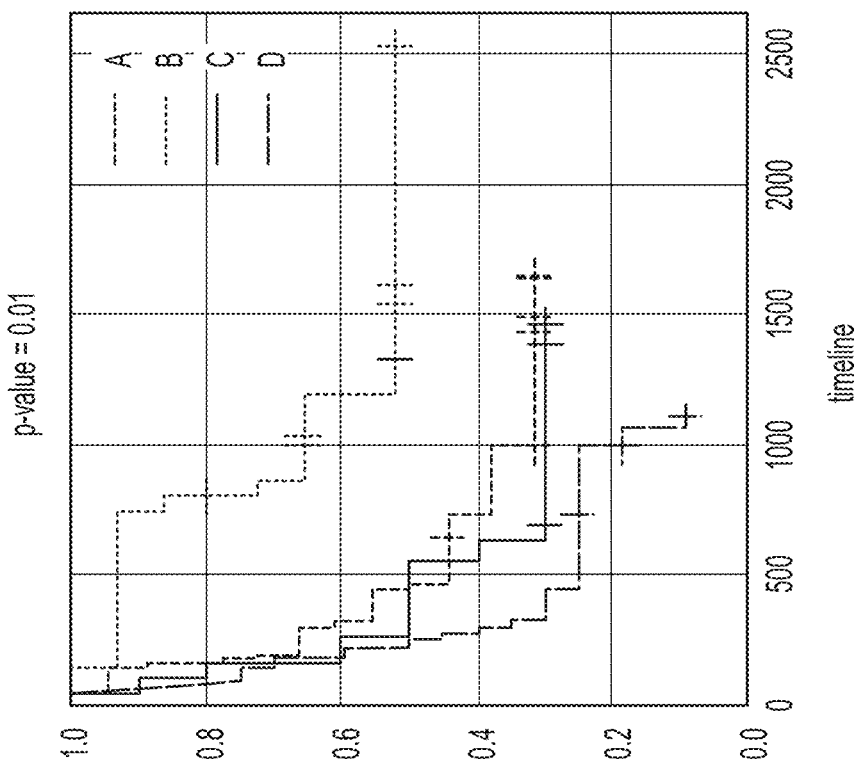
FIG. 46G shows Kaplan-Meier survival curves for melanoma patients treated with anti-CTLA4 therapy split into cohorts according to the their determined MF profile type (Types A-D; $1^{st}$-$4^{th}$ MF profile clusters, respectively), in accordance with some embodiments of the technology described herein.

Application of MF profiles to datasets of patients treated with anti-CTLA-4 and anti-PD-1 therapies resulted in 0.72 and 0.76 AUC scores for response prediction respectively (FIG. 46F). With regard to response to treatment, patients with type B tumors displayed the most favorable survival rate, and patients with type C tumors displayed unfavorable survival rates (FIGS. 46G-46H).

The efficacy of therapeutic MAGEA3-vaccine use depended on the tumor MF-type (FIG. 46F; AUC score of 0.72). As similarly determined for checkpoint inhibitor therapies, type B tumors are associated with increased response to vaccination (FIG. 46C). Non-responders had "immune desert" type D tumors, which have no immune infiltration to drive anti-tumor immune response (FIG. 46C).

MF profiles were also associated with a targeted therapy outcome. An individual patient's mutational status seemed to be the most important characteristic when choosing appropriate targeted therapy, but some targeted therapies also affected the tumor microenvironment and thus response to them was found to strongly depend on the tumor organization.

Patients treated with cetuximab (EGFR inhibitor) from two independent cohorts (GSE5851, GSE65021) were arranged by tumor type from the most immune to the least immune (B, A, D, C) and stratified by EGFR expression status. Patients with tumor types A and B (first and second MF profile clusters, respectively) were unlikely to benefit from anti-EGFR therapy (FIG. 46D). On the contrary, among patients with tumor types C and D (third and fourth MF profile clusters, respectively) the number of responders was higher (FIG. 46D). These tumor types seemed to be strongly dependent on the activity of growth factors which act via EGFR. In fact, the combination of the tumor MF-type classification (types D and C) with EGFR-expression status increased response prediction up to 80% of patients and had an overall AUC score of 0.8 (FIGS. 46D and 46F).

The above examples show that additional personalization of the patient tumor MF profile by combining the tumor type with traits like mutational burden or EGFR expression status lead to the possibility of using portraits in different cancers and for prediction of response to various therapies.

Figure 46I:
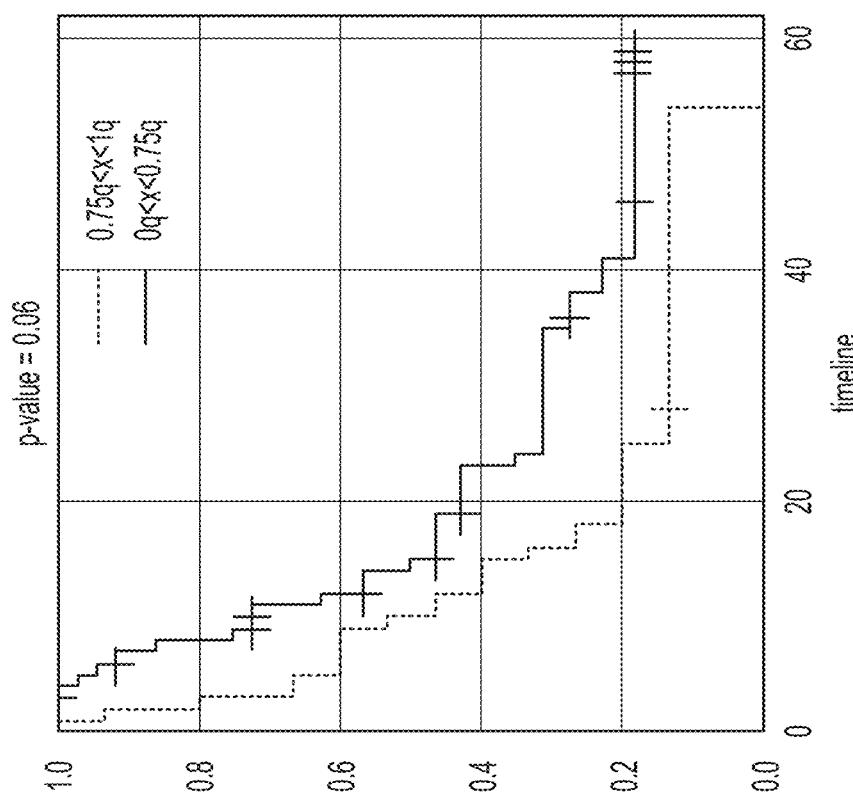
FIG. 46I shows Kaplan-Meier survival curves for sunitinib treated patients having tumors with a high proliferation rate or a low proliferation rate, in accordance with some embodiments of the technology described herein.

Alternatively, just one of the processes comprised in the tumor MF profile could serve a key predictor of certain therapy effectiveness. For instance, treatment efficacy of sunitinib, a pan-tyrosine kinase inhibitor, was dependent only on tumor proliferation rate (AUC score 0.91) which constitutes a single process of MF profile (FIGS. 46E-46F and FIG. 46I).

Example 6

Dynamic Evolution of Tumor MF Profile Predicts Response to Immune Checkpoint Inhibitors A dataset of 3 non-responder and 2 responder melanoma patients treated with anti-PD-1 therapy whose tumors were measured before and after treatment was obtained. The dynamics of each patient's tumor were plotted on a map created using 470 melanoma patients (TCGA).

Figure 47A:
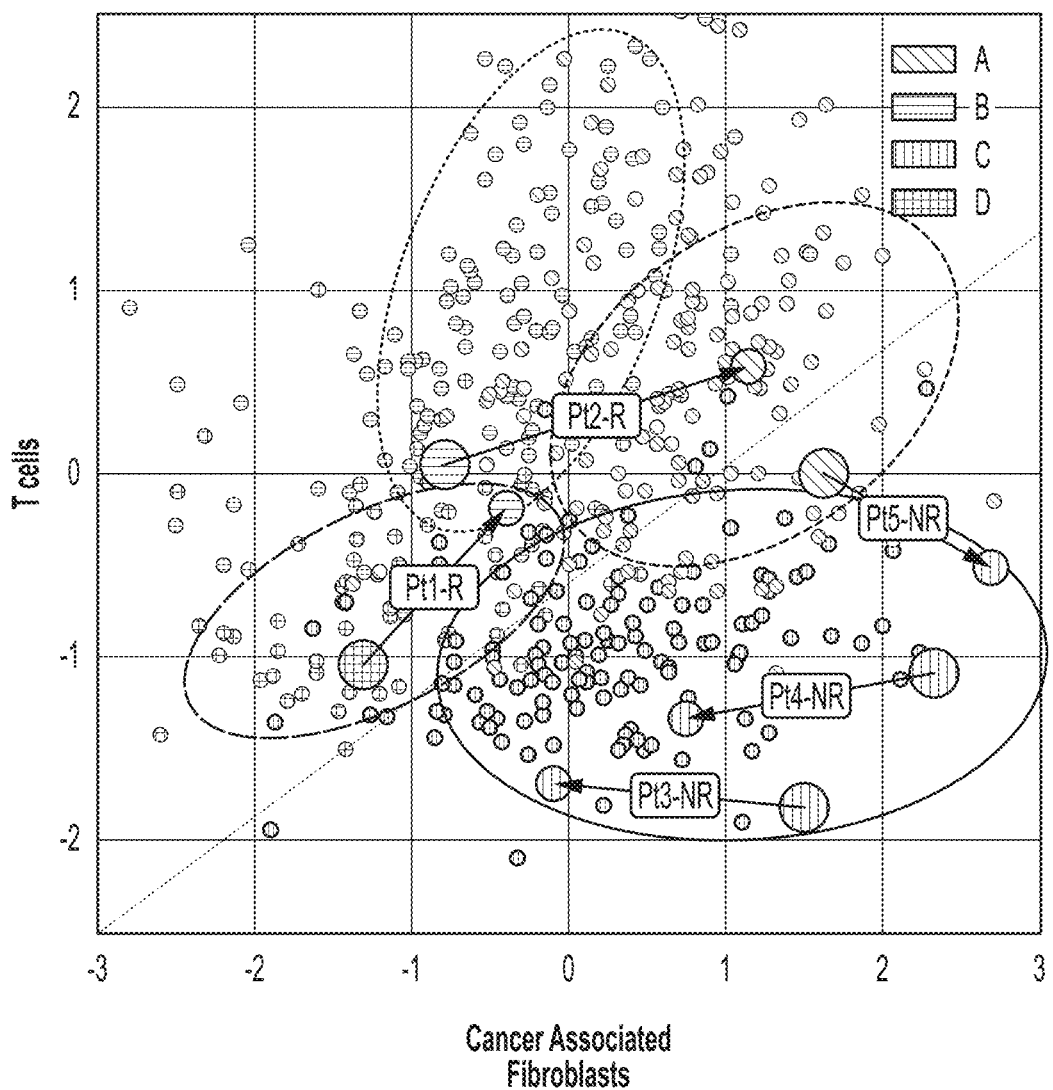
FIG. 47A shows a graphical representation of melanoma patients (dots) on two-dimensional coordinates of T cells and Cancer Associated Fibroblast process intensity from MF profile (z-scores), in accordance with some embodiments of the technology described herein. MF profile type (Types A-D; $1^{st}$-$4^{th}$ MF profile clusters, respectively) is indicated for each patient. Dynamic changes in tumor MF profiles of five patients are shown by arrows. Larger dots indicate pre-treatment tumors.
Figure 47B:
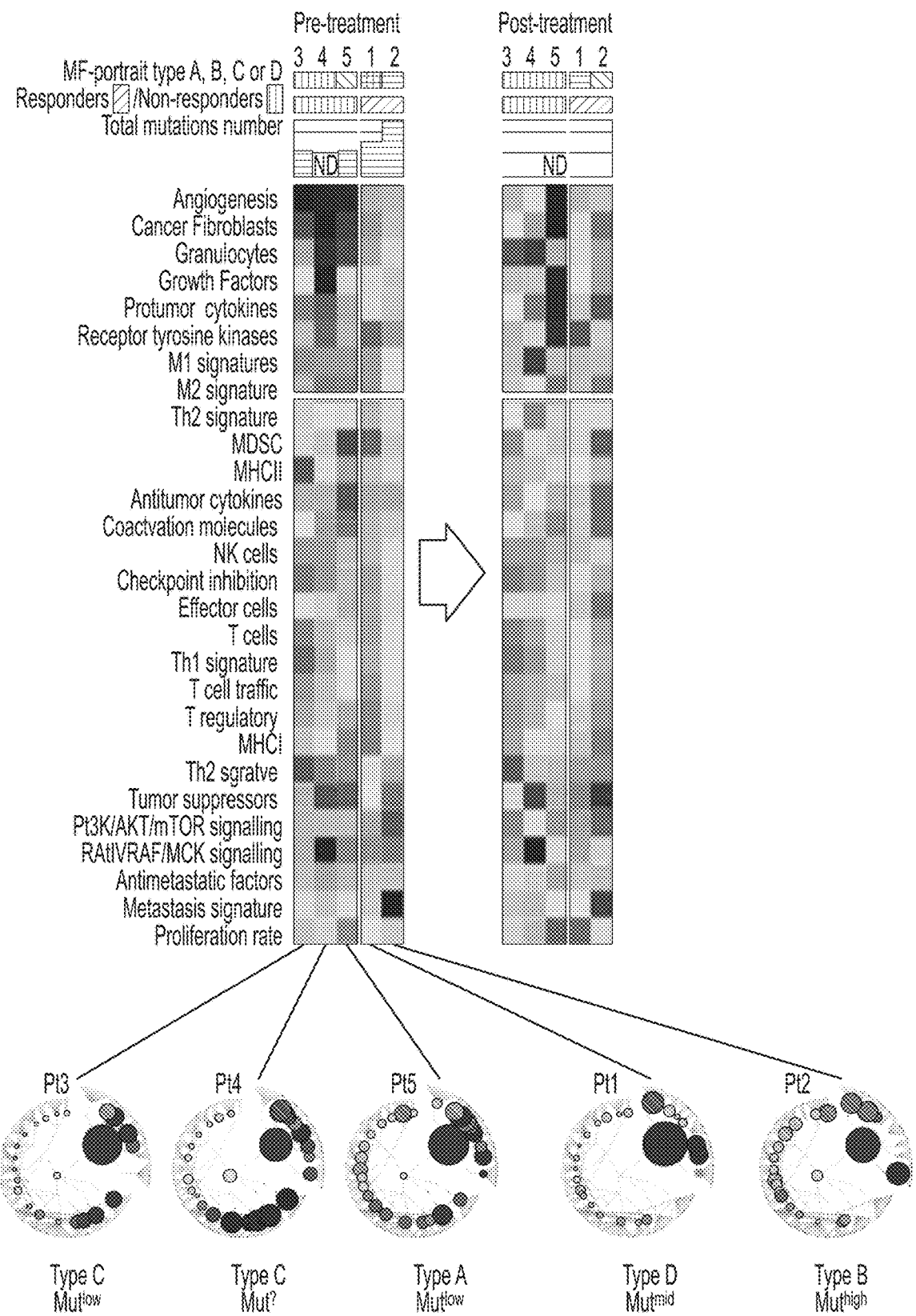
FIG. 47B shows a heatmap showing processes of determined MF profile type (Types A-D; $1^{st}$-$4^{th}$ MF profile clusters, respectively) for melanoma patients before and after treatment with anti-PD-1 therapy, in accordance with some embodiments of the technology described herein. Annotation of responders and non-responders, MF profile classification and total number of mutations is shown above the heatmap. Pre-treatment MF profiles for each patient are shown under the heatmap.

Pre-treatment tumors for three non-responding patients were classified according to their MF profiles as type C (Pt3, Pt4) and type A (Pt5) tumors. These tumor types were associated with low mutation burden, which, according to the analysis of Hugo et al. dataset, was associated with the absence of response. Evolution of non-responder tumors can be clearly seen on the map of melanoma patients plotted on the PCA and colored according to MF profile types (FIG. 47A). The non-responding patients (Pt3, Pt4, Pt5) move deeply into the type C tumors that constitute a "bad" zone of non-responders according to the analysis of the Hugo et al. dataset (FIGS. 47A-47B).

Figure 47C:
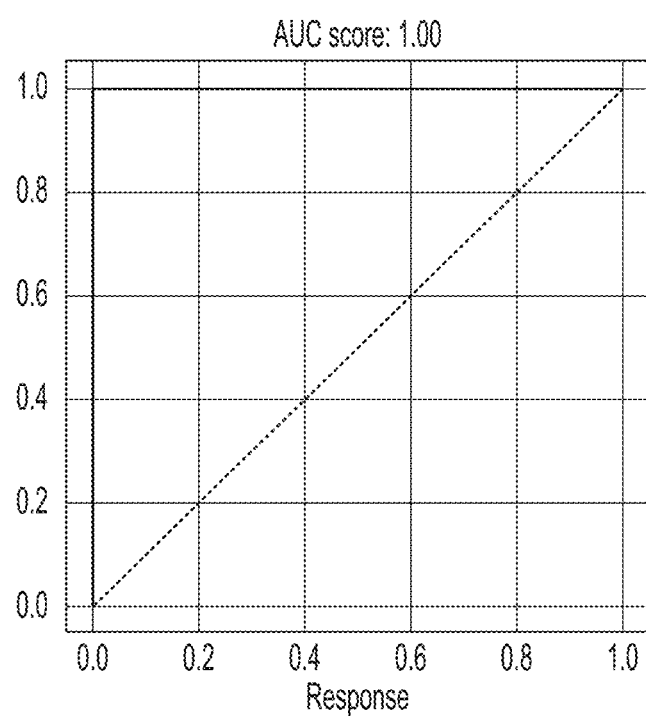
FIG. 47C shows a graph of receiver operating characteristics for therapy response prediction based on tumor classification before treatment, in accordance with some embodiments of the technology described herein.

Alternatively, responder tumors were classified as immune enriched type B (Pt2) and immune desert type D (Pt1) with high and mid number of mutations before treatment. After the treatment responder tumors moved even further to the zone of "best responders" of tumor types B (Pt1) and A (Pt2) (FIG. 47A). In a type D patient (Pt1) the number of immune cells were increased, and the patient's tumor became type B (FIG. 47B). Receiver operating characteristics for therapy response prediction based on tumor classification before treatment with AUC scores was determined (FIG. 47C).

Example 7

Application of Tumor MF Profiles for Personalized Combination Therapy Design

Tumor molecular-functional portraits (MF profiles) can facilitate development of combination therapies. For example, if there is no visible tumor infiltration with MDSC, there is no reason to use remedies directed against MDSC. Conversely, when there are clear signs in the tumor of an overexpressed vascular network this indicates a reasonable demand for anti-angiogenic agents to be applied during treatment. In addition, if a functional module is substantial, then a therapy directed at regulating that functional module may be selected. In another example, if a tumor module is absent, then a therapy can be selected to induce the appearance of the module, should an appropriate inducer exist.

To facilitate development of specific combination therapies, the MF profile was complemented with a list of known pharmaceutical compounds directed to particular functional modules (FIGS. 48A-48D). The MF profile enabled the user to specify which functional module to target. Ultimately, it is the clinician's decision whether or not to use a particular option, and if so, how to use it. The schematic shown in FIGS. 48A-48D is a representation of the interface created in order to allow a user to objectively evaluate a patient's tumor for the presence or absence of primary molecular and cellular targets for the existing modes of therapeutic intervention. Importantly, the schematic readily discards those remedies that would be irrelevant to this particular patient because of the absence of functional modules to which these remedies are directed.

Prevalent MF profiles for Types A-D ($1^{st}$-$4^{th}$ MF profile clusters, respectively) tumors form the basis for designing therapeutic protocols relevant to each of these four tumor types. Described herein are pre-compiled combination therapy designs for tumors having MF profiles of types A, B, C and D ($1^{st}$-$4^{th}$ MF profile clusters, respectively), starting with the latter as having the simplest molecular-functional organization.

Figure 42A:
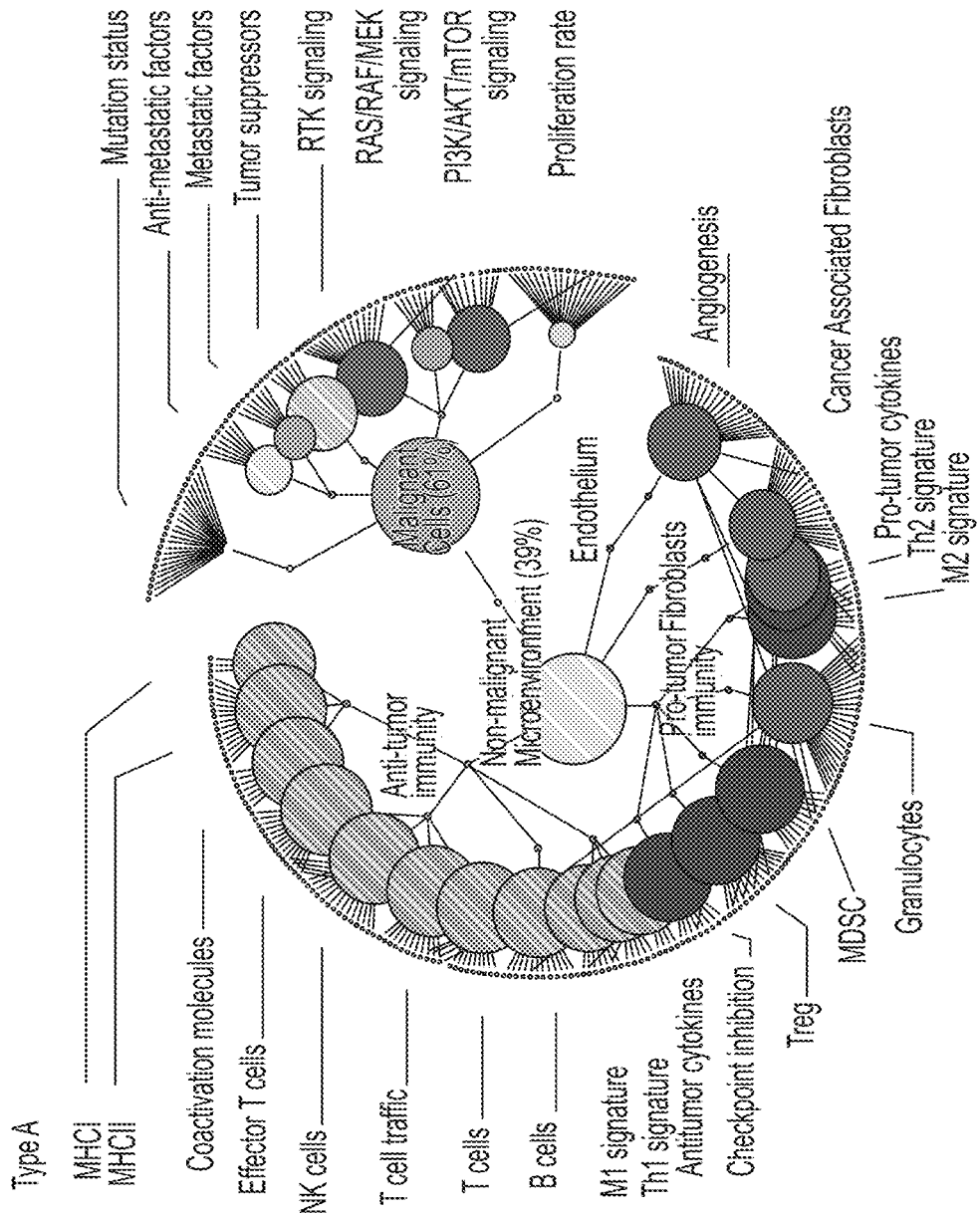
FIG. 42A shows a MF profile type A (first type) as determined in accordance with some embodiments of the technology described herein.
Figure 42B:
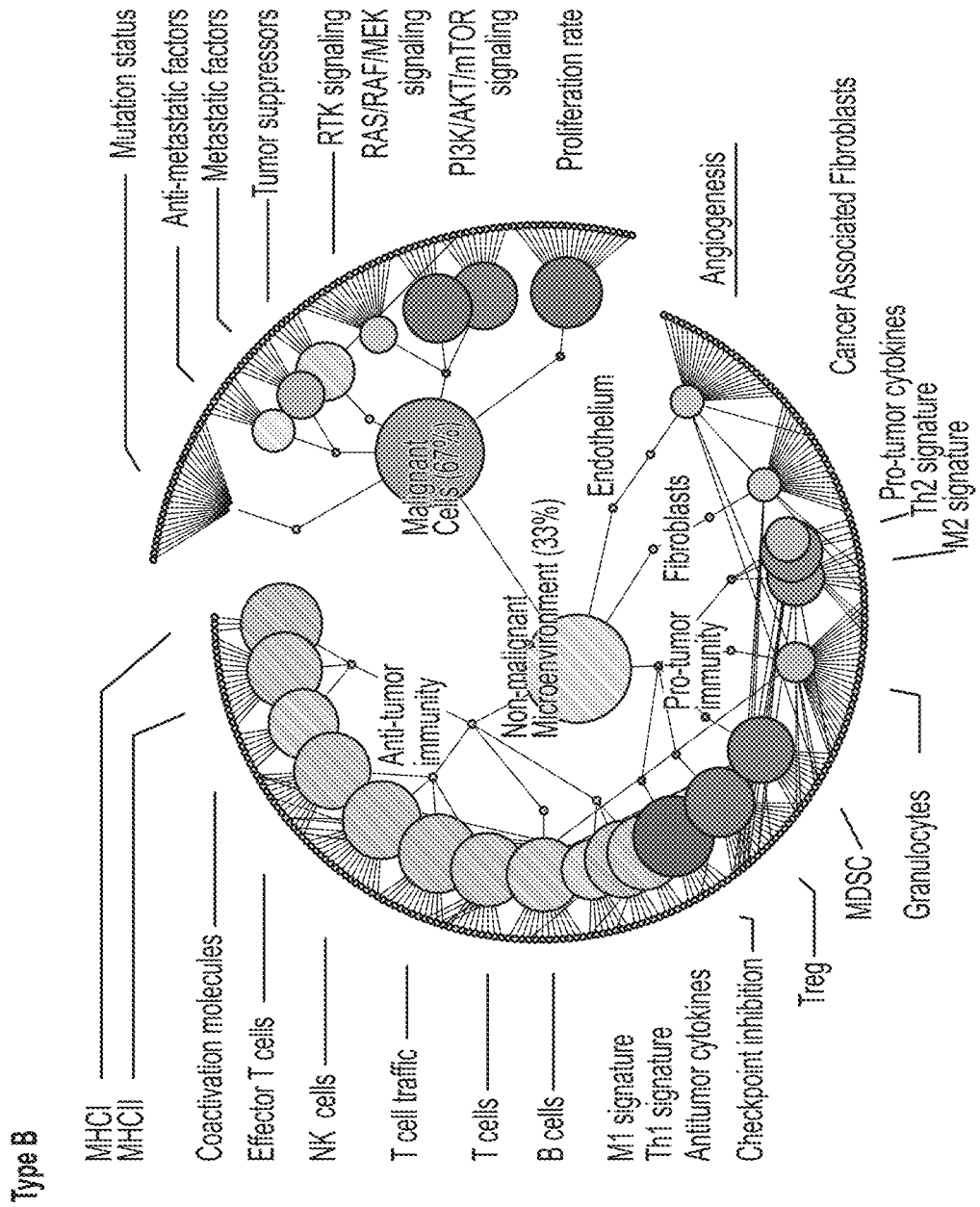
FIG. 42B shows a MF profile type B (second type), as determined in accordance with some embodiments of the technology described herein.
Figure 42C:
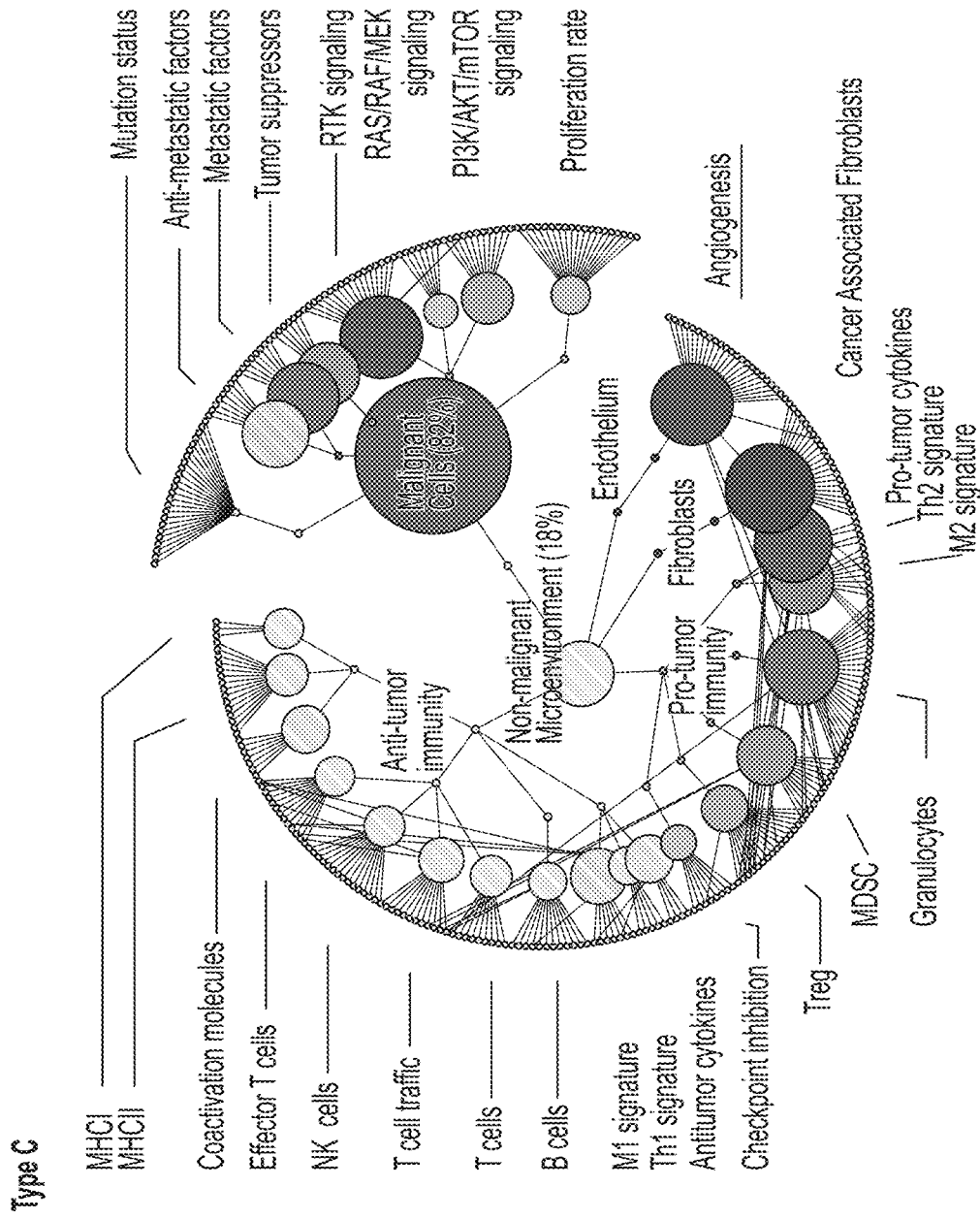
FIG. 42C shows a MF profile type C (third type), as determined in accordance with some embodiments of the technology described herein.
Figure 42D:
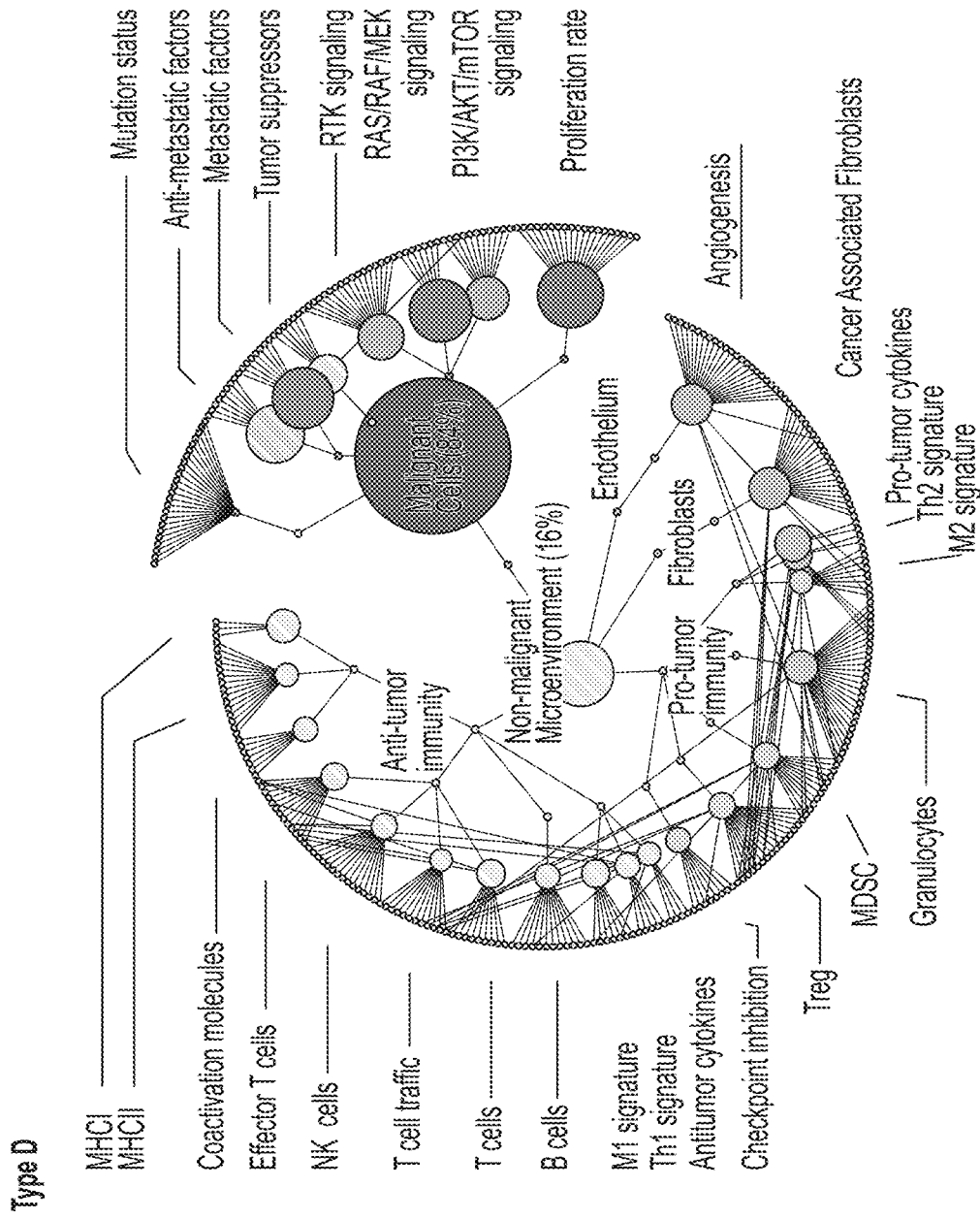
FIG. 42D shows a MF profile type D (fourth type), as determined in accordance with some embodiments of the technology described herein.

Type D tumors (the fourth MF profile cluster) represent the simplest MF profile that are nearly devoid of any modules but have an increased expression of cancer signaling pathways and a high proliferative activity of malignant cells (FIG. 42D). For patients with Type D tumors, one can apply a chemotherapeutic regimen, radiotherapy, targeted tyrosine kinase, or cyclin-dependent kinase inhibitors to block cell divisions, but most probably none of these standard care therapies will be curative and tumors will likely recur. In such patients, there is a need to evoke the immune system as a way of destroying the tumor cell variants that could escape conventional therapies. Treatment options that would effectively attract cytotoxic T cells, Th1, and NK cells into the tumor could be useful for such "non-inflamed" cancers.

Type C tumors were also identified to be "uninflamed" or "non-inflamed" (FIG. 42C). At the same time, they have increased expression of cancer signaling pathways and/or metastatic capabilities. Type C tumors are also characterized by the prominence of tumor-promoting CAFs, an extensively developed network of tumor vasculature, and increased expression of tumor-promoting cytokines. In addition, myeloid lineage compartments (MDSC, granulocytes, M2 macrophages) that greatly promote tumor progression are pronounced in Type C tumors. Accordingly, when designing a combination therapy for Type C tumor patients (FIG. 48B), therapies interfering with the refined cancer-signaling pathways, as well as inhibitors of angiogenesis, CAFs and/or immunosuppressive factors (e.g., TGFβ) that are produced by these cells would likely be used. In addition, remedies that are capable of M2 macrophages and MDSC reprogramming would likely be useful in combination therapies for patients having Type C tumors.

Treatment strategies for "inflamed" tumors are more multifarious. For patients with Type B tumors (FIG. 48C) checkpoint inhibitors in combination with blockaders of Treg, MDSC and immunosuppressive (e.g., TGFβ, IDO-1) factors could be used. Compared to Type B (second type) tumors, Type A (first type) tumors (FIG. 42A) require the addition of angiogenesis and CAF inhibitors. As the infiltrating T cell compartments are well expressed in Types A and B (first and second type tumors, respectively) tumors, they could be fully exploited by the application of either personalized vaccines or vaccines based on the shared tumor-specific antigens, or both. In addition, for the treatment of Types A and B tumors (first and second type, respectively), a combination of the referenced therapies with therapies that inhibit metastatic or growth-signaling activities of malignant cells, or therapies that block the action of tumor growth factors if they are prominently expressed in the particular patient's MF profile could be used.

Therapeutic combinations compiled for Types A, B, C and D tumors (first-fourth type tumors, respectively) can be adapted for a particular patient. The identified and described cancer MF profiles provide an objective basis for choosing a functionally relevant combination of therapeutic components. Specific combinations of therapies for Types A-D ($1^{st}$-$4^{th}$ type, respectively) tumors ("treatment standards") can be pre-designed and tuned by adding or excluding certain remedies based on the unique characteristics of a patient's tumor.

Figure 48A:
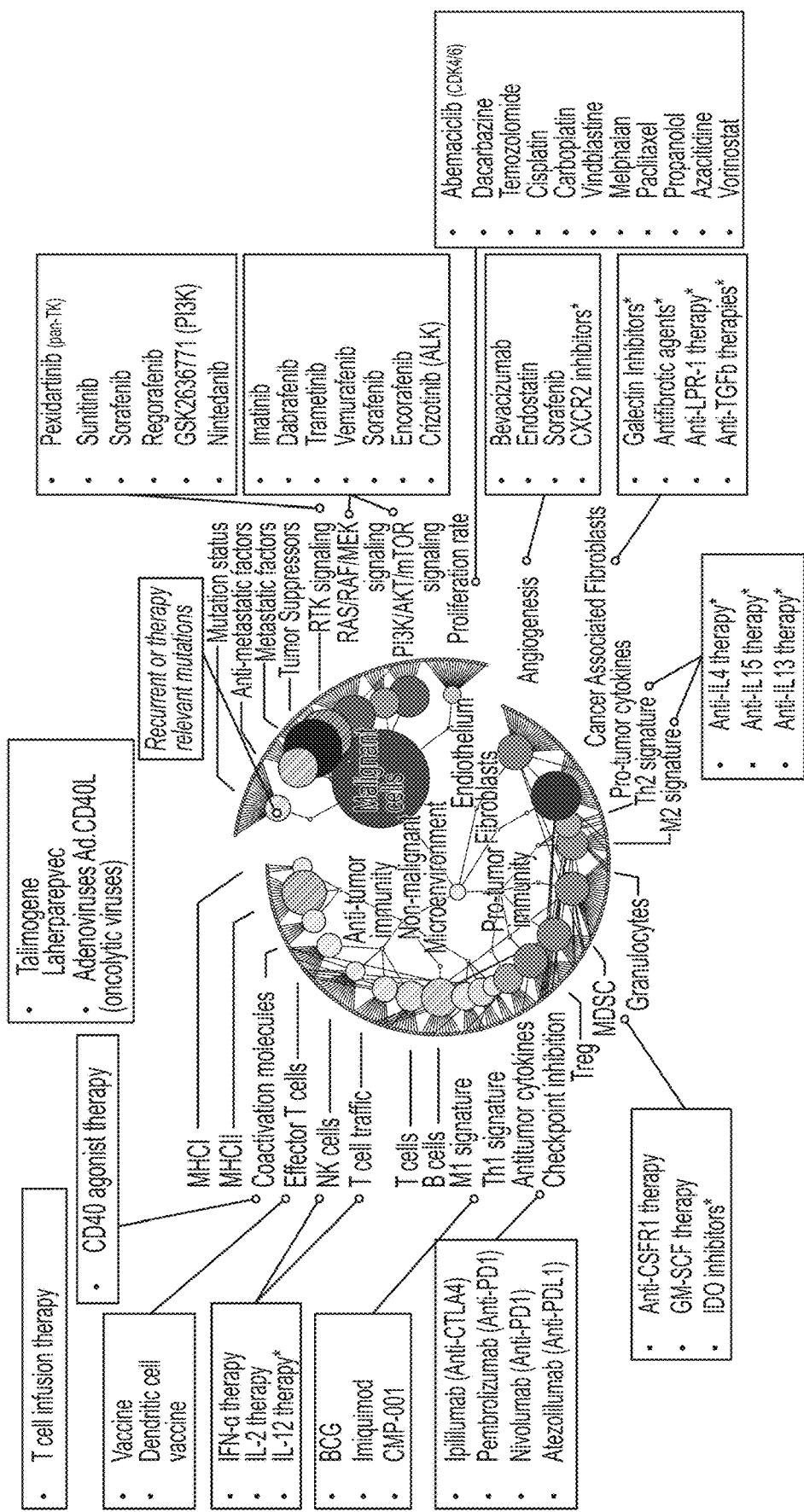
FIG. 48A shows an exemplary MF profile useful for designing a combination therapy, in accordance with some embodiments of the technology described herein.
Figure 48B:
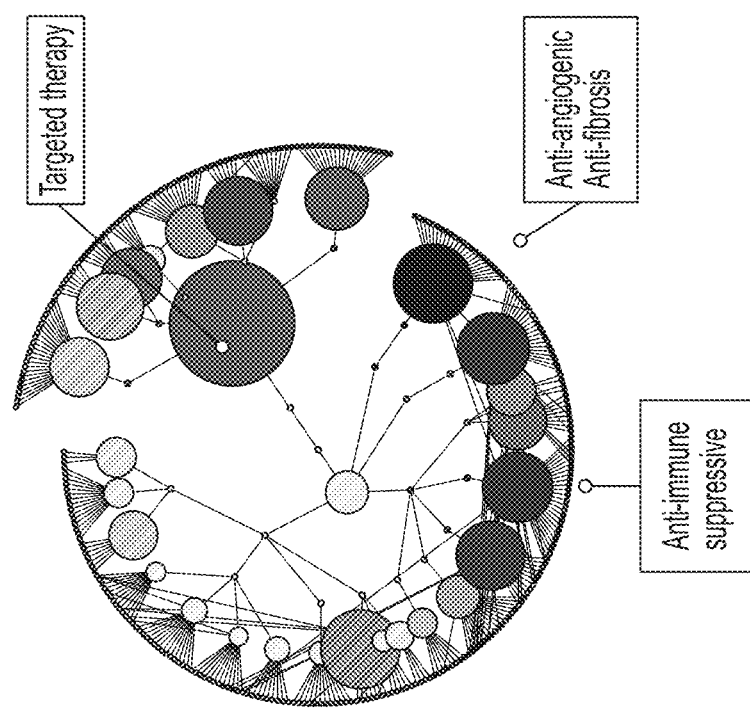
FIG. 48B shows an exemplary MF profile type B useful for designing a combination therapy, in accordance with some embodiments of the technology described herein.
Figure 48C:
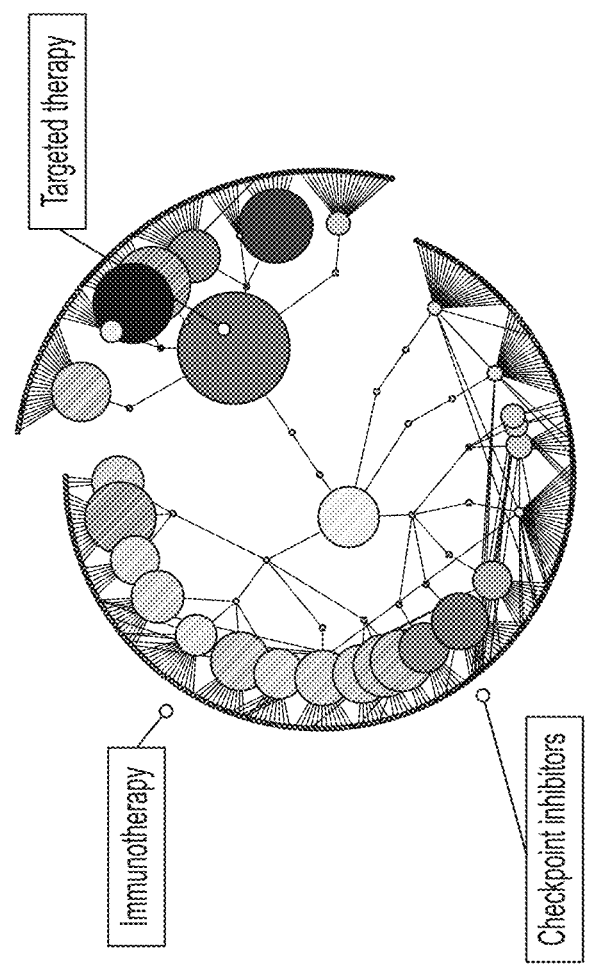
FIG. 48C shows an exemplary MF profile type C useful for designing a combination therapy, in accordance with some embodiments of the technology described herein.
Figure 48D:
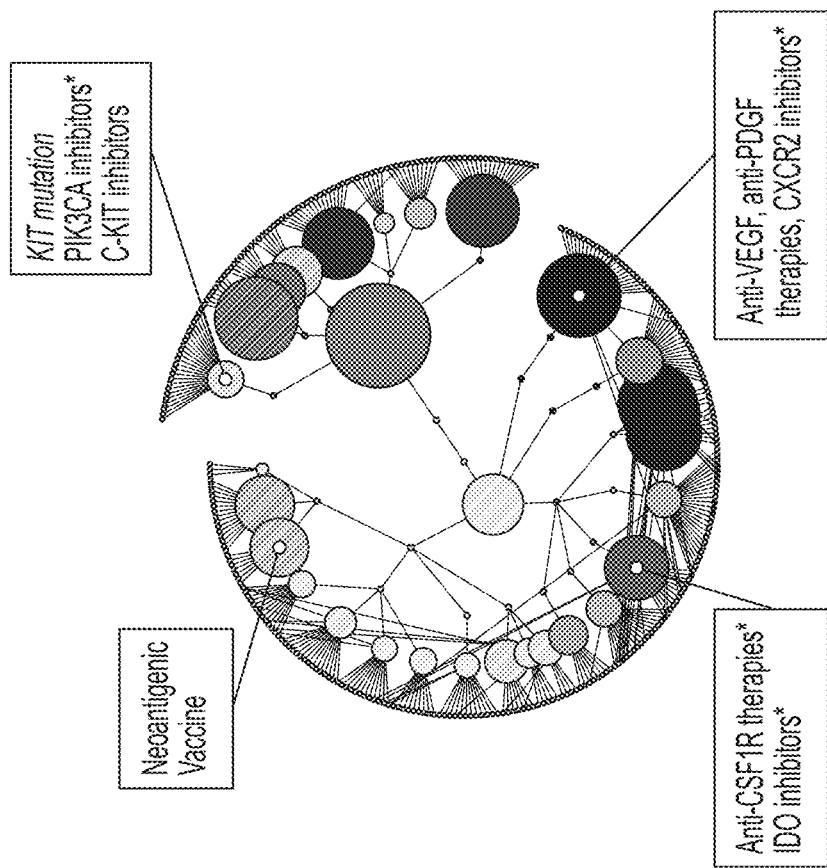
FIG. 48D shows an exemplary MF profile type D useful for designing a combination therapy, in accordance with some embodiments of the technology described herein.

Given the efficiency and wide application of targeted inhibitors, the MF profiles were further expanded to include a mutation status module that represented the most important recurrent and therapy relevant mutations in oncogenes. The presence of these mutations may be used as a biomarker for selecting targeted inhibitors. In another example, a MF profile was modified to design a combination therapy that included targeted inhibitors, relevant to the driver mutation (KIT) found in the tumor of a melanoma patient (FIG. 48D). Identified mutations could also provide useful information for designing of personalized neoantigen vaccine.

Example 8

MF Profile Complexity

Figure 49A:
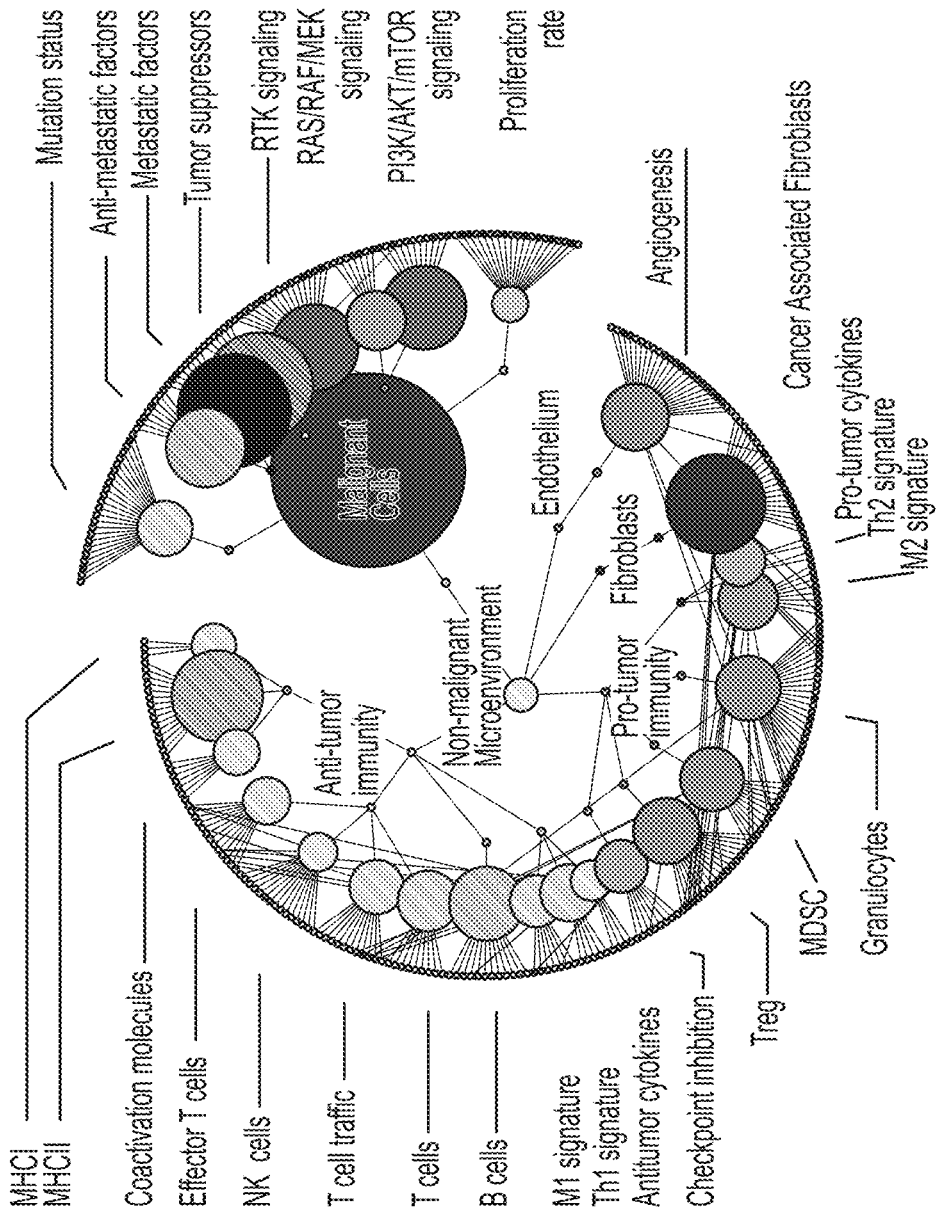
FIG. 49A is a graphical representation of an exemplary MF profile having 28 functional processes, in accordance with some embodiments of the technology described herein.
Figure 49B:
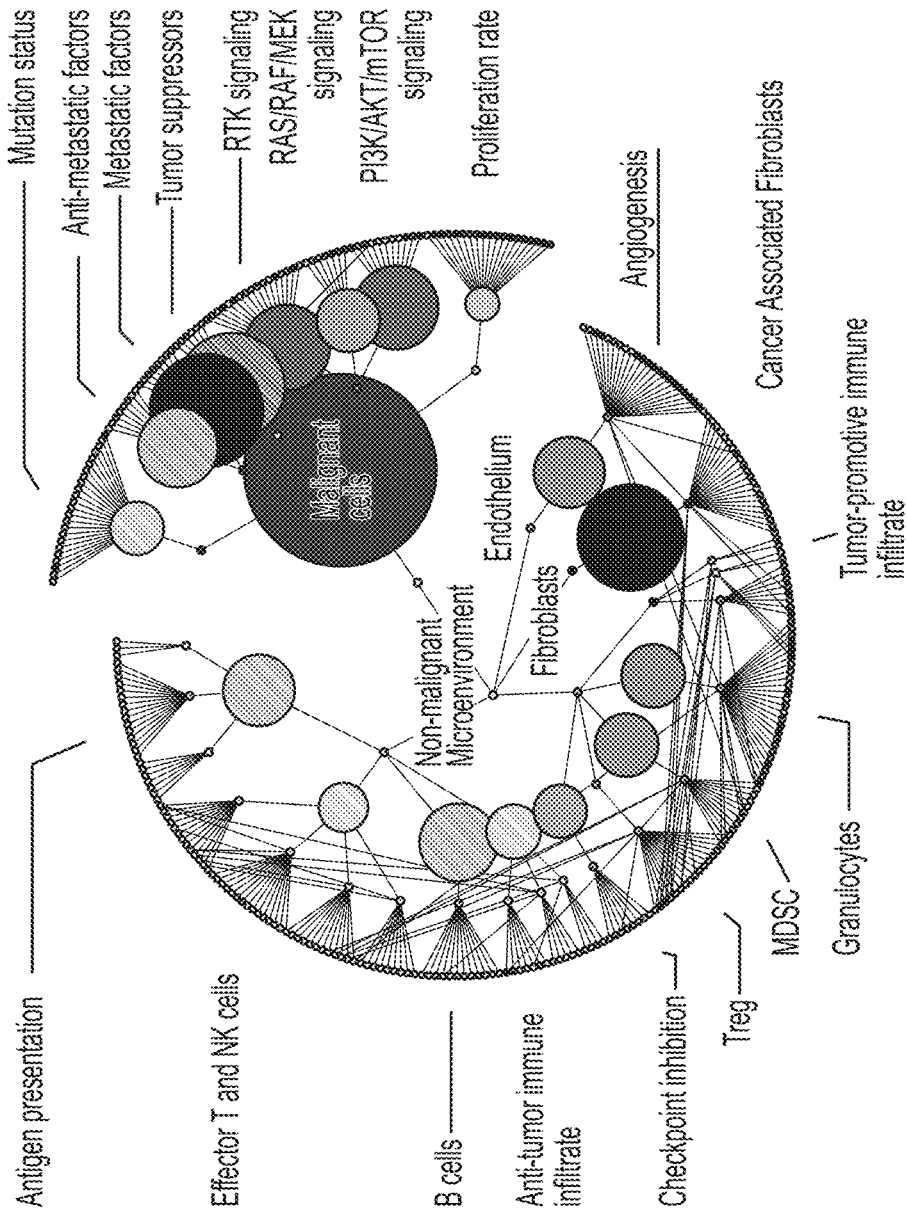
FIG. 49B is a graphical representation showing a visualization of a MF profile having 19 functional processes, in accordance with some embodiments of the technology described herein.
Figure 49C:
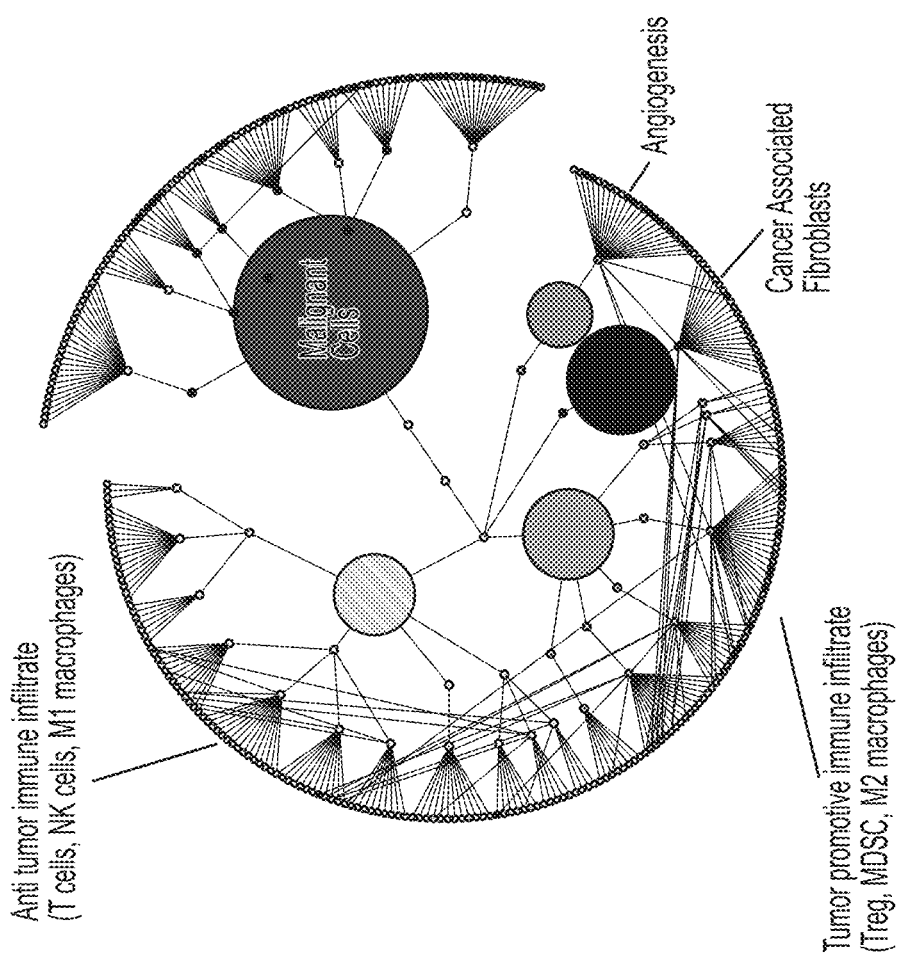
FIG. 49C is a graphical representation showing a visualization of a MF profile having 5 functional processes, in accordance with some embodiments of the technology described herein.

The degree of detail of MF profiles was decreased from 28 modules (FIG. 49A) down to 19 modules (FIG. 49B) or 5 modules (FIG. 49C) by collapsing related functional processes. A reduction of model complexity was achieved by merging inherently related modules. For example, the T cell, T cell traffic and Cytotoxic T cell modules were be merged with NK cell module in the combined Effector T and NK cell module. Similarly, Th2 cells, M2 macrophages and Pro-tumor cytokines were joined within the Tumor-promoting immune infiltrate module.

The level of detail can be selected depending on the task. For example, the most simplified MF profile can serve to classify a tumor principal type, e.g., "non-inflamed" or "inflamed," or having extensive angiogenesis, or containing an excess of cancer-associated fibroblasts, or exhibiting hypertrophy of suppressor cells. A more sophisticated MF profile can be employed for the refined analysis of a tumor functional organization, specifically to identify the composition of infiltrating immune cells, intensity of anticancer cytotoxic mechanisms, types of immunosuppressive cells and molecules, the number, differentiation phase and activity of CAFs, and finally, malignancy details of cancerous cells.

Example 9

Analysis of Relationships Between Functional Modules

The MF profiles of Types A-D tumors ($1^{st}$-$4^{th}$ type tumors, respectively) differ by the intensity of processes assigned to 28 functional modules. These processes reflect the presence and functional activity of certain cell types—malignant, endothelial, fibroblasts, as well as leukocytes/lymphocytes of various differentiation lineages. The presence and functional status of each cell type influences the presence and function of other cell types in the tumor microenvironment, which in turn influences the presence and function of the former cell type.

Three principal variants of mutual interaction among cell types occur, and thus influences interaction between functional modules. The first variant is a synergistic action of two particular cell types or two functional modules, which means that activation of one module promotes activation of the other. The second variant is an antagonism of two particular cell types or two functional modules, when activation of one module suppresses the other module. The third variant is the absence of any mutual influence of two modules on each other.

In the case of a positive relationship, functionally connected modules could be either co-activated or co-extinguished (e.g., not activated). The intensity of antagonistic functional modules should be the opposite—one active, the other not. In the absence of mutual influence, modules should randomly vary from portrait to portrait with no signs of connection.

Figure 50A:
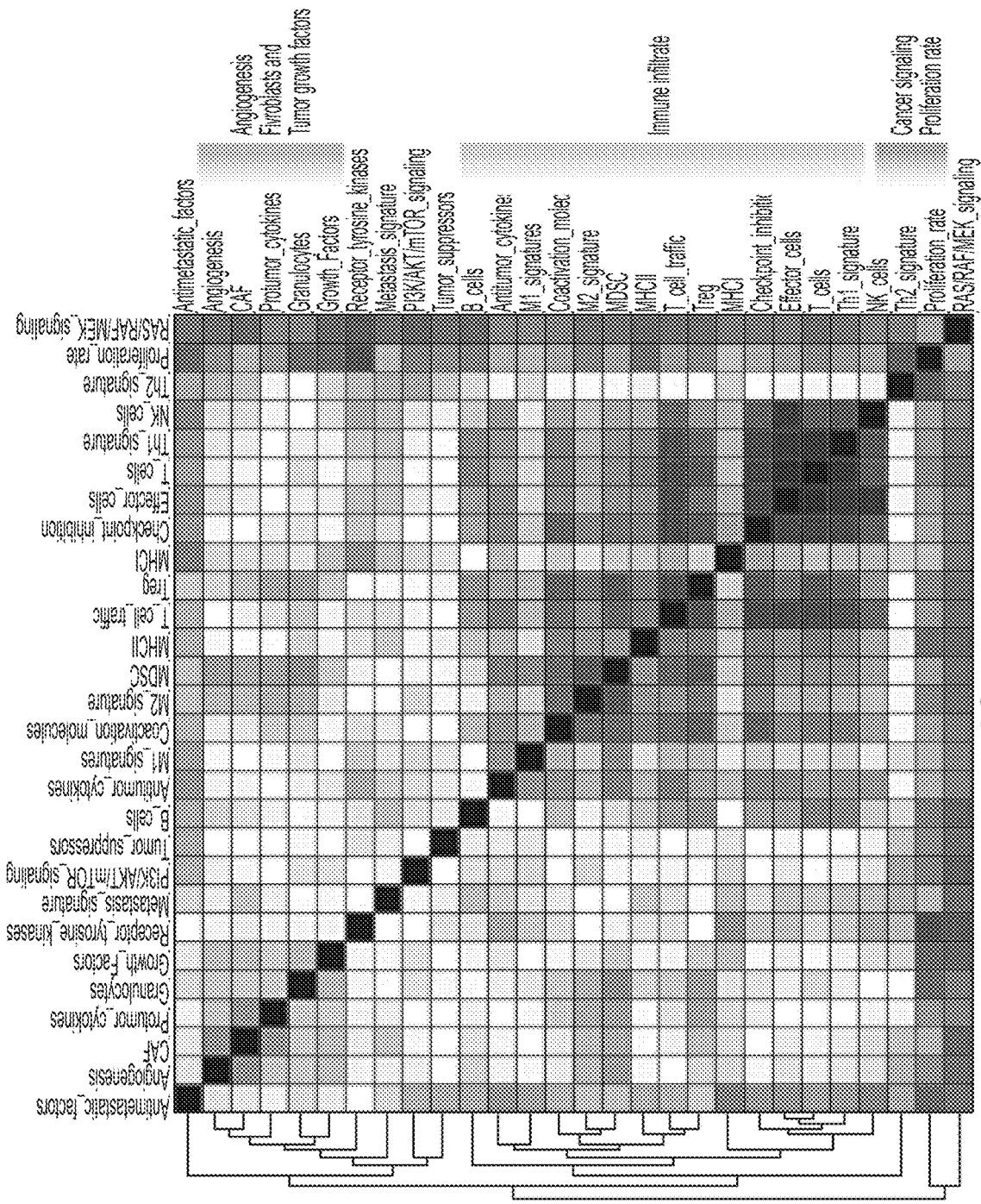
FIG. 50A shows data from a Pearson correlation analysis of functional modules which form the basis for the tumor MF profiles, in accordance with some embodiments of the technology described herein.
Figure 50B:
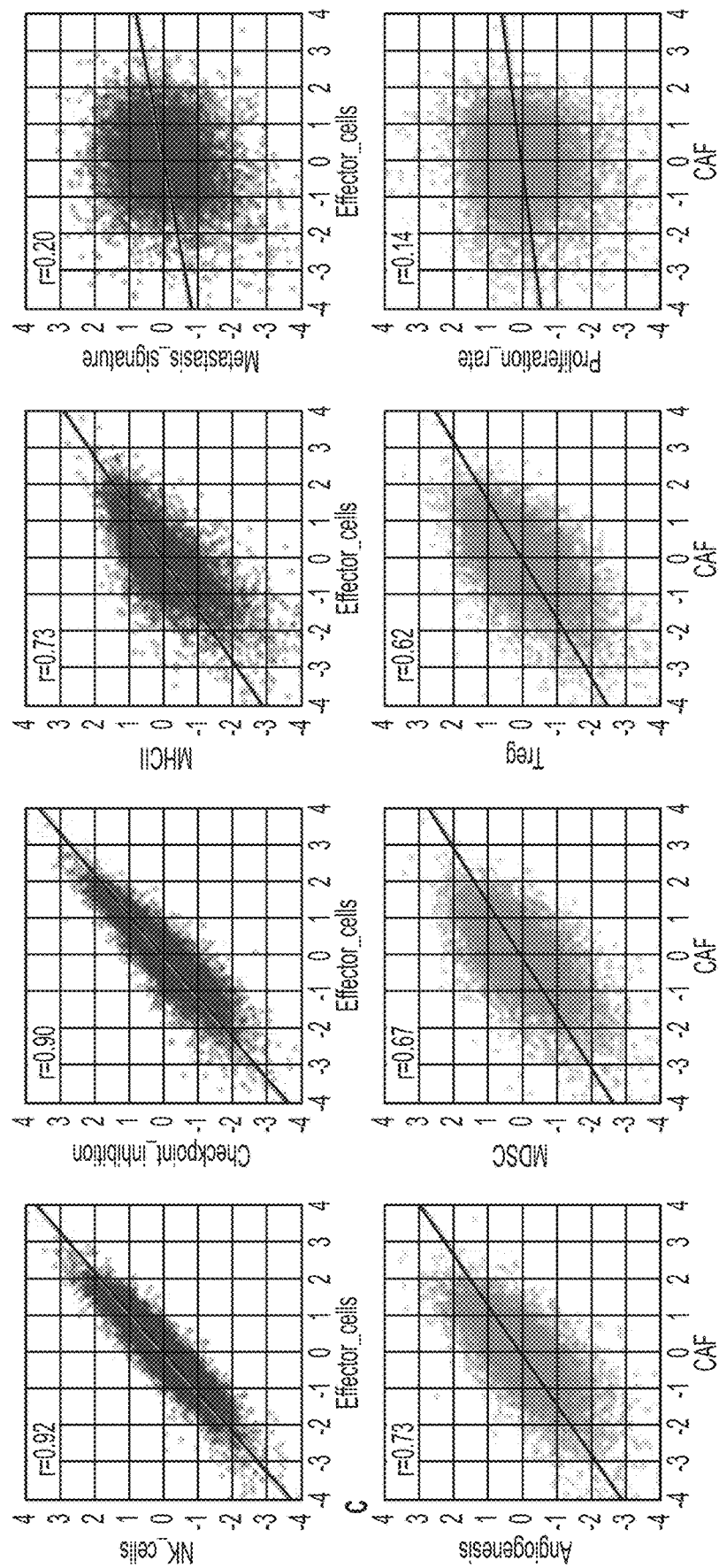
FIG. 50B shows data from a Pearson correlation analysis of Effector cells functional activity module with NK cells, Checkpoint inhibition, MHC class II and Metastasis modules, in accordance with some embodiments of the technology described herein.
Figure 50C:
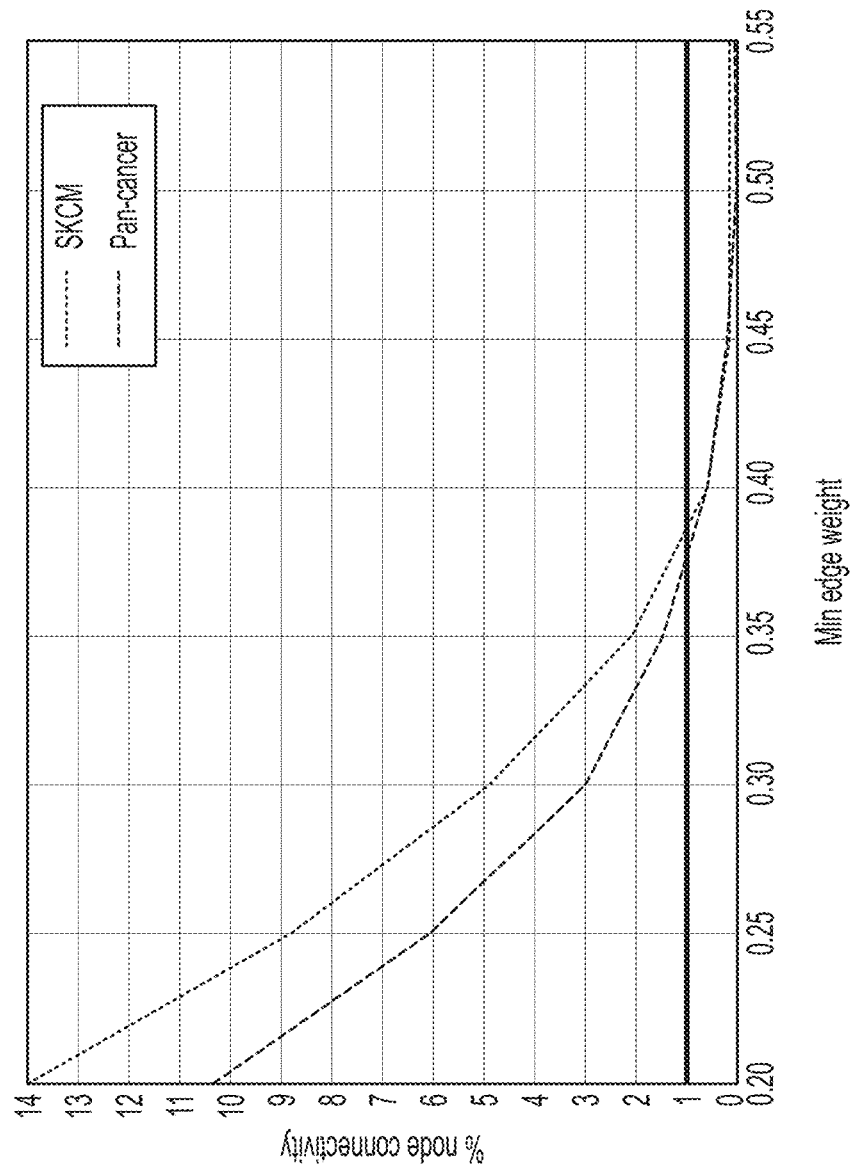
FIG. 50C shows a graph showing SKCM and pan-cancer graph node connectivity percent (%) on different edge weight thresholds, in accordance with some embodiments of the technology described herein. The solid line shows 1% node connectivity.

Pearson correlation analysis of relationships between any two of the 28 functional modules revealed two groups of modules bound by positive correlations (FIGS. 50A-50C). Modules in the first group having a positive relationship included T cell signatures, T cell trafficking, Th1 cells, Effector T cells, NK cells, MHC class II expression as well as the Checkpoint inhibition and Treg modules. With lower positive correlation coefficients, MHC Class I, Co-activation molecules, Anti-tumor cytokines and B cells modules were adjacent to this group of modules. Modules of this first group were generally related to effective anti-tumor responses. Remarkably, these modules had negative correlation with the tumor malignancy modules such as the Tumor proliferation rate and Cancer signaling (RAS/RAF/MEK) modules. In other words, the worse the malignancy of the tumor, the less developed the immune responses were within the tumor. Conversely, if the tumor had no prominent malignancy signs, an intensive immune response was observed.

Modules in the second group having an antagonistic relationship included CAFs, Angiogenesis and the Tumor-promoting growth factors, as well as Pro-tumor cytokines, M2 macrophages, Granulocytes and MDSC modules. This second group of modules functions to promote tumor growth, survival and metastasis while suppressing immune responses that control tumor outgrowth. In addition, this second group of modules were negatively correlated with cancer signaling (RAS/RAF/MEK) and proliferation modules.

Taken together, the relationship between modules suggested that tumors comprising driver mutations and/or high proliferation rates were devoid of tumor immune defenses and tumor-promoting modules (e.g., CAFs, angiogenesis, M2, MDSC). Thus, the malignancy of certain cells forms a basis for the development of "non-inflamed" tumors, wherein the activity of the microenvironment is reduced to a minimum.

EXAMPLE EMBODIMENTS

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising gene groups associated with cancer malignancy and different gene groups associated with cancer microenvironment; and identifying, from among multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using RNA expression data obtained from biological samples from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising gene groups associated with cancer malignancy and different gene groups associated with cancer microenvironment; and identifying, from among multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using RNA expression data obtained from biological samples from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising gene groups associated with cancer malignancy and different gene groups associated with cancer microenvironment; and identifying, from among multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using RNA expression data obtained from biological samples from the plurality of subjects, each of the plurality of MF profiles containing a gene group expression level for each gene group in the set of gene groups; and clustering the plurality of MF profiles to obtain the MF profile clusters.

In some embodiments, the gene groups associated with cancer malignancy is the tumor properties group; and the MF profile for the subject comprises determining a gene group expression level for the tumor properties group. In some embodiments, the gene groups associated with cancer microenvironment are the tumor-promoting immune microenvironment group, the anti-tumor immune microenvironment group, the angiogenesis group, and the fibroblasts group; and determining the MF profile for the subject comprises determining a gene group expression level for each of the tumor-promoting immune microenvironment group, the anti-tumor immune microenvironment group, the angiogenesis group, and the fibroblasts group. In some embodiments, the gene groups associated with cancer malignancy comprise at least three genes from the following group: the tumor properties group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL.

In some embodiments, determining the MF portrait comprises: determining the gene group expression level for the tumor properties group using the gene expression level obtained from the RNA sequence data for at least three genes in the tumor properties group. In certain embodiments, the gene groups associated with cancer microenvironment comprise at least three genes from each of the following groups: the anti-tumor immune microenvironment group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the tumor-promoting immune microenvironment group: PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDOL ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1; the fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; and the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMPS. In some embodiments, determining the MF portrait comprises: determining the gene group expression level for the anti-tumor immune microenvironment group using the gene expression level obtained from the RNA sequence data for at least three genes in the anti-tumor immune microenvironment group; determining the gene group expression level for the tumor-promoting immune microenvironment group using the gene expression level obtained from the RNA sequence data for at least three genes in the tumor-promoting immune microenvironment group; determining the gene group expression level for the fibroblasts group using the gene expression level obtained from the RNA sequence data for at least three genes in the fibroblasts group; and determining the gene group expression level for the angiogenesis group using the gene expression level obtained from the RNA sequence data for at least three genes in the angiogenesis group. In certain embodiments, the gene groups associated with cancer malignancy are: the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining the MF profile for the subject comprises determining a gene group expression level for each of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group. In some embodiments, the gene groups associated with cancer microenvironment are: the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and determining the MF profile for the subject comprises determining a gene group expression level for each of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group.

In certain embodiments, the gene groups associated with cancer malignancy comprise at least three genes from each of the following groups: the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In certain embodiments, determining the MF portrait comprises: determining the gene group expression level for the proliferation rate group using the gene expression level obtained from the RNA sequence data for at least three genes in the proliferation rate group; determining the gene group expression level for the PI3K/AKT/mTOR signaling group using the gene expression level obtained from the RNA sequence data for at least three genes in the PI3K/AKT/mTOR signaling group; determining the gene group expression level for the RAS/RAF/MEK signaling group using the gene expression level obtained from the RNA sequence data for at least three genes in the RAS/RAF/MEK signaling group; determining the gene group expression level for the receptor tyrosine kinases expression group using the gene expression level obtained from the RNA sequence data for at least three genes in the receptor tyrosine kinases expression group; determining the gene group expression level for the tumor suppressors group using the gene expression level obtained from the RNA sequence data for at least three genes in the tumor suppressors group; determining the gene group expression level for the metastasis signature group using the gene expression level obtained from the RNA sequence data for at least three genes in the metastasis signature group; determining the gene group expression level for the anti-metastatic factors group using the gene expression level obtained from the RNA sequence data for at least three genes in the anti-metastatic factors group; and determining the gene group expression level for the mutation status group using the gene expression level obtained from the RNA sequence data for at least three genes in the mutation status group. In certain embodiments, the gene groups associated with cancer microenvironment comprise at least three genes from each of the following groups: the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the antigen presentation group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, and CD28; the cytotoxic T and NK cells group: IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the anti-tumor microenvironment group: NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the checkpoint inhibition group: PDCD1, CD274, CTLA4, LAG5, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the tumor-promotive immune group: IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1. In certain embodiments, determining the MF portrait comprises: determining the gene group expression level for the cancer associated fibroblasts group using the gene expression level obtained from the RNA sequence data for at least three genes in the cancer associated fibroblasts group; determining the gene group expression level for the angiogenesis group using the gene expression level obtained from the RNA sequence data for at least three genes in the angiogenesis group; determining the gene group expression level for the antigen presentation group using the gene expression level obtained from the RNA sequence data for at least three genes in the antigen presentation group; determining the gene group expression level for the cytotoxic T and NK cells group using the gene expression level obtained from the RNA sequence data for at least three genes in the cytotoxic T and NK cells group; determining the gene group expression level for the B cells group using the gene expression level obtained from the RNA sequence data for at least three genes in the B cells group; determining the gene group expression level for the anti-tumor microenvironment group using the gene expression level obtained from the RNA sequence data for at least three genes in the anti-tumor microenvironment group; determining the gene group expression level for the checkpoint inhibition group using the gene expression level obtained from the RNA sequence data for at least three genes in the checkpoint inhibition group; determining the gene group expression level for the Treg group using the gene expression level obtained from the RNA sequence data for at least three genes in the Treg group; determining the gene group expression level for the MDSC group using the gene expression level obtained from the RNA sequence data for at least three genes in the MDSC group; determining the gene group expression level for the granulocytes group using the gene expression level obtained from the RNA sequence data for at least three genes in the granulocytes group; and determining the gene group expression level for the tumor-promotive immune group using the gene expression level obtained from the RNA sequence data for at least three genes in the tumor-promotive immune group.

In some embodiments, the gene groups associated with cancer malignancy are: the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining the MF profile for the subject comprises determining a gene group expression level for each of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group. In certain embodiments, the gene groups associated with cancer microenvironment are: the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; and determining the MF profile for the subject comprises determining a gene group expression level for each of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group. In certain embodiments, the gene groups associated with cancer malignancy comprise at least three genes from each of the following groups: the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the growth factors group: NGF, CSF3, CSF2, FGF7, IGF1, IGF2, IL7, and FGF2; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In certain embodiments, determining the MF portrait comprises: determining the gene group expression level for the proliferation rate group using the gene expression level obtained from the RNA sequence data for at least three genes in the proliferation rate group; determining the gene group expression level for the PI3K/AKT/mTOR signaling group using the gene expression level obtained from the RNA sequence data for at least three genes in the PI3K/AKT/mTOR signaling group; determining the gene group expression level for the RAS/RAF/MEK signaling group using the gene expression level obtained from the RNA sequence data for at least three genes in the RAS/RAF/MEK signaling group; determining the gene group expression level for the receptor tyrosine kinases expression group using the gene expression level obtained from the RNA sequence data for at least three genes in the receptor tyrosine kinases expression group; determining the gene group expression level for the growth factors group using the gene expression level obtained from the RNA sequence data for at least three genes in the growth factors group; determining the gene group expression level for the tumor suppressors group using the gene expression level obtained from the RNA sequence data for at least three genes in the tumor suppressors group; determining the gene group expression level for the metastasis signature group using the gene expression level obtained from the RNA sequence data for at least three genes in the metastasis signature group; determining the gene group expression level for the anti-metastatic factors group using the gene expression level obtained from the RNA sequence data for at least three genes in the anti-metastatic factors group; and determining the gene group expression level for the mutation status group using the gene expression level obtained from the RNA sequence data for at least three genes in the mutation status group.

In some embodiments, the gene groups associated with cancer microenvironment comprise at least three genes from each of the following groups: the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the MHCI group: HLA-A, HLA-B, HLA-C, B2M, TAP1, and TAP2; the MHCII group: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; the coactivation molecules group: CD80, CD86, CD40, CD83, TNFRSF4, ICOSLG, and CD28; the effector cells group: IFNG, GZMA, GZMB, PRF1, LCK, GZMK, ZAP70, GNLY, FASLG, TBX21, EOMES, CD8A, and CD8B; the NK cells group: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5; the T cell traffic group: CXCL9, CXCL10, CXCR3, CX3CL1, CCR7, CXCL11, CCL21, CCL2, CCL3, CCL4, and CCL5; the T cells group: EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the M1 signatures group: NOS2, IL12A, IL12B, IL23A, TNF, IL1B, and SOCS3; the Th1 signature group: IFNG, IL2, CD40LG, IL15, CD27, TBX21, LTA, and IL21; the antitumor cytokines group: HMGB1, TNF, IFNB1, IFNA2, CCL3, TNFSF10, and FASLG; the checkpoint inhibition group: PDCD1, CD274, CTLA4, LAG3, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the M2 signature group: IL10, VEGFA, TGFB1, IDO1, PTGES, MRC1, CSF1, LRP1, ARG1, PTGS1, MSR1, CD163, and CSF1R; the Th2 signature group: IL4, IL5, IL13, IL10, IL25, and GATA3; the protumor cytokines group: IL10, TGFB1, TGFB2, TGFB3, IL22, and MIF; and the complement inhibition group: CFD, CFI, CD55, CD46, and CR1. In certain embodiments, determining the MF portrait comprises: determining the gene group expression level for the cancer associated fibroblasts group using the gene expression level obtained from the RNA sequence data for at least three genes in the cancer associated fibroblasts group; determining the gene group expression level for the angiogenesis group using the gene expression level obtained from the RNA sequence data for at least three genes in the angiogenesis group; determining the gene group expression level for the MHCI group using the gene expression level obtained from the RNA sequence data for at least three genes in the MHCI group; determining the gene group expression level for the MHCII group using the gene expression level obtained from the RNA sequence data for at least three genes in the MHCII group; determining the gene group expression level for the coactivation molecules group using the gene expression level obtained from the RNA sequence data for at least three genes in the coactivation molecules group; determining the gene group expression level for the effector cells group using the gene expression level obtained from the RNA sequence data for at least three genes in the effector cells group; determining the gene group expression level for the NK cells group using the gene expression level obtained from the RNA sequence data for at least three genes in the NK cells group; determining the gene group expression level for the T cell traffic group using the gene expression level obtained from the RNA sequence data for at least three genes in the T cell traffic group; determining the gene group expression level for the T cells group using the gene expression level obtained from the RNA sequence data for at least three genes in the T cells group; determining the gene group expression level for the B cells group using the gene expression level obtained from the RNA sequence data for at least three genes in the B cells group; determining the gene group expression level for the M1 signatures group using the gene expression level obtained from the RNA sequence data for at least three genes in the M1 signatures group; determining the gene group expression level for the Th1 signature group using the gene expression level obtained from the RNA sequence data for at least three genes in the Th1 signature group; determining the gene group expression level for the antitumor cytokines group using the gene expression level obtained from the RNA sequence data for at least three genes in the antitumor cytokines group; determining the gene group expression level for the checkpoint inhibition group using the gene expression level obtained from the RNA sequence data for at least three genes in the checkpoint inhibition group; determining the gene group expression level for the Treg group using the gene expression level obtained from the RNA sequence data for at least three genes in the Treg group; determining the gene group expression level for the MDSC group using the gene expression level obtained from the RNA sequence data for at least three genes in the MDSC group; determining the gene group expression level for the granulocytes group using the gene expression level obtained from the RNA sequence data for at least three genes in the granulocytes group; determining the gene group expression level for the M2 signature group using the gene expression level obtained from the RNA sequence data for at least three genes in the M2 signature group; determining the gene group expression level for the Th2 signature group using the gene expression level obtained from the RNA sequence data for at least three genes in the Th2 signature group; determining the gene group expression level for the protumor cytokines group using the gene expression level obtained from the RNA sequence data for at least three genes in the protumor cytokines group; and determining the gene group expression level for the complement inhibition group using the gene expression level obtained from the RNA sequence data for at least three genes in the complement inhibition group.

In some embodiments, the system, method, or computer-readable storage medium further comprises identifying at least one first therapy for the subject based on the identified MF profile cluster. In some embodiments, identifying at least one first therapy consists of identifying a single therapy. In some embodiments, identifying at least one first therapy consists of identifying two or more therapies. In some embodiments, identifying the at least one therapy comprises identifying at least one therapy selected from the group consisting of: chemotherapy, antibody drug conjugates, hormonal therapy, viral therapy, genetic therapy, non-immune protein therapy, antiangiogenic agents, anti-cancer vaccines, radiotherapy, soluble receptor therapy, cell based therapies, immunotherapy, and targeted therapy. In certain embodiments, identifying the at least one therapy comprises identifying at least one therapy selected from the group consisting of: HGFR inhibitors, EGFR inhibitors, VEGF inhibitors, PDGF inhibitors, CXR2 inhibitors, CXCR4 inhibitors, DPP-4 inhibitors, galectin inhibitors, antifibrotic agents, LPR1 inhibitors, TGF-beta inhibitors, IL5 inhibitors, IL4 inhibitors, IL13 inhibitors, IL22 inhibitors, CSF1R inhibitors, IDO inhibitors, LPR1 inhibitors, CD25 inhibitors, GITR inhibitors, PD-1 inhibitors, CTLA1 inhibitors, PDL1 inhibitors, LAG3 inhibitors, TIM3 inhibitors, vaccines, PRIMA-1 analogues, CD40 agonists, ICOS agonists, OX40 agonists, Bcl-2 inhibitors, AKT inhibitors, MYC-targeting siRNA, pan-tyrosine kinase inhibitors, CDK4/6 inhibitors, Aurora A inhibitors, vaccines, LAG3 inhibitors, and any antibody-drug conjugate. In certain embodiments, identifying the at least one therapy comprises identifying at least one therapy selected from the group consisting of: HGFR inhibitors, EGFR inhibitors, VEGF inhibitors, PDGF inhibitors, CXR2 inhibitors, galectin inhibitors, antifibrotic agents, LPR1 inhibitors, TGF-beta inhibitors, IL5 inhibitors, IL4 inhibitors, IL13 inhibitors, IL22 inhibitors, CSF1R inhibitors, IDO inhibitors, CXCR4 inhibitors, CD25 inhibitors, GITR inhibitors, PD-1 inhibitors, CTLA1 inhibitors, PDL1 inhibitors, LAG3 inhibitors, TIM3 inhibitors, and vaccines. In certain embodiments, identifying the at least one therapy comprises identifying at least one therapy selected from the group consisting of: HGFR inhibitors, EGFR inhibitors, PRIMA-1 analogues, TGF-beta inhibitors, IL22 inhibitors, CSF1R inhibitors, IDO inhibitors, LPR1 inhibitors, CXCR4 inhibitors, CD25 inhibitors, GITR inhibitors, CD40 agonists, ICOS agonists, OX40 agonists, and vaccines. In some embodiments, identifying the at least one therapy comprises identifying at least one therapy selected from the group consisting of: Bcl-2 inhibitors, AKT inhibitors, MYC-targeting siRNA, PRIMA-1 analogues, VEGF inhibitors, PDGF inhibitors, CXR2 inhibitors, galectin inhibitors, antifibrotic agents, LPR1 inhibitors, TGF-beta inhibitors, IL5 inhibitors, IL4 inhibitors, IL13 inhibitors, CSF1R inhibitors, IDO inhibitors, CXCR4 inhibitors, and vaccines.

In some embodiments, identifying the at least one therapy comprises identifying at least one therapy selected from the group consisting of: antibody-drug conjugates, HGFR inhibitors, EGFR inhibitors, VEGF inhibitors, PDGF inhibitors, CXCR2 inhibitors, galectin inhibitors, antifibrotic agents, LPR1 inhibitors, TGF-beta inhibitors, IL22 inhibitors, and CXCL10 disrupting inhibitors. In certain embodiments, identifying the at least one therapy comprises identifying at least one therapy selected from the group consisting of: Bcl-2 inhibitors, AKT inhibitors, MYC-targeting siRNA, chemotherapy, pan-tyrosine kinase inhibitors, CDK4/6 inhibitors, Aurora A inhibitors, and DPP-4 inhibitors.

In some embodiments, obtaining the RNA expression data is performed using whole transcriptome sequencing or mRNA sequencing. In certain embodiments, each of the biological samples is from a tumor or tissue known or suspected of having cancerous cells.

In some embodiments, the system, method, or computer-readable storage medium further comprises generating the MF profile clusters, the generating comprising: obtaining RNA expression data from biological samples obtained from a plurality of subjects; determining a respective plurality of MF profiles for the plurality of subjects, each of the plurality of MF profiles containing a gene group expression level for each gene group in the set of gene groups; and clustering the plurality of MF profiles to obtain the MF profile clusters. In certain embodiments, clustering the plurality of MF profiles is performed by using a k-means clustering technique.

In some embodiments, the system, method, or computer-readable storage medium further comprises: determining at least one visual characteristic of a first graphical user interface (GUI) element using a first gene group expression level for at least one gene group associated with cancer malignancy and at least one visual characteristic of a second GUI element using a second gene group expression level for at least one gene group associated with cancer microenvironment; generating a personalized GUI personalized to the subject, the GUI comprising: a first portion associated with cancer malignancy and containing the first GUI element; and a second portion associated with cancer microenvironment and containing the second GUI element, wherein the second portion is different from the first portion; and presenting the generated personalized GUI to a user. In some embodiments, determining the at least one visual characteristic of the first GUI element comprises determining size of the first GUI element using the first gene group expression level. In certain embodiments, determining the at least one visual characteristic of the first GUI element comprises determining color of the first GUI element using the first gene group expression level. In certain embodiments, the first portion comprises a first plurality of GUI elements representing a respective plurality of gene groups associated with cancer malignancy. In certain embodiments, the second portion comprises a second plurality of GUI elements representing a respective plurality of gene groups associated with cancer microenvironment.

In some embodiments, the system, method, or computer-readable storage medium further comprises: obtaining RNA expression data for at least one additional biological sample obtained from the subject subsequent to administration of at least one first therapy; determining, using the RNA expression data for at least one additional biological sample obtained from the subject subsequent to administration of at least one therapy, a second MF profile for the subject, wherein the second MF profile is determined at least in part by determining, using the RNA expression data for at least one additional biological sample obtained from the subject subsequent to administration of at least one therapy, a gene group expression level for each gene group in a set of gene groups, the set of gene groups comprising gene groups associated with cancer malignancy and different gene groups associated with cancer microenvironment; and identifying, from among the MF profile clusters, an MF profile cluster with which to associate the MF profile for the subject.

In certain embodiments, the system, method, or computer-readable storage medium further comprises determining that the at least one first therapy is effectively treating the subject. In some embodiments, the system, method, or computer-readable storage medium further comprises: determining that the at least one first therapy is not effectively treating the subject; and identifying at least one second therapy for the subject based on the second MF profile cluster. In certain embodiments, determining the MF profile for the subject comprises: determining a first gene group expression level for a first gene group of the gene groups associated with cancer malignancy using a gene set enrichment analysis (GSEA) technique; and determining a second gene group expression level for a second gene group of the gene groups associated with cancer microenvironment using the gene set enrichment analysis (GSEA) technique.

In some embodiments, determining the MF profile for the subject comprises: determining a first gene group expression level for a first gene group of the gene groups associated with cancer malignancy using a mutation count technique; and determining a second gene group expression level for a second gene group of the gene groups associated with cancer microenvironment using the mutation count technique. In some embodiments, the WES data is used to quantify tumor burden (purity), identify specific mutations, and/or to calculate the number of neoantigens.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data from biological samples from a plurality of subjects, at least some of the subjects having a cancer of a particular type; determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample; and storing the plurality of MF profiles in association with information identifying the particular cancer type.

In one aspect, provided herein is a method, comprising: using at least one computer hardware processor to perform: obtaining RNA expression data and/or whole exome sequencing (WES) data from biological samples from a plurality of subjects, at least some of the subjects having a cancer of a particular type; determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample; and storing the plurality of MF profiles in association with information identifying the particular cancer type.

In one aspect, provided herein is at least one non-transitory computer-readable storage medium storing processor-executable instructions that, when executed by at least one computer hardware processor, cause at least one computer hardware processor to perform: obtaining RNA expression data and/or whole exome sequencing (WES) data from biological samples from a plurality of subjects, at least some of the subjects having a cancer of a particular type; determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample; and storing the plurality of MF profiles in association with information identifying the particular cancer type.

In some embodiments, the system, method, or computer-readable storage medium further comprises: obtaining RNA expression data for at least one biological sample obtained from an additional subject; determining, using the RNA expression data for the at least one additional biological sample obtained from the additional subject, an MF profile for the additional subject, wherein the MF profile for the additional subject is determined at least in part by determining, using the RNA expression data for the at least one additional biological sample obtained from the additional subject, a gene group expression level for each gene group in a set of gene groups, the set of gene groups comprising gene groups associated with cancer malignancy and different gene groups associated with cancer microenvironment; and identifying, from among the MF profile clusters, an MF profile cluster with which to associate the MF profile for the additional subject.

In some embodiments, the system, method, or computer-readable storage medium further comprises: determining at least one visual characteristic of a first graphical user interface (GUI) element using a first gene group expression level for at least one gene group associated with cancer malignancy and at least one visual characteristic of a second GUI element using a second gene group expression level for at least one gene group associated with cancer microenvironment; generating a personalized GUI personalized to the additional subject, the GUI comprising: a first portion associated with cancer malignancy and containing the first GUI element; and a second portion associated with cancer microenvironment and containing the second GUI element, wherein the second portion is different from the first portion; and presenting the generated personalized GUI to a user.

In certain embodiments, the first portion comprises a first plurality of GUI elements representing a respective plurality of gene groups associated with cancer malignancy. In certain embodiments, the second portion comprises a second plurality of GUI elements representing a respective plurality of gene groups associated with cancer microenvironment. In some embodiments, determining the respective gene group expression level for each group in the set of gene groups is performed using a gene set enrichment analysis (GSEA) technique. In some embodiments, determining the respective gene group expression level for each group in the set of gene groups is performed using a mutation count technique. In certain embodiments, the clustering is performed using a community detection clustering technique. In certain embodiments, the clustering is performed using a k-means clustering technique.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising a first gene group associated with cancer malignancy and a second gene group associated with cancer microenvironment, wherein the first and second gene groups are different, the determining comprising: determining a first gene group expression level for the first gene group, and determining a second gene group expression level for the second gene group; determining a first visual characteristic for a first graphical user interface (GUI) element using the first gene group expression level; determining a second visual characteristic for a second GUI element using the second gene group expression level; generating a personalized GUI personalized to the subject, the GUI comprising: a first GUI portion associated with cancer malignancy and containing the first GUI element having the first visual characteristic, and a second GUI portion associated with cancer microenvironment and containing the second GUI element having the second visual characteristic; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising a first gene group associated with cancer malignancy and a second gene group associated with cancer microenvironment, wherein the first and second gene groups are different, the determining comprising: determining a first gene group expression level for the first gene group, and determining a second gene group expression level for the second gene group; determining a first visual characteristic for a first graphical user interface (GUI) element using the first gene group expression level; determining a second visual characteristic for a second GUI element using the second gene group expression level; generating a personalized GUI personalized to the subject, the GUI comprising: a first GUI portion associated with cancer malignancy and containing the first GUI element having the first visual characteristic, and a second GUI portion associated with cancer microenvironment and containing the second GUI element having the second visual characteristic; and presenting the generated personalized GUI to a user.

In one aspect, provided herein is at least one non-transitory computer-readable storage medium storing processor-executable instructions that, when executed by at least one computer hardware processor, cause at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups, the set of gene groups comprising a first gene group associated with cancer malignancy and a second gene group associated with cancer microenvironment, wherein the first and second gene groups are different, the determining comprising: determining a first gene group expression level for the first gene group, and determining a second gene group expression level for the second gene group; determining a first visual characteristic for a first graphical user interface (GUI) element using the first gene group expression level; determining a second visual characteristic for a second GUI element using the second gene group expression level; generating a personalized GUI personalized to the subject, the GUI comprising: a first GUI portion associated with cancer malignancy and containing the first GUI element having the first visual characteristic, and a second GUI portion associated with cancer microenvironment and containing the second GUI element having the second visual characteristic; and presenting the generated personalized GUI to a user.

In some embodiments, determining the first visual characteristic for the first GUI element comprises determining size of the first GUI element using the first gene group expression level; and determining the second visual characteristic for the second GUI element comprises determining size of the second GUI element using the second gene group expression level. In some embodiments, determining the first visual characteristic for the first GUI element comprises determining color and/or pattern of the first GUI element using the first gene group expression level; and determining the second visual characteristic for the second GUI element comprises determining color and/or pattern of the second GUI element using the second gene group expression level. In some embodiments, determining the first visual characteristic for the first GUI element comprises determining shape of the first GUI element using the first gene group expression level; and determining the second visual characteristic for the second GUI element comprises determining shape of the second GUI element using the second gene group expression level. In certain embodiments, in response to a user selection of the first GUI element, the GUI is configured to present information about at least one additional gene group associated with cancer malignancy. In certain embodiments, in response to a user selection of the second GUI element, the GUI is configured to present information about at least one additional gene group associated with cancer microenvironment.

In some embodiments, generating the personalized GUI comprises generating the GUI comprising: a first portion associated with cancer malignancy and containing the first GUI element; and a second portion associated with cancer microenvironment and containing the second GUI element, wherein the second portion is different from the first portion.

In some embodiments, the first portion comprises a first plurality of GUI elements including a GUI element for each of the gene groups associated with cancer malignancy, wherein the first plurality of GUI elements comprises the first GUI element; and the second portion comprises a second plurality of GUI elements including a GUI element for each of the gene groups associated with cancer microenvironment, wherein the second plurality of GUI elements comprises the second GUI element.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the tumor properties group; and determining, using the RNA expression data and the reference RNA expression data, a gene group expression level for each gene group in a second set of gene groups associated with cancer microenvironment and consisting of the tumor-promoting immune microenvironment group, the anti-tumor immune microenvironment group, the angiogenesis group, and the fibroblasts group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the tumor properties group; and determining, using the RNA expression data and the reference RNA expression data, a gene group expression level for each gene group in a second set of gene groups associated with cancer microenvironment and consisting of the tumor-promoting immune microenvironment group, the anti-tumor immune microenvironment group, the angiogenesis group, and the fibroblasts group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the tumor properties group; and determining, using the RNA expression data and the reference RNA expression data, a gene group expression level for each gene group in a second set of gene groups associated with cancer microenvironment and consisting of the tumor-promoting immune microenvironment group, the anti-tumor immune microenvironment group, the angiogenesis group, and the fibroblasts group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological sample, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is a method, comprising: using at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject having a particular type of cancer; determining a molecular-functional (MF) profile for the subject at least in part by: determining, using the RNA expression data and reference RNA expression data, a gene group expression level for each gene group in a first set of gene groups associated with cancer malignancy and consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and determining, using the RNA expression data and the reference RNA expression data, a gene group expression level for each gene group in a second set of gene groups associated with cancer microenvironment and consisting of the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group; and accessing information specifying multiple MF profile clusters for the particular cancer type; identifying, from among the multiple MF profile clusters, an MF profile cluster with which to associate the MF profile for the subject, the MF profile clusters comprising: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by: determining a plurality of MF profiles for a respective plurality of subjects using the reference RNA expression data and RNA expression data from biological samples obtained from the plurality of subjects, each of the plurality of MF profiles containing a gene group expression level for each gene group in the set of gene groups; and clustering the plurality of MF profiles to obtain the MF profile clusters.

In some embodiments, the gene groups associated with cancer malignancy comprise at least three genes from each of the following groups: the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the growth factors group: NGF, CSF3, CSF2, FGF7, IGF1, IGF2, IL7, and FGF2; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL.

In some embodiments, determining the MF portrait comprises: determining the gene group expression level for the proliferation rate group using the gene expression level obtained from the RNA sequence data for at least three genes in the proliferation rate group; determining the gene group expression level for the PI3K/AKT/mTOR signaling group using the gene expression level obtained from the RNA sequence data for at least three genes in the PI3K/AKT/mTOR signaling group; determining the gene group expression level for the RAS/RAF/MEK signaling group using the gene expression level obtained from the RNA sequence data for at least three genes in the RAS/RAF/MEK signaling group; determining the gene group expression level for the receptor tyrosine kinases expression group using the gene expression level obtained from the RNA sequence data for at least three genes in the receptor tyrosine kinases expression group; determining the gene group expression level for the growth factors group using the gene expression level obtained from the RNA sequence data for at least three genes in the growth factors group; determining the gene group expression level for the tumor suppressors group using the gene expression level obtained from the RNA sequence data for at least three genes in the tumor suppressors group; determining the gene group expression level for the metastasis signature group using the gene expression level obtained from the RNA sequence data for at least three genes in the metastasis signature group; determining the gene group expression level for the anti-metastatic factors group using the gene expression level obtained from the RNA sequence data for at least three genes in the anti-metastatic factors group; and determining the gene group expression level for the mutation status group using the gene expression level obtained from the RNA sequence data for at least three genes in the mutation status group.

In some embodiments, determining the MF profile for the subject comprises: determining a first gene group expression level for a first gene group of the first set of gene groups associated with cancer malignancy using a gene set enrichment analysis (GSEA) technique; and determining a second gene group expression level for a second gene group of the second set of gene groups associated with cancer microenvironment using the gene set enrichment analysis (GSEA) technique.

In some embodiments, determining the MF profile for the subject comprises: determining a first gene group expression level for a first gene group of the first set of gene groups associated with cancer malignancy using a mutation count technique; and determining a second gene group expression level for a second gene group of the second set of gene groups associated with cancer microenvironment using the mutation count technique.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining first RNA expression data and/or first whole exome sequencing (WES) data from biological samples from a plurality of subjects; determining a respective plurality of molecular-functional (MF) profiles for the plurality of subjects at least in part by, for each of the plurality of subjects, determining, using the first RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters including: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples; obtaining second RNA expression data for a biological sample from a subject; determining a molecular-functional (MF) profile for the subject at least in part by determining, using the second RNA expression data, a gene group expression level for each group in the set of gene groups; and identifying, from among the MF profile clusters, a particular MF profile cluster with which to associate the MF profile for the subject.

In one aspect, provided herein is a method, comprising: using at least one computer hardware processor to perform: obtaining first RNA expression data and/or first whole exome sequencing (WES) data from biological samples from a plurality of subjects; determining a respective plurality of molecular-functional (MF) profiles for the plurality of subjects at least in part by, for each of the plurality of subjects, determining, using the first RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters including: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples; obtaining second RNA expression data for a biological sample from a subject; determining a molecular-functional (MF) profile for the subject at least in part by determining, using the second RNA expression data, a gene group expression level for each group in the set of gene groups; and identifying, from among the MF profile clusters, a particular MF profile cluster with which to associate the MF profile for the subject.

In one aspect, provided herein is at least one non-transitory computer-readable storage medium storing processor-executable instructions that, when executed by at least one computer hardware processor, cause the at least one computer hardware processor to perform: obtaining first RNA expression data and/or first whole exome sequencing (WES) data from biological samples from a plurality of subjects; determining a respective plurality of molecular-functional (MF) profiles for the plurality of subjects at least in part by, for each of the plurality of subjects, determining, using the first RNA expression data, a respective gene group expression level for each group in a set of gene groups, the set of gene groups comprising gene groups associated with cancer malignancy and different gene groups associated with cancer microenvironment; clustering the plurality of MF profiles to obtain MF profile clusters including: a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples; obtaining second RNA expression data for a biological sample from a subject; determining a molecular-functional (MF) profile for the subject at least in part by determining, using the second RNA expression data, a gene group expression level for each group in the set of gene groups; and identifying, from among the MF profile clusters, a particular MF profile cluster with which to associate the MF profile for the subject.

In some embodiments, the first portion comprises a first plurality of GUI elements representing a respective plurality of gene groups associated with cancer malignancy; and the second portion comprises a second plurality of GUI elements representing a respective plurality of gene groups associated with cancer microenvironment.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the tumor properties group; and second gene groups associated with cancer microenvironment consisting of the tumor-promoting immune microenvironment group, the anti-tumor immune microenvironment group, the angiogenesis group, and the fibroblasts group, determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the tumor properties group; and second gene groups associated with cancer microenvironment consisting of the tumor-promoting immune microenvironment group, the anti-tumor immune microenvironment group, the angiogenesis group, and the fibroblasts group, determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the tumor properties group; and second gene groups associated with cancer microenvironment consisting of the tumor-promoting immune microenvironment group, the anti-tumor immune microenvironment group, the angiogenesis group, and the fibroblasts group, determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In some embodiments, determining the first set of visual characteristics for the first plurality of GUI elements determining sizes for each of the first plurality of GUI elements using the gene expression levels determined for the first gene groups; and determining the second set of visual characteristics for the first plurality of GUI elements determining sizes for each of the second plurality of GUI elements using the gene expression levels determined for the second gene groups.

In some embodiments, determining the MF profile for the subject comprises determining the gene expression levels for each of the first gene groups using a gene set enrichment analysis (GSEA) technique; and determining the MF profile for the subject comprises determining the gene expression levels for each of the second gene groups using the gene set enrichment analysis (GSEA) technique.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and second gene groups associated with cancer microenvironment consisting of the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and second gene groups associated with cancer microenvironment consisting of the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and second gene groups associated with cancer microenvironment consisting of the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and second gene groups associated with cancer microenvironment consisting of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is a method, comprising: using at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and second gene groups associated with cancer microenvironment consisting of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

In one aspect, provided herein is at least one non-transitory computer-readable storage medium storing processor-executable instructions that, when executed by at least one computer hardware processor, cause the at least one computer hardware processor to perform: obtaining RNA expression data and/or whole exome sequencing (WES) data for a biological sample from a subject; determining a molecular-functional (MF) profile for the subject at least in part by determining, using the RNA expression data, a gene group expression level for each gene group in a set of gene groups comprising: first gene groups associated with cancer malignancy consisting of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group; and second gene groups associated with cancer microenvironment consisting of the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group; determining a first set of visual characteristics for a first plurality of graphical user interface (GUI) elements using the gene group expression levels determined for the first gene groups; determining a second set of visual characteristics for a second plurality of GUI elements using the gene group expression levels determined for the second gene groups; generating a personalized GUI personalized to the subject, the generating comprising: generating a first GUI portion associated with cancer malignancy and containing the first plurality of GUI elements having the determined first set of visual characteristics; and generating a second GUI portion associated with cancer microenvironment and containing the second plurality of GUI elements having the determined second set of visual characteristics; and presenting the generated personalized GUI to a user.

EQUIVALENTS AND SCOPE

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the technology described herein need not reside on a single computer or processor, but may be distributed in a modular fashion among different computers or processors to implement various aspects of the technology described herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as an example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the described methods and systems encompass all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the systems and methods described herein (or aspects thereof) are referred to as comprising particular elements and/or features, certain embodiments of the systems and methods or aspects of the same consist, or consist essentially of, such elements and/or features. For purposes of simplicity, those embodiments have not been specifically set forth in haec verba herein.

It is also noted that the terms "including," "comprising," "having," "containing", "involving", are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the described systems and methods, to the tenth of the unit of the lower limit of the range, unless the context clearly dictates otherwise.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

Additionally, as used herein the terms "patient" and "subject" may be used interchangeably. Such terms may include, but are not limited to, human subjects or patients. Such terms may also include non-human primates or other animals.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that fall within the prior art may be explicitly excluded from any one or more of the claims. Because such embodiments are deemed to be known to one of ordinary skill in the art, they may be excluded even if the exclusion is not set forth explicitly herein. Any particular embodiment of the systems and methods described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:
1. A system, comprising:
at least one computer hardware processor; and
at least one non-transitory computer-readable storage medium storing processor-executable instructions that, when executed by the at least one computer hardware processor, cause the at least one computer hardware processor to perform:
 obtaining RNA expression data from biological samples from a plurality of subjects, at least some of the plurality of subjects having a cancer of a particular type;
 determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment, wherein the gene groups associated with cancer microenvironment include: a cancer associated fibroblasts group, an angiogenesis group, a MHCI group, a MHCII group, a coactivation molecules group, an effector cells group, a NK cells group, a T cells group, a B cells group, a M1 signatures group, a Th1 signature group, an antitumor cytokines group, a checkpoint inhibition group, a Treg group, a MDSC group, a granulocytes group, a Th2 signature group, and a protumor cytokines group; and wherein determining the respective plurality of MF profiles for the plurality of subjects comprises determining a gene group expression level for each of the cancer associated fibroblasts group, the angiogenesis group, the MHCI group, the MHCII group, the coactivation molecules group, the effector cells group, the NK cells group, the T cells group, the B cells group, the M1 signatures group, the Th1 signature group, the antitumor cytokines group, the checkpoint inhibition group, the Treg group, the MDSC group, the granulocytes group, the Th2 signature group, and the protumor cytokines group, wherein determining the gene group expression level for the M1 signatures group comprises using a gene expression level obtained from the RNA expression data for at least three genes in the M1 signatures group;
 clustering the respective plurality of MF profiles to obtain MF profile clusters comprising:
  a first MF profile cluster associated with inflamed and vascularized biological samples and/or inflamed and fibroblast-enriched biological samples,
  a second MF profile cluster associated with inflamed and non-vascularized biological samples and/or inflamed and non-fibroblast-enriched biological samples,
  a third MF profile cluster associated with non-inflamed and vascularized biological samples and/or non-inflamed and fibroblast-enriched biological samples, and
  a fourth MF profile cluster associated with non-inflamed and non-vascularized biological samples and/or non-inflamed and non-fibroblast-enriched biological samples;

storing the respective plurality of MF profiles in association with information identifying the particular cancer type; and determining at least one visual characteristic of a first graphical user interface (GUI) element using a first gene group expression level for at least one gene group associated with cancer malignancy and at least one visual characteristic of a second GUI element using a second gene group expression level for at least one gene group associated with cancer microenvironment;

generating a personalized GUI personalized to a subject of the plurality of subjects, the personalized GUI comprising:

a first portion associated with cancer malignancy and containing the first GUI element; and a second portion associated with cancer microenvironment and containing the second GUI element, wherein the second portion is different from the first portion; and presenting the generated personalized GUI to a user.

2. The system of claim 1, wherein the gene groups associated with cancer malignancy comprise a tumor properties group; and wherein determining the respective plurality of MF profiles comprises determining a gene group expression level for the tumor properties group; and/or wherein the gene groups associated with cancer microenvironment comprise a tumor-promoting immune microenvironment group, an anti-tumor immune microenvironment group, and a fibroblasts group; and wherein determining the respective plurality of MF profiles comprises determining a gene group expression level for each of the tumor-promoting immune microenvironment group, the anti-tumor immune microenvironment group, and the fibroblasts group.

3. The system of claim 2, wherein the gene groups associated with cancer malignancy comprise at least three genes from the following group:

the tumor properties group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL.

4. The system of claim 3, wherein determining the respective plurality of MF profiles comprises:

determining the gene group expression level for the tumor properties group using a gene expression level obtained from the RNA expression data for at least three genes in the tumor properties group.

5. The system of claim 2, wherein the gene groups associated with cancer microenvironment comprise at least three genes from each of the following groups:

the anti-tumor immune microenvironment group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG;

the tumor-promoting immune microenvironment group: PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDO1, ARG1, IL4R, IL10, TGFB1, TGFB2, TGFB3, NOS2, CYBB, CXCR4, CD33, CXCL1, CXCL5, CCL2, CCL4, CCL5, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1;

the fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; and the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; optionally wherein determining the respective plurality of MF profiles comprises:

determining the gene group expression level for the anti-tumor immune microenvironment group using a gene expression level obtained from the RNA expression data for at least three genes in the anti-tumor immune microenvironment group;

determining the gene group expression level for the tumor-promoting immune microenvironment group using a gene expression level obtained from the RNA expression data for at least three genes in the tumor-promoting immune microenvironment group;

determining the gene group expression level for the fibroblasts group using a gene expression level obtained from the RNA expression data for at least three genes in the fibroblasts group; and determining the gene group expression level for the angiogenesis group using a gene expression level obtained from the RNA expression data for at least three genes in the angiogenesis group.

6. The system of claim 1, wherein the gene groups associated with cancer malignancy comprise: a proliferation rate group, a PI3K/AKT/mTOR signaling group, a RAS/RAF/MEK signaling group, a receptor tyrosine kinases expression group, a tumor suppressors group, a metastasis signature group, an anti-metastatic factors group, and a mutation status group; and wherein determining the respective plurality of MF profiles comprises determining a gene group expression level for each of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group; and/or wherein the gene groups associated with cancer microenvironment comprise: an antigen presentation group, a cytotoxic T and NK cells group, an anti-tumor microenvironment group, and a tumor-promotive immune group; and wherein determining the respective plurality of MF profiles comprises determining a gene group expression level for each of the antigen presentation group, the cytotoxic T and NK cells group, the anti-tumor microenvironment group, and the tumor-promotive immune group.

7. The system of claim 6, wherein the gene groups associated with cancer malignancy comprise at least three genes from each of the following groups:

the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6;

the PI3K/AKT/mTOR signaling group: PIK3CA, PIK3CB, PIK3CG, PIK3CD, AKT1, MTOR, PTEN, PRKCA, AKT2, and AKT3;

the RAS/RAF/MEK signaling group: BRAF, FNTA, FNTB, MAP2K1, MAP2K2, MKNK1, and MKNK2;

the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB;

the tumor suppressors group: TP53, SIK1, PTEN, DCN, MTAP, AIM2, and RB1;

the metastasis signature group: ESRP1, CTSL, HOXA1, SMARCA4, SNAI2, TWIST1, NEDD9, PAPPA, and HPSE;

the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL; optionally wherein determining the respective plurality of MF profiles comprises:

determining the gene group expression level for the proliferation rate group using a gene expression level obtained from the RNA expression data for at least three genes in the proliferation rate group;

determining the gene group expression level for the PI3K/AKT/mTOR signaling group using a gene expression level obtained from the RNA expression data for at least three genes in the PI3K/AKT/mTOR signaling group;

determining the gene group expression level for the RAS/RAF/MEK signaling group using a gene expression level obtained from the RNA expression data for at least three genes in the RAS/RAF/MEK signaling group;

determining the gene group expression level for the receptor tyrosine kinases expression group using a gene expression level obtained from the RNA expression data for at least three genes in the receptor tyrosine kinases expression group;

determining the gene group expression level for the tumor suppressors group using a gene expression level obtained from the RNA expression data for at least three genes in the tumor suppressors group;

determining the gene group expression level for the metastasis signature group using a gene expression level obtained from the RNA expression data for at least three genes in the metastasis signature group;

determining the gene group expression level for the anti-metastatic factors group using a gene expression level obtained from the RNA expression data for at least three genes in the anti-metastatic factors group; and determining the gene group expression level for the mutation status group using a gene expression level obtained from the RNA expression data for at least three genes in the mutation status group.

8. The system of claim 6, wherein the gene groups associated with cancer microenvironment comprise at least three genes from each of the following groups:

the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3;

the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3;

the antigen presentation group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, and CD28;

the cytotoxic T and NK cells group: IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, and TRAT1;

the B cells group: CD19, MS4A1, TNFRSF13C, CD27, CD24, CR2, TNFRSF17, TNFRSF13B, CD22, CD79A, CD79B, and BLK;

the anti-tumor microenvironment group: NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNF SF 10, and FASLG;

the checkpoint inhibition group: PDCD1, CD274, CTLA4, LAG3, PDCD1LG2, BTLA, HAVCR2, and VSIR;

the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28;

the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8;

the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG;

the tumor-promotive immune group: IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1; optionally wherein determining the respective plurality of MF profiles comprises:

determining the gene group expression level for the cancer associated fibroblasts group using a gene expression level obtained from the RNA expression data for at least three genes in the cancer associated fibroblasts group;

determining the gene group expression level for the angiogenesis group using a gene expression level obtained from the RNA expression data for at least three genes in the angiogenesis group;

determining the gene group expression level for the antigen presentation group using a gene expression level obtained from the RNA expression data for at least three genes in the antigen presentation group;

determining the gene group expression level for the cytotoxic T and NK cells group using a gene expression level obtained from the RNA expression data for at least three genes in the cytotoxic T and NK cells group;

determining the gene group expression level for the B cells group using a gene expression level obtained from the RNA expression data for at least three genes in the B cells group;

determining the gene group expression level for the anti-tumor microenvironment group using a gene expression level obtained from the RNA expression data for at least three genes in the anti-tumor microenvironment group;

determining the gene group expression level for the checkpoint inhibition group using a gene expression level obtained from the RNA expression data for at least three genes in the checkpoint inhibition group;

determining the gene group expression level for the Treg group using a gene expression level obtained from the RNA expression data for at least three genes in the Treg group;

determining the gene group expression level for the MDSC group using a gene expression level obtained from the RNA expression data for at least three genes in the MDSC group;

determining the gene group expression level for the granulocytes group using a gene expression level obtained from the RNA expression data for at least three genes in the granulocytes group; and determining the gene group expression level for the tumor-promotive immune group using a gene expression level obtained from the RNA expression data for at least three genes in the tumor-promotive immune group.

9. The system of claim 1,
wherein the gene groups associated with cancer malignancy include: a proliferation rate group, a PI3K/AKT/mTOR signaling group, a RAS/RAF/MEK signaling group, a receptor tyrosine kinases expression group, a growth factors group, a tumor suppressors group, a metastasis signature group, an anti-metastatic factors group, and a mutation status group; and wherein determining the respective plurality of MF profiles comprises determining a gene group expression level for each of the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group.

10. The system of claim 9, wherein the gene groups associated with cancer malignancy comprise at least three genes from each of the following groups:

the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6;

the PI3K/AKT/mTOR signaling group: PIK3CA, PIK3CB, PIK3CG, PIK3CD, AKT1, MTOR, PTEN, PRKCA, AKT2, and AKT3;

the RAS/RAF/MEK signaling group: BRAF, FNTA, FNTB, MAP2K1, MAP2K2, MKNK1, and MKNK2;

the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB;

the growth factors group: NGF, CSF3, CSF2, FGF7, IGF1, IGF2, IL7, and FGF2;

the tumor suppressors group: TP53, SIK1, PTEN, DCN, MTAP, AIM2, and RB1;

the metastasis signature group: ESRP1, CTSL, HOXA1, SMARCA4, SNAI2, TWIST1, NEDD9, PAPPA, and HPSE;

the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL; optionally wherein determining the respective plurality of MF profiles comprises:

determining the gene group expression level for the proliferation rate group using a gene expression level obtained from the RNA expression data for at least three genes in the proliferation rate group;

determining the gene group expression level for the PI3K/AKT/mTOR signaling group using a gene expression level obtained from the RNA expression data for at least three genes in the PI3K/AKT/mTOR signaling group;

determining the gene group expression level for the RAS/RAF/MEK signaling group using a gene expression level obtained from the RNA expression data for at least three genes in the RAS/RAF/MEK signaling group;

determining the gene group expression level for the receptor tyrosine kinases expression group using a gene expression level obtained from the RNA expression data for at least three genes in the receptor tyrosine kinases expression group;

determining the gene group expression level for the growth factors group using a gene expression level obtained from the RNA expression data for at least three genes in the growth factors group;

determining the gene group expression level for the tumor suppressors group using a gene expression level obtained from the RNA expression data for at least three genes in the tumor suppressors group;

determining the gene group expression level for the metastasis signature group using a gene expression level obtained from the RNA expression data for at least three genes in the metastasis signature group;

determining the gene group expression level for the anti-metastatic factors group using a gene expression level obtained from the RNA expression data for at least three genes in the anti-metastatic factors group; and determining the gene group expression level for the mutation status group using a gene expression level obtained from the RNA expression data for at least three genes in the mutation status group.

11. The system of claim 1, wherein the gene groups associated with cancer microenvironment comprise at least three genes from each of the following groups:

the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3;

the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3;

the MHCI group: HLA-A, HLA-B, HLA-C, B2M, TAP1, and TAP2;

the MHCII group: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6;

the coactivation molecules group: CD80, CD86, CD40, CD83, TNFRSF4, ICOSLG, and CD28;

the effector cells group: IFNG, GZMA, GZMB, PRF1, LCK, GZMK, ZAP70, GNLY, FASLG, TBX21, EOMES, CD8A, and CD8B;

the NK cells group: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5;

a T cell traffic group: CXCL9, CXCL10, CXCR3, CX3CL1, CCR7, CXCL11, CCL21, CCL2, CCL3, CCL4, and CCL5;

the T cells group: EOMES, TBX21, ITK, CD3D, CD3E, CD3G, TRAC, TRBC1, TRBC2, LCK, UBASH3A, and TRAT1;

the B cells group: CD19, MS4A1, TNFRSF13C, CD27, CD24, CR2, TNFRSF17, TNFRSF13B, CD22, CD79A, CD79B, and BLK;

the M1 signatures group: NOS2, IL12A, IL12B, IL23A, TNF, IL1B, and SOCS3;

the Th1 signature group: IFNG, IL2, CD40LG, IL15, CD27, TBX21, LTA, and IL21;

the antitumor cytokines group: HMGB1, TNF, IFNB1, IFNA2, CCL3, TNFSF10, and FASLG;

the checkpoint inhibition group: PDCD1, CD274, CTLA4, LAG3, PDCD1LG2, BTLA, HAVCR2, and VSIR;

the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28;

the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8;

the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG;

a M2 signature group: IL10, VEGFA, TGFB1, IDO1, PTGES, MRC1, CSF1, LRP1, ARG1, PTGS1, MSR1, CD163, and CSF1R;

the Th2 signature group: IL4, IL5, IL13, IL10, IL25, and GATA3;

the protumor cytokines group: IL10, TGFB1, TGFB2, TGFB3, IL22, and MIF; and a complement inhibition group: CFD, CFI, CD55, CD46, and CR1; optionally wherein determining the respective plurality of MF profiles comprises:

determining the gene group expression level for the cancer associated fibroblasts group using a gene expression level obtained from the RNA expression data for at least three genes in the cancer associated fibroblasts group;

determining the gene group expression level for the angiogenesis group using a gene expression level obtained from the RNA expression data for at least three genes in the angiogenesis group;

determining the gene group expression level for the MHCI group using a gene expression level obtained from the RNA expression data for at least three genes in the MHCI group;

determining the gene group expression level for the MHCII group using a gene expression level obtained from the RNA expression data for at least three genes in the MHCII group;

determining the gene group expression level for the coactivation molecules group using a gene expression level obtained from the RNA expression data for at least three genes in the coactivation molecules group;

determining the gene group expression level for the effector cells group using a gene expression level obtained from the RNA expression data for at least three genes in the effector cells group;

determining the gene group expression level for the NK cells group using a gene expression level obtained from the RNA expression data for at least three genes in the NK cells group;

determining the gene group expression level for the T cell traffic group using a gene expression level obtained from the RNA expression data for at least three genes in the T cell traffic group;

determining the gene group expression level for the T cells group using a gene expression level obtained from the RNA expression data for at least three genes in the T cells group;

determining the gene group expression level for the B cells group using a gene expression level obtained from the RNA expression data for at least three genes in the B cells group;

determining the gene group expression level for the Th1 signature group using a gene expression level obtained from the RNA expression data for at least three genes in the Th1 signature group;

determining the gene group expression level for the antitumor cytokines group using a gene expression level obtained from the RNA expression data for at least three genes in the antitumor cytokines group;

determining the gene group expression level for the checkpoint inhibition group using a gene expression level obtained from the RNA expression data for at least three genes in the checkpoint inhibition group;

determining the gene group expression level for the Treg group using a gene expression level obtained from the RNA expression data for at least three genes in the Treg group;

determining the gene group expression level for the MDSC group using a gene expression level obtained from the RNA expression data for at least three genes in the MDSC group;

determining the gene group expression level for the granulocytes group using a gene expression level obtained from the RNA expression data for at least three genes in the granulocytes group;

determining the gene group expression level for the M2 signature group using a gene expression level obtained from the RNA expression data for at least three genes in the M2 signature group;

determining the gene group expression level for the Th2 signature group using a gene expression level obtained from the RNA expression data for at least three genes in the Th2 signature group;

determining the gene group expression level for the protumor cytokines group using a gene expression level obtained from the RNA expression data for at least three genes in the protumor cytokines group; and determining the gene group expression level for the complement inhibition group using a gene expression level obtained from the RNA expression data for at least three genes in the complement inhibition group.

12. The system of claim 1, wherein:
(a) obtaining the RNA expression data is performed using whole transcriptome sequencing or mRNA sequencing; and/or
(b) each of the biological samples is from a tumor or tissue known or suspected of having cancerous cells.

13. The system of claim 1, wherein the system further comprises:
obtaining RNA expression data for at least one biological sample obtained from an additional subject;
determining, using the RNA expression data for the at least one biological sample obtained from the additional subject, an MF profile for the additional subject, wherein the MF profile for the additional subject is determined at least in part by determining, using the RNA expression data for the at least one biological sample obtained from the additional subject, a gene group expression level for each gene group in the set of gene groups; and identifying, from among the MF profile clusters, an MF profile cluster with which to associate the MF profile for the additional subject.

14. The system of claim 1, wherein determining the at least one visual characteristic of the first GUI element comprises determining size of the first GUI element using the first gene group expression level; and/or wherein determining the at least one visual characteristic of the first GUI element comprises determining color of the first GUI element using the first gene group expression level.

15. The system of claim 1, wherein the first portion comprises a first plurality of GUI elements representing a respective plurality of gene groups associated with cancer malignancy; and/or wherein the second portion comprises a second plurality of GUI elements representing a respective plurality of gene groups associated with cancer microenvironment.

16. The system of claim 1, wherein determining the respective gene group expression level for each group in the set of gene groups is performed using a gene set enrichment analysis (GSEA) technique and/or a mutation count technique.

17. The system of claim 1, wherein the clustering is performed using a community detection clustering technique and/or a k-means clustering technique.

18. The system of claim 1, wherein the at least one computer hardware processor is further configured to perform:
obtaining whole exome sequencing (WES) data; and
based on the WES data, quantifying tumor burden identifying specific mutations, and/or calculating the number of neoantigens.

19. At least one non-transitory computer-readable storage medium storing processor-executable instructions that, when executed by at least one computer hardware processor, cause the at least one computer hardware processor to perform:
obtaining RNA expression data from biological samples from a plurality of subjects, at least some of the plurality of subjects having a cancer of a particular type;
determining a respective plurality of molecular-functional (MF) profiles for the plurality of subjects at least in part by, for each of the plurality of subjects,
determining, using the RNA expression data, a respective gene group expression level for each group in a set of gene groups, the set of gene groups comprising gene groups associated with cancer malignancy and different gene groups associated with cancer microenvironment, wherein the gene groups associated with cancer microenvironment include: a cancer associated fibroblasts group, an angiogenesis group, a MHCI group, a MHCII group, a coactivation molecules group, an effector cells group, a NK cells group, a T cells group, a B cells group, a M1 signatures group, a Th1 signature group, an antitumor cytokines group, a checkpoint inhibition group, a Treg group, a MDSC group, a granulocytes group, a Th2 signature group, and a protumor cytokines group; and wherein determining the respective plurality of MF profiles for the plurality of subjects comprises determining a gene group expression level for each of the cancer associated fibroblasts group, the angiogenesis group, the MHCI group, the MHCII group, the coactivation molecules group, the effector cells group, the NK cells group, the T cells group, the B cells group, the M1 signatures group, the Th1 signature group, the antitumor cytokines group, the checkpoint inhibition group, the Treg group, the MDSC group, the granulocytes group, the Th2 signature group, and the protumor cytokines group, wherein determining the gene group expression level for the M1 signatures group comprises using a gene expression level obtained from the RNA expression data for at least three genes in the M1 signatures group;

clustering the respective plurality of MF profiles to obtain MF profile clusters comprising:
  a first MF profile cluster associated with inflamed and vascularized biological samples and/or inflamed and fibroblast-enriched biological samples,
  a second MF profile cluster associated with inflamed and non-vascularized biological samples and/or inflamed and non-fibroblast-enriched biological samples,
  a third MF profile cluster associated with non-inflamed and vascularized biological samples and/or non-inflamed and fibroblast-enriched biological samples, and
  a fourth MF profile cluster associated with non-inflamed and non-vascularized biological samples and/or non-inflamed and non-fibroblast-enriched biological samples;

storing the respective plurality of MF profiles in association with information identifying the particular cancer type; and determining at least one visual characteristic of a first graphical user interface (GUI) element using a first gene group expression level for at least one gene group associated with cancer malignancy and at least one visual characteristic of a second GUI element using a second gene group expression level for at least one gene group associated with cancer microenvironment;

generating a personalized GUI personalized to a subject of the plurality of subjects, the personalized GUI comprising:
  a first portion associated with cancer malignancy and containing the first GUI element; and
  a second portion associated with cancer microenvironment and containing the second GUI element, wherein the second portion is different from the first portion; and presenting the generated personalized GUI to a user.

20. A method, comprising:
using at least one computer hardware processor to perform:
  obtaining RNA expression data from biological samples from a plurality of subjects, at least some of the plurality of subjects having a cancer of a particular type;
  determining a respective plurality of molecular-functional (MF) profiles for the plurality of subjects at least in part by, for each of the plurality of subjects, determining, using the RNA expression data, a respective gene group expression level for each group in a set of gene groups, the set of gene groups comprising gene groups associated with cancer malignancy and different gene groups associated with cancer microenvironment, wherein the gene groups associated with cancer microenvironment include: a cancer associated fibroblasts group, an angiogenesis group, a MHCI group, a MHCII group, a coactivation molecules group, an effector cells group, a NK cells group, a T cells group, a B cells group, a M1 signatures group, a Th1 signature group, an antitumor cytokines group, a checkpoint inhibition group, a Treg group, a MDSC group, a granulocytes group, a Th2 signature group, and a protumor cytokines group; and wherein determining the respective plurality of MF profiles for the plurality of subjects comprises determining a gene group expression level for each of the cancer associated fibroblasts group, the angiogenesis group, the MHCI group, the MHCII group, the coactivation molecules group, the effector cells group, the NK cells group, the T cells group, the B cells group, the M1 signatures group, the Th1 signature group, the antitumor cytokines group, the checkpoint inhibition group, the Treg group, the MDSC group, the granulocytes group, the Th2 signature group, and the protumor cytokines group, wherein determining the gene group expression level for the M1 signatures group comprises using a gene expression level obtained from the RNA expression data for at least three genes in the M1 signatures group;

clustering the respective plurality of MF profiles to obtain MF profile clusters comprising:
    a first MF profile cluster associated with inflamed and vascularized biological samples and/or inflamed and fibroblast-enriched biological samples,
    a second MF profile cluster associated with inflamed and non-vascularized biological samples and/or inflamed and non-fibroblast-enriched biological samples,
    a third MF profile cluster associated with non-inflamed and vascularized biological samples and/or non-inflamed and fibroblast-enriched biological samples, and
    a fourth MF profile cluster associated with non-inflamed and non-vascularized biological samples and/or non-inflamed and non-fibroblast-enriched biological samples;

storing the respective plurality of MF profiles in association with information identifying the particular cancer type; and determining at least one visual characteristic of a first graphical user interface (GUI) element using a first gene group expression level for at least one gene group associated with cancer malignancy and at least one visual characteristic of a second GUI element using a second gene group expression level for at least one gene group associated with cancer microenvironment;

generating a personalized GUI personalized to a subject of the plurality of subjects, the personalized GUI comprising:
    a first portion associated with cancer malignancy and containing the first GUI element; and
    a second portion associated with cancer microenvironment and containing the second GUI element, wherein the second portion is different from the first portion; and presenting the generated personalized GUI to a user.

* * * * *

UNITED STATES PATENT AND TRADEMARK OFFICE
CERTIFICATE OF CORRECTION

PATENT NO. : 11,984,200 B2
APPLICATION NO. : 16/006481
DATED : May 14, 2024
INVENTOR(S) : Alexander Bagaev et al.

It is certified that error appears in the above-identified patent and that said Letters Patent is hereby corrected as shown below:

In the Claims

Column 140, Line 32 Claim 5:
"CXCL5, CCL2, CCL4, CCL5, CCR2, CCL3, CCL5"
Should read:
--CXCL5, CCL2, CCL4, CCL8, CCR2, CCL3, CCL5--

Signed and Sealed this
Second Day of July, 2024

Katherine Kelly Vidal
*Director of the United States Patent and Trademark Office*